(12) United States Patent
Rudolf et al.

(10) Patent No.: US 7,700,589 B2
(45) Date of Patent: Apr. 20, 2010

(54) CGRP ANTAGONISTS

(75) Inventors: Klaus Rudolf, Warthausen (DE);
Stephan Georg Mueller, Warthausen (DE); Dirk Stenkamp, Biberach (DE);
Philipp Lustenberger, Basel (CH);
Alexander Dreyer, Gutenzell-Huerbel (DE); Eckhart Bauer, Biberach (DE);
Marcus Schindler, Biberach (DE);
Kirsten Arndt, Biberach (DE); Henri Doods, Warthausen (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 11/757,743

(22) Filed: Jun. 4, 2007

(65) Prior Publication Data

US 2007/0244099 A1    Oct. 18, 2007

Related U.S. Application Data

(63) Continuation of application No. 10/685,921, filed on Oct. 15, 2003, now abandoned.

(60) Provisional application No. 60/426,167, filed on Nov. 14, 2002.

(30) Foreign Application Priority Data

Oct. 25, 2002    (DE)    ................. 102 50 082

(51) Int. Cl.
*C07D 403/14* (2006.01)
*A61K 31/551* (2006.01)
(52) U.S. Cl. ...................... 514/221; 540/500
(58) Field of Classification Search ............... 540/500; 514/221
See application file for complete search history.

(56) References Cited

U.S. PATENT DOCUMENTS

| 5,442,044 | A  | 8/1995 | Hoover et al. |
| 6,344,449 | B1 | 2/2002 | Rudolf et al. |
| 6,653,478 | B2 | 11/2003 | Urbanski et al. |
| 7,205,294 | B2 | 4/2007 | Rudolf et al. |
| 7,279,471 | B2 | 10/2007 | Mueller |
| 7,439,237 | B2 | 10/2008 | Rudolf |
| 7,479,488 | B2 | 1/2009 | Mueller |
| 2004/0192729 | A1 | 9/2004 | Rudolf et al. |
| 2005/0256099 | A1 | 11/2005 | Mueller |
| 2006/0252750 | A1 | 11/2006 | Mueller |
| 2006/0252931 | A1 | 11/2006 | Mueller et al. |
| 2007/0049581 | A1 | 3/2007 | Mueller |
| 2007/0072847 | A1 | 3/2007 | Mueller |
| 2007/0099903 | A1 | 5/2007 | Mueller |
| 2007/0238715 | A1 | 10/2007 | Rudolf |
| 2007/0275951 | A1 | 11/2007 | Mueller |
| 2008/0280887 | A1 | 11/2008 | Mueller |

FOREIGN PATENT DOCUMENTS

| DE | 19911039 A1 | 9/2000 |
| EP | 0438233 A2 | 7/1991 |
| WO | 9811128 | 3/1998 |
| WO | 03104236 A1 | 12/2003 |
| WO | 2005084672 | 9/2005 |
| WO | 2005100360 | 10/2005 |
| WO | 2005103037 | 11/2005 |
| WO | 2006100009 | 9/2006 |
| WO | 2006100026 | 9/2006 |
| WO | 2007020261 | 2/2007 |
| WO | 2007036532 | 4/2007 |
| WO | 2007036533 | 4/2007 |
| WO | 2007045672 | 4/2007 |
| WO | 2005100343 | 10/2008 |

OTHER PUBLICATIONS

Doods, et al; Pharmacological profile of BIBN4096BS, the first selective small molecule CGRP antagonist; British Journal of Pharmacology; 2000; vol. 129; pp. 420-423; Macmillan Publishers Ltd.
Mallee, et al; Receptor Activity-modifying Protein 1 Determines the Species Selectivity of Non-peptide CGRP Receptor Antagonists; The Journal of Biological Chemistry; Apr. 19, 2002; vol. 277; No. 16; pp. 14294-14298; The American Society for Biochemistry and Molecular Biology, Inc.

*Primary Examiner*—Kahsay T Habte
(74) *Attorney, Agent, or Firm*—Michael P. Morris; Mary-Ellen M. Devlin; Alan R. Stempel

(57) ABSTRACT

CGRP antagonists of the formula

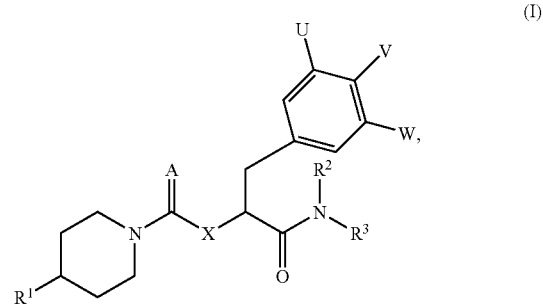

of which the following are exemplary:
(1) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,
(2) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-piperazin-1-yl)-piperidin-1-yl]-2-oxo-ethyl}-amide.

6 Claims, No Drawings

CGRP ANTAGONISTS

RELATED APPLICATIONS

This is a continuation of U.S. application Ser. No. 10/685,921 filed on Oct. 15, 2003, which claims, as does the present application, priority benefit of U.S. Provisional Application Ser. No. 60/426,167, filed on Nov. 14, 2002, and DE 10250082, filed on Oct. 25, 2002.

FIELD OF THE INVENTION

The present invention relates to CGRP antagonists of general formula

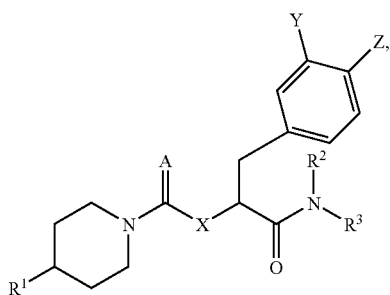

(I)

the tautomers, diastereomers, enantiomers, hydrates, mixtures thereof and the salts thereof as well as the hydrates of the salts, particularly the physiologically acceptable salts thereof with inorganic or organic acids, pharmaceutical compositions containing these compounds, the use thereof and processes for the preparation thereof.

In the above general formula (I) in a first embodiment

A denotes an oxygen or sulphur atom, a phenylsulphonylimino or cyanoimino group, X denotes an oxygen or sulphur atom, an imino group optionally substituted by a $C_{1-6}$-alkyl group or a methylene group optionally substituted by a $C_{1-6}$-alkyl group, Y and Z independently of one another each denote a straight-chain or branched $C_{1-6}$-alkyl group wherein each methylene group may be substituted by up to 2 fluorine atoms and each methyl group may be substituted by up to 3 fluorine atoms, while the above-mentioned alkyl groups together with the carbon atom to which they are bound, may be joined to one another, forming a 4- to 8-membered ring, $R^1$ denotes a saturated, mono- or diunsaturated 5- to 7-membered aza, diaza, triaza, oxaza, thiaza, thiadiaza or S,S-dioxido-thiadiaza heterocyclic group, in which the above-mentioned heterocycles are linked via a carbon or nitrogen atom, contain one or two carbonyl or thiocarbonyl groups adjacent to a nitrogen atom, may be substituted at one of the nitrogen atoms by an alkyl group, may be substituted at one or at two carbon atoms by an alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, while the substituents may be identical or different, and while an olefinic double bond of one of the above-mentioned unsaturated heterocycles may be fused to a phenyl, naphthyl, pyridine, diazine, 1,3-oxazole, thienyl, furan, thiazole, pyrrole, N-methylpyrrole or quinoline ring, to a 1H-quinolin-2-one ring optionally substituted at the nitrogen atom by an alkyl group or to an imidazole or N-methylimidazole ring or also two olefinic double bonds of one of the above-mentioned unsaturated heterocycles may each be fused to a phenyl ring, while the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in $R^1$ as well as benzo-, thieno-, pyrido- and diazino-fused heterocycles in the carbon skeleton may additionally be mono-, di- or trisubstituted by fluorine, chlorine, bromine or iodine atoms, by alkyl, alkoxy, nitro, alkylthio, alkylsulphinyl, alkylsulphonyl, alkylsulphonylamino, phenyl, difluoromethyl, trifluoromethyl, alkoxycarbonyl, carboxy, hydroxy, amino, alkylamino, dialkylamino, acetyl, acetylamino, propionylamino, aminocarbonyl, alkylaminocarbonyl, dialkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, difluoromethoxy, trifluoromethoxy, trifluoromethylthio, trifluoromethylsulphinyl or trifluoromethylsulphonyl groups, while the substituents may be identical or different, $R^2$ denotes the hydrogen atom, a phenylmethyl group or a $C_{2-7}$-alkyl group which may be substituted in the ω position by a cyclohexyl, phenyl, pyridinyl, diazinyl, hydroxy, amino, alkylamino, dialkylamino, carboxy, alkoxycarbonyl, aminocarbonyl, aminocarbonylamino, acetylamino, 1-pyrrolidinyl, 1-piperidinyl, 4-(1-piperidinyl)-1-piperidinyl, 4-morpholinyl, hexahydro-1H-1-azepinyl, [bis-(2-hydroxyethyl)]amino, 4-alkyl-1-piperazinyl or 4-(ω-hydroxy-$C_{2-7}$-alkyl)-1-piperazinyl group, a phenyl or pyridinyl group, while the above-mentioned heterocyclic groups and phenyl groups may additionally be mono- di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, methylsulphonyloxy, difluoromethoxy, trifluoromethoxy, trifluoromethylthio, trifluoromethylsulphinyl, trifluoromethylsulphonyl, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group optionally substituted by a phenyl or pyridinyl group, while the $C_{1-3}$-alkyl group may be linked to an alkyl group present in $R^2$ or a phenyl or pyridyl ring present in $R^2$ and the nitrogen atom to which they are bound, forming a ring, or $R^2$ and $R^3$ together with the enclosed nitrogen atom denote a group of general formula

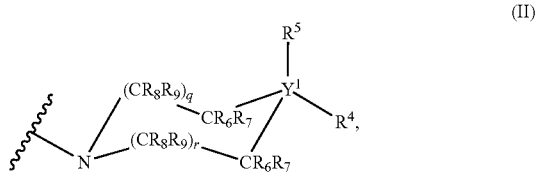

(II)

wherein

Y$^1$ denotes the carbon atom or, if R$^5$ is a pair of free electrons, it may also denote the nitrogen atom, q and r, if Y$^1$ denotes the carbon atom, represent the numbers 0, 1 or 2, or q and r, if Y$^1$ denotes the nitrogen atom, represent the numbers 1 or 2, R$^4$ denotes the hydrogen atom, an amino, alkylamino, dialkylamino, alkyl, cycloalkyl, amino-C$_{2-7}$-alkyl, alkylamino-C$_{2-7}$-alkyl, dialkylamino-C$_{2-7}$-alkyl, aminoiminomethyl, aminocarbonylamino, alkylaminocarbonylamino, cycloalkylaminocarbonylamino, phenylaminocarbonylamino, aminocarbonylalkyl, aminocarbonylaminoalkyl, alkoxycarbonyl, alkoxycarbonylalkyl or carboxyalkyl group, or, if Y$^1$ does not denote the nitrogen atom, the carboxy, aminomethyl, alkylaminomethyl or dialkylaminomethyl group, a phenyl, pyridinyl, diazinyl, 1-naphthyl, 2-naphthyl, pyridinylcarbonyl or phenylcarbonyl group which may each be mono-, di- or trisubstituted in the carbon skeleton by fluorine, chlorine, bromine or iodine atoms, by alkyl, alkoxy, methylsulphonyloxy, difluoromethyl, trifluoromethyl, hydroxy, amino, acetylamino, aminocarbonyl, aminocarbonylamino, aminocarbonylaminomethyl, cyano, carboxy, alkoxycarbonyl, carboxyalkyl, alkoxycarbonylalkyl, alkanoyl, ω-(dialkylamino)alkanoyl, ω-(dialkylamino)alkyl, ω-(dialkylamino)hydroxyalkyl, ω-(carboxy)alkanoyl, difluoromethoxy, trifluoromethoxy, trifluoromethylthio, trifluoromethylsulphinyl or trifluoromethylsulphonyl groups, while the substituents may be identical or different, a 4- to 10-membered azacycloalkyl group, a 6- to 10-membered oxaza, thiaza or diazacycloalkyl group, a 6- to 10-membered azabicycloalkyl group, a 1-alkyl-4-piperidinylcarbonyl or 4-alkyl-1-piperazinylcarbonyl group, while the above-mentioned mono- and bicyclic heterocycles are bound via a nitrogen or carbon atom, in the above-mentioned mono- and bicyclic heterocycles any methylene group not directly bound to a nitrogen, oxygen or sulphur atom may be substituted by one or two fluorine atoms, the above-mentioned mono- and bicyclic heterocycles as well as the 1-alkyl-4-piperidinylcarbonyl- and 4-alkyl-1-piperazinylcarbonyl group in the ring may be mono- or polysubstituted by a C$_{1-7}$-alkyl group, monosubstituted by a phenyl-C$_{1-3}$-alkyl, alkanoyl, dialkylamino, phenylcarbonyl, pyridinylcarbonyl, carboxy, carboxyalkanoyl, carboxyalkyl, alkoxycarbonylalkyl, alkoxycarbonyl, aminocarbonyl, alkylaminocarbonyl, alkylsulphonyl, cycloalkyl or cycloalkylalkyl group, or substituted by a cycloalkylcarbonyl, azacycloalkylcarbonyl, diazacycloalkyl-carbonyl or oxazacycloalkylcarbonyl group optionally alkyl-substituted in the ring, while the alicyclic moieties contained in these substituents each comprise 3 to 10 ring members and the heteroalicyclic moieties each comprise 4 to 10 ring members and the phenyl and pyridinyl groups contained in the above-mentioned groups may in turn be mono-, di- or trisubstituted by fluorine, chlorine, bromine or iodine atoms, by alkyl, alkoxy, methylsulphonyloxy, difluoromethyl, trifluoromethyl, hydroxy, amino, acetylamino, aminocarbonyl, aminocarbonylamino, aminocarbonylaminomethyl, cyano, carboxy, alkoxycarbonyl, carboxyalkyl, alkoxycarbonylalkyl, alkanoyl, ω-(dialkylamino)alkanoyl, ω-(carboxy)alkanoyl, difluoromethoxy, trifluoromethoxy, trifluoromethylthio, trifluoromethylsulphinyl or trifluoromethylsulphonyl groups, while the substituents may be identical or different, R$^5$ denotes a hydrogen atom, a C$_{1-4}$-alkyl group, while an unbranched alkyl group may be substituted in the ω position by a phenyl, pyridinyl, diazinyl, amino, alkylamino, dialkylamino, 1-pyrrolidinyl, 1-piperidinyl, 4-methyl-1-piperazinyl, 4-morpholinyl or hexahydro-1H-1-azepinyl group, an alkoxycarbonyl, the cyano or aminocarbonyl group or also, if Y$^1$ denotes a nitrogen atom, a pair of free electrons, or, if Y$^1$ does not denote a nitrogen atom, also the fluorine atom, or R$^4$ together with R$^5$ and Y$^1$ denote a 4- to 7-membered cycloaliphatic ring, in which a methylene group may be replaced by a —NH or —N(alkyl)-group while a hydrogen atom bound to a nitrogen atom within the above-mentioned group R$^4$ may be replaced by a protecting group, R$^6$ and R$^7$, which may be identical or different, in each case denote a hydrogen atom, a C$_{1-3}$-alkyl or dialkylamino group or also, if Y$^1$ does not denote a nitrogen atom, the fluorine atom and R$^8$ and R$^9$, which may be identical or different, in each case denote a hydrogen atom or a C$_{1-3}$-alkyl group, while, unless otherwise stated, all the above-mentioned alkyl and alkoxy groups as well as the alkyl groups present within the other groups specified comprise 1 to 7 carbon atoms and may be straight-chain or branched, while each methylene group may be substituted by up to 2 fluorine atoms and each methyl group may be substituted by up to 3 fluorine atoms, all the above-mentioned cycloalkyl groups as well as the cycloalkyl groups present within the other groups specified, unless otherwise stated, may comprise 3 to 10 carbon atoms, while each methylene group may be substituted by up to 2 fluorine atoms, all the above-mentioned aromatic and heteroaromatic groups may additionally be mono-di- or trisubstituted by fluorine, chlorine or bromine atoms, by cyano or hydroxy groups and the substituents may be identical or different and by the protective groups mentioned in the foregoing and subsequent definitions are meant the protective groups familiar from peptide chemistry, particularly a phenylalkoxycarbonyl group with 1 to 3 carbon atoms in the alkoxy moiety optionally substituted in the phenyl nucleus by a halogen atom, by a nitro or phenyl group or by one or two methoxy groups, for example the benzyloxycarbonyl, 2-nitro-benzyloxycarbonyl, 4-nitro-benzyloxycarbonyl, 4-methoxy-benzyloxycarbonyl, 2-chloro-benzyloxycarbonyl, 3-chlorobenzyloxycarbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety,
for example the methoxycarbonyl, ethoxycarbonyl, n-propoxycarbonyl, isopropoxycarbonyl, n-butoxycarbonyl, 1-methylpropoxycarbonyl, 2-methylpropoxy-carbonyl or tert.butyloxycarbonyl group, the allyloxycarbonyl, 2,2,2-trichloro-(1,1-dimethylethoxy) carbonyl or 9-fluorenylmethoxycarbonyl group or
the formyl, acetyl or trifluoroacetyl group.

A second embodiment of the present invention comprises the compounds of the above general formula (I), wherein
A, X, Y, Z, $R^2$ and $R^3$ are defined as mentioned in the first embodiment hereinbefore and
$R^1$ denotes a mono- or diunsaturated 5- to 7-membered aza, diaza, triaza or thiaza heterocyclic group,
in which the above-mentioned heterocycles are linked via a carbon or nitrogen atom,
contain one or two carbonyl groups adjacent to a nitrogen atom,
may be substituted at a carbon atom by a phenyl, pyridinyl, diazinyl, thienyl, pyrrolyl, 1,3-thiazolyl, isoxazolyl, pyrazolyl or 1-methylpyrazolyl group and
an olefinic double bond of one of the above-mentioned unsaturated heterocycles may be fused to a phenyl, naphthyl, pyridine, diazine, thienyl or quinoline ring or to a 1H-quinolin-2-one ring optionally substituted at the nitrogen atom by a methyl group,
while the phenyl, pyridinyl, diazinyl, thienyl, pyrrolyl, 1,3-thiazolyl, isoxazolyl, pyrazolyl or 1-methylpyrazolyl groups contained in $R^1$ as well as the benzo-, pyrido- and diazino-fused heterocycles in the carbon skeleton may additionally be mono-, di- or trisubstituted by fluorine, chlorine, bromine or iodine atoms, by alkyl, alkoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, while the above-mentioned alkyl groups or the alkyl groups contained in the above-mentioned groups, unless otherwise stated, contain 1 to 7 carbon atoms and may be branched or unbranched, while each methylene group may be substituted by up to 2 fluorine atoms and each methyl group may be substituted by up to 3 fluorine atoms, and
the above-mentioned aromatic and heteroaromatic groups may additionally be mono- di- or trisubstituted by fluorine, chlorine or bromine atoms or by cyano or hydroxy groups and the substituents may be identical or different.

A third embodiment of the present invention comprises the compounds of the above general formula (I), wherein
A, X, Y, Z, $R^2$ and $R^3$ are defined as hereinbefore in the first embodiment and
$R^1$ denotes a monounsaturated 5- to 7-membered diaza or triaza heterocyclic group,
while the above-mentioned heterocycles are linked via a nitrogen atom,
contain a carbonyl group adjacent to a nitrogen atom,
may additionally be substituted at a carbon atom by a phenyl group and
an olefinic double bond of one of the above-mentioned unsaturated heterocycles may be fused to a phenyl, thienyl or quinoline ring,
while the phenyl groups contained in $R^1$ as well as benzo-fused heterocycles in the carbon skeleton may additionally be mono-, di- or trisubstituted by fluorine, chlorine, bromine or iodine atoms, by methyl, methoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, but are preferably unsubstituted, or monosubstituted by a fluorine, chlorine or bromine atom or by a methyl or methoxy group, while, unless otherwise stated, all the above-mentioned alkyl groups as well as the alkyl groups present within the other groups comprise 1 to 7 carbon atoms and may be straight-chain or branched and the above-mentioned aromatic and heteroaromatic groups may additionally be mono- di- or trisubstituted by fluorine, chlorine or bromine atoms or by cyano or hydroxy groups and the substituents may be identical or different.

A fourth embodiment of the present invention comprises the compounds of the above general formula (I), wherein
A, X, Y, Z, $R^2$ and $R^3$ are defined as hereinbefore in the first embodiment and
$R^1$ denotes a 4-(2-oxo-1,2,4,5-tetrahydro-1,3-benzodiazepin-3-yl)-piperidin-1-yl, 4-(2-oxo-1,4-dihydro-2H-quinazolin-3-yl)-piperidin-1-yl, 4-(5-oxo-3-phenyl-4,5-dihydro-1,2,4-triazol-1-yl)-piperidin-1-yl, 4-(2-oxo-1,2-dihydro-imidazo[4,5-c]quinolin-3-yl)-piperidin-1-yl, 4-(2-oxo-1,2-dihydro-4H-thieno[3,4-d]pyrimidin-3-yl)-piperidin-1-yl, 4-(2-oxo-1,4-dihydro-2H-thieno[3,2-d]pyrimidin-3-yl)-piperidin-1-yl, 4-(5-oxo-4,5,7,8-tetrahydro-2-thia-4,6-diaza-azulen-6-yl)-piperidin-1-yl, 4-(2-oxo-1,2,4,5-tetrahydro-thieno[3,2-d]-1,3-diazepin-3-yl)-piperidin-1-yl, 4-(2-oxo-1,2,4,5-tetrahydro-thieno[2,3-d]-1,3-diazepin-3-yl)-piperidin-1-yl or 4-(2-oxo-1,4-dihydro-2H-thieno[2,3-d]pyrimidin-3-yl)-piperidin-1-yl group,
while the above-mentioned mono- and bicyclic heterocycles in the carbon skeleton may additionally be monosubstituted by a methoxy group,
while the above-mentioned aromatic and heteroaromatic groups by fluorine, chlorine or bromine atoms, by cyano or hydroxy groups may additionally be mono- di- or trisubstituted and the substituents may be identical or different.

A fifth embodiment of the present invention comprises the compounds of the above general formula (I), wherein
A, X, Y, Z and $R^1$ are defined as hereinbefore in the first embodiment and
$R^2$ denotes the hydrogen atom or
a phenylmethyl group or a $C_{2-7}$-alkyl group which may be substituted in the ω position by a phenyl, pyridinyl, hydroxy, amino, alkylamino, dialkylamino, carboxy, alkoxycarbonyl, aminocarbonyl, aminocarbonylamino, acetylamino, 1-pyrrolidinyl, 1-piperidinyl, 4-morpholinyl, [bis-(2-hydroxyethyl)]amino group
while the above-mentioned heterocyclic groups and phenyl groups may additionally be mono-, di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group, while the $C_{1-3}$-alkyl group may be linked to an alkyl group present in $R^2$ or a phenyl or pyridyl ring present in $R^2$ and the nitrogen atom to which they are bound, forming a 5- to 7-membered ring, or $R^2$ and $R^3$ together with the enclosed nitrogen atom denote a group of general formula

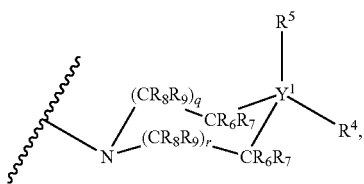

(II)

wherein
- $Y^1$ denotes the carbon atom or, if $R^5$ denotes a pair of free electrons, it may also denote the nitrogen atom,
- q and r, if $Y^1$ denotes the carbon atom, represent the numbers 0 or 1 or,
- q and r, if $Y^1$ denotes the nitrogen atom, represent the numbers 1 or 2,
- $R^4$ denotes the hydrogen atom, an amino, alkylamino or dialkylamino group,
- or, if $Y^1$ does not denote the nitrogen atom, a dialkylaminomethyl group,
- a phenyl, pyridinyl or diazinyl group which may be substituted in each case by a fluorine, chlorine or bromine atom or by a trifluoromethylcarbonyl, methyl or methoxy group,
- a 4- to 7-membered azacycloalkyl group, a 6- to 7-membered oxaza or diazacycloalkyl group or a 7- to 9-membered azabicycloalkyl group,
    - while the above-mentioned mono- and bicyclic heterocycles are bound via a nitrogen or carbon atom,
    - in the above-mentioned mono- and bicyclic heterocycles any methylene group not directly bound to a nitrogen, oxygen or sulphur atom may be substituted by one or two fluorine atoms and
    - the above-mentioned mono- and bicyclic heterocycles may be substituted by a $C_{1-3}$-alkyl group, by a benzyl, $C_{3-6}$-cycloalkylalkyl, $C_{1-4}$-alkanoyl, di-($C_{1-3}$-alkyl)-amino or $C_{1-3}$-alkylsulphonyl, by an alkoxycarbonyl, alkoxycarbonylalkyl, carboxy or carboxyalkyl group,
- $R^5$ denotes a hydrogen atom, a $C_{1-3}$-alkyl group or,
- if $Y^1$ denotes a nitrogen atom, it may also denote a pair of free electrons,
- $R^6$ and $R^7$, which may be identical or different, in each case denote a hydrogen atom or a $C_{1-3}$-alkyl group or di-($C_{1-3}$-alkyl)-amino group and
- $R^8$ and $R^9$, which may be identical or different, in each case denote a hydrogen atom or a $C_{1-3}$-alkyl group, while, unless otherwise stated, all the above-mentioned alkyl groups as well as the alkyl groups present within the other groups comprise 1 to 7 carbon atoms and may be straight-chain or branched and the above-mentioned aromatic and heteroaromatic groups may additionally be mono-, di- or trisubstituted by fluorine, chlorine or bromine atoms or by cyano or hydroxy groups and the substituents may be identical or different.

A sixth embodiment of the present invention comprises the compounds of the above general formula (I), wherein A, X, Y, Z and $R^1$ are defined as hereinbefore in the first embodiment and $R^2$ denotes a phenylmethyl group or a $C_{2-7}$-alkyl group which may be substituted in the ω position by a phenyl, amino, alkylamino or dialkylamino group,
    while the above-mentioned phenyl group may be substituted by an amino-$C_{1-3}$-alkyl, $C_{1-3}$-alkylamino-$C_{1-3}$-alkyl or di-($C_{1-3}$-alkyl)-amino-$C_{1-3}$-alkyl group, or
$R^3$ denotes the hydrogen atom or a $C_{1-3}$-alkyl group,
$R^2$ and $R^3$ together with the nitrogen atom to which they are bound denote a 7-dimethylaminomethyl-1,2,4,5-tetrahydro-3-benzazepin-3-yl group or
$R^2$ and $R^3$ together with the enclosed nitrogen atom denote a group of general formula

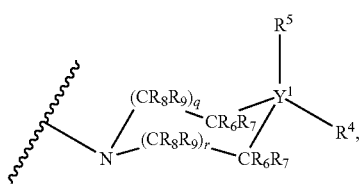

(II)

wherein
- $Y^1$ denotes the carbon atom or, if $R^5$ denotes a pair of free electrons, it may also denote the nitrogen atom,
- q and r, if $Y^1$ denotes the carbon atom, represent the numbers 0 or 1 or
- q and r, if $Y^1$ denotes the nitrogen atom, represent the numbers 1 or 2,
- $R^4$ denotes the hydrogen atom,
- a phenyl or pyridinyl group which may be substituted in each case by a fluorine, chlorine or bromine atom, by a trifluoromethylcarbonyl, methyl or methoxy group,
- a dimethylamino, diethylamino, perhydro-azepin-1-yl, 4-methyl-perhydro-1,4-diazepin-1-yl, 1-methyl-piperidin-4-yl, 1-ethylpiperidin-4-yl, piperazin-1-yl, 4-acetyl-piperazin-1-yl, 4-cyclopropylmethyl-piperazin-1-yl, pyrrolidin-1-yl, 4-ethyl-piperazin-1-yl, 4-isopropyl-piperazin-1-yl, piperidin-1-yl, piperidin-4-yl, morpholin-4-yl, 4,4-difluoro-piperidin-1-yl, 8-methyl-8-aza-bicyclo[3.2.1]oct-3-yl, pyridin-4-yl, 3-dimethylamino-piperidin-1-yl, 1-ethyl-piperidin-4-yl, 4-amino-piperidin-1-yl, 4-(dimethylamino)-piperidin-1-yl, 4-(diethylaminomethyl)-piperidin-1-yl, p-trifluoromethylcarbonyl-phenyl, 1-benzyl-piperidin-4-yl, 4-benzyl-piperazin-1-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-carboxymethyl-piperidin-4-yl, 4-carboxymethyl-piperazin-1-yl, 4-methylsulphonyl-piperazin-1-yl or 4-methyl-piperazin-1-yl group,
- $R^5$ denotes a hydrogen atom or, if $Y^1$ denotes a nitrogen atom, it may also denote a pair of free electrons,
- $R^6$ and $R^7$ in each case denote a hydrogen atom or a dimethylamino group and
- $R^8$ and $R^9$ in each case denote the hydrogen atom, while, unless otherwise stated, all the above-mentioned alkyl groups as well as the alkyl groups present within the other groups comprise 1 to 7 carbon atoms and may be straight-chain or branched and the above-mentioned aromatic and heteroaromatic groups may additionally be mono-, di- or trisubstituted by fluorine, chlorine or bromine atoms, by cyano or hydroxy groups and the substituents may be identical or different, while in all the embodiments mentioned above those compounds wherein
(i) A denotes an oxygen atom, a cyanoimino or phenylsulphonylimino group,
X denotes an oxygen atom, an imino or methylene group and
Y and Z independently of one another each denote a straight-chain or branched $C_{1-4}$-alkyl group wherein each methylene group may be substituted by up to 2 fluorine atoms and each methyl group may be substituted by up to 3 fluorine atoms,
while the above-mentioned alkyl groups together with the carbon atoms to which they are bound may be joined to one another, forming a 5- to 7-membered ring,
are of exceptional importance and
those compounds wherein
(ii) A denotes an oxygen atom or a cyanoimino group,
X denotes an oxygen atom, an imino or methylene group and
Y and Z independently of one another each denote a methyl or ethyl group wherein each methylene group may be substituted by up to 2 fluorine atoms and the methyl group may be substituted by up to 3 fluorine atoms,
while the above-mentioned methyl and ethyl groups together with the carbon atoms to which they are bound may be joined to one another, forming a 5- to 6-membered ring,
are of particularly outstanding importance.

A seventh embodiment of the present invention comprises the compounds of the above general formula (I) wherein
A denotes an oxygen atom, a cyanoimino or phenylsulphonylimino group,
X denotes an oxygen or sulphur atom, an imino group optionally substituted by a $C_{1-6}$-alkyl group or a methylene group optionally substituted by a $C_{1-6}$-alkyl group,
Y and Z independently of one another each denote a straight-chain or branched $C_{1-6}$-alkyl group wherein each methylene group may be substituted by up to 2 fluorine atoms and each methyl group may be substituted by up to 3 fluorine atoms,
while the above-mentioned alkyl groups together with the carbon atoms to which they are bound may be joined to one another, forming a 4- to 8-membered ring,
$R^1$ denotes a monounsaturated 5- to 7-membered diaza or triaza heterocyclic group,
while the above-mentioned heterocycles are linked via a nitrogen atom,
contain a carbonyl group adjacent to a nitrogen atom,
may additionally be substituted at a carbon atom by a phenyl group and
an olefinic double bond of one of the above-mentioned unsaturated heterocycles may be fused to a phenyl, thienyl or quinoline ring,
while the phenyl groups contained in $R^1$ as well as benzo-fused heterocycles in the carbon skeleton may additionally be mono-, di- or trisubstituted by fluorine, chlorine, bromine or iodine atoms, by methyl, methoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, but are preferably unsubstituted or are monosubstituted by a fluorine, chlorine or bromine atom or by a methyl or methoxy group,
$R^2$ denotes the hydrogen atom or
a phenylmethyl group or a $C_{2-7}$-alkyl group which may be substituted in the ω position by a phenyl, pyridinyl, hydroxy, amino, alkylamino, dialkylamino, alkoxycarbonyl, carboxy, aminocarbonyl, aminocarbonylamino, acetylamino, 1-pyrrolidinyl, 1-piperidinyl, 4-morpholinyl or [bis-(2-hydroxyethyl)]amino group,
while the above-mentioned heterocyclic groups and phenyl groups may additionally be mono-, di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different,
$R^3$ denotes the hydrogen atom or a $C_{1-3}$-alkyl group,
while the $C_{1-3}$-alkyl group may be linked to an alkyl group present in $R^2$ or a phenyl or pyridyl ring present in $R^2$ and the nitrogen atom to which they are bound, forming a 5- to 7-membered ring, or
$R^2$ and $R^3$ together with the enclosed nitrogen atom denote a group of general formula

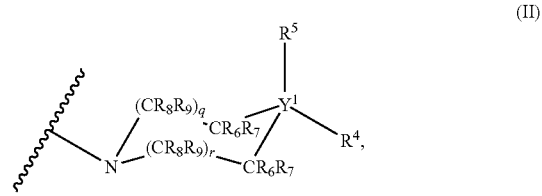

(II)

wherein
$Y^1$ denotes the carbon atom or, if $R^5$ denotes a pair of free electrons, it may also denote the nitrogen atom,
q and r, if $Y^1$ denotes the carbon atom, represent the numbers 0, 1 or
q and r, if $Y^1$ denotes the nitrogen atom, represent the numbers 1 or 2,
$R^4$ denotes the hydrogen atom, an amino, alkylamino or dialkylamino group,
or, if $Y^1$ does not denote the nitrogen atom, it denotes a dialkylaminomethyl group,
a phenyl, pyridinyl or diazinyl group which may be substituted in each case by a fluorine, chlorine or bromine atom, by a trifluoromethylcarbonyl, methyl or methoxy group,
a 4- to 7-membered azacycloalkyl group, a 6- to 7-membered oxaza or diazacycloalkyl group or a 7- to 9-membered azabicycloalkyl group,
while the above-mentioned mono- and bicyclic heterocycles are bound via a nitrogen or carbon atom,
in the above-mentioned mono- and bicyclic heterocycles any methylene group not directly bound to a nitrogen, oxygen or sulphur atom may be substituted by one or two fluorine atoms,
the above-mentioned mono- and bicyclic heterocycles may be substituted by a $C_{1-3}$-alkyl group, by a benzyl, $C_{3-6}$-cycloalkylalkyl, $C_{1-4}$-alkanoyl, di-($C_{1-3}$-alkyl)-amino or $C_{1-3}$-alkylsulphonyl, by an alkoxycarbonyl, alkoxycarbonylalkyl, carboxy or carboxyalkyl group,
$R^5$ denotes a hydrogen atom, a $C_{1-3}$-alkyl group or,
if $Y^1$ denotes a nitrogen atom, it may also denote a pair of free electrons,
$R^6$ and $R^7$, which may be identical or different, in each case denote the hydrogen atom or a $C_{1-3}$-alkyl or di-($C_{1-3}$-alkyl)-amino group and R[8] and R[9], which may be identical or different, in each case denote the hydrogen atom or a $C_{1-3}$-alkyl group, while, unless otherwise stated, the above-mentioned alkyl groups or the alkyl groups contained in the above-mentioned groups contain 1 to 7 carbon atoms and may be branched or unbranched and the above-mentioned aromatic and heteroaromatic groups may additionally be mono-, di- or trisubstituted by fluorine, chlorine or bromine atoms, by cyano or hydroxy groups and the substituents may be identical or different.

An eighth embodiment of the present invention comprises the compounds of the above general formula (I), wherein A denotes an oxygen atom, a cyanoimino or phenylsulphonylimino group, X denotes an oxygen atom, an imino or methylene group, Y and Z independently of one another each denote a straight-chain or branched $C_{1-4}$-alkyl group wherein each methylene group may be substituted by up to 2 fluorine atoms and each methyl group may be substituted by up to 3 fluorine atoms, while the above-mentioned alkyl groups together with the carbon atoms to which they are bound may be joined to one another, forming a 5- to 7-membered ring, R[1] denotes a 4-(2-oxo-1,2,4,5-tetrahydro-1,3-benzodiazepin-3-yl)-piperidin-1-yl, 4-(2-oxo-1,4-dihydro-2H-quinazolin-3-yl)-piperidin-1-yl, 4-(5-oxo-3-phenyl-4,5-dihydro-1,2,4-triazol-1-yl)-piperidin-1-yl, 4-(2-oxo-1,2-dihydro-imidazo[4,5-c]quinolin-3-yl)-piperidin-1-yl, 4-(2-oxo-1,2-dihydro-4H-thieno[3,4-d]pyrimidin-3-yl)-piperidin-1-yl, 4-(2-oxo-1,4-dihydro-2H-thieno[3,2-d]pyrimidin-3-yl)-piperidin-1-yl, 4-(5-oxo-4,5,7,8-tetrahydro-2-thia-4,6-diaza-azulen-6-yl)-piperidin-1-yl, 4-(2-oxo-1,2,4,5-tetrahydro-thieno[3,2-d]-1,3-diazepin-3-yl)-piperidin-1-yl, 4-(2-oxo-1,2,4,5-tetrahydro-thieno[2,3-d]-1,3-diazepin-3-yl)-piperidin-1-yl or 4-(2-oxo-1,4-dihydro-2H-thieno[2,3-d]pyrimidin-3-yl)-piperidin-1-yl group, while the above-mentioned mono- and bicyclic heterocycles in the carbon skeleton may additionally be mono-substituted by a methoxy group, R[2] denotes a phenylmethyl group or a $C_{2-7}$-alkyl group which may be substituted in the ω position by a phenyl, amino, alkylamino or dialkylamino group, while the above-mentioned phenyl group may be substituted by an amino-$C_{1-3}$-alkyl, $C_{1-3}$-alkylamino-$C_{1-3}$-alkyl or di-($C_{1-3}$-alkyl)-amino-$C_{1-3}$-alkyl group, or R[3] denotes the hydrogen atom or a $C_{1-3}$-alkyl group, R[2] and R[3] together with the nitrogen atom to which they are bound denote a 7-dimethylaminomethyl-1,2,4,5-tetrahydro-3-benzazepin-3-yl group or R[2] and R[3] together with the enclosed nitrogen atom denote a group of general formula

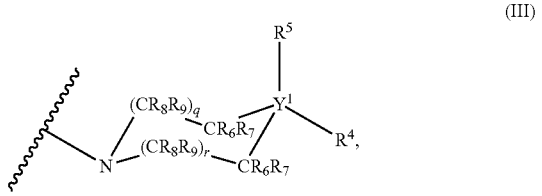

(III)

wherein

Y[1] represents the carbon atom or, if R[5] denotes a pair of free electrons, it may also denote the nitrogen atom, q and r, if Y[1] denotes the carbon atom, represent the numbers 0 or 1 or q and r, if Y[1] denotes the nitrogen atom, represent the numbers 1 or 2, R[4] denotes the hydrogen atom, a phenyl or pyridinyl group which may be substituted in each case by a fluorine, chlorine or bromine atom, by a trifluoromethylcarbonyl, methyl or methoxy group, a dimethylamino, diethylamino, perhydro-azepin-1-yl, 4-methyl-perhydro-1,4-diazepin-1-yl, 1-methyl-piperidin-4-yl, 1-ethyl-piperidin-4-yl, piperazin-1-yl, 4-acetyl-piperazin-1-yl, 4-cyclopropylmethyl-piperazin-1-yl, pyrrolidin-1-yl, 4-ethyl-piperazin-1-yl, 4-isopropyl-piperazin-1-yl, piperidin-1-yl, piperidin-4-yl, 4-morpholin-4-yl, 4,4-difluoro-1-piperidin-1-yl, 8-methyl-8-aza-bicyclo[3.2.1]oct-3-yl, pyridin-4-yl, 3-dimethylamino-piperidin-1-yl, 1-ethyl-piperidin-4-yl, 4-amino-piperidin-1-yl, 4-(dimethylamino)-piperidin-1-yl, 4-(diethylaminomethyl)-piperidin-1-yl, p-trifluoromethylcarbonyl-phenyl, 1-benzyl-piperidin-4-yl, 4-benzyl-piperazin-1-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-carboxymethyl-piperidin-4-yl, 4-carboxymethyl-piperazin-1-yl, 4-methylsulphonyl-piperazin-1-yl or 4-methyl-piperazin-1-yl group, R[5] denotes a hydrogen atom or, if Y[1] denotes a nitrogen atom, it may also denote a pair of free electrons, R[6] and R[7] in each case denote a hydrogen atom or a dimethylamino group and R[8] and R[9] in each case denote the hydrogen atom, while, unless otherwise stated, all the above-mentioned alkyl groups as well as the alkyl groups present within the other groups comprise 1 to 7 carbon atoms and may be straight-chain or branched and the above-mentioned aromatic and heteroaromatic groups may additionally be mono-, di- or trisubstituted by fluorine, chlorine or bromine atoms or by cyano or hydroxy groups and the substituents may be identical or different.

A ninth embodiment of the present invention comprises the compounds of the above general formula (I), wherein A denotes an oxygen atom or a cyanoimino group, X denotes an oxygen atom, an imino or methylene group, Y and Z independently of one another in each case denote a methyl or ethyl group wherein each methylene group may be substituted by up to 2 fluorine atoms and the methyl group may be substituted by up to 3 fluorine atoms, while the above-mentioned methyl and ethyl groups together with the carbon atoms to which they are bound may be joined together, forming a 5- to 6-membered ring, R[1] denotes a 4-(2-oxo-1,2,4,5-tetrahydro-1,3-benzodiazepin-3-yl)-piperidin-1-yl, 4-(2-oxo-1,4-dihydro-2H-quinazolin-3-yl)-piperidin-1-yl, 4-(5-oxo-3-phenyl-4,5-dihydro-1,2,4-triazol-1-yl)-piperidin-1-yl, 4-(2-oxo-1,2-dihydro-imidazo[4,5-c]quinolin-3-yl)-piperidin-1-yl, 4-(2-oxo-1,2-dihydro-4H-thieno[3,4-d]pyrimidin-3-yl)-piperidin-1-yl, 4-(2-oxo-1,4-dihydro-2H-thieno[3,2-d]pyrimidin-3-yl)-piperidin-1-yl, 4-(5-oxo-4,5,7,8-tetrahydro-2-thia-4,6-diaza-azulen-6-yl)-piperidin-1-yl, 4-(2-oxo-1,2,4,5-tetrahydro-thieno[3,2-d]-1,3-diazepin-3-yl)-piperidin-1-yl, 4-(2-oxo-1,2,4,5-tetrahydro-thieno[2,3-d]-1,3-diazepin-3-yl)-piperidin-1-yl or 4-(2-oxo-1,4-dihydro-2H-thieno[2,3-d]pyrimidin-3-yl)-piperidin-1-yl group, while the above-mentioned mono- and bicyclic heterocycles may additionally be monosubstituted in the carbon skeleton by a methoxy group, $R^2$ denotes a phenylmethyl group or a $C_{2-7}$-alkyl group which may be substituted in the ω position by a phenyl, amino, alkylamino or dialkylamino group, while the above-mentioned phenyl group may be substituted by an amino-$C_{1-3}$-alkyl, $C_{1-3}$-alkylamino-$C_{1-3}$-alkyl or di-($C_{1-3}$-alkyl)-amino-$C_{1-3}$-alkyl group, or $R^3$ denotes the hydrogen atom or a $C_{1-3}$-alkyl group, $R^2$ and $R^3$ together with the nitrogen atom to which they are bound denote a 7-dimethylaminomethyl-1,2,4,5-tetrahydro-3-benzazepin-3-yl group or $R^2$ and $R^3$ together with the enclosed nitrogen atom denote a group of general formula

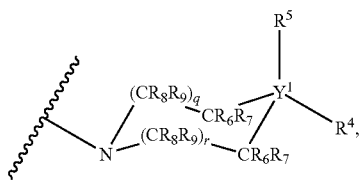

(III)

wherein
    $Y^1$ denotes the carbon atom or, if $R^5$ denotes a pair of free electrons, it may also denote the nitrogen atom,
    q and r, if $Y^1$ denotes the carbon atom, represent the numbers 0 or 1 or
    q and r, if $Y^1$ denotes the nitrogen atom, represent the numbers 1 or 2,
    $R^4$ denotes the hydrogen atom,
        a phenyl or pyridinyl group which may be substituted in each case by a fluorine, chlorine or bromine atom, by a trifluoromethylcarbonyl, methyl or methoxy group,
        a dimethylamino, diethylamino, perhydro-azepin-1-yl, 4-methyl-perhydro-1,4-diazepin-1-yl, 1-methyl-piperidin-4-yl, 1-ethyl-piperidin-4-yl, piperazin-1-yl, 4-acetyl-piperazin-1-yl, 4-cyclopropylmethyl-piperazin-1-yl, pyrrolidin-1-yl, 4-ethyl-piperazin-1-yl, 4-isopropyl-piperazin-1-yl, piperidin-1-yl, piperidin-4-yl, 4-morpholin-4-yl, 4,4-difluoro-piperidin-1-yl, 8-methyl-8-aza-bicyclo[3.2.1]oct-3-yl, pyridin-4-yl, 3-dimethylamino-piperidin-1-yl, 1-ethyl-piperidin-4-yl, 4-amino-piperidin-1-yl, 4-(dimethylamino)-piperidin-1-yl, 4-(diethylaminomethyl)-piperidin-1-yl, p-trifluoromethylcarbonyl-phenyl, 1-benzyl-piperidin-4-yl, 4-benzyl-piperazin-1-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-carboxymethyl-piperidin-4-yl, 4-carboxymethyl-piperazin-1-yl, 4-methylsulphonyl-piperazin-1-yl or
    4-methyl-piperazin-1-yl group,
    $R^5$ denotes a hydrogen atom or, if $Y^1$ denotes a nitrogen atom, it may also denote a pair of free electrons,
    $R^6$ and $R^7$ in each case denote a hydrogen atom or a dimethylamino group and
    $R^8$ and $R^9$ in each case denote the hydrogen atom, while, unless otherwise stated, all the above-mentioned alkyl groups as well as the alkyl groups present within the other groups comprise 1 to 7 carbon atoms and may be straight-chain or branched and the above-mentioned aromatic and heteroaromatic groups may additionally be mono-, di- or trisubstituted by fluorine, chlorine or bromine atoms or by cyano or hydroxy groups and the substituents may be identical or different.

The following are mentioned as examples of most particularly preferred compounds of the above general formula (I):

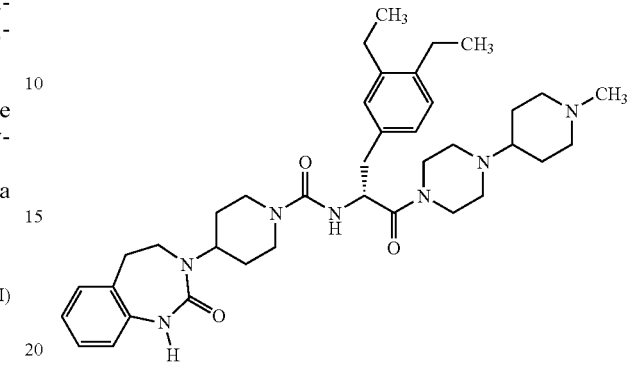

(1)

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

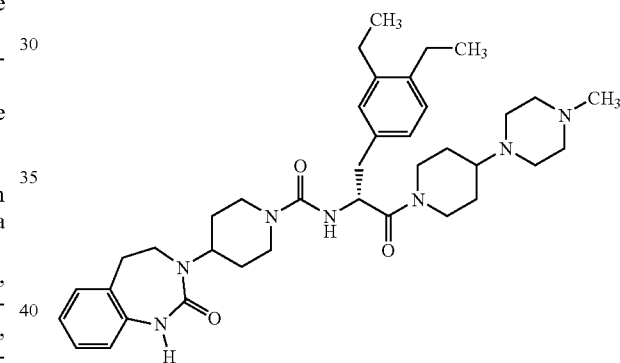

(2)

4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-piperazin-1-yl)-piperidin-1-yl]-2-oxo-ethyl}-amide

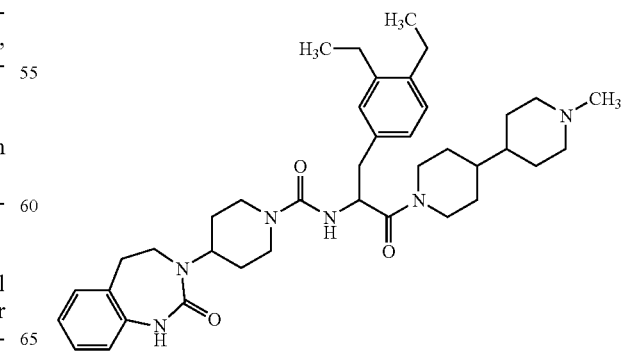

(3)

4-(2-oxo-1,2,4,5-tetrahydro-1,3-benzodiazepin-3-yl)-piperidine-1-carboxylic acid-[1-(3,4-diethyl-benzyl)-2-(1'-methyl-4,4'-bipiperidinyl-1-yl)-2-oxo-ethyl]-amide 4-(2-oxo-1,2,4,5-tetrahydro-1,3-benzodiazepin-3-yl)-piperidine-1-carboxylic acid-[2-1,4'-bipiperidinyl-1'-yl-1-(3,4-diethyl-benzyl)-2-oxo-ethyl]-amide (6)

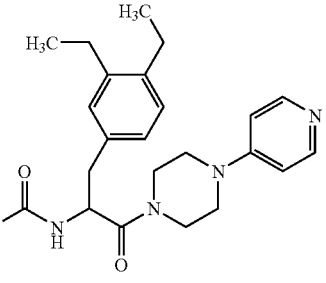

(4)

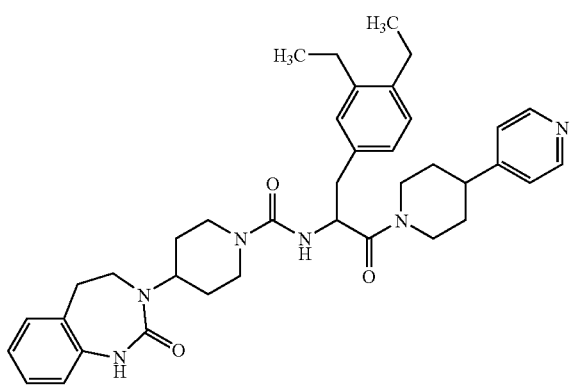

4-(2-oxo-1,2,4,5-tetrahydro-1,3-benzodiazepin-3-yl)-piperidine-1-carboxylic acid-[1-(3,4-diethyl-benzyl)-2-oxo-2-(4-pyridin-4-yl-piperazin-1-yl)-ethyl]-amide (7)

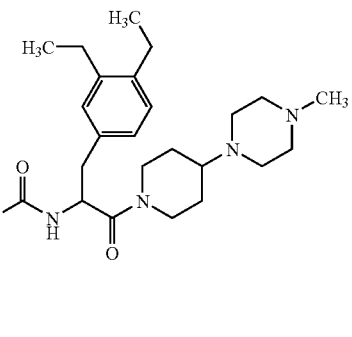

4-(2-oxo-1,2,4,5-tetrahydro-1,3-benzodiazepin-3-yl)-piperidine-1-carboxylic acid-[1'-(3,4-diethyl-benzyl)-2-oxo-2-(3,4,5,6-tetrahydro-2H-4,4'-bipyridinyl-1'-yl)-ethyl]-amide 4-(2-oxo-1,4-dihydro-2H-quinazolin-3-yl)-piperidine-1-carboxylic acid-{1-(3,4-diethyl-benzyl)-2-[4-(4-methyl-piperazin-1-yl)-piperidin-1-yl]-2-oxo-ethyl}-amide (5)

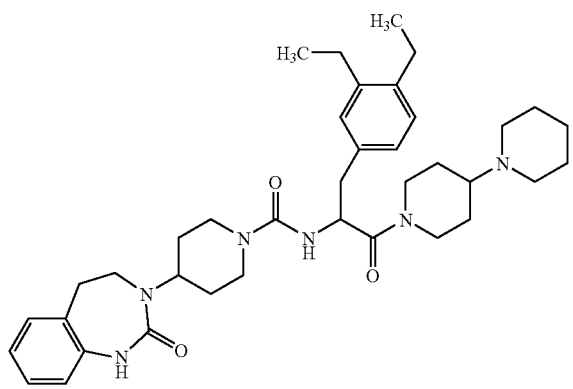

(8)

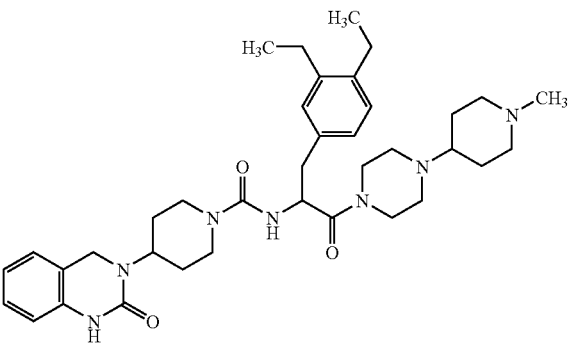

17

4-(2-oxo-1,4-dihydro-2H-quinazolin-3-yl)-piperidine-1-carboxylic acid-{1-(3,4-diethyl-benzyl)-2-[4-(1-methyl-piperidin-4-yl)-piperazin-1-yl]-2-oxo-ethyl}-amide (9)

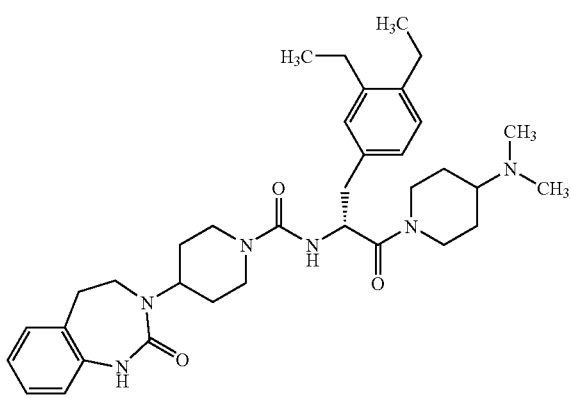

4-(2-oxo-1,2,4,5-tetrahydro-1,3-benzodiazepin-3-yl)-piperidine-1-carboxylic acid-[(R)-1-(3,4-diethyl-benzyl)-2-(4-dimethylamino-piperidin-1-yl)-2-oxo-ethyl]-amide (10)

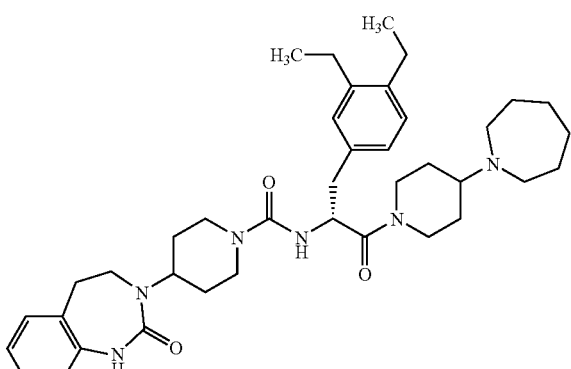

18

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-perhydro-azepin-1-yl-piperidin-1-yl)-ethyl]-amide (11)

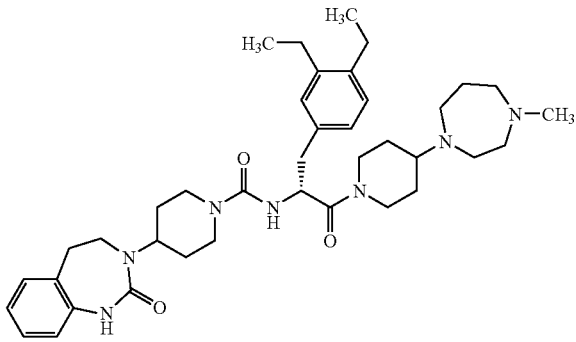

4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-perhydro-1,4-diazepin-1-yl)-piperidin-1-yl]-2-oxo-ethyl}-amide (12)

4-(2-oxo-1,2,4,5-tetrahydro-1,3-benzodiazepin-3-yl)-piperidine-1-carboxylic acid-[(R)-1-(3,4-diethyl-benzyl)-2-(1'-methyl-4,4'-bipiperidinyl-1-yl)-2-oxo-ethyl]-amide (13)

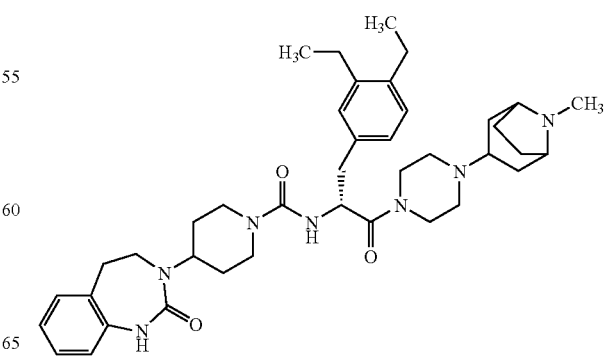

19

4-(2-oxo-1,2,4,5-tetrahydro-1,3-benzodiazepin-3-yl)-piperidine-1-carboxylic acid-{(R)-1-(3,4-diethyl-benzyl)-2-[4-(8-methyl-8-aza-bicyclo[3.2.1]oct-3-yl)-piperazin-1-yl]-2-oxo-ethyl}-amide (14)

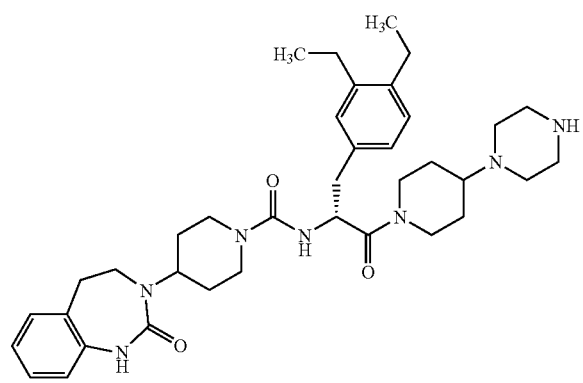

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperazin-1-yl-piperidin-1-yl)-ethyl]-amide (15)

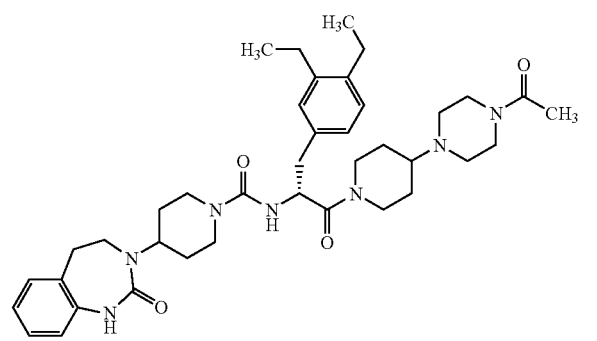

20

4-(2-oxo-1,2,4,5-tetrahydro-1,3-benzodiazepin-3-yl)-piperidine-1-carboxylic acid-[(R)-2-[4-(4-acetyl-piperazin-1-yl)-piperidin-1-yl]-1-(3,4-diethyl-benzyl)-2-oxo-ethyl]-amide (16)

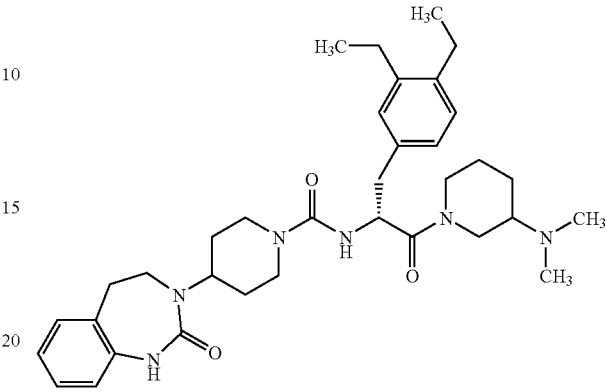

4-(2-oxo-1,2,4,5-tetrahydro-1,3-benzodiazepin-3-yl)-piperidine-1-carboxylic acid-[(R)-1-(3,4-diethyl-benzyl)-2-(3-dimethylamino-piperidin-1-yl)-2-oxo-ethyl]-amide (17)

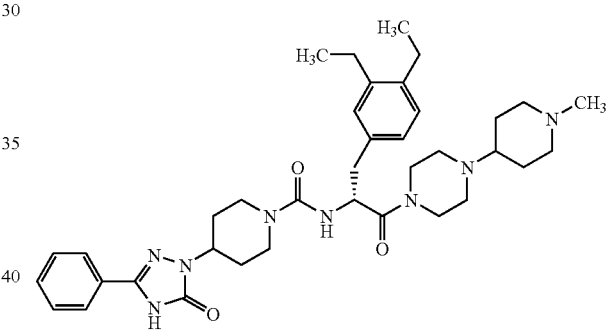

4-(5-oxo-3-phenyl-4,5-dihydro-1,2,4-triazol-1-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (18)

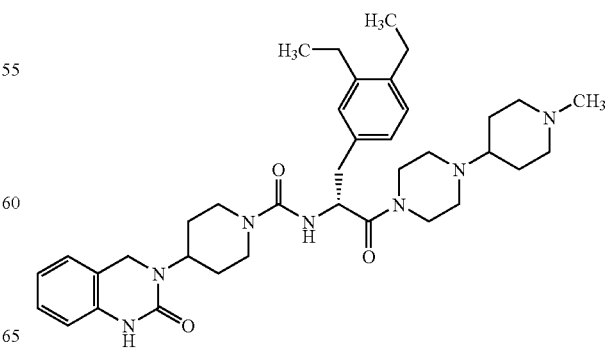

4-(2-oxo-1,4-dihydro-2H-quinazolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (19)

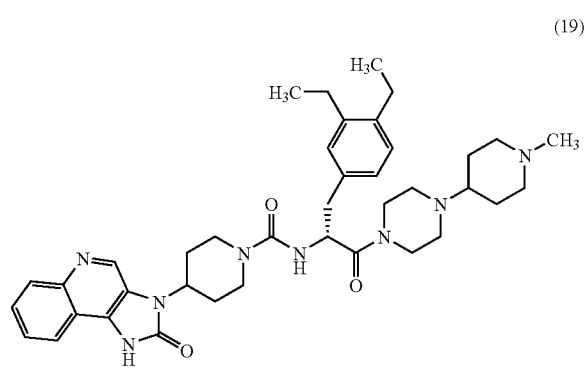

4-(2-oxo-1,2-dihydro-imidazo[4,5-c]quinolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (20)

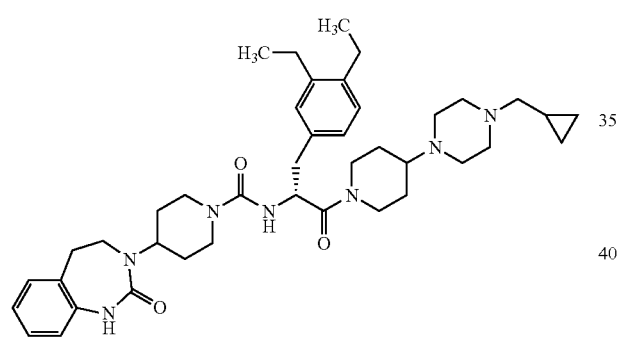

4-(2-oxo-1,2,4,5-tetrahydro-1,3-benzodiazepin-3-yl)-piperidine-1-carboxylic acid-[(R)-2-[4-(4-cyclopropylmethyl-piperazin-1-yl)-piperidin-1-yl]-1-(3,4-diethyl-benzyl)-2-oxo-ethyl]-amide (21)

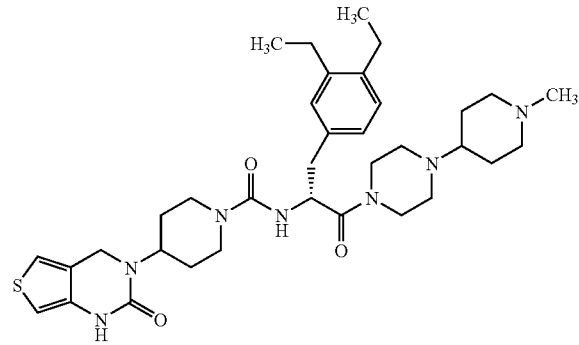

4-(2-oxo-1,2-dihydro-4H-thieno[3,4-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (22)

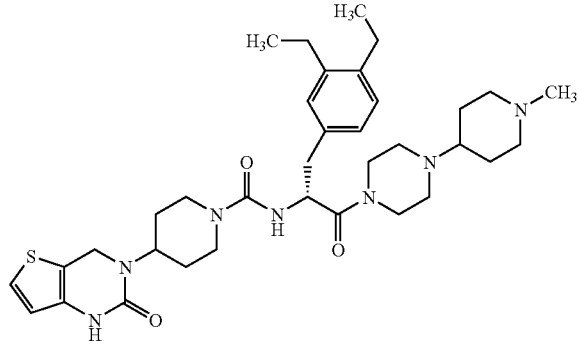

4-(2-oxo-1,4-dihydro-2H-thieno[3,2-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (23)

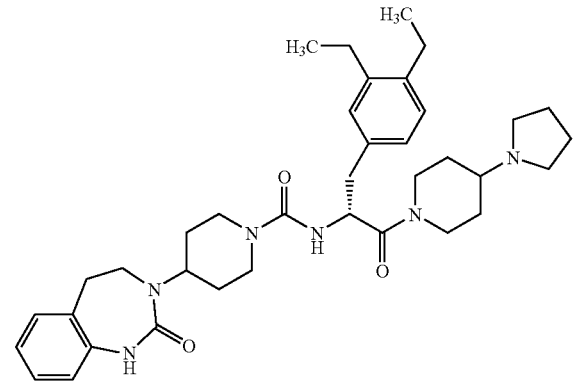

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyrrolidin-1-yl-piperidin-1-yl)-ethyl]-amide (24)

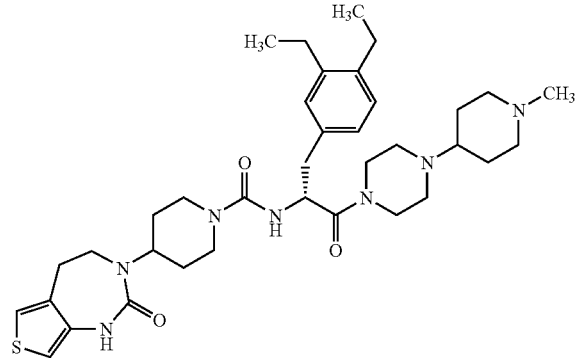

4-(5-oxo-4,5,7,8-tetrahydro-2-thia-4,6-diaza-azulen-6-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide 4-(2-oxo-1,4-dihydro-2H-thieno[2,3-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (25)

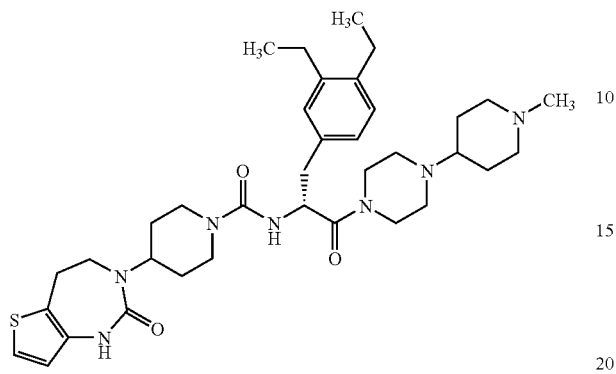

4-(2-oxo-1,2,4,5-tetrahydro-thieno[3,2-d]-1,3-diazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (28)

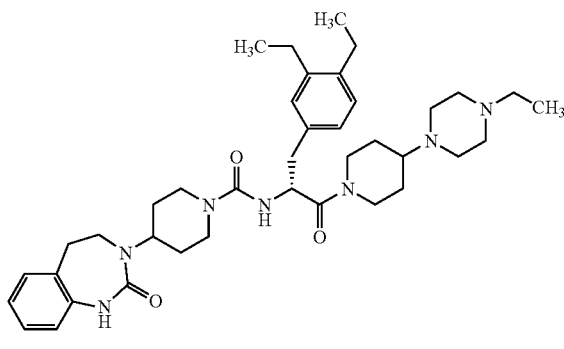

4-(2-oxo-1,2,4,5-tetrahydro-1,3-benzodiazepin-3-yl)-piperidine-1-carboxylic acid-{(R)-1-(3,4-diethyl-benzyl)-2-[4-(4-ethyl-piperazin-1-yl)-piperidin-1-yl]-2-oxo-ethyl}-amide (26)

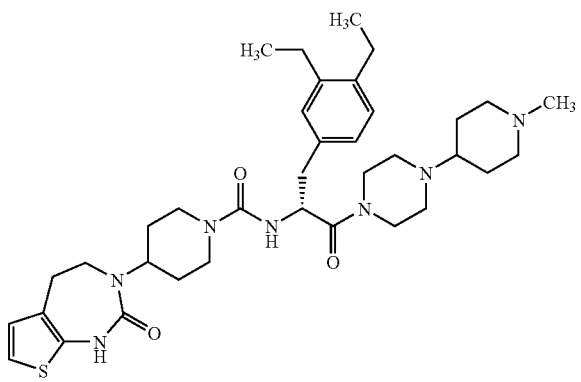

4-(2-oxo-1,2,4,5-tetrahydro-thieno[2,3-d]-1,3-diazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide (29)

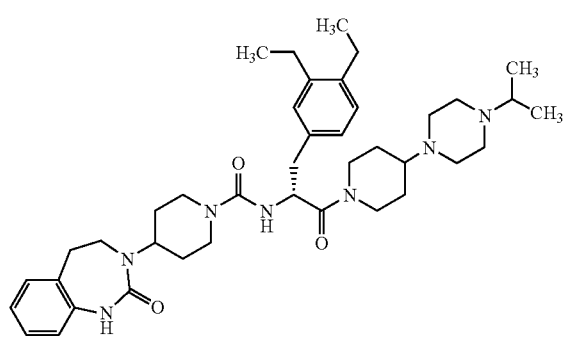

4-(2-oxo-1,2,4,5-tetrahydro-1,3-benzodiazepin-3-yl)-piperidine-1-carboxylic acid-{(R)-1-(3,4-diethyl-benzyl)-2-[4-(4-isopropyl-piperazin-1-yl)-piperidin-1-yl]-2-oxo-ethyl}-amide (27)

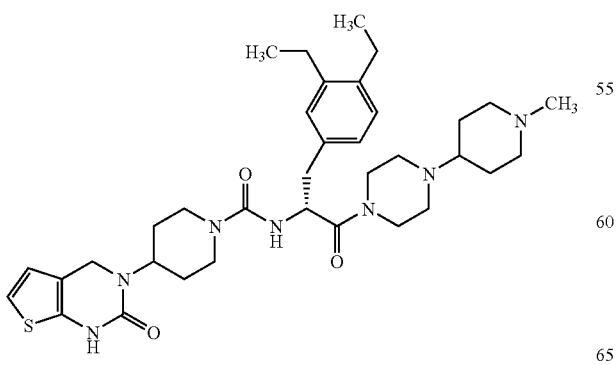

(30)

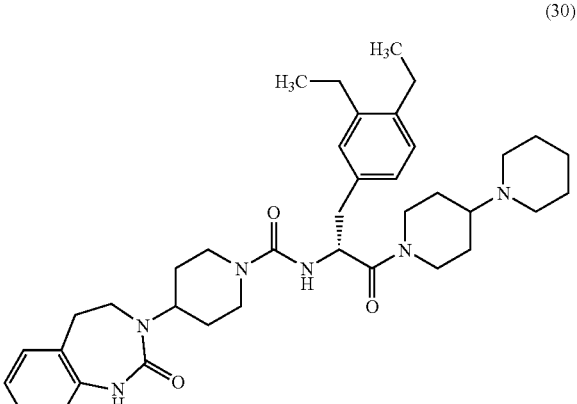

25

4-(2-oxo-1,2,4,5-tetrahydro-1,3-benzodiazepin-3-yl)-piperidine-1-carboxylic acid-[(R)-2-1,4'-bipiperidinyl-1'-yl-1-(3,4-diethyl-benzyl)-2-oxo-ethyl]-amide (31)

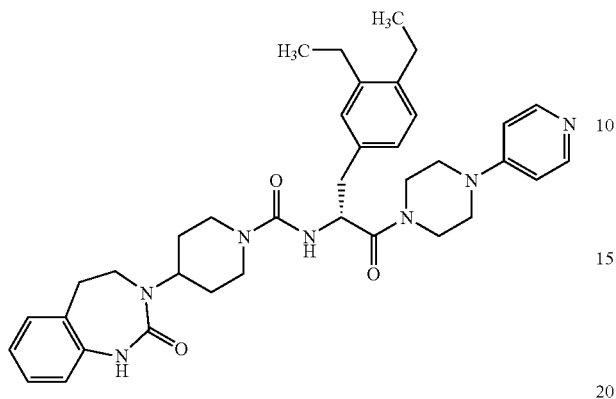

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyridin-4-yl-piperazin-1-yl)-ethyl]-amide (32)

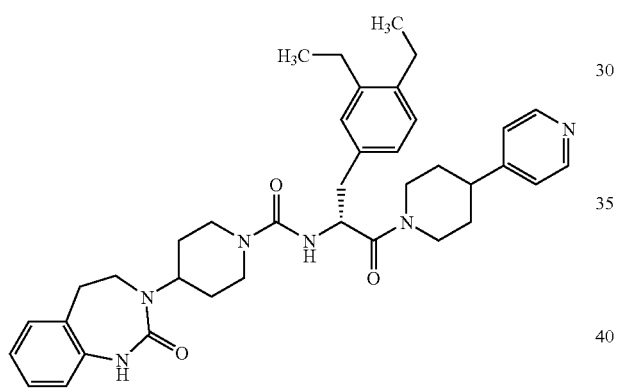

4-(2-oxo-1,2,4,5-tetrahydro-1,3-benzodiazepin-3-yl)-piperidine-1'-carboxylic acid-[(R)-1-(3,4-diethyl-benzyl)-2-oxo-2-(3,4,5,6-tetrahydro-2H-4,4'-bipyridinyl-1-yl)-ethyl]-amide (33)

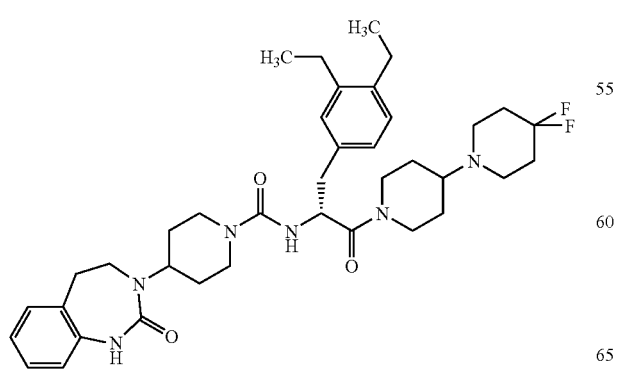

26

4-(2-oxo-1,2,4,5-tetrahydro-1,3-benzodiazepin-3-yl)-piperidine-1-carboxylic acid-[(R)-1-(3,4-diethyl-benzyl)-2-(4,4-difluoro-1,4'-bipiperidinyl-1'-yl)-2-oxo-ethyl]-amide (34)

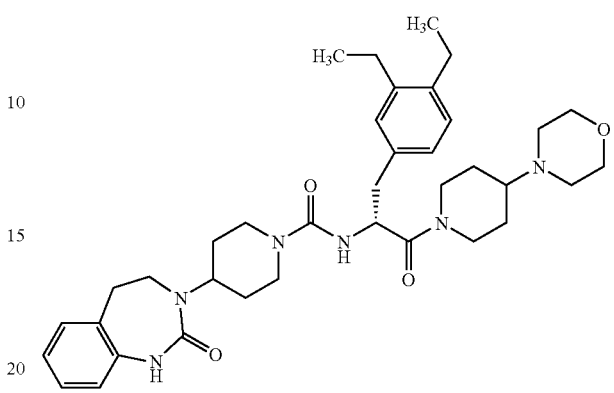

4-(2-oxo-1,2,4,5-tetrahydro-1,3-benzodiazepin-3-yl)-piperidine-1-carboxylic acid-[(R)-1-(3,4-diethyl-benzyl)-2-(4-morpholin-4-yl-piperidin-1-yl)-2-oxo-ethyl]-amide (35)

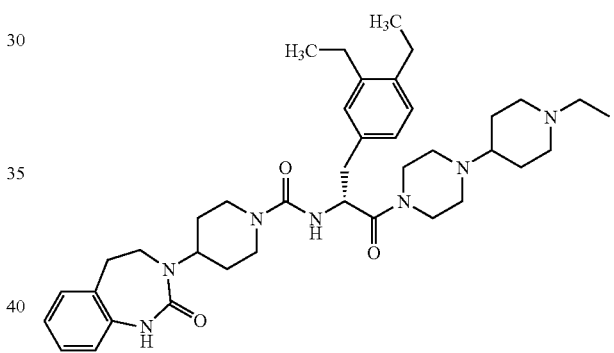

4-(2-oxo-1,2,4,5-tetrahydro-1,3-benzodiazepin-3-yl)-piperidine-1-carboxylic acid {(R)-1-(3,4-diethyl-benzyl)-2-[4-(1-ethyl-piperidin-4-yl)-piperazin-1-yl]-2-oxo-ethyl}-amide (36)

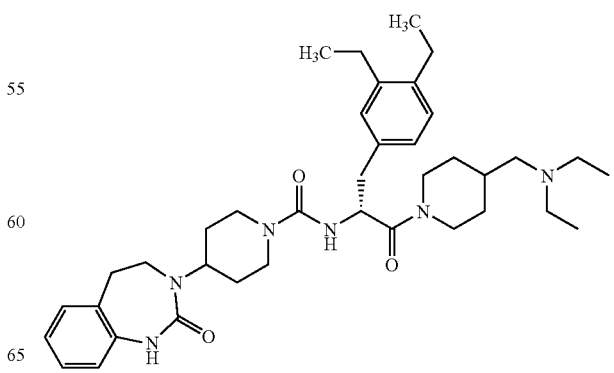

27

4-(2-oxo-1,2,4,5-tetrahydro-1,3-benzodiazepin-3-yl)-piperidine-1-carboxylic acid [(R)-2-(4-diethylaminomethyl-piperidin-1-yl)-1-(3,4-diethyl-benzyl)-2-oxo-ethyl]-amide (37)

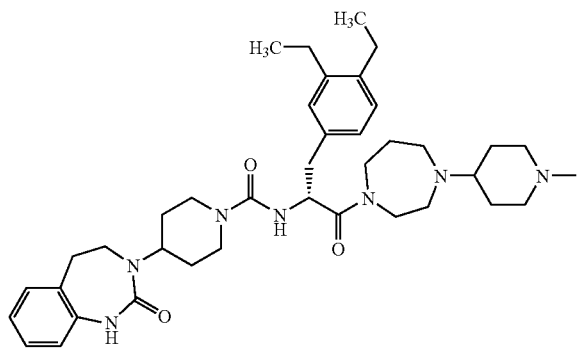

4-(2-oxo-1,2,4,5-tetrahydro-1,3-benzodiazepin-3-yl)-piperidine-1-carboxylic acid {(R)-1-(3,4-diethyl-benzyl)-2-[4-(1-methyl-piperidin-4-yl)-[1,4]diazepan-1-yl]-2-oxo-ethyl}-amide (38)

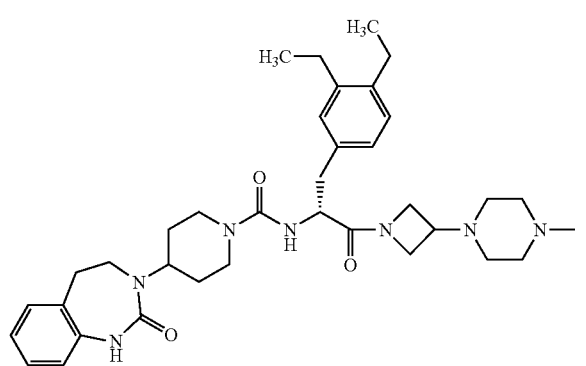

4-(2-oxo-1,2,4,5-tetrahydro-1,3-benzodiazepin-3-yl)-piperidine-1-carboxylic acid {(R)-1-(3,4-diethyl-benzyl)-2-[3-(4-methyl-piperazin-1-yl)-azetidin-1-yl]-2-oxo-ethyl}-amide (39)

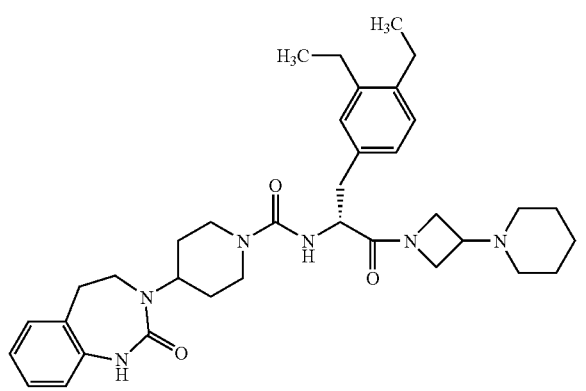

28

4-(2-oxo-1,2,4,5-tetrahydro-1,3-benzodiazepin-3-yl)-piperidine-1-carboxylic acid [(R)-1-(3,4-diethyl-benzyl)-2-oxo-2-(3-piperidin-1-yl-azetidin-1-yl)-ethyl]-amide (40)

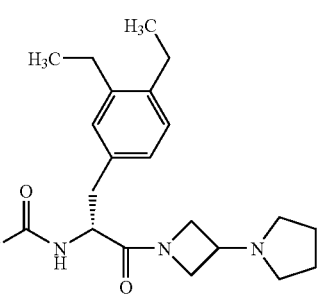

4-(2-oxo-1,2,4,5-tetrahydro-1,3-benzodiazepin-3-yl)-piperidine-1-carboxylic acid [(R)-1-(3,4-diethyl-benzyl)-2-oxo-2-(3-pyrrolidin-1-yl-azetidin-1-yl)-ethyl]-amide (41)

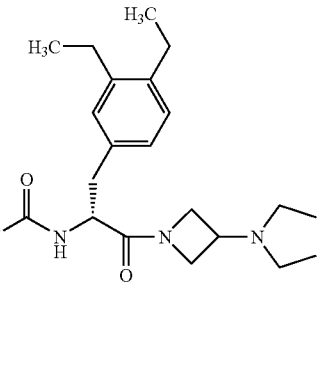

4-(2-oxo-1,2,4,5-tetrahydro-1,3-benzodiazepin-3-yl)-piperidine-1-carboxylic acid [(R)-2-(3-diethylamino-azetidin-1-yl)-1-(3,4-diethyl-benzyl)-2-oxo-ethyl]-amide

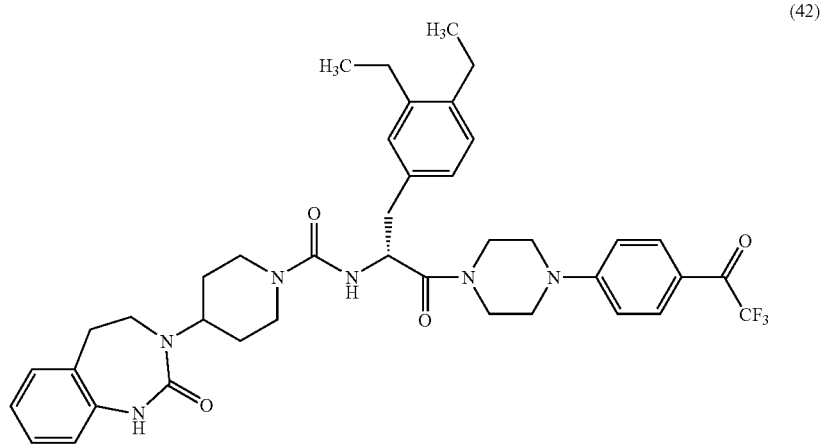

(42)

4-(2-oxo-1,2,4,5-tetrahydro-1,3-benzodiazepin-3-yl)-piperidine-1-carboxylic acid ((R)-1-(3,4-diethyl-benzyl)-2-oxo-2-{4-[4-(2,2,2-trifluoro-acetyl)-phenyl]-piperazin-1-yl}-ethyl)-amide 4-(2-oxo-1,2,4,5-tetrahydro-1,3-benzodiazepin-3-yl)-piperidine-1-carboxylic acid [(R)-1-(3-aminomethyl-benzylcarbamoyl)-2-(3,4-diethylphenyl)-ethyl]-amide

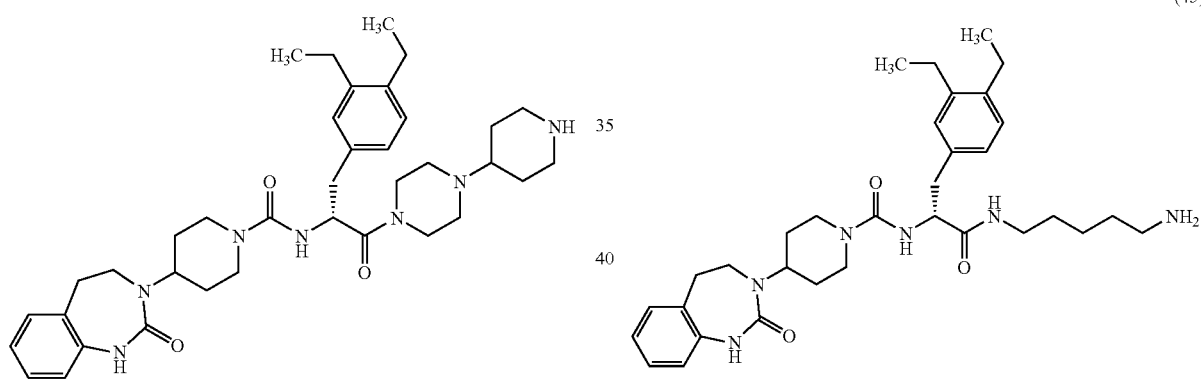

(43)

(45)

4-(2-oxo-1,2,4,5-tetrahydro-1,3-benzodiazepin-3-yl)-piperidine-1-carboxylic acid [(R)-1-(3,4-diethyl-benzyl)-2-oxo-2-(4-piperidin-4-yl-piperazin-1-yl)-ethyl]-amide 4-(2-oxo-1,2,4,5-tetrahydro-1,3-benzodiazepin-3-yl)-piperidine-1-carboxylic acid [(R)-1-(5-amino-pentyl-carbamoyl)-2-(3,4-diethyl-phenyl)-ethyl]-mide (44)

(46)

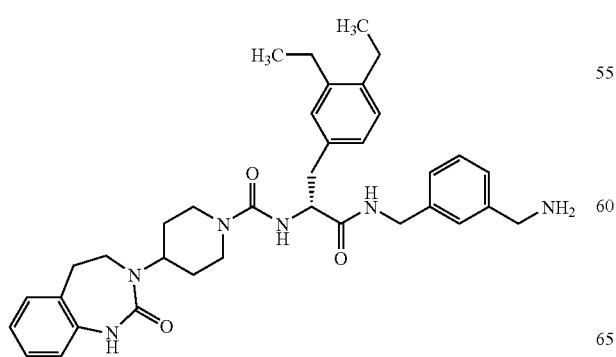

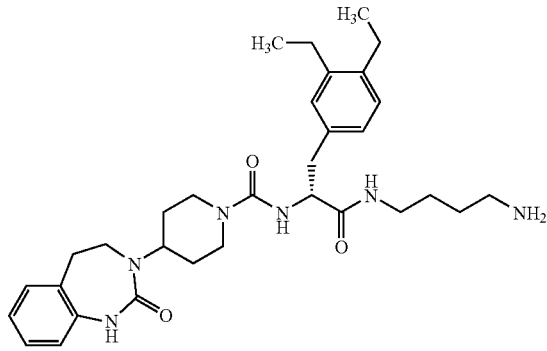

31

4-(2-oxo-1,2,4,5-tetrahydro-1,3-benzodiazepin-3-yl)-piperidine-1-carboxylic acid-[(R)-1-(4-amino-butyl-carbamoyl)-2-(3,4-diethyl-phenyl)-ethyl]-amide (47)

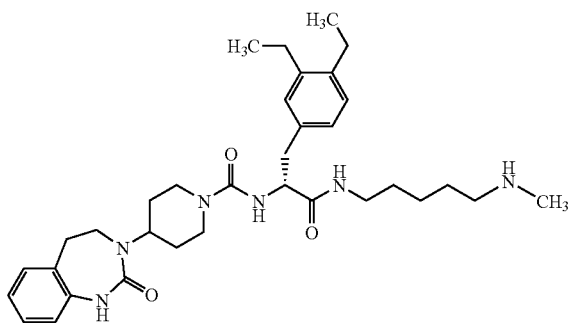

4-(2-oxo-1,2,4,5-tetrahydro-1,3-benzodiazepin-3-yl)-piperidine-1-carboxylic acid-[(R)-2-(3,4-diethyl-phenyl)-1-(5-methylamino-pentylcarbamoyl)-ethyl]-amide (48)

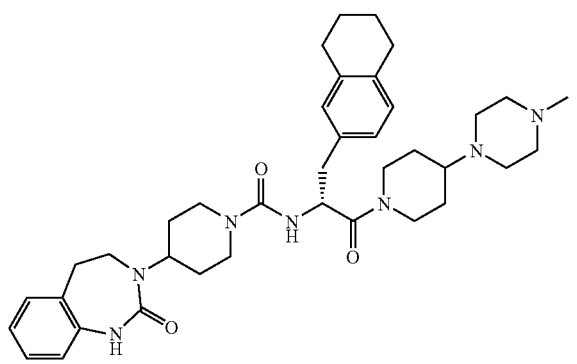

32

4-(2-oxo-1,2,4,5-tetrahydro-1,3-benzodiazepin-3-yl)-piperidine-1-carboxylic acid [(R)-2-[4-(4-methyl-piperazin-1-yl)-piperidin-1-yl]-2-oxo-1-(5,6,7,8-tetrahydro-naphthalen-2-ylmethyl)-ethyl]-amide (49)

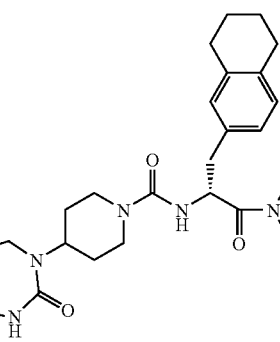

4-(2-oxo-1,2,4,5-tetrahydro-1,3-benzodiazepin-3-yl)-piperidine-1-carboxylic acid [(R)-2-[4-(1-methyl-piperidin-4-yl)-piperazin-1-yl]-2-oxo-1-(5,6,7,8-tetrahydro-naphthalen-2-ylmethyl)-ethyl]-amide (50)

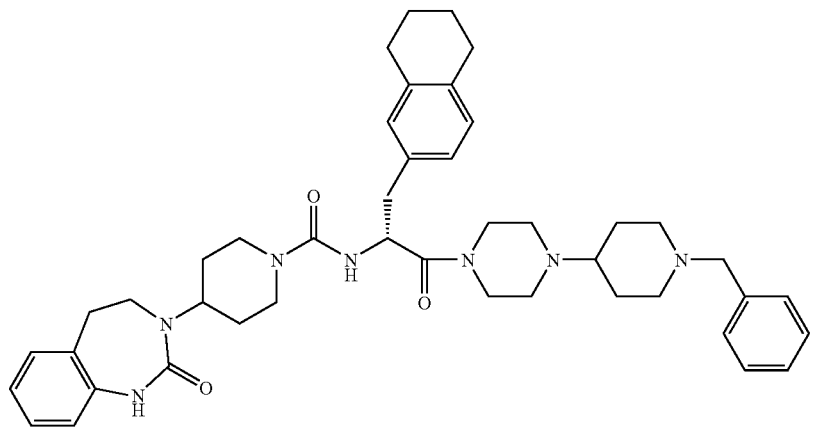

4-(2-oxo-1,2,4,5-tetrahydro-1,3-benzodiazepin-3-yl)-piperidine-1-carboxylic acid [(R)-2-[4-(1-benzyl-piperidin-4-yl)-piperazin-1-yl]-2-oxo-1-(5,6,7,8-tetrahydro-naphthalen-2-ylmethyl)-ethyl]-amide

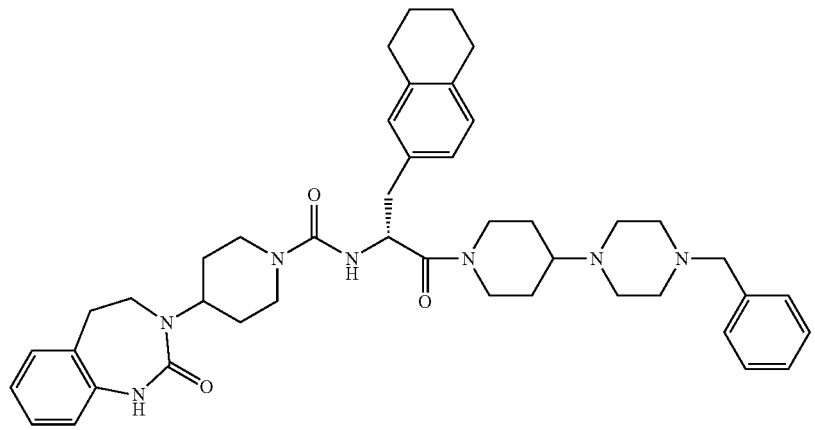

(51)

4-(2-oxo-1,2,4,5-tetrahydro-1,3-benzodiazepin-3-yl)-piperidine-1-carboxylic acid [(R)-2-[4-(4-benzyl-piperazin-1-yl)-piperidin-1-yl]-2-oxo-1-(5,6,7,8-tetrahydro-naphthalen-2-ylmethyl)-ethyl]-amide 4-(2-oxo-1,2,4,5-tetrahydro-1,3-benzodiazepin-3-yl)-piperidine-1-carboxylic acid [(R)-2-oxo-2-(4-piperidin-4-yl-piperazin-1-yl)-1-(5,6,7,8-tetrahydronaphthalen-2-ylmethyl)-ethyl]-amide

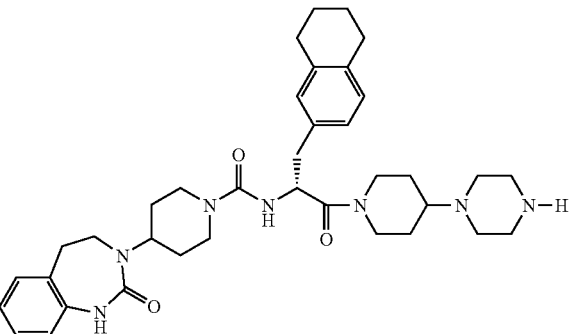

(52)

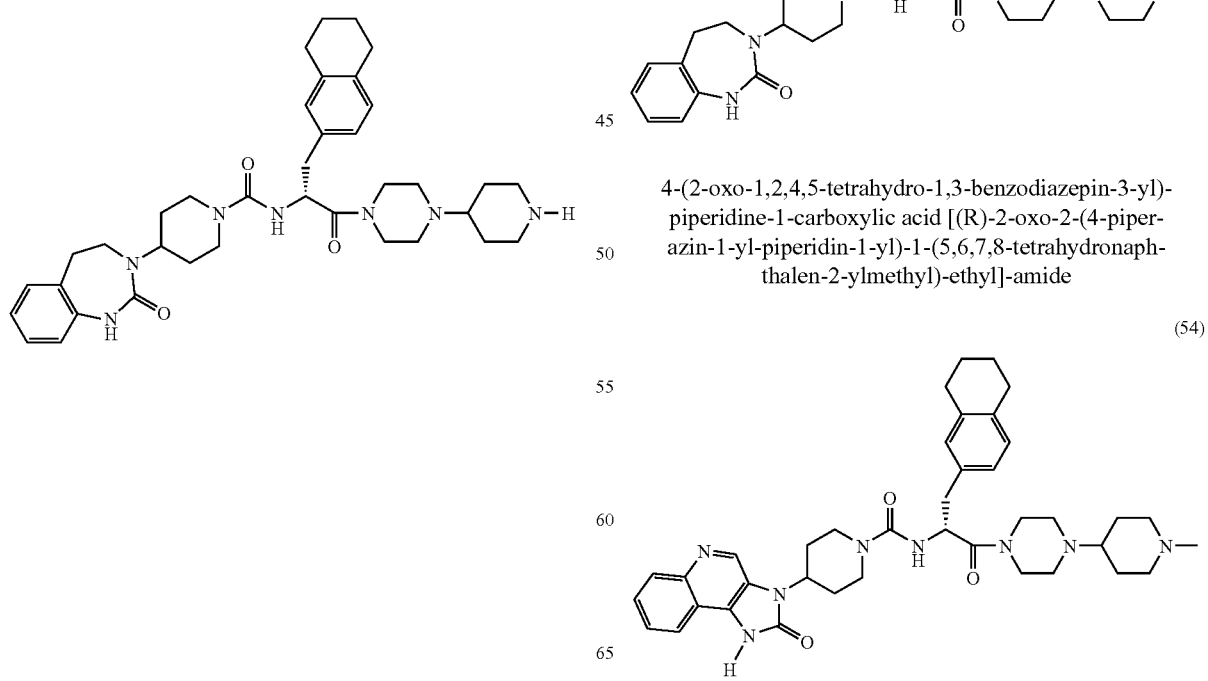

(53)

4-(2-oxo-1,2,4,5-tetrahydro-1,3-benzodiazepin-3-yl)-piperidine-1-carboxylic acid [(R)-2-oxo-2-(4-piperazin-1-yl-piperidin-1-yl)-1-(5,6,7,8-tetrahydronaphthalen-2-ylmethyl)-ethyl]-amide (54)

4-(2-oxo-1,2-dihydro-imidazo[4,5-c]quinolin-3-yl)-piperidine-1-carboxylic acid [(R)-2-[4-(1-methyl-piperidin-4-yl)-piperazin-1-yl]-2-oxo-1-(5,6,7,8-tetrahydronaphthalen-2-ylmethyl)-ethyl]-amide (55)

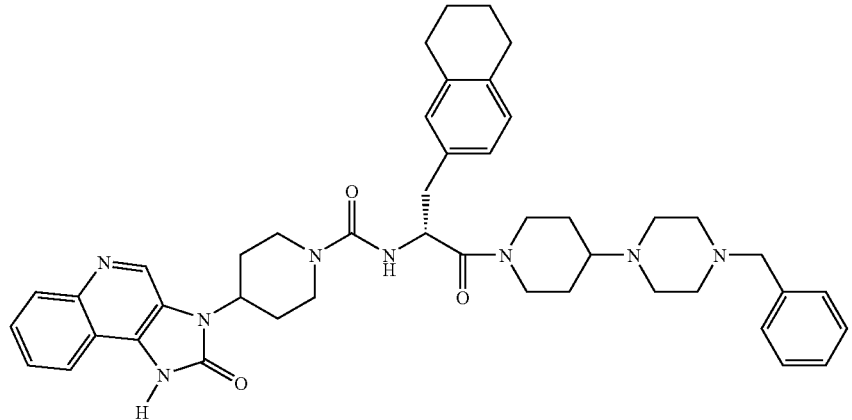

4-(2-oxo-1,2-dihydro-imidazo[4,5-c]quinolin-3-yl)-piperidine-1-carboxylic acid [(R)-2-[4-(4-benzyl-piperazin-1-yl)-piperidin-1-yl]-2-oxo-1-(5,6,7,8-tetrahydronaphthalen-2-ylmethyl)-ethyl]-amide 4-(2-oxo-1,2-dihydro-imidazo[4,5-c]quinolin-3-yl)-piperidine-1-carboxylic acid [(R)-2-oxo-2-(4-piperazin-1-yl-piperidin-1-yl)-1-(5,6,7,8-tetrahydro-naphthalen-2-ylmethyl)-ethyl]-amide (57)

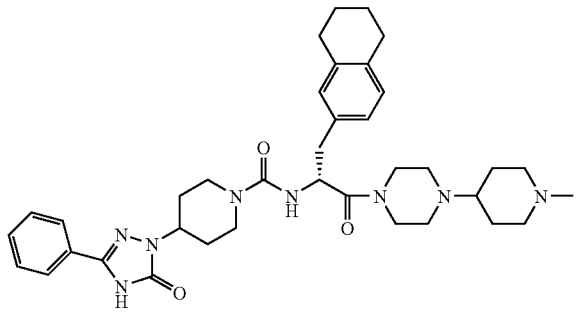

(56)

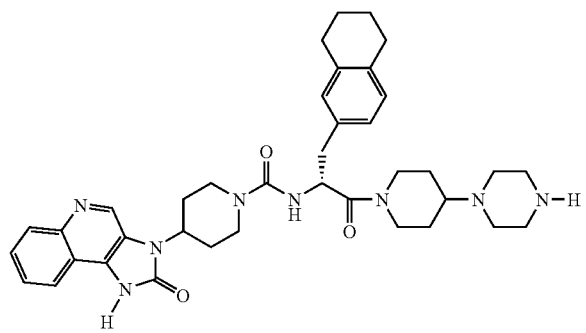

4-(5-oxo-3-phenyl-4,5-dihydro-[1,2,4]triazol-1-yl)-piperidine-1-carboxylic acid [(R)-2-[4-(1-methyl-piperidin-4-yl)-piperazin-1-yl]-2-oxo-1-(5,6,7,8-tetrahydronaphthalen-2-ylmethyl)-ethyl]-amide (58)

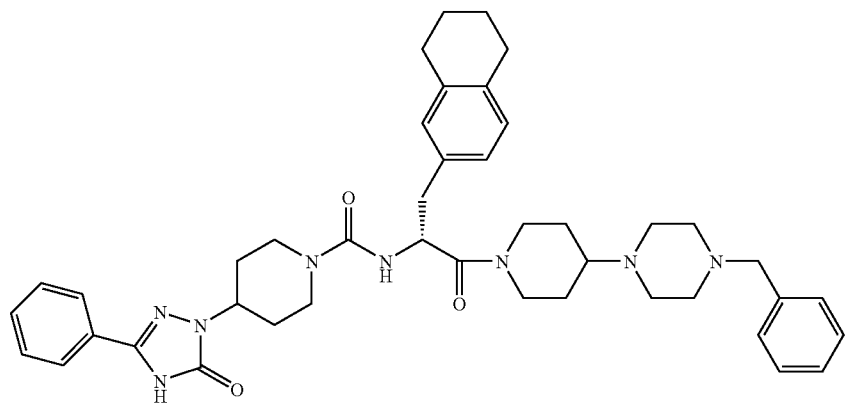

37

4-(5-oxo-3-phenyl-4,5-dihydro-[1,2,4]triazol-1-yl)-piperidine-1-carboxylic acid-[(R)-2-[4-(4-benzyl-piperazin-1-yl)-piperidin-1-yl]-2-oxo-1-(5,6,7,8-tetrahydronaphthalen-2-ylmethyl)-ethyl]-amide

38

4-(2-oxo-1,2,4,5-tetrahydro-1,3-benzodiazepin-3-yl)-piperidine-1-carboxylic acid-[(R)-1-(3,4-diethyl-benzyl)-2-(7-dimethylaminomethyl-1,2,4,5-tetrahydro-3-benzazepin-3-yl)-2-oxo-ethyl]-amide (59)

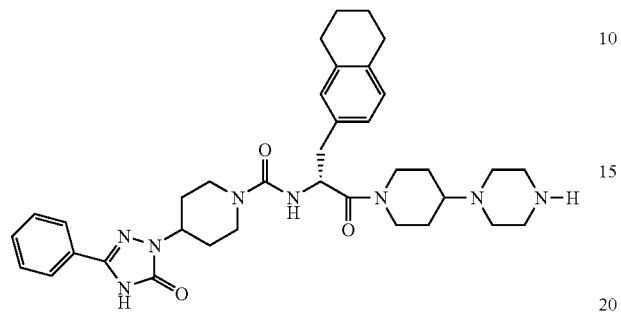

4-(5-oxo-3-phenyl-4,5-dihydro-[1,2,4]triazol-1-yl)-piperidine-1-carboxylic acid-[(R)-2-oxo-2-(4-piperazin-1-yl-piperidin-1-yl)-1-(5,6,7,8-tetrahydro-naphthalen-2-ylmethyl)-ethyl]-amide (62)

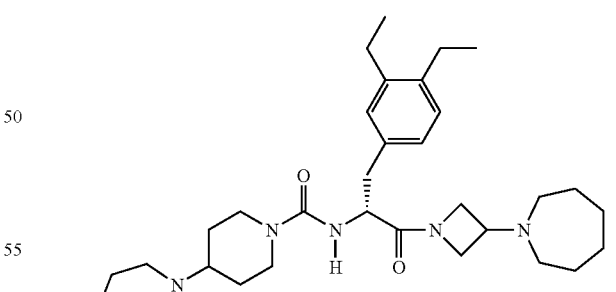

(60)

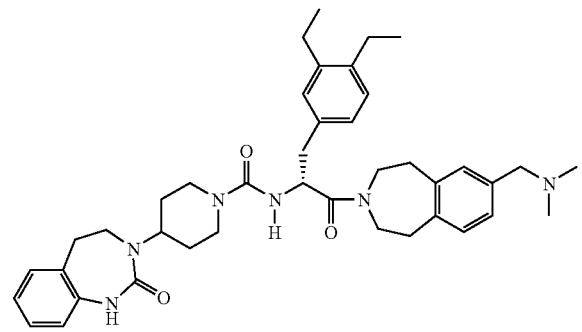

(R)-1-(3,4-diethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate 4-(2-oxo-1,2,4,5-tetrahydro-1,3-benzodiazepin-3-yl)-piperidine-1-carboxylic acid-[(R)-2-(4-azetidin-1-yl-piperidin-1-yl)-1-(3,4-diethyl-benzyl)-2-oxo-ethyl]-amide (61)

(63)

4-(2-oxo-1,2,4,5-tetrahydro-1,3-benzodiazepin-3-yl)-piperidine-1-carboxylic acid [(R)-2-(3-azepan-1-yl-azetidin-1-yl)-1-(3,4-diethyl-benzyl)-2-oxo-ethyl]-amide (64)

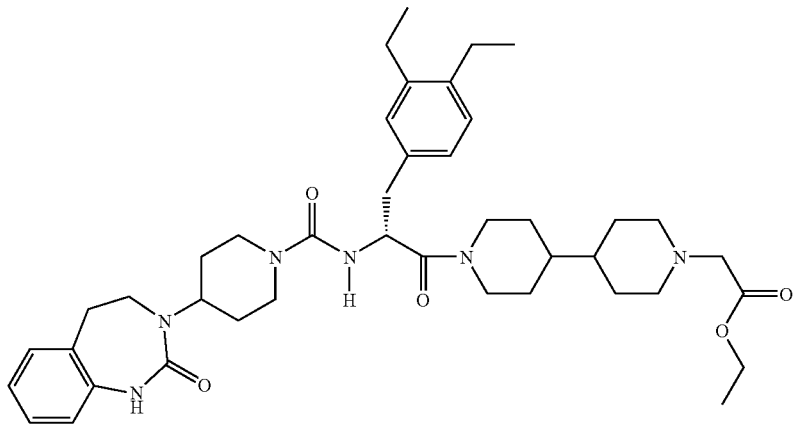

ethyl [1'-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-[4,4']bipiperidinyl-1-yl]-acetate (65)

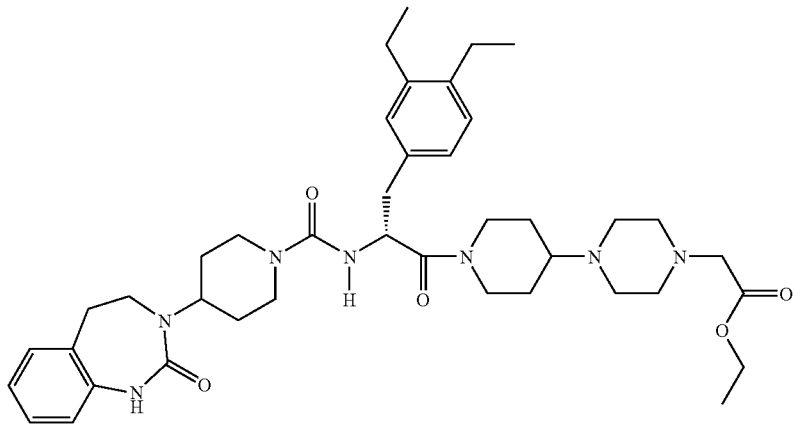

ethyl {4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetate (66)

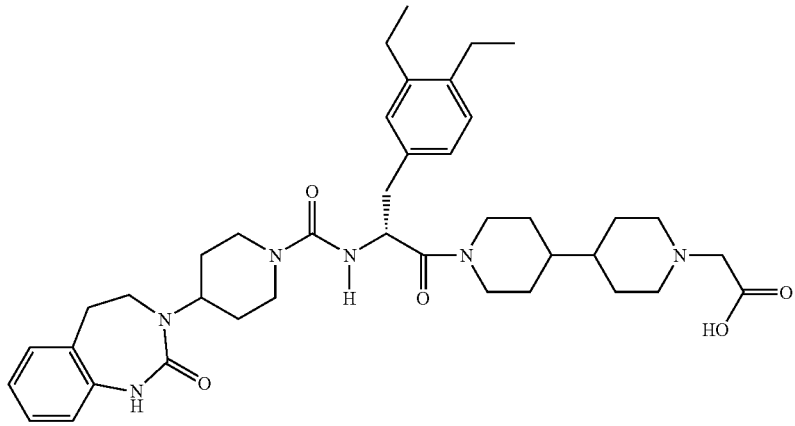

[1'-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-[4,4']bipiperidinyl-1-yl]-acetic acid (67)

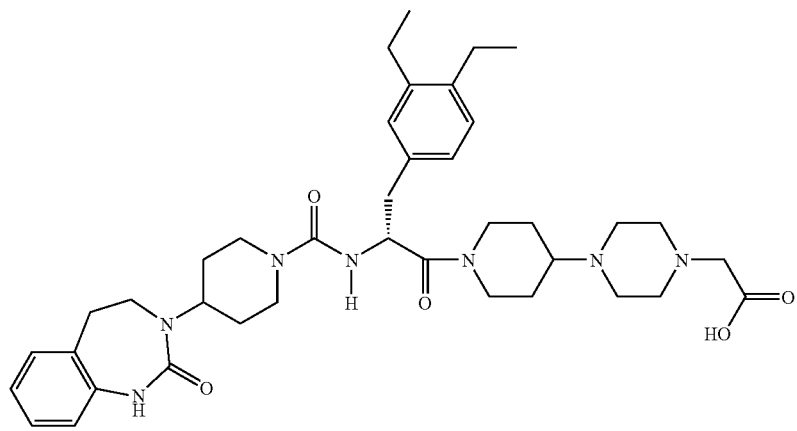

{4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetic acid (68)

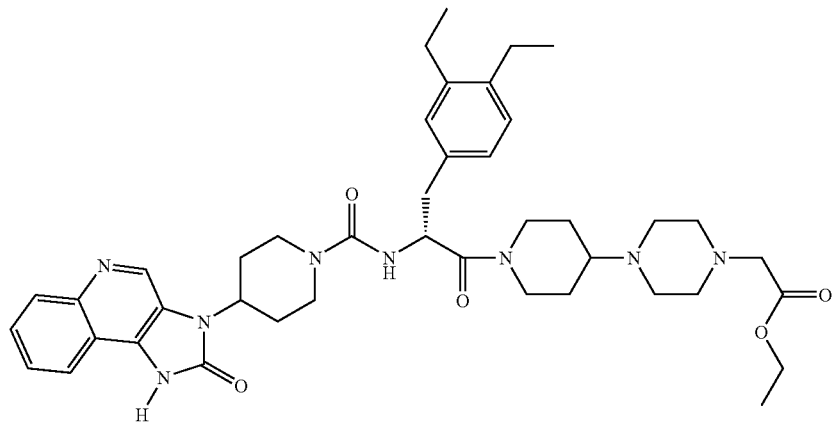

ethyl {4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetate (69)

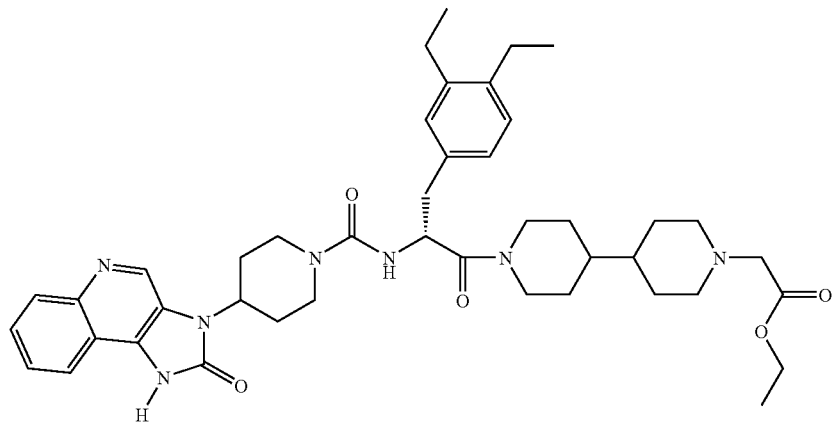

ethyl [1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetate
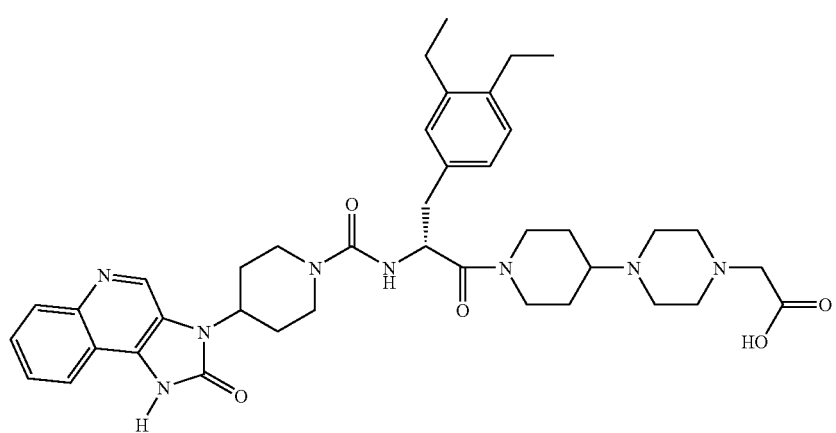
(70)
{4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetic acid
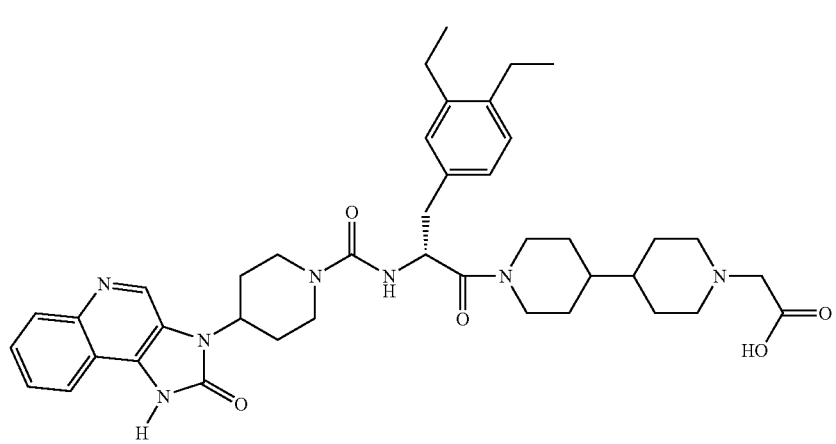
(71)

45

[1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetic acid (72)

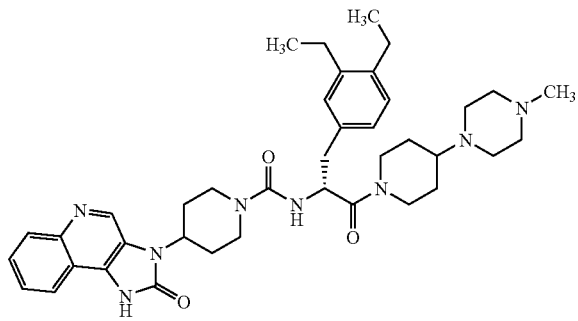

4-(2-oxo-1,2-dihydro-imidazo[4,5-c]quinolin-3-yl)-piperidine-1-carboxylic acid {(R)-1-(3,4-diethyl-benzyl)-2-[4-(4-methyl-piperazin-1-yl)-piperidin-1-yl]-2-oxo-ethyl}-amide (73)

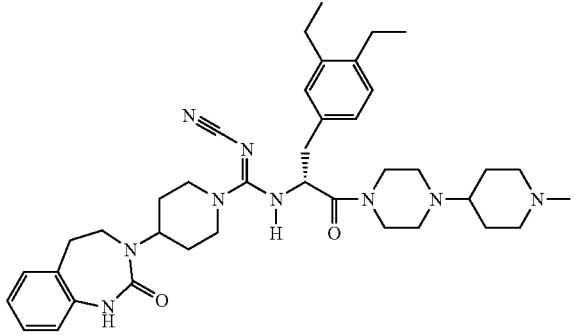

N-[1-{(R)-1-(3,4-diethyl-benzyl)-2-[4-(1-methyl-piperidin-4-yl)-piperazin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide (74)

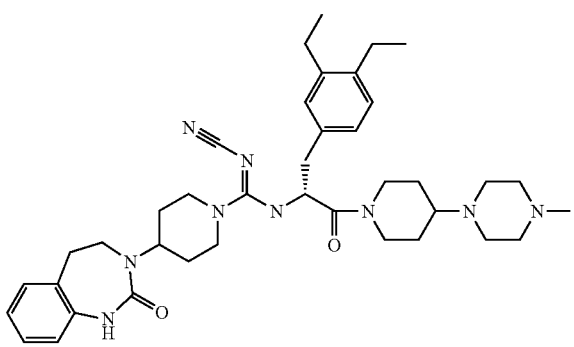

46

N-[1-{(R)-1-(3,4-diethyl-benzyl)-2-[4-(4-methyl-piperazin-1-yl)-piperidin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide (75)

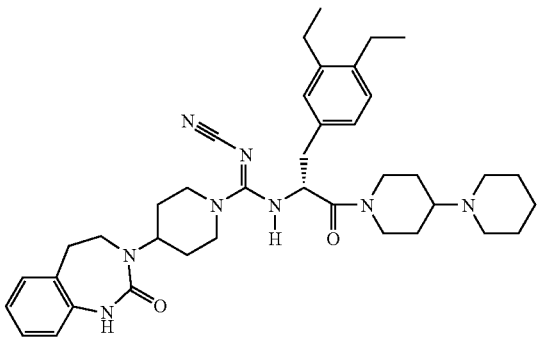

N-[1-[(R)-2-[1,4']bipiperidinyl-1'-yl-1-(3,4-diethyl-benzyl)-2-oxo-ethylamino]-1-[4-(2-oxo-1,2,4,5-tetrahydro-1,3-benzodiazepin-3-yl)-piperidin-1-yl]-meth-(Z)-ylidene]-cyanamide (76)

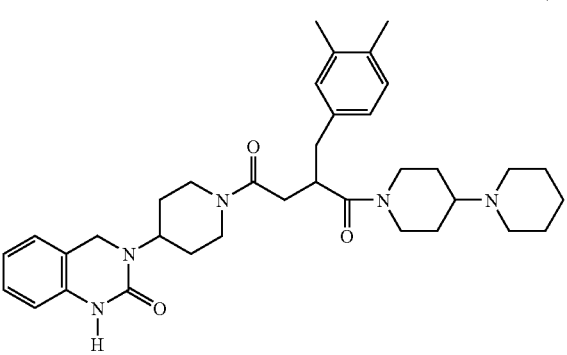

1-[1,4']bipiperidinyl-1'-yl-2-(3,4-dimethyl-benzyl)-4-[4-(2-oxo-1,4-dihydro-2H-quinazolin-3-yl)-piperidin-1-yl]-butan-1,4-dione (77)

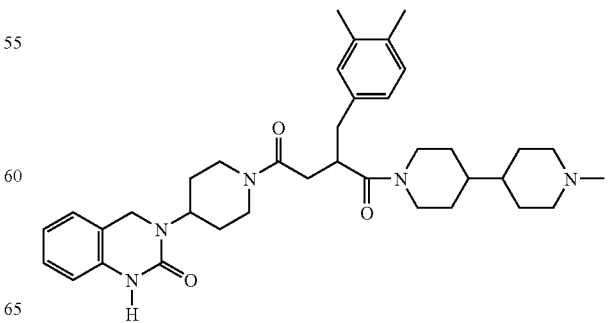

47

2-(3,4-dimethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione (78)

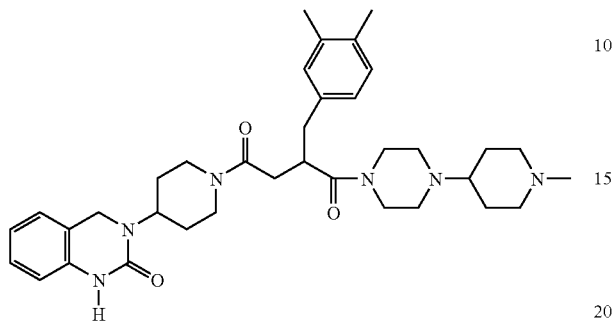

2-(3,4-dimethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione (79)

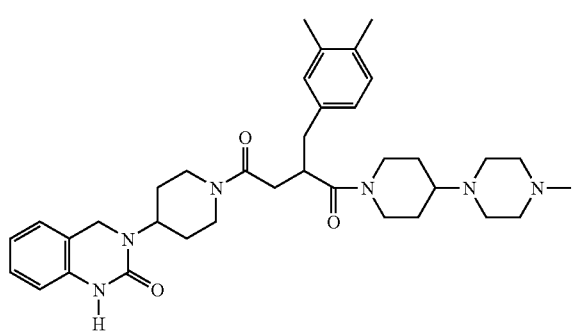

2-(3,4-dimethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione (80)

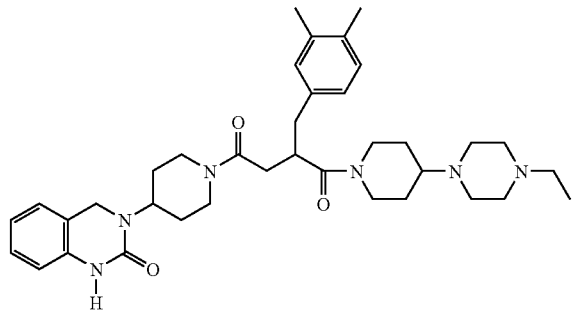

48

2-(3,4-dimethyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione (81)

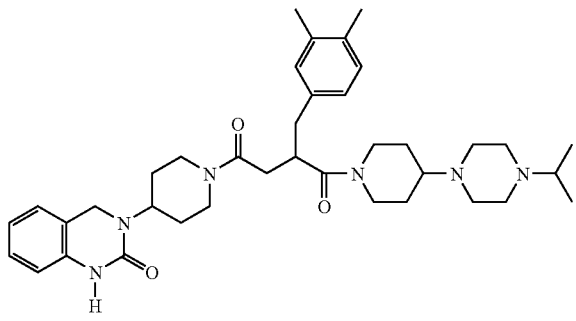

2-(3,4-dimethyl-benzyl)-1-[4-(4-isopropyl-piperazin-1-yl)-piperidin-1-yl]-4-[4-(2-oxo-1,4-dihydro-2H-quinazolin-3-yl)-piperidin-1-yl]-butan-1,4-dione (82)

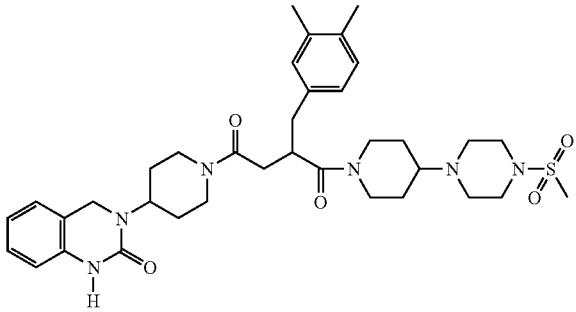

2-(3,4-dimethyl-benzyl)-1-[4-(4-methanesulphonyl-piperazin-1-yl)-piperidin-1-yl]-4-[4-(2-oxo-1,4-dihydro-2H-quinazolin-3-yl)-piperidin-1-yl]-butan-1,4-dione (83)

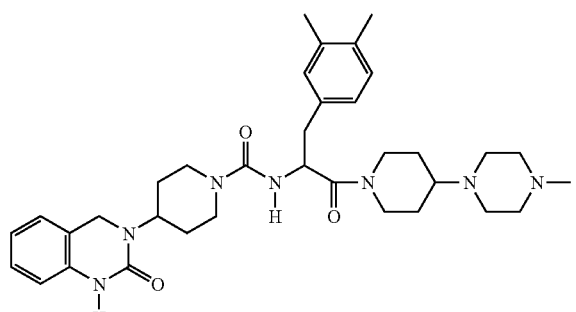

49

4-(2-oxo-1,4-dihydro-2H-quinazolin-3-yl)-piperidine-1'-carboxylic acid {1-(3,4-dimethyl-benzyl)-2-[4-(4-methyl-piperazin-1-yl)-piperidin-1-yl]-2-oxo-ethyl}-amide

50

4-(2-oxo-1,4-dihydro-2H-quinazolin-3-yl)-piperidine-1-carboxylic acid [1-(3,4-dimethyl-benzyl)-2-(1'-methyl-[4,4']bipiperidinyl-1-yl)-2-oxo-ethyl]-amide

(84)

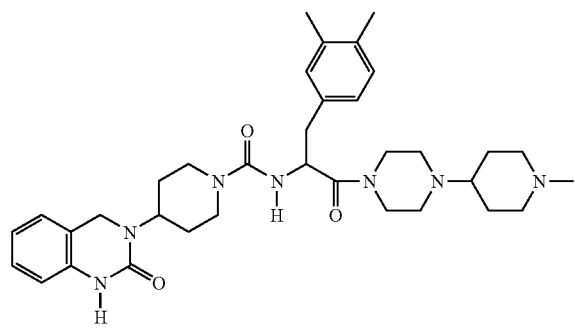

4-(2-oxo-1,4-dihydro-2H-quinazolin-3-yl)-piperidine-1-carboxylic acid {1-(3,4-dimethyl-benzyl)-2-[4-(1-methyl-piperidin-4-yl)-piperazin-1-yl]-2-oxo-ethyl}-amide (86)

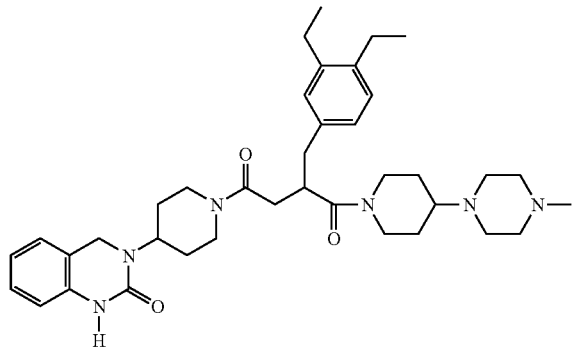

2-(3,4-diethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione (85)

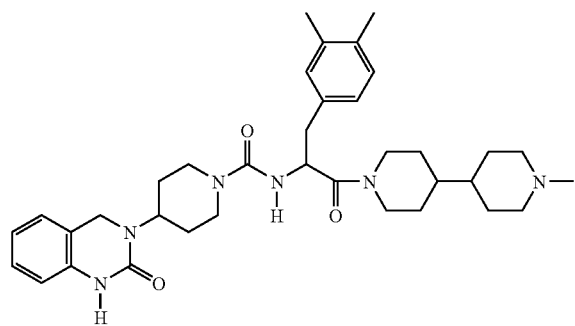

(87)

2-(3,4-diethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione (88)

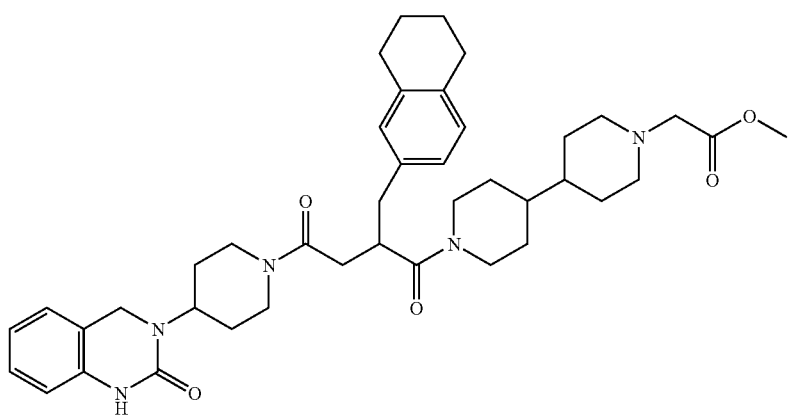

methyl {1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetate
(89)
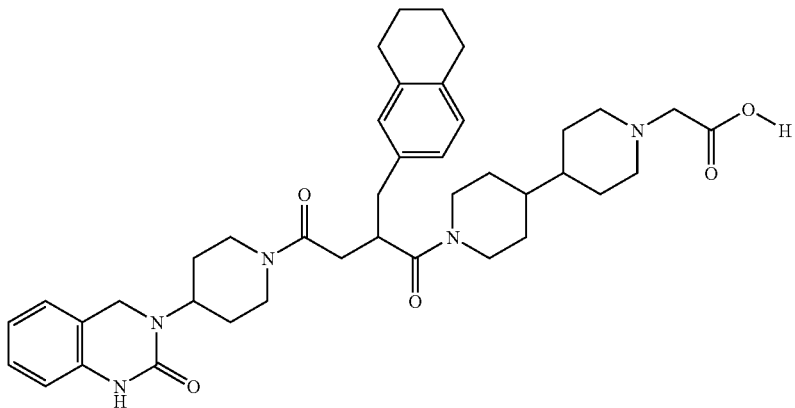
{1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetic acid
(90)
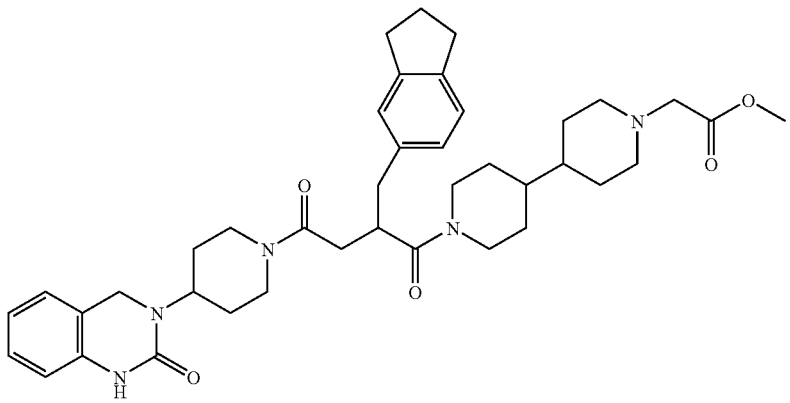
methyl (1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetate
(91)
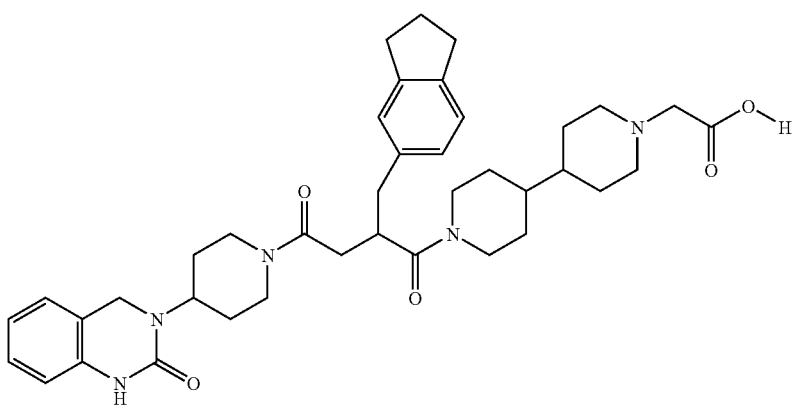

53

((1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetic acid

54

2-indan-5-ylmethyl-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione (92)

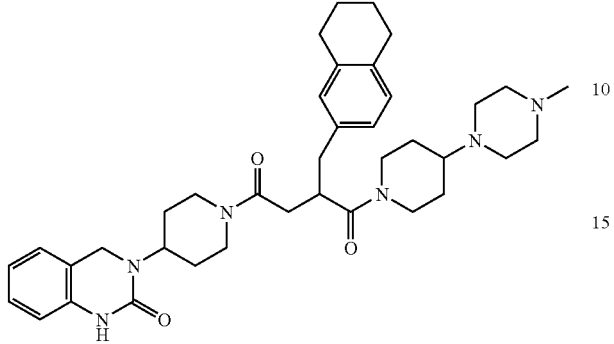

1-[4-(4-methyl-piperazin-1-yl)-piperidin-1-yl]-4-[4-(2-oxo-1,4-dihydro-2H-quinazolin-3-yl)-piperidin-1-yl]-2-(5,6,7,8-tetrahydro-naphthalen-2-ylmethyl)-butan-1,4-dione (95)

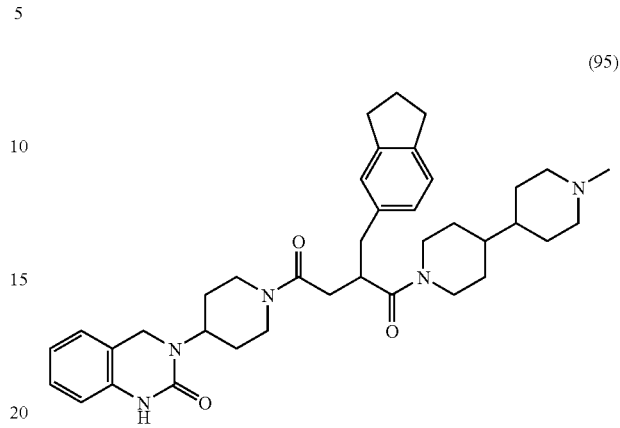

2-indan-5-ylmethyl-1-(1'-methyl-[4,4']bipiperidinyl-1-yl)-4-[4-(2-oxo-1,4-dihydro-2H-quinazolin-3-yl)-piperidin-1-yl]-butan-1,4-dione (93)

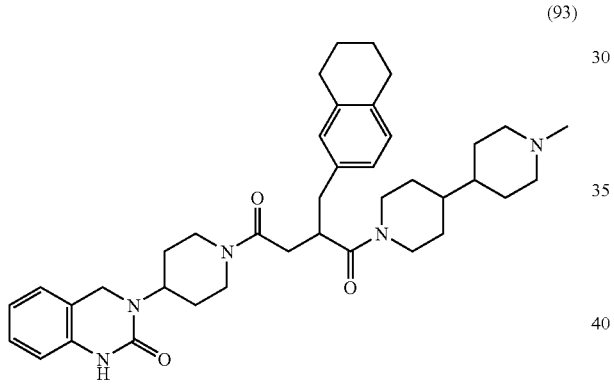

1-(1'-methyl-[4,4']bipiperidinyl-1-yl)-4-[4-(2-oxo-1,4-dihydro-2H-quinazolin-3-yl)-piperidin-1-yl]-2-(5,6,7,8-tetrahydro-naphthalen-2-ylmethyl)-butan-1,4-dione (96)

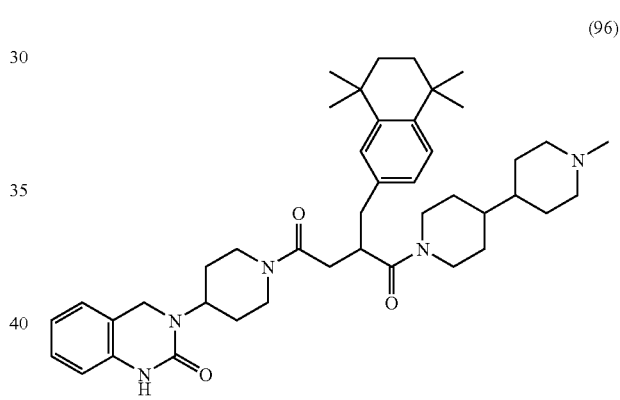

1-(1'-methyl-[4,4']bipiperidinyl-1-yl)-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione (94)

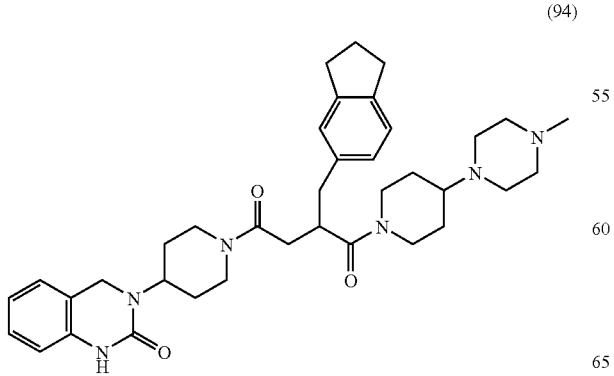

(97)

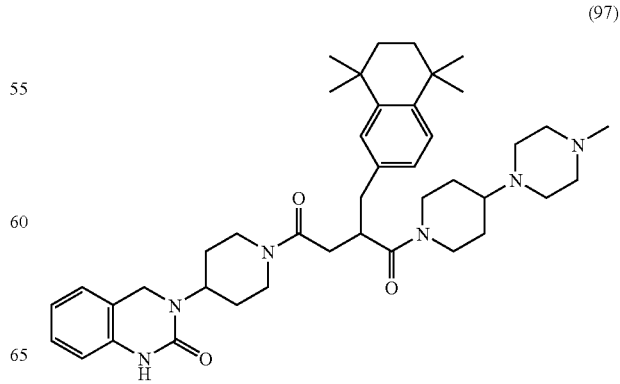

55

1-[4-(4-methyl-piperazin-1-yl)-piperidin-1-yl]-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione (98)

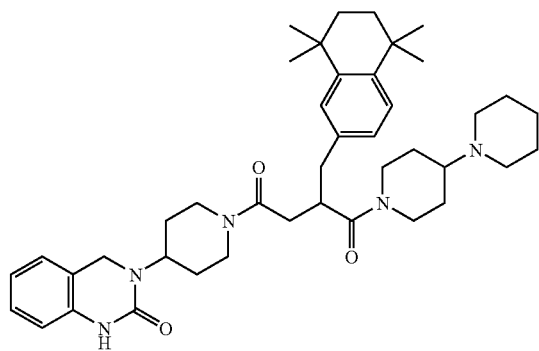

1-[1,4']bipiperidinyl-1'-yl-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione (99)

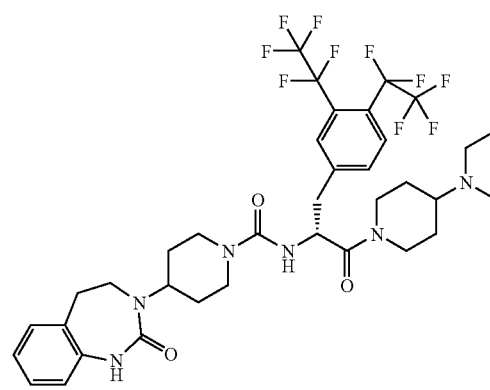

4-(2-oxo-1,2,4,5-tetrahydro-1,3-benzodiazepin-3-yl)-piperidine-1-carboxylic acid {(R)-1-(3,4-bis-pentafluoroethyl-benzyl)-2-[4-(4-methyl-piperazin-1-yl)-piperidin-1-yl]-2-oxo-ethyl}-amide (100)

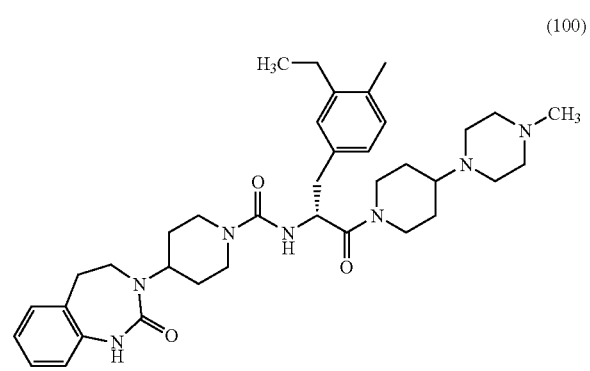

56

4-(2-oxo-1,2,4,5-tetrahydro-1,3-benzodiazepin-3-yl)-piperidine-1-carboxylic acid {(R)-1-(3-ethyl-4-methyl-benzyl)-2-[4-(4-methyl-piperazin-1-yl)-piperidin-1-yl]-2-oxo-ethyl}-amide (101)

(R)-1-(3,4-diethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate (102)

(R)-1-(3,4-diethyl-benzyl)-2-[4-(1-ethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (103)

| 57 | 58 |
|---|---|
| (R)-2-oxo-2-(4-piperazin-1-yl-piperidin-1-yl)-1-(5,6,7,8-tetrahydro-naphthalen-2-ylmethyl)-ethyl 4-(2-oxo-1,2,4,5-tetrahydro-1,3-benzodiazepin-3-yl)-piperidine-1-carboxylate | (S)-2-(3,4-diethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione |

(104)

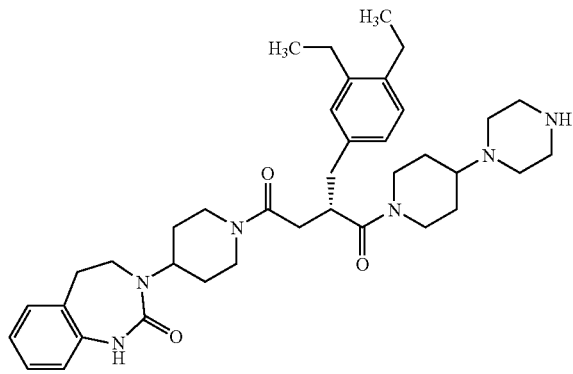

(S)-2-(3,4-diethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione (107)

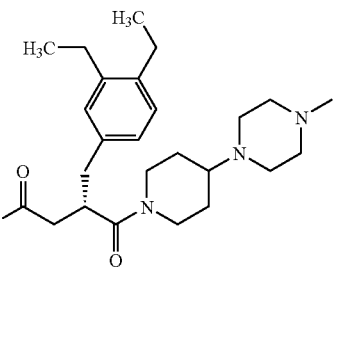

(S)-2-(3,4-diethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione (105)

(S)-2-(3,4-diethyl-benzyl)-4-[4-(2-oxo-1,2,4,5-tetrahydro-1,3-benzodiazepin-3-yl)-piperidin-1-yl]-1-(4-piperidin-4-yl-piperazin-1-yl)-butan-1,4-dione (108)

(S)-1-[1,4']bipiperidinyl-1'-yl-2-(3,4-diethyl-benzyl)-4-[4-(2-oxo-1,2,4,5-tetrahydro-1,3-benzodiazepin-3-yl)-piperidin-1-yl]-butan-1,4-dione (106)

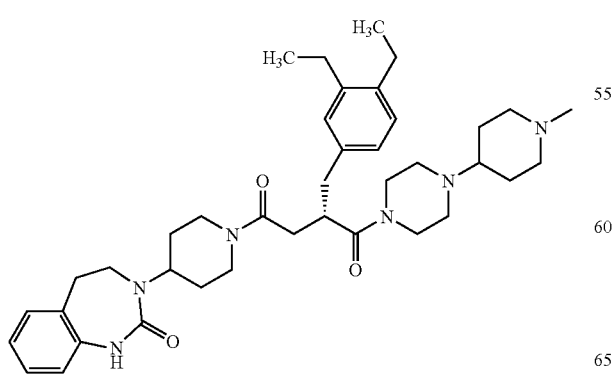

(109)

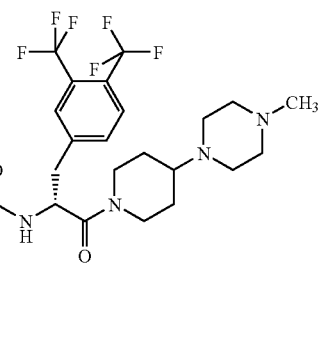

59

4-(2-oxo-1,2,4,5-tetrahydro-1,3-benzodiazepin-3-yl)-piperidine-1-carboxylic acid {(R)-1-(3,4-bis-trifluoromethyl-benzyl)-2-[4-(4-methyl-piperazin-1-yl)-piperidin-1-yl]-2-oxo-ethyl}-amide (110)

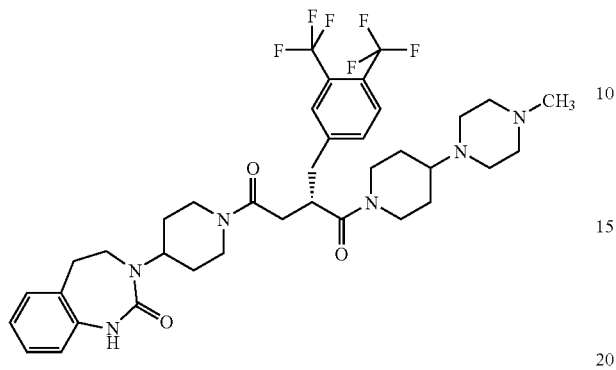

(S)-2-(3,4-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione (111)

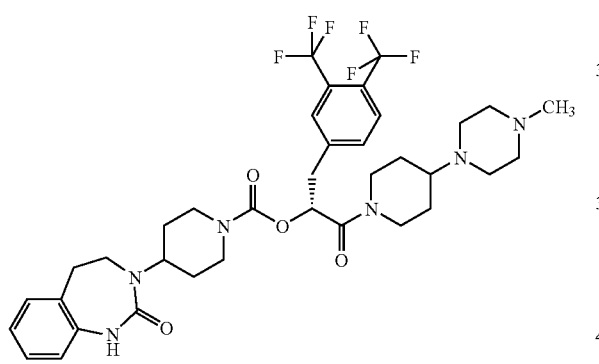

(R)-1-(3,4-bis-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate (112)

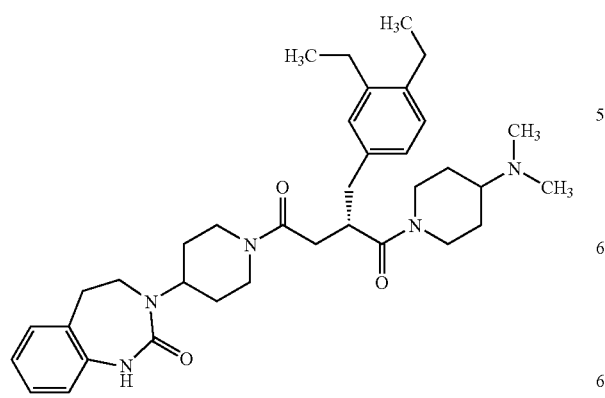

60

(S)-2-(3,4-diethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione (113)

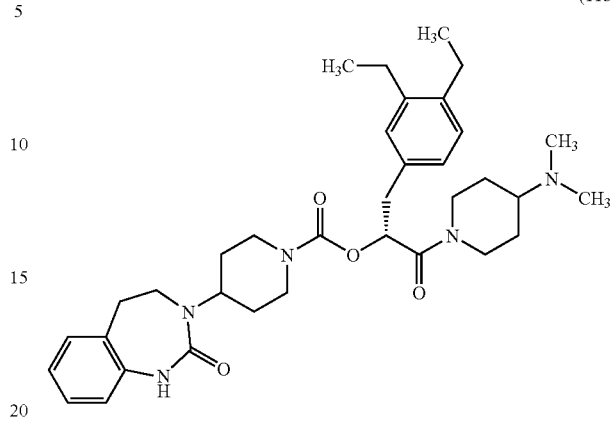

(R)-1-(3,4-diethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate (114)

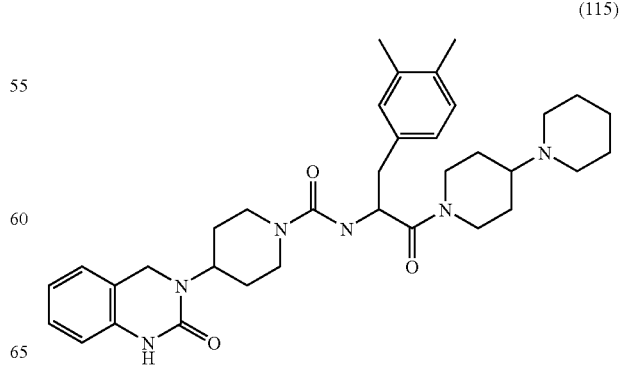

4-(2-oxo-1,2,4,5-tetrahydro-1,3-benzodiazepin-3-yl)-piperidine-1-carboxylic acid [(R)-2-(4-amino-piperidin-1-yl)-1-(3,4-diethyl-benzyl)-2-oxo-ethyl]-amide (115)

| 61 | 62 |
|---|---|
| 4-(2-oxo-1,4-dihydro-2H-quinazolin-3-yl)-piperidine-1-carboxylic acid [2-[1,4']bipiperidinyl-1'-yl-1-(3,4-dimethyl-benzyl)-2-oxo-ethyl]-amide | 4-(2-oxo-1,2,4,5-tetrahydro-1,3-benzodiazepin-3-yl)-piperidine-1-carboxylic acid-{(R)-1-(4-ethyl-3-trifluoromethyl-benzyl)-2-[4-(4-methyl-piperazin-1-yl)-piperidin-1-yl]-2-oxo-ethyl}-amide |

(116)

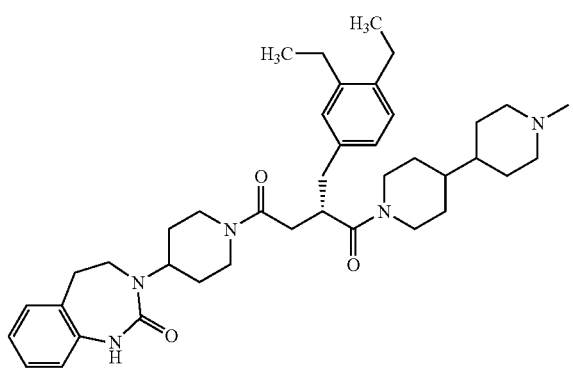

(S)-2-(3,4-diethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione (119)

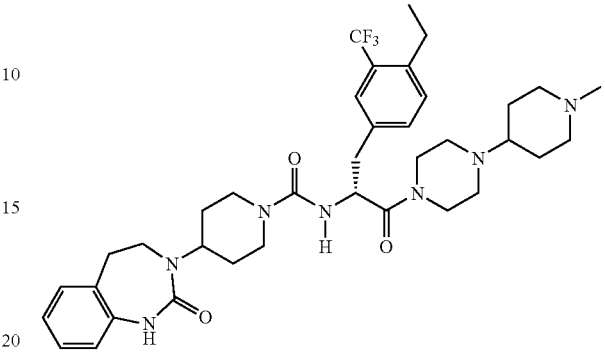

4-(2-oxo-1,2,4,5-tetrahydro-1,3-benzodiazepin-3-yl)-piperidine-1-carboxylic acid-{(R)-1-(4-ethyl-3-trifluoromethyl-benzyl)-2-[4-(1-methyl-piperidin-4-yl)-piperazin-1-yl]-2-oxo-ethyl}-amide (117)

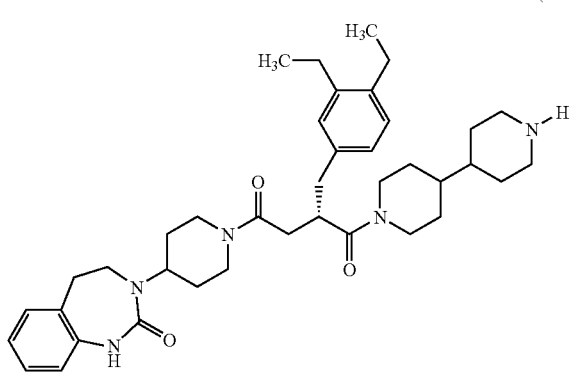

(S)-1-4,4'-bipiperidinyl-1-yl-2-(3,4-diethyl-benzyl)-4-[4-(2-oxo-1,2,4,5-tetrahydro-1,3-benzodiazepin-3-yl)-piperidin-1-yl]-butan-1,4-dione (120)

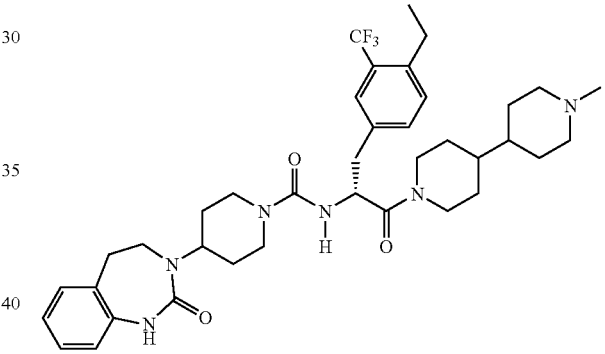

4-(2-oxo-1,2,4,5-tetrahydro-1,3-benzodiazepin-3-yl)-piperidine-1-carboxylic acid-[(R)-1-(4-ethyl-3-trifluoromethyl-benzyl)-2-(1'-methyl-4,4'-bipiperidinyl-1-yl)-2-oxo-ethyl]-amide (118)

(121)

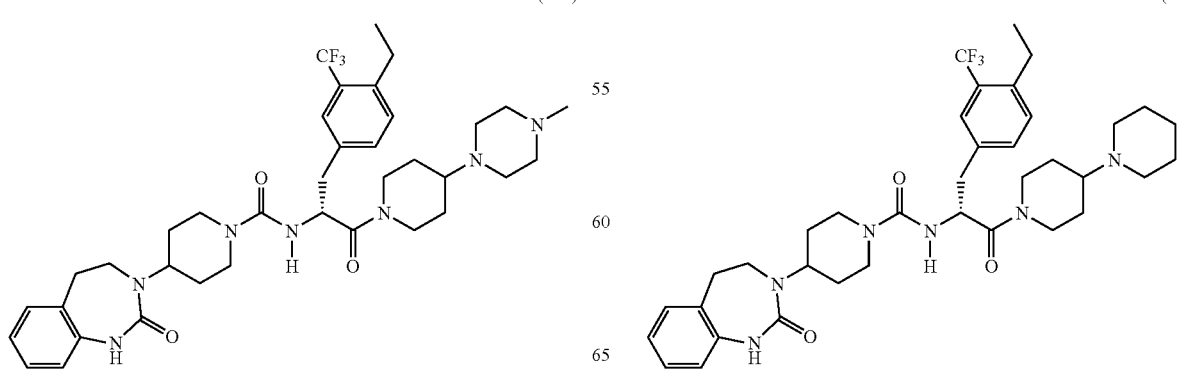

63

4-(2-oxo-1,2,4,5-tetrahydro-1,3-benzodiazepin-3-yl)-piperidine-1-carboxylic acid-[(R)-2-1,4'-bipiperidi-nyl-1'-yl-1-(4-ethyl-3-trifluoromethyl-benzyl)-2-oxo-ethyl]-amide (122)

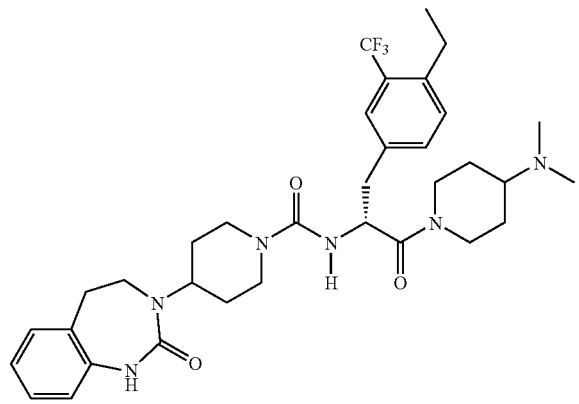

4-(2-oxo-1,2,4,5-tetrahydro-1,3-benzodiazepin-3-yl)-piperidine-1-carboxylic acid-[(R)-2-(4-dimethy-lamino-piperidin-1-yl)-1-(4-ethyl-3-trifluoromethyl-benzyl)-2-oxo-ethyl]-amide (123)

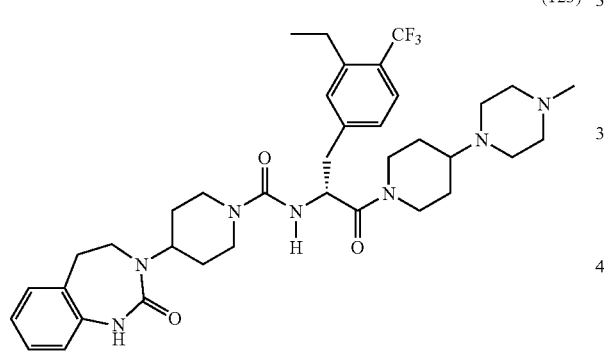

4-(2-oxo-1,2,4,5-tetrahydro-1,3-benzodiazepin-3-yl)-piperidine-1-carboxylic acid-{(R)-1-(3-ethyl-4-trif-luoromethyl-benzyl)-2-[4-(4-methyl-piperazin-1-yl)-piperidin-1-yl]-2-oxo-ethyl}-amide (124)

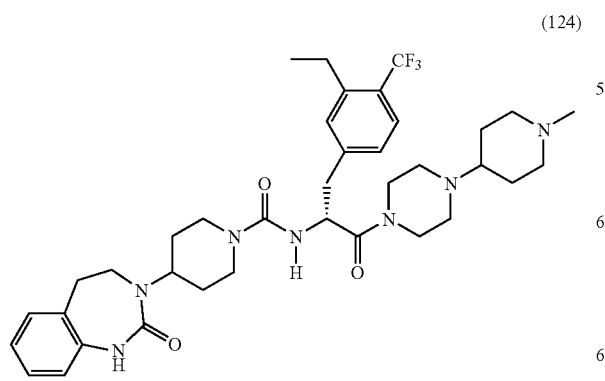

64

4-(2-oxo-1,2,4,5-tetrahydro-1,3-benzodiazepin-3-yl)-piperidine-1-carboxylic acid-{(R)-1-(3-ethyl-4-trif-luoromethyl-benzyl)-2-[4-(1-methyl-piperidin-4-yl)-piperazin-1-yl]-2-oxo-ethyl}-amide (125)

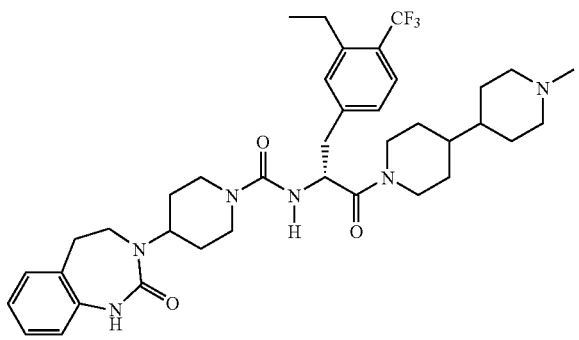

4-(2-oxo-1,2,4,5-tetrahydro-1,3-benzodiazepin-3-yl)-piperidine-1-carboxylic acid-[(R)-1-(3-ethyl-4-trif-luoromethyl-benzyl)-2-(1'-methyl-4,4'-bipiperidinyl-1-yl)-2-oxo-ethyl]-amide (126)

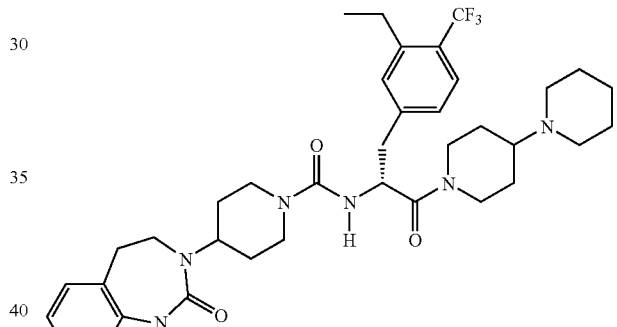

4-(2-oxo-1,2,4,5-tetrahydro-1,3-benzodiazepin-3-yl)-piperidine-1-carboxylic acid-[(R)-2-1,4'-bipiperidi-nyl-1'-yl-1-(3-ethyl-4-trifluoromethyl-benzyl)-2-oxo-ethyl]-amide (127)

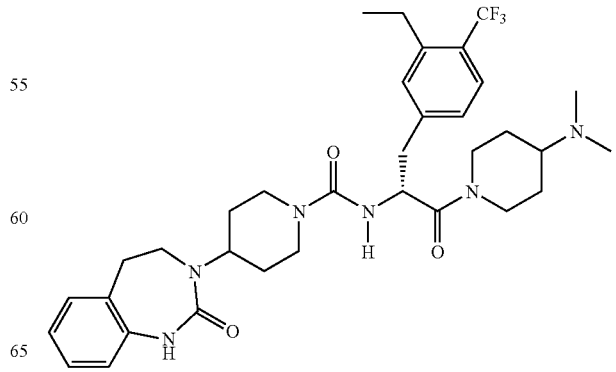

4-(2-oxo-1,2,4,5-tetrahydro-1,3-benzodiazepin-3-yl)-piperidine-1-carboxylic acid-[(R)-2-(4-dimethylamino-piperidin-1-yl)-1-(3-ethyl-4-trifluoromethyl-benzyl)-2-oxo-ethyl]-amide, the enantiomers, the diastereomers and the salts thereof, while the compounds (1) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide, (2) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-piperazin-1-yl)-piperidin-1-yl]-2-oxo-ethyl}-amide, (3) 4-(2-oxo-1,2,4,5-tetrahydro-1,3-benzodiazepin-3-yl)-piperidine-1-carboxylic acid-[1-(3,4-diethyl-benzyl)-2-(1'-methyl-4,4'-bipiperidinyl-1-yl)-2-oxo-ethyl]-amide, (4) 4-(2-oxo-1,2,4,5-tetrahydro-1,3-benzodiazepin-3-yl)-piperidine-1-carboxylic acid-[2-1,4'-bipiperidinyl-1'-yl-1-(3,4-diethyl-benzyl)-2-oxo-ethyl]-amide, (5) 4-(2-oxo-1,2,4,5-tetrahydro-1,3-benzodiazepin-3-yl)-piperidine-1-carboxylic acid-[1-(3,4-diethyl-benzyl)-2-oxo-2-(4-pyridin-4-yl-piperazin-1-yl)-ethyl]-amide, (6) 4-(2-oxo-1,4-dihydro-2H-quinazolin-3-yl)-piperidine-1-carboxylic acid-{1-(3,4-diethyl-benzyl)-2-[4-(4-methyl-piperazin-1-yl)-piperidin-1-yl]-2-oxo-ethyl}-amide, (7) 4-(2-oxo-1,4-dihydro-2H-quinazolin-3-yl)-piperidine-1-carboxylic acid-{1-(3,4-diethyl-benzyl)-2-[4-(1-methyl-piperidin-4-yl)-piperazin-1-yl]-2-oxo-ethyl}-amide, (8) 4-(2-oxo-1,2,4,5-tetrahydro-1,3-benzodiazepin-3-yl)-piperidine-1-carboxylic acid-[(R)-1-(3,4-diethyl-benzyl)-2-(4-dimethylamino-piperidin-1-yl)-2-oxo-ethyl]-amide, (9) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-perhydro-azepin-1-yl-piperidin-1-yl)-ethyl]-amide,

(10) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-perhydro-1,4-diazepin-1-yl)-piperidin-yl]-2-oxo-ethyl}-amide,

(11) 4-(2-oxo-1,2,4,5-tetrahydro-1,3-benzodiazepin-3-yl)-piperidine-1-carboxylic acid-[(R)-1-(3,4-diethyl-benzyl)-2-(1'-methyl-4,4'-bipiperidinyl-1-yl)-2-oxo-ethyl]-amide,

(12) 4-(2-oxo-1,2,4,5-tetrahydro-1,3-benzodiazepin-3-yl)-piperidine-1-carboxylic acid-{(R)-1-(3,4-diethyl-benzyl)-2-[4-(8-methyl-8-aza-bicyclo[3.2.1]oct-3-yl)-piperazin-1-yl]-2-oxo-ethyl}-amide,

(13) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperazin-1-yl-piperidin-1-yl)-ethyl]-amide,

(14) 4-(2-oxo-1,2,4,5-tetrahydro-1,3-benzodiazepin-3-yl)-piperidine-1-carboxylic acid-[(R)-2-[4-(4-acetyl-piperazin-1-yl)-piperidin-1-yl]-1-(3,4-diethyl-benzyl)-2-oxo-ethyl]-amide,

(15) 4-(5-oxo-3-phenyl-4,5-dihydro-1,2,4-triazol-1-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,

(16) 4-(2-oxo-1,4-dihydro-2H-quinazolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,

(17) 4-(2-oxo-1,2-dihydro-imidazo[4,5-c]quinolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,

(18) 4-(2-oxo-1,2,4,5-tetrahydro-1,3-benzodiazepin-3-yl)-piperidine-1-carboxylic acid-[(R)-2-[4-(4-cyclopropylmethyl-piperazin-1-yl)-piperidin-1-yl]-1-(3,4-diethyl-benzyl)-2-oxo-ethyl]-amide,

(19) 4-(2-oxo-1,2-dihydro-4H-thieno[3,4-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,

(20) 4-(2-oxo-1,4-dihydro-2H-thieno[3,2-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,

(21) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyrrolidin-1-yl-piperidin-1-yl)-ethyl]-amide,

(22) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-ethyl-piperazin-1-yl)-piperidin-1-yl]-2-oxo-ethyl}-amide,

(23) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-isopropyl-piperazin-1-yl)-piperidin-1-yl]-2-oxo-ethyl}-amide,

(24) 4-(2-oxo-1,2,4,5-tetrahydro-1,3-benzodiazepin-3-yl)-piperidine-1-carboxylic acid-[(R)-2-1,4'-bipiperidinyl-1'-yl-1-(3,4-diethyl-benzyl)-2-oxo-ethyl]-amide,

(25) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyridin-4-yl-piperazin-1-yl)-ethyl]-amide,

(26) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(3,4,5,6-tetrahydro-2H-4,4'-bipyridinyl-1-yl)-ethyl]-amide,

(27) 4-(2-oxo-1,2,4,5-tetrahydro-1,3-benzodiazepin-3-yl)-piperidine-1-carboxylic acid-[(R)-1-(3,4-diethyl-benzyl)-2-(4-morpholin-4-yl-piperidin-1-yl)-2-oxo-ethyl]-amide,

(28) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-ethyl-piperidin-4-yl)-piperazin-1-yl]-2-oxo-ethyl}-amide,

(29) 4-(2-oxo-1,2,4,5-tetrahydro-1,3-benzodiazepin-3-yl)-piperidine-1-carboxylic acid-[(R)-2-(4-diethylaminomethyl-piperidin-1-yl)-1-(3,4-diethyl-benzyl)-2-oxo-ethyl]-amide,

(30) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-[1,4]diazepan-1-yl]-2-oxo-ethyl}-amide,

(31) 4-(2-oxo-1,2,4,5-tetrahydro-1,3-benzodiazepin-3-yl)-piperidine-1-carboxylic acid-{(R)-1-(3,4-diethyl-benzyl)-2-[3-(4-methyl-piperazin-1-yl)-azetidin-1-yl]-2-oxo-ethyl}-amide,

(32) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperidin-4-yl-piperazin-1-yl)-ethyl]-amide,

(33) 4-(2-oxo-1,2,4,5-tetrahydro-1,3-benzodiazepin-3-yl)-piperidine-1-carboxylic acid-[(R)-2-[4-(4-methyl-piperazin-1-yl)-piperidin-1-yl]-2-oxo-1-(5,6,7,8-tetrahydronaphthalen-2-ylmethyl)-ethyl]-amide,

(34) 4-(2-oxo-1,2,4,5-tetrahydro-1,3-benzodiazepin-3-yl)-piperidine-1-carboxylic acid-[(R)-2-[4-(1-methyl-piperidin-4-yl)-piperazin-1-yl]-2-oxo-1-(5,6,7,8-tetrahydronaphthalen-2-ylmethyl)-ethyl]-amide,

(35) 4-(2-oxo-1,2,4,5-tetrahydro-1,3-benzodiazepin-3-yl)-piperidine-1-carboxylic acid-[(R)-2-oxo-2-(4-piperidin-4-yl-piperazin-1-yl)-1-(5,6,7,8-tetrahydro-naphthalen-2-ylmethyl)-ethyl]-amide,

(36) 4-(2-oxo-1,2,4,5-tetrahydro-1,3-benzodiazepin-3-yl)-piperidine-1-carboxylic acid-[(R)-2-oxo-2-(4-piperazin-1-yl-piperidin-1-yl)-1-(5,6,7,8-tetrahydro-naphthalen-2-ylmethyl)-ethyl]-amide,

(37) 4-(2-oxo-1,2-dihydro-imidazo[4,5-c]quinolin-3-yl)-piperidine-1-carboxylic acid-[(R)-2-[4-(1-methyl-piperidin-4-yl)-piperazin-1-yl]-2-oxo-1-(5,6,7,8-tetrahydronaphthalen-2-ylmethyl)-ethyl]-amide,

(38) 4-(2-oxo-1,2-dihydro-imidazo[4,5-c]quinolin-3-yl)-piperidine-1-carboxylic acid-[(R)-2-[4-(4-benzyl-piperazin-1-yl)-piperidin-1-yl]-2-oxo-1-(5,6,7,8-tetrahydronaphthalen-2-ylmethyl)-ethyl]-amide,

(39) 4-(2-oxo-1,2-dihydro-imidazo[4,5-c]quinolin-3-yl)-piperidine-1-carboxylic acid-[(R)-2-oxo-2-(4-piperazin-1-yl-piperidin-1-yl)-1-(5,6,7,8-tetrahydro-naphthalen-2-ylmethyl)-ethyl]-amide,

(40) 4-(5-oxo-3-phenyl-4,5-dihydro-[1,2,4]triazol-1-yl)-piperidine-1-carboxylic acid-[(R)-2-[4-(1-methyl-piperidin-4-yl)-piperazin-1-yl]-2-oxo-1-(5,6,7,8-tetrahydronaphthalen-2-ylmethyl)-ethyl]-amide,

(41) 4-(5-oxo-3-phenyl-4,5-dihydro-[1,2,4]triazol-1-yl)-piperidine-1-carboxylic acid-[(R)-2-oxo-2-(4-piperazin-1-yl-piperidin-1-yl)-1-(5,6,7,8-tetrahydro-naphthalen-2-ylmethyl)-ethyl]-amide,

(42) (R)-1-(3,4-diethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate,

(43) 4-(2-oxo-1,2,4,5-tetrahydro-1,3-benzodiazepin-3-yl)-piperidine-1-carboxylic acid-[(R)-2-(4-azetidin-1-yl-piperidin-1-yl)-1-(3,4-diethyl-benzyl)-2-oxo-ethyl]-amide,

(44) {4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetic acid,

(45) ethyl {4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetate,

(46) ethyl [1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetate,

(47) {4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetic acid,

(48) 4-(2-oxo-1,2-dihydro-imidazo[4,5-c]quinolin-3-yl)-piperidine-1-carboxylic acid-{(R)-1-(3,4-diethyl-benzyl)-2-[4-(4-methyl-piperazin-1-yl)-piperidin-1-yl]-2-oxo-ethyl}-amide,

(49) N-[1-{(R)-1-(3,4-diethyl-benzyl)-2-[4-(1-methyl-piperidin-4-yl)-piperazin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide,

(50) N-[1-{(R)-1-(3,4-diethyl-benzyl)-2-[4-(4-methyl-piperazin-1-yl)-piperidin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide,

(51) N-[1-[(R)-2-[1,4']bipiperidinyl-1'-yl-1-(3,4-diethyl-benzyl)-2-oxo-ethylamino]-1-[4-(2-oxo-1,2,4,5-tetrahydro-1,3-benzodiazepin-3-yl)-piperidin-1-yl]-meth-(Z)-ylidene]-cyanamide,

(52) 2-(3,4-dimethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione,

(53) 2-(3,4-dimethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione,

(54) 2-(3,4-dimethyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione,

(55) 4-(2-oxo-1,4-dihydro-2H-quinazolin-3-yl)-piperidine-1-carboxylic acid-{1-(3,4-dimethyl-benzyl)-2-[4-(4-methyl-piperazin-1-yl)-piperidin-1-yl]-2-oxo-ethyl}-amide,

(56) 4-(2-oxo-1,4-dihydro-2H-quinazolin-3-yl)-piperidine-1-carboxylic acid-{1-(3,4-dimethyl-benzyl)-2-[4-(1-methyl-piperidin-4-yl)-piperazin-1-yl]-2-oxo-ethyl}-amide,

(57) 4-(2-oxo-1,4-dihydro-2H-quinazolin-3-yl)-piperidine-1-carboxylic acid-[1-(3,4-dimethyl-benzyl)-2-(1'-methyl-[4,4']bipiperidinyl-1-yl)-2-oxo-ethyl]-amide,

(58) 2-(3,4-diethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione,

(59) 2-(3,4-diethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione, the enantiomers, the diastereomers and the salts thereof are particularly preferred.

The compounds of general formula (I) are prepared by methods known in principle. The following methods have proved particularly satisfactory for preparing the compounds of general formula (I) according to the invention:

(a) In order to prepare compounds of general formula (I) wherein X denotes an oxygen atom or the NH group and $R^1$ to $R^3$ are as hereinbefore defined, with the proviso that these groups do not contain any free carboxylic acid function:

Reacting piperidines of general formula

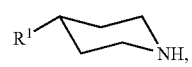

(III)

wherein $R^1$ is as hereinbefore defined, (i) with carbonic acid derivatives of general formula

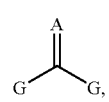

(IV)

wherein A is as hereinbefore defined and G denotes a nucleofugic group, preferably the phenoxy, 1H-imidazol-1-yl, 1H-1,2,4-triazol-1-yl, trichloromethoxy or the 2,5-dioxopyrrolidin-1-yloxy group, with the proviso that X denotes the NH group, or (ii) with carbonic acid derivatives of general formula

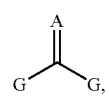

(IV)

wherein A denotes the oxygen atom and G denotes a nucleofugic group which may be identical or different, preferably the chlorine atom or the p-nitrophenoxy or trichloromethoxy group, with the proviso that X denotes the oxygen atom, and with compounds of general formula

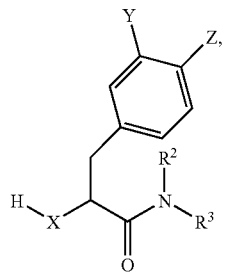
(V)

wherein X denotes an oxygen atom or an —NH group and Y, Z, $R^2$ and $R^3$ are as hereinbefore defined, with the proviso that $R^2$ and $R^3$ do not contain any free carboxylic acid, any other free primary or secondary aliphatic amino function or any other free hydroxy function.

The fundamentally two-step reactions are normally carried out as one-pot processes, in which, preferably, in the first step, one of the two components (III) or (V) is reacted with equimolar amounts of the carbonic acid derivative of general formula (IV) in a suitable solvent at lower temperature, then at least equimolar amounts of the other component (III) or (V) are added and the reaction is completed at a higher temperature. The reactions with bis-(trichloromethyl)-carbonate are preferably carried out in the presence of at least 2 equivalents (based on bis-(trichloromethyl)-carbonate) of a tertiary base, for example triethylamine, N-ethyldiisopropylamine, pyridine, 1,5-diaza-bicyclo-[4,3,0]-non-5-ene, 1,4-diazabicyclo [2,2,2]octane or 1,8-diazabicyclo-[5,4,0]-undec-7-ene. The solvents used, which should be anhydrous, may be for example tetrahydrofuran, dioxane, dimethylformamide, dimethylacetamide, N-methyl-2-pyrrolidone, 1,3-dimethyl-2-imidazolidinone or acetonitrile, while if bis-(trichloromethyl)-carbonate is used as the carbonyl component anhydrous chlorohydrocarbons, for example dichloromethane, 1,2-dichloroethane or trichloroethylene are preferred. The reaction temperatures for the first reaction step are between −30° C. and +25° C., preferably −5° C. and +10° C., for the second reaction step between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Praparativen Organischen Chemie, Volume V, p. 53-93, Verlag Chemie, Weinheim/Bergstr., 1967; P. Majer and R. S. Randad, J. Org. Chem. 59, p. 1937-1938 (1994); K. Takeda, Y. Akagi, A. Saiki, T. Sukahara and H. Ogura, Tetrahedron Letters 24 (42), 4569-4572 (1983)); S. R. Sandler and W. Karo in "Organic Functional Group Preparations", Vol. II, S. 223-245, Academic Press, New York 1971).

(b) In order to prepare compounds of general formula (I) wherein X denotes the methylene group and $R^1$ to $R^3$ are as hereinbefore defined, with the proviso that these groups do not contain any free carboxylic acid and/or other free primary or secondary aliphatic amino function:

Coupling a carboxylic acid of general formula

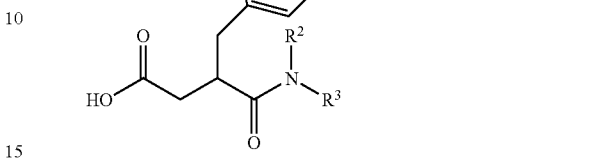
(VI)

wherein Y, Z, $R^2$ and $R^3$ are as hereinbefore defined, to a piperidine of general formula

(III)

wherein $R^1$ has the meanings given hereinbefore.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hûnig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the above-mentioned solvents and at temperatures between −20 and +25° C., preferably 0° C. and +25° C.

(c) In order to prepare compounds of general formula (I) wherein X denotes the methylene group and $R^2$ and $R^3$ are as hereinbefore defined, with the proviso that these groups do not contain any free primary or secondary amine:

Coupling a compound of general formula

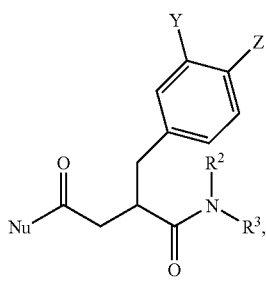

(VII)

wherein Y, Z, R² and R³ are as hereinbefore defined, with the proviso that R² and R³ do not contain any free primary or secondary amine, and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzotriazol-1-yloxy or azide group, with a piperidine of general formula

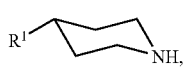

(III)

wherein R¹ is as hereinbefore defined.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof, if alkali metal or alkaline earth metal hydroxides, alkali metal carbonates or acetates are used as the auxiliary bases, water may also be added to the reaction mixture as cosolvent.

(d) In order to prepare compounds of general formula (I) wherein all the groups are as hereinbefore defined:

Coupling a carboxylic acid of general formula

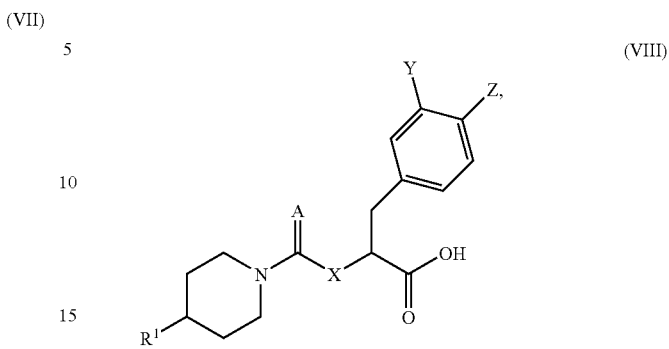

(VIII)

wherein all the groups are as hereinbefore defined, with an amine of general formula HNR²R³, wherein R² and are as hereinbefore defined, with the proviso that it does not contain any free carboxylic acid and/or other free primary or secondary aliphatic amino function.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the above-mentioned solvents and at temperatures between −20 and +25° C., preferably 0° C. and +25° C.

(e) In order to prepare compounds of general formula (I) wherein R¹ is as hereinbefore defined, with the proviso that no free primary or secondary amine is present:

Coupling a compound of general formula

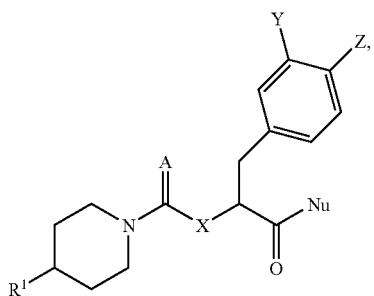

(IX)

wherein all the groups are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with an amine of general formula $HNR^2R^3$, wherein $R^2$ and $R^3$ are as hereinbefore defined, with the proviso that no free carboxylic acid and/or other free primary or secondary aliphatic amino function is present.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof, if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formula (III) may be obtained, if they are not known from the literature or even commercially available, according to the processes described in WO 98/11128 and DE 199 52 146. The starting compounds of general formula (IV) are commercially available. Compounds of general formula (V) may be obtained by methods familiar to the peptide chemist from protected phenylalanines and amines of general formula $HNR^2R^3$.

The phenylalanine derivatives needed to prepare the optically pure compounds of general formula (V) may be prepared from the compounds of general formula

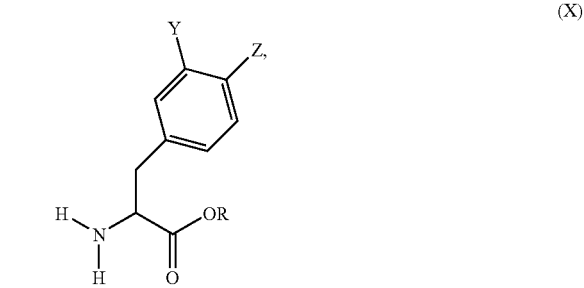

(X)

wherein Y and Z are as hereinbefore defined and R denotes an unbranched alkyl group, preferably the methyl or ethyl group, by racemate cleavage.

This racemate cleavage can be carried out using enzymatic methods, while only one enantiomer of the racemate is transformed and the mixture produced is then separated using physicochemical methods, preferably using chromatographic methods. A suitable enzyme system for this step consists of the enzyme Alcalase 2.4 L FG (Novozymes A/S; DK 2880 Bagsvaerd). The compounds of general formula (X) can then be converted into the enantiomerically pure compounds of general formula (V) by methods familiar to the peptide chemist.

If the group X in compounds of general formula (V) denotes the oxygen atom, the hydroxycarboxylic acids needed for the synthesis, of general formula

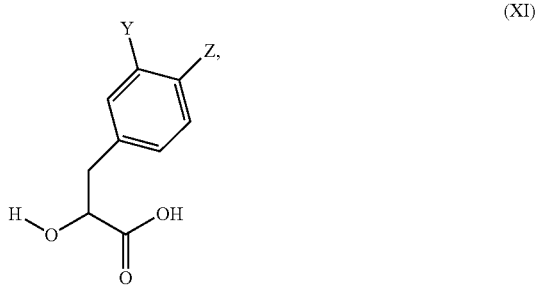

(XI)

wherein Y and Z are as hereinbefore defined, may be prepared from compounds of general formula (X), with the proviso that R denotes the hydrogen atom.

The compounds of general formula (XI) may be obtained by diazotisation of compounds of general formula (X) with a suitable diazotising reagent, preferably sodium nitrite in an acidic medium. If enantiomerically pure compounds are used, the corresponding enantiomerically pure hydroxycarboxylic acid compounds are obtained, and the configuration is retained during the reaction.

Another method of obtaining compounds of general formula (XI) comprises alkylating the compound

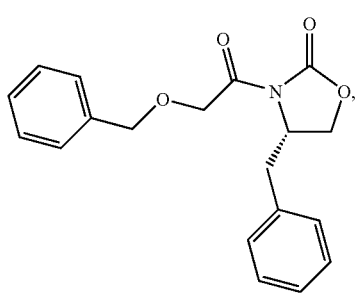

(XII)

with correspondingly substituted benzyl chlorides, benzyl bromides or benzyl iodides of general formula

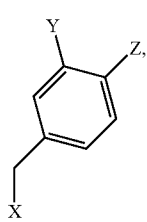

(XIII)

wherein X denotes a chlorine, bromine or iodine atom, analogously to methods known from the literature (Michael T. Crimmins, Kyle A. Emmitte and Jason D. Katz, Org. Lett. 2, 2165-2167 [2000]).

The diastereomeric products obtained can then be separated by physicochemical methods, preferably using chromatographic methods. The hydrolytic cleaving of the chiral auxiliary, coupling with amines of general formula $HNR^2R^3$ and cleaving the benzyl protecting group also provides access to enantiomerically pure hydroxycarboxylic acid compounds of general formula (V).

The starting compounds of general formula (VI) are obtained for example by reacting amines of general formula $HNR^2R^3$ with 2-(alkoxycarbonylmethyl)-3-aryl-propanoic acids and subsequently hydrolytically cleaving the alkyl group. The 2-(alkoxycarbonylmethyl)-3-aryl-propanoic acids required may be prepared analogously to methods known from the literature (David A. Evans, Leester D. Wu, John J. M. Wiener, Jeffrey S. Johnson, David H. B. Ripin and Jason S. Tedrow, J. Org. Chem. 64, 6411-6417 [1999]; Saul G. Cohen and Aleksander Milovanovic, J. Am. Chem. Soc. 90, 3495-3502 [1968]; Hiroyuki Kawano, Youichi Ishii, Takao Ikariya, Masahiko Saburi, Sadao Yoshikawa, Yasuzo Uchida and Hidenori Kumobayashi, Tetrahedron Letters 28, 1905-1908 [1987]). Carboxylic acids of general formula (VIII) may be prepared from generally available starting materials in accordance with the processes described in WO 98/11128.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain a carboxylic acid function, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds of general formula I and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 µM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds mentioned hereinbefore show IC$_{50}$ values ≦ 10000 nM in the test described.

B. CGRP Antagonism in SK-N-MC Cells

SK-N-MC cells (1 million cells) are washed twice with 250 µl incubation buffer (Hanks'HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations (10$^{-11}$ to 10$^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds of general formula I exhibit CGRP-antagonistic properties in the in vitro test model described, in a dosage range between 10$^{-12}$ and 10$^{-5}$ M.

In view of their pharmacological properties the compounds of general formula I and the salts thereof with physiologically acceptable acids are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect. The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone substitution, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinine antagonists, anti-convulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, 5-HT$_{1B/1D}$ agonists or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, Experimental Section As a rule, IR, $^1$H-NMR and/or mass spectra have been obtained for the compounds prepared. Unless otherwise stated, R$_f$ values were obtained using ready-made silica gel TLC plates 60 F254 (E. Merck, Darmstadt, Item no. 1.05714) without chamber saturation. The R$_f$ values obtained under the name Alox were obtained using ready-made aluminium oxide 60 F254 TLC plates (E. Merck, Darmstadt, item no. 1.05713) without chamber saturation. The ratios given for the eluants relate to units by volume of the solvent in question. The units by volume given for NH$_3$ are based on a concentrated solution of NH$_3$ in water.

Unless otherwise stated the acid, base and saline solutions used for working up the reaction solutions are aqueous solutions having the concentrations specified. For chromatographic purification, silica gel made by Millipore (MATREX™, 35-70 μm) was used. For chromatographic purification Alox (E. Merck, Darmstadt, standardised aluminium oxide 90, 63-200 μm, Article no. 1.01097.9050) is used.

The HPLC data provided are measured using the parameters specified below:

Analytical column: Zorbax column (Agilent Technologies), SB (Stable Bond)-C18; 3.5 μm; 4.6×75 mm; column temperature: 30° C.; flow: 0.8 mL/min; injection volume: 5 μL; detection at 254 nm water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenyloin, valproate, amityptiline, lidocaine or diltiazem and other 5-HT$_{1B/1D}$-agonists such as, for example, almotriptan, avitriptan, eletriptan, frovatriptan, naratriptan, rizatriptan, sumatriptan and zolmitriptan.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Method A:

| time (min) | percent by volume of water (with 0.1% formic acid) | percent by volume of acetonitrile (with 0.1% formic acid) |
| --- | --- | --- |
| 0 | 90 | 10 |
| 9 | 10 | 90 |
| 10 | 10 | 90 |
| 11 | 90 | 10 |

In preparative HPLC purifications as a rule the same gradients are used as were used to raise the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:

| | |
| --- | --- |
| abs. | absolute |
| Boc | tert.-butoxycarbonyl |
| CDI | N,N'-carbonyldiimidazole |
| CDT | 1,1'-carbonyldi-(1,2,4-triazole) |
| Cyc | cyclohexane |
| DCM | dichloromethane |
| DMF | N,N-dimethylformamide |
| EtOAc | ethyl acetate |
| EtOH | ethanol |
| h | hour |
| semiconc. | semiconcentrated |
| HCl | hydrochloric acid |
| HOAc | acetic acid |
| HOBt | 1-hydroxybenzotriazole-hydrate |
| i. vac. | in vacuo (in a vacuum) |
| KOH | potassium hydroxide |
| conc. | concentrated |
| MeOH | methanol |
| NaCl | sodium chloride |
| NaOH | sodium hydroxide |
| org. | organic |
| PE | petroleum ether |
| RT | room temperature |
| TBTU | 2-(1H-benzotriazol-1-yl)-1,1,3,3-tetramethyluronium-tetrafluoroborate |
| tert. | tertiary |
| TFA | trifluoroacetic acid |
| THF | tetrahydrofuran |

EXAMPLE 1

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

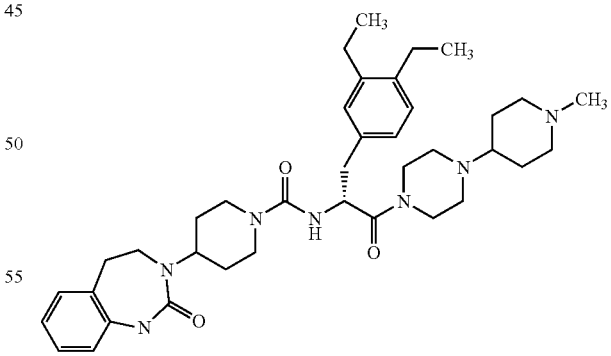

1a) 3,4-diethylbenzoic acid 152.8 mL (3.0 mol) of bromine was slowly added dropwise to an ice-cooled solution of 394.8 g (9.87 mol) of NaOH in 3.3 L of water. Then at 10° C. a solution of 174 g (0.99 mol) of 1-(3,4-diethyl-phenyl)-ethanone in 400 mL of 1,4-dioxane was added dropwise to this solution. It was stirred for 2 h at RT, the bromoform obtained was separated off, the aqueous phase washed twice with 400 mL of diethyl ether and adjusted to pH 3 with semiconcentrated HCl. The precipitated product was suction filtered, washed with water and recrystallised from PE. The desired product was obtained in the form of a white solid.

| Yield: | 100.0 g (57% of theory) |
|---|---|
| ESI-MS: | (M − H)⁻ 177 |

1b) 3,4-(diethyl-phenyl)-methanol

A solution of 90 g (0.51 mol) of 3,4-diethylbenzoic acid in 300 mL of THF was added dropwise at RT to the suspension of 20.8 g (0.55 mol) of lithium aluminium hydride in 1500 mL THF. The mixture was stirred for 30 min at RT and refluxed for 1 h. While cooling with ice 15 mL of 20% NaOH was added dropwise and then sufficient water until a granular precipitate was formed. The precipitate was suction filtered, washed twice with THF and the filtrate was evaporated down under reduced pressure. The desired product was obtained in the form of a yellow oil.

| Yield: | 75.0 g (90% of theory) |
|---|---|
| ESI-MS: | (M − H)⁻ 163 |

1c) 4-bromomethyl-1,2-diethyl-benzene 16.1 mL (0.17 mol) of phosphorus tribromide was added dropwise to the solution of 81.0 g (0.49 mol) of 3,4-(diethyl-phenyl)-methanol in 500 mL of diethyl ether while cooling with ice. The reaction mixture was stirred for 30 min at 30° C., carefully poured onto ice, neutralised by the addition of $NaHCO_3$ solution and exhaustively extracted with diethyl ether. The combined diethyl ether extracts were dried and evaporated down under reduced pressure. 104.0 g (92%) of an oil were obtained, which was further reacted without any further purification.

| EI-MS: | M⁺ 226/228 (Br) |
|---|---|

1d) (R)-2-amino-3-(3,4-diethyl-phenyl)-N-((1S,2S)-2-hydroxy-1-methyl-2-phenyl-ethyl)-N-methyl-propionamide In a three-necked flask 250 mL of a 1 molar solution of lithium-bis-(trimethylsilyl)-amide (250 mmol) and 15.4 g (64.1 mmol) of (1S,2S)-pseudoephedrine-glycinamide hydrate were added to 500 mL of THF under a nitrogen atmosphere and while cooling with ice. The mixture was stirred for 1.5 h at 0° C., slowly combined with 15.4 g (67.1 mmol) of 4-bromomethyl-1,2-diethyl-benzene, dissolved in 10 mL of THF, and stirred for 2 h at 0° C. While cooling with ice 10 mL of water and 6 mL semiconcentrated HCl were added dropwise, stirred for a further 20 min and made alkaline with concentrated ammonia solution. The reaction mixture was exhaustively extracted with EtOAc, the combined organic phases were dried and evaporated down under reduced pressure. The residue remaining was purified through silica gel. The desired product was obtained in the form of a solid.

| Yield: | 7.4 g (31% of theory) |
|---|---|
| ESI-MS: | (M + H)⁺ 369 |

1e) (R)-2-amino-3-(3,4-diethyl-phenyl)-propionic acid

A mixture of 7.8 g (21.2 mmol) of (R)-2-amino-3-(3,4-diethyl-phenyl)-N-((1S,2S)-2-hydroxy-1-methyl-2-phenyl-ethyl)-N-methyl-propionamide, 50 mL of water and 50 mL of 1,4-dioxane was refluxed for 7 days. The reaction mixture was evaporated down under reduced pressure, the residue remaining was stirred with EtOH and suction filtered. The desired product was obtained in the form of a white solid.

| Yield: | 4.0 g (85% of theory) |
|---|---|
| ESI-MS: | (M + H)⁺ 222; (M − H)⁻ 220 |
| $R_f$: | 0.25 (silica gel, DCM/MeOH/cyc/NH₃ 70:15:15:2) |

1f) (R)-2-tert-butoxycarbonylamino-3-(3,4-diethyl-phenyl)-propionic acid

A mixture of 4.0 g (18.1 mmol) of (R)-2-amino-3-(3,4-diethyl-phenyl)-propionic acid, 4.2 g (39.2 mmol) of $Na_2CO_3$, 100 mL of water and 25 mL of THF was combined with 5.0 g (22.2 mmol) of di-tert.-butyldicarbonate, dissolved in 25 mL of THF, while cooling with ice. It was stirred for 30 min while cooling with ice and for 3 h at RT. The organic phase was separated off and the aqueous phase was repeatedly extracted with diethyl ether. The combined organic phases were extracted with 15% $K_2CO_3$ solution, the combined aqueous phases were acidified with 1 M $KHSO_4$ solution and exhaustively extracted with EtOAc. The combined organic extracts were dried over $MgSO_4$ and evaporated down under reduced pressure. The desired product was obtained in the form of a colourless oil.

| Yield: | 4.9 g (84% of theory) |
|---|---|
| ESI-MS: | (M + H)⁺ 320 |
| $R_f$: | 0.33 (silica gel, DCM/MeOH/cyc/NH₃ 70:15:15:2) |

1g) tert. butyl {(R)-1-(3,4-diethyl-benzyl)-2-[4-(1-methyl-piperidin-4-yl)-piperazin-1-yl]-2-oxo-ethyl}-carbaminate A mixture of 4.9 g (15.25 mmol) of (R)-2-tert.-butoxycarbonylamino-3-(3,4-diethyl-phenyl)-propionic acid, 5.3 g (16.5 mmol) of TBTU, 2.1 g (15.23 mmol) of HOBt, 17 mL N-ethyldiisopropylamine, 15 mL of DMF and 150 mL of THF was stirred for 30 min at RT, combined with 6.2 g (19.9 mmol) of 1-(1-methyl-piperidin-4-yl)-piperazine and stirred for a further 4 h. The reaction mixture was evaporated down under reduced pressure, the residue remaining was combined with 15% $K_2CO_3$ solution and extracted three times with DCM. The combined organic extracts were dried over $MgSO_4$, evaporated down and the residue remaining was purified through silica gel. The desired product was obtained in the form of a pale yellow oil.

| Yield: | 5.0 g (67% of theory) |
|---|---|
| EI-MS: | M⁺ 486 |
| $R_f$: | 0.56 (silica gel, DCM/MeOH/cyc/NH$_3$ 70:15:15:2) |

1 h) (R)-2-amino-3-(3,4-diethyl-phenyl)-1-[4-(1-methyl-piperidin-4-yl)-piperazin-1-yl]-propan-1-one A mixture of 5.0 g (10.27 mmol) of tert. butyl {(R)-1-(3,4-diethyl-benzyl)-2-[4-(1-methyl-piperidin-4-yl)-piperazin-1-yl]-2-oxo-ethyl}-carbaminate, 100 mL of DCM and 20 mL of TFA was stirred for 1.5 h at RT. The reaction mixture was then evaporated down under reduced pressure, the residue combined with 15% K$_2$CO$_3$ solution and extracted exhaustively with DCM. The combined organic extracts were dried and evaporated down under reduced pressure. The desired product was obtained in the form of a bright yellow oil.

| Yield: | 3.6 g (91% of theory) |
|---|---|
| ESI-MS: | (M + H)⁺ 387 |
| $R_f$: | 0.22 (silica gel, DCM/MeOH/cyc/NH$_3$ 70:15:15:2) |

1i) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide 1.70 g (4.39 mmol) of (R)-2-amino-3-(3,4-diethyl-phenyl)-1-[4-(1-methyl-piperidin-4-yl)-piperazin-1-yl]-propan-1-one, dissolved in 25 mL of THF, was slowly added dropwise to the ice-cooled mixture of 75 mL of THF and 0.80 g (4.63 mmol) of CDT. Then the mixture was stirred for 30 min in the ice bath and for a further 45 min at RT before the solution of 1.1 g (4.48 mmol) of 3-piperidin-4-yl-1,3,4,5-tetrahydro-1,3-benzodiazepin-2-one in 20 mL of DMF was added and refluxed for 4 h. The reaction mixture was evaporated down under reduced pressure, the residue was combined with 50 mL of 15% K$_2$CO$_3$ solution and exhaustively extracted with DCM. The combined organic extracts were washed with water, dried over MgSO$_4$, evaporated down and purified through silica gel. The crystallisation was from acetone. The desired product was obtained in the form of a crystalline solid.

| Yield: | 1.2 g (42% of theory) |
|---|---|
| ESI-MS: | (M + H)⁺ 658 |
| $R_f$: | 0.28 (silica gel, DCM/MeOH/cyc/NH$_3$ 70:15:15:2) |

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleinate 0.5 g (0.76 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 0.176 g (1.52 mmol) maleic acid were suspended in 20 mL acetone and after the addition of 5 mL methanol the mixture was refluxed for. The precipitate formed after cooling to ambient temperature was filtered off, washed with acetone and dried.

| Yield: | 0.5 g (74% of theory) |
|---|---|
| melting point: | 165° C. (decomp.) |

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate 1.0 g (1.52 mmol) of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 0.24 g (1.52 mmol) benzenesulphonic acid were refluxed in 20 mL isopropanol. Then the solution was continuously cooled over three days from 50° C. to 25° C., during which time a crystalline precipitate was formed. The solid formed was filtered off, washed with isopropanol and dried.

| Yield: | 0.58 g (47% of theory) |
|---|---|
| melting point: | 192° C. (decomp.) |

EXAMPLE 2

4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-piperazin-1-yl)-piperidin-1-yl]-2-oxo-ethyl}-amide

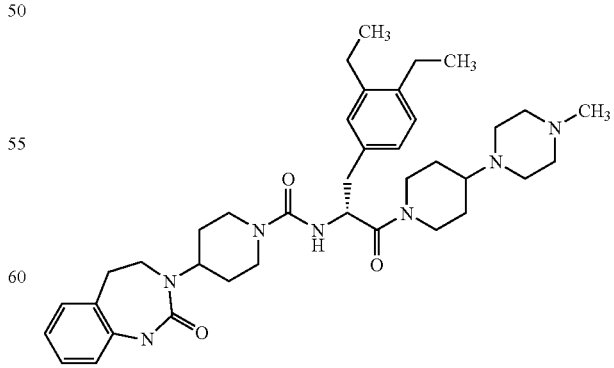

2a) tert. butyl {(R)-1-(3,4-diethyl-benzyl)-2-[4-(4-methyl-piperazin-1-yl)-piperidin-1-yl]-2-oxo-ethyl}-carbaminate 4.2 mL ethyldiisopropylamine were added to a mixture of 3.7 g (11.52 mmol) of (R)-2-tert.-butoxycarbonylamino-3-(3,4-diethyl-phenyl)-propionic acid, 3.9 g (12 mmol) of TBTU, 1.7 g (12 mmol) of HOBt and 2.2 g (11.6 mmol) of 1-methyl-4-piperidin-4-yl-piperazine in 100 mL of THF and the reaction mixture was stirred overnight at RT. The reaction mixture was evaporated down under reduced pressure, the residue remaining was combined with Na$_2$CO$_3$ solution and extracted with EtOAc. The combined organic extracts were dried over Na$_2$SO$_4$ and evaporated down. The desired product was obtained in the form of a pale yellow oil.

| Yield: | 5.5 g (97% of theory) |
|---|---|
| R$_f$= | 0.5 (Alox, DCM/MeOH = 30/1) |

2b) (R)-2-amino-3-(3,4-diethyl-phenyl)-1-[4-(4-methyl-piperazin-1-yl)-piperidin-1-yl]-propan-1-one A mixture of 5.4 g (11.1 mmol) of tert. butyl {(R)-1-(3,4-diethyl-benzyl)-2-[4-(4-methylpiperazin-1-yl)-piperidin-1-yl]-2-oxo-ethyl}-carbaminate, 100 mL of DCM and 20 mL of TFA was stirred for 4 h at RT. The reaction mixture was added dropwise to a Na$_2$CO$_3$ solution, stirred for 10 min, the organic phase was then separated off and dried over Na$_2$SO$_4$. The solvent was removed in vacuo. The desired product was obtained in the form of a bright yellow oil.

| Yield: | 4.2 g (98% of theory) |
|---|---|
| R$_f$= | 0.54 (Alox, DCM/MeOH = 19/1) |

2c) 4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-piperazin-1-yl)-piperidin-1-yl]-2-oxoethyl}-amide 4.1 g (10.61 mmol) of (R)-2-amino-3-(3,4-diethyl-phenyl)-1-[4-(4-methyl-piperazin-1-yl)-piperidin-1-yl]-propan-1-one, dissolved in 50 mL of THF, were slowly added dropwise to the ice-cooled mixture of 150 mL of THF and 1.9 g (11.2 mmol) of CDT. Then the mixture was stirred for 30 min in the ice bath and for a further 45 min at RT before the solution of 2.7 g (11.0 mmol) of 3-piperidin-4-yl-1,3,4,5-tetrahydro-1,3-benzodiazepin-2-one in 20 mL of DMF was added and the mixture was refluxed for 4 h. The reaction mixture was evaporated down under reduced pressure, the residue was combined with Na$_2$CO$_3$ solution and exhaustively extracted with EtOAc. The combined organic extracts were washed with water, dried over Na$_2$SO$_4$, evaporated down and purified over aluminium oxide. The product was obtained as a solid.

| Yield: | 4.2 g (60% of theory) |
|---|---|
| R$_f$= | 0.32 (Alox, DCM/MeOH = 30/1) |

EXAMPLE 3

4-(2-oxo-1,2,4,5-tetrahydro-1,3-benzodiazepin-3-yl)-piperidine-1-carboxylic acid-[1-(3,4-diethyl-benzyl)-2-(1'-methyl-4,4'-bipiperidinyl-1-yl)-2-oxo-ethyl]-amide

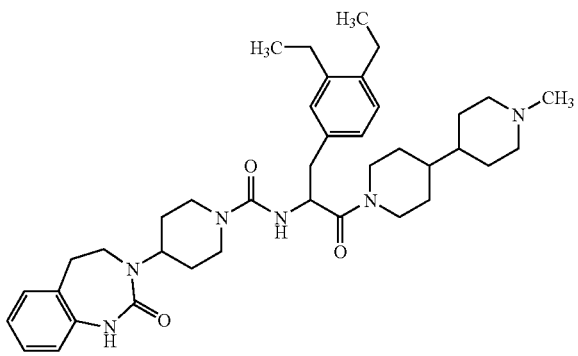

3a) diethyl 2-acetylamino-2-(3,4-diethyl-benzyl)-malonate

Under a nitrogen atmosphere 8.14 g (354 mmol) of sodium were added batchwise to 200 mL of absolute EtOH and stirred until completely dissolved. 76.9 g (354 mmol) of diethyl 2-acetylaminomalonate were added to this solution, whereupon the sodium salt formed was precipitated. After the addition of 150 mL of 1,4-dioxane a solution of 80 g (352 mmol) of 4-bromomethyl-1,2-diethyl-benzene in 500 mL of 1,4-dioxane was added dropwise to this suspension. The reaction solution was kept for 2 h at 50° C. and then stirred overnight at RT. The solvent was distilled off in vacuo, the oily residue was combined with water, whereupon the product was obtained in the form of white crystals. These were suction filtered, washed with water and reacted without any further purification.

R$_f$=0.35 (silica gel, PE/EtOAc=2/1)

3b) (R,S)-2-amino-3-(3,4-diethyl-phenyl)-propionic acid

The crude product described in Example 3a) was dissolved in 250 mL of AcOH and combined with 250 mL of concentrated HCl and 150 mL of water. The reaction solution was refluxed for 3 h, the solvents were concentrated by evaporation in vacuo, the residue was taken up in EtOH, the precipitate formed was suction filtered and washed with diethyl ether.

| Yield: | 45 g (57% of theory) |
|---|---|
| ESI-MS: | (M + H)$^+$ 222 |
| R$_f$= | 0.35 (silica gel, EtOAc/MeOH/AcOH = 90:10:3) |

3c) methyl 2-amino-3-(3,4-diethyl-phenyl)-propionate 41 g (159 mmol) of (R,S)-2-amino-3-(3,4-diethyl-phenyl)-propionic acid were combined with 300 mL of HCl-saturated MeOH and left to stand overnight at RT, during which time the desired hydrochloride precipitated out. It was heated to 50° C., whereupon HCl was given off and the product went back into solution. The solution was evaporated down to ⅓ of its original volume in vacuo, the precipitated product was stirred with diethyl ether, suction filtered and washed twice with diethyl ether. The crude product was reacted without any further purification.

| Yield: | 42 g (97% of theory) |
|---|---|
| ESI-MS: | (M + H)⁺ 236 |
| $R_f =$ | 0.7 (silica gel, MeOH) |

3d) methyl 3-(3,4-diethyl-phenyl)-2-{[4-(2-oxo-1,2,4,5-tetrahydro-1,3-benzodiazepin-3-yl)-piperidine-1-carbonyl]-amino}-propionate 7.4 g (45 mmol) of CDT were added to a solution of 10.5 g (44.6 mmol) of methyl 2-amino-3-(3,4-diethyl-phenyl)-propionate in 250 mL of THF cooled to 0° C. and stirred for a further 30 min at this temperature. Then 10.9 g (44.6 mmol) of 3-piperidin-4-yl-1,3,4,5-tetrahydro-1,3-benzodiazepin-2-one was added and the reaction solution was kept for a further 20 min at this temperature before being refluxed for 30 min. The solvent was removed in vacuo, the residue was taken up in saturated NaHCO₃ solution, exhaustively extracted with diethyl ether/EtOAc (1:1) and dried over MgSO₄. After elimination of the desiccant and solvent the crude product was reacted without any further purification.

| Yield: | quantitative |
|---|---|
| $R_f =$ | 0.6 (silica gel: EtOAc/petroleum ether = 6:4) |

3e) 3-(3,4-diethyl-phenyl)-2-{[4-(2-oxo-1,2,4,5-tetrahydro-1,3-benzodiazepin-3-yl)-piperidine-1-carbonyl]-amino}-propionic acid 26 g of the crude product described in 3d) were dissolved in 200 mL EtOH, combined with 2.3 g (55 mmol) of lithium hydroxide hydrate and stirred overnight at RT. The reaction solution was concentrated by evaporation in vacuo, the residue was taken up with water, extracted with diethyl ether, acidified with citric acid solution and exhaustively extracted with EtOAc. The combined organic phases were dried over MgSO₄ and evaporated down in vacuo.

| Yield: | 19 g (75% of theory) |
|---|---|
| $R_f$: | 0.1 (silica gel, EtOAc/petroleum ether 6:4) |

3f) 4-(2-oxo-1,2,4,5-tetrahydro-1,3-benzodiazepin-3-yl)-piperidine-1-carboxylic acid-[1-(3,4-diethyl-benzyl)-2-(1'-methyl-4,4'-bipiperidinyl-1-yl)-2-oxo-ethyl]-amide 0.3 mL of triethylamine, 323 mg (1.01 mmol) of TBTU, 155 mg (1.01 mmol) of HOBt and 184 mg (1.01 mmol) of methyl-[4,4']bipiperidinyl were added to a solution of 500 mg (1.02 mmol) of 3-(3,4-diethyl-phenyl)-2-{[4-(2-oxo-1,2,4,5-tetrahydro-1,3-benzodiazepin-3-yl)-piperidine-1-carbonyl]-amino}-propionic acid in 50 mL of THF and stirred for 4 h at RT and 2 h at 40° C. The reaction mixture was evaporated down, the residue was stirred with 40 mL of saturated NaHCO₃ solution, the precipitated product was suction filtered, washed twice with water and triturated with EtOH. The white substance precipitated was suction filtered and washed twice with diethyl ether.

| Yield: | 420 mg (63% of theory) |
|---|---|
| ESI-MS: | (M + H)⁺ 657 |
| $R_f =$ | 0.45 (silica gel, MeOH) |

EXAMPLE 4

4-(2-oxo-1,2,4,5-tetrahydro-1,3-benzodiazepin-3-yl)-piperidine-1-carboxylic acid-[1-(3,4-diethyl-benzyl)-2-oxo-2-(3,4,5,6-tetrahydro-2H-4,4'-bipyridinyl-1-yl)-ethyl]-amide

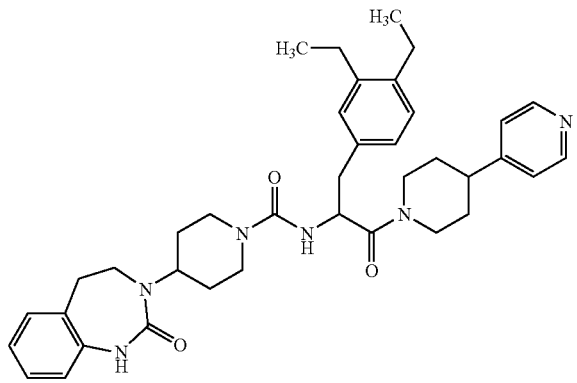

Prepared analogously to Example 3f) from 3-(3,4-diethyl-phenyl)-2-{[4-(2-oxo-1,2,4,5-tetrahydro-1,3-benzodiazepin-3-yl)-piperidine-1-carbonyl]-amino}-propionic acid and 1,2,3,4,5,6-hexahydro-[4,4']bipyridinyl.

| Yield: | 270 mg (42% of theory) |
|---|---|
| ESI-MS: | (M + H)⁺ 637 |
| $R_f =$ | 0.55 (silica gel, MeOH) |

EXAMPLE 5

4-(2-oxo-1,2,4,5-tetrahydro-1,3-benzodiazepin-3-yl)-piperidine-1-carboxylic acid-[2-1,4'-bipiperidinyl-1'-yl-1-(3,4-diethyl-benzyl)-2-oxo-ethyl]-amide

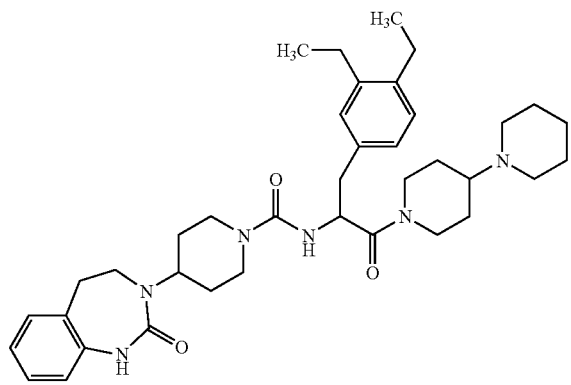

Prepared analogously to Example 3f) from 3-(3,4-diethyl-phenyl)-2-{[4-(2-oxo-1,2,4,5-tetrahydro-1,3-benzodiazepin-3-yl)-piperidine-1-carbonyl]-amino}-propionic acid and [1,4']-bipiperidinyl.

| Yield: | 37% of theory |
| ESI-MS: | (M + H)⁺ 643 |
| $R_f$: | 0.55 (silica gel, MeOH) |

EXAMPLE 6

4-(2-oxo-1,2,4,5-tetrahydro-1,3-benzodiazepin-3-yl)-piperidine-1-carboxylic acid-[1-(3,4-diethyl-benzyl)-2-oxo-2-(4-pyridin-4-yl-piperazin-1-yl)-ethyl]-amide

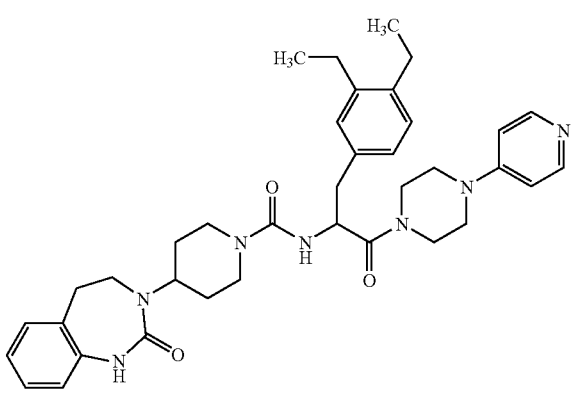

Prepared analogously to Example 3f) from 3-(3,4-diethyl-phenyl)-2-{[4-(2-oxo-1,2,4,5-tetrahydro-1,3-benzodiazepin-3-yl)-piperidine-1-carbonyl]-amino}-propionic acid and 1-pyridin-4-yl-piperazine.

| Yield: | 57% of theory |
| ESI-MS: | (M + H)⁺ 638 |
| $R_f$: | 0.45 (silica gel, MeOH) |

EXAMPLE 7

4-(2-oxo-1,4-dihydro-2H-quinazolin-3-yl)-piperidine-1-carboxylic acid-{1-(3,4-diethyl-benzyl)-2-[4-(4-methyl-piperazin-1-yl)-piperidin-1-yl]-2-oxo-ethyl}-amide

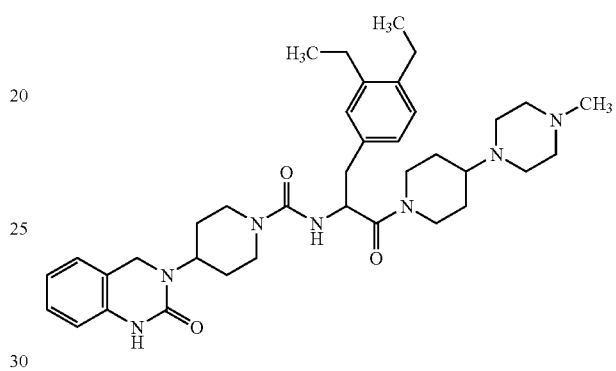

7a) methyl 3-(3,4-diethyl-phenyl)-2-{[4-(2-oxo-1,4-dihydro-2H-quinazolin-3-yl)-piperidine-1-carbonyl]-amino}-propionate 3.3 mL ethyldiisopropyl-amine and 2.06 g (12.6 mmol) of CDT were added to an ice-cooled solution of 2.95 g (12.54 mmol) of methyl 2-amino-3-(3,4-diethyl-phenyl)-propionate in 200 mL of THF and stirred for a further 90 min at 0-10° C. Then 20 mL of DMF were added, the mixture was stirred for a further 30 min, 2.91 g (12.6 mmol) of 3-piperidin-4-yl-3,4-dihydro-1H-quinazolin-2-one were added and the suspension was refluxed for 10 h. The reaction mixture was evaporated down in vacuo, combined with semisaturated NaHCO₃ solution, exhaustively extracted with EtOAc and dried over MgSO₄. After elimination of the desiccant and solvent the crude product was reacted without any further purification.

| Yield: | 6.0 g (97% of theory) |
| $R_f$: | 0.8 (silica gel, EtOAc/MeOH/AcOH 30:10:1) |

7b) 3-(3,4-diethyl-phenyl)-2-{[4-(2-oxo-1,4-dihydro-2H-quinazolin-3-yl)-piperidine-1-carbonyl]-amino}-propionic acid The crude product (6 g, 11.84 mmol) described in 7a) was placed in 120 mL MeOH, combined with 40 mL 1M NaOH (40 mmol) and refluxed for 5 h. The reaction mixture was concentrated by evaporation in vacuo, the residue was combined with 150 mL of water and 40 mL 1M HCl, exhaustively extracted with DCM and the combined organic phases were dried over MgSO₄. After elimination of the desiccant and solvent the residue was triturated with diisopropylether and suction filtered.

| Yield: | 3.5 g (62% of theory) |
| --- | --- |
| ESI-MS: | (M + H)⁺ 479 |
| $R_f$: | 0.5 (silica gel, PE/EtOAc/AcOH 70:30:3) |

7c) 4-(2-oxo-1,4-dihydro-2H-quinazolin-3-yl)-piperidine-1-carboxylic acid-{1-(3,4-diethyl-benzyl)-2-[4-(4-methyl-piperazin-1-yl)-piperidin-1-yl]-2-oxo-ethyl}-amide 336 mg (1.05 mmol) of TBTU, 161 mg (1.05 mmol) of HOBt, 0.75 mL of triethylamine and 192 mg (1.05 mmol) of 1-methyl-4-piperidin-4-yl-piperazine were added to a solution of 500 mg (1.05 mmol) of 3-(3,4-diethyl-phenyl)-2-{[4-(2-oxo-1,4-dihydro-2H-quinazolin-3-yl)-piperidine-1-carbonyl]-amino}-propionic acid in 100 mL of THF, and stirred for 4 h at RT and 2 h at 40° C. The solvent was removed in vacuo, the residue taken up in 40 mL of saturated NaHCO₃ solution, exhaustively extracted with EtOAc and dried over MgSO₄. After elimination of the desiccant and solvent the crude product was purified by chromatography (silica gel, MeOH/NH₃ 100:3).

| Yield: | 350 mg (52% of theory) |
| --- | --- |
| ESI-MS: | (M + H)⁺ 644 |
| $R_f$: | 0.3 (silica gel, MeOH/NH₃ 100:3) |

EXAMPLE 8

4-(2-oxo-1,4-dihydro-2H-quinazolin-3-yl)-piperidine-1-carboxylic acid-{1-(3,4-diethyl-benzyl)-2-[4-(1-methyl-piperidin-4-yl)-piperazin-1-yl]-2-oxo-ethyl}-amide

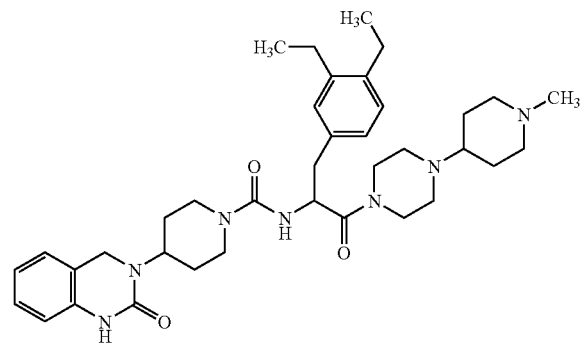

336 mg (1.05 mmol) of TBTU, 161 mg (1.05 mmol) of HOBt, 1.02 mL triethylamine and 326 mg (1.05 mmol) of 1-(1-methyl-piperidin-4-yl)-piperazine (used as the tris-hydrochloride) were added to a solution of 500 mg (1.05 mmol) of 3-(3,4-diethyl-phenyl)-2-{[4-(2-oxo-1,4-dihydro-2H-quinazolin-3-yl)-piperidine-1-carbonyl]-amino}-propionic acid in 100 mL of THF, stirred for 4 h at RT and 2 h at 40° C. The solvent was removed in vacuo, the residue was stirred with 40 mL of saturated NaHCO₃ solution, the precipitated product was suction filtered, taken up in MeOH and purified by chromatography over silica gel (MeOH). The product fractions were evaporated down, the residue triturated with diethyl ether, suction filtered, washed twice with diethyl ether and dried.

| Yield: | 120 mg (18% of theory) |
| --- | --- |
| ESI-MS: | (M + H)⁺ 644 |
| $R_f$: | 0.35 (silica gel, MeOH/NH₃ 100:3) |

EXAMPLE 9

4-(2-oxo-1,2,4,5-tetrahydro-1,3-benzodiazepin-3-yl)-piperidine-1-carboxylic acid-[(R)-1-(3,4-diethyl-benzyl)-2-(4-dimethylamino-piperidin-1-yl)-2-oxo-ethyl]-amide

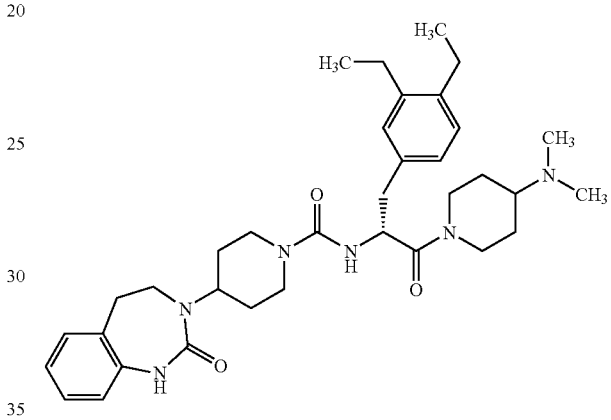

9a) diethyl 2-acetylamino-2-(3,4-diethyl-benzyl)-malonate 6.7 g (0.29 mol) sodium were added to 300 mL EtOH under an argon atmosphere. 60.0 g (0.27 mol) ethyl acetamidomalonate were added to the resulting solution, stirred for 1.5 h and then 62.0 g (0.27 mol) 4-bromomethyl-1,2-diethyl-benzene were slowly added dropwise. The reaction mixture was stirred overnight at RT, poured onto 1 L of water and vigorously stirred for 1 h at RT. The precipitate formed was suction filtered, suspended twice with a little water, suction filtered and dried.

| Yield: | 93.5 g (95% of theory) |
| --- | --- |
| ESI-MS: | (M + H)⁺ 364 |
| $R_f$: | 0.72 (silica gel, DCM/MeOH 19:1) |

9b) monoethyl 2-acetylamino-2-(3,4-diethyl-benzyl)-malonate

A solution of 50 g (138 mmol) diethyl 2-acetylamino-2-(3,4-diethyl-benzyl)-malonate in 300 mL EtOH was combined with 5.8 g (138.2 mmol) lithium hydroxide hydrate dissolved in 46 mL water and the reaction mixture was stirred for 19 h at RT. The solvent was evaporated down under reduced pressure, the residue was combined with 100 mL water and washed twice with tert-butylmethylether. The aqueous phase was then acidified by the addition of 2 M HCl while being cooled, the precipitate was suction filtered, washed with water and dried.

| | |
|---|---|
| Yield: | 37.2 g (81% of theory) |
| ESI-MS: | (M + H)+ 336 |
| R_f: | 0.10 (silica gel, DCM/MeOH/cyc/NH_3 70:15:15:2) |

9c) ethyl 2-acetylamino-3-(3,4-diethyl-phenyl)-propionate

A mixture of 35.2 g (104.9 mmol) monoethyl 2-acetylamino-2-(3,4-diethyl-benzyl)-malonate and 400 mL toluene was refluxed for 15 h. The reaction mixture was evaporated down under reduced pressure, the residue was taken up in DCM and the organic phase washed with saturated NaHCO_3 solution. The organic phase was then dried and evaporated down under reduced pressure.

| | |
|---|---|
| Yield: | 29.7 g (97% of theory) |
| ESI-MS: | (M + H)+ 290 |
| R_f: | 0.70 (silica gel, DCM/MeOH/cyc/NH_3 70:15:15:2) |

9d) ethyl (R)-2-acetylamino-3-(3,4-diethyl-phenyl)-propionate 27 mL Alcalase 2.4 L FG (Novozymes A/S; DK 2880 Bagsvaerd) were added to a solution of 38.0 g (213.5 mmol) disodium hydrogen phosphate dihydrate in 500 mL water at a temperature of 37° C. and the pH was adjusted to 7.5 by the addition of sodium dihydrogen phosphate dihydrate. Then at 37° C. with stirring 29.7 g (101.9 mmol) ethyl 2-acetylamino-3-(3,4-diethyl-phenyl)-propionate dissolved in 150 mL acetone was added dropwise. The pH value of the reaction mixture was kept constantly kept in the range from pH 7.4 to pH 7.6 by the addition of 1 M NaOH. After the addition had ended the mixture was stirred for 4 h at 37° C. The reaction mixture was extracted three times with tert-butylmethylether, the combined organic extracts were washed with 15% K_2CO_3 solution, dried and evaporated down under reduced pressure.

| | |
|---|---|
| Yield: | 13.8 g (47% of theory) |
| ESI-MS: | (M + H)+ 292 |
| R_f: | 0.77 (silica gel, EtOAc) |
| ee value: | >99% [HPLC: Chiralpak AD, 10 μm, 4.6 × 250 mm; eluant: EtOH/hexane 15:85 + 0.1% diethylamine] |

9e) (R)-2-amino-3-(3,4-diethyl-phenyl)-propionic acid

A mixture of 13.8 g (47.4 mmol) ethyl (R)-2-acetylamino-3-(3,4-diethyl-phenyl)-propionate and 160 mL 6 M HCl was refluxed in the oil bath for 3 h. The reaction mixture was cooled in the ice bath and the precipitate formed was suction filtered.

| | |
|---|---|
| Yield: | 10.6 g (87% of theory) |
| ESI-MS: | (M + H)+ 222 |

9f) methyl (R)-2-amino-3-(3,4-diethyl-phenyl)-propionate 44 mL (607 mmol) thionyl chloride were added dropwise to 600 mL methanol within 1.5 h while cooling with ice. Then while cooling with ice 40.2 g (156 mmol) (R)-2-amino-3-(3,4-diethyl-phenyl)-propionic acid was added, and the mixture was stirred overnight at RT. The reaction mixture was evaporated down under reduced pressure, stirred twice with tert-butylmethylether, suction filtered and dried.

| | |
|---|---|
| Yield: | 41.7 g (98% of theory) |

9g) methyl (R)-3-(3,4-diethyl-phenyl)-2-{[4-(2-oxo-1,2,4,5-tetrahydro-1,3-benzodiazepin-3-yl)-piperidine-1-carbonyl]-amino}-propionate The mixture of 41.7 g (0.153 mol) methyl (R)-2-amino-3-(3,4-diethyl-phenyl)-propionate, 800 mL THF and 28 mL (0.161 mol) ethyldiisopropylamine was combined with 25.4 g (0.157 mol) CDT and then 38.0 g (0.155 mol) 3-piperidin-4-yl-1,3,4,5-tetrahydro-1,3-benzodiazepin-2-one while cooling with an ice bath and refluxed for 3 h with stirring. The reaction mixture was then extracted with 300 mL 10% citric acid solution, three times with 100 mL aliquots of water and 200 mL saturated NaCl solution, dried and evaporated down under reduced pressure.

| | |
|---|---|
| Yield: | 74.4 g (96% of theory) |

9h) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid 74.4 g (0.147 mol) methyl (R)-3-(3,4-diethyl-phenyl)-2-{[4-(2-oxo-1,2,4,5-tetrahydro-1,3-benzodiazepin-3-yl)-piperidine-1-carbonyl]-amino}-propionate dissolved in 600 mL THF was combined with 5.4 g (0.221 mol) lithium hydroxide hydrate in 300 mL water while cooling with an ice bath and stirred overnight at RT. The reaction mixture was evaporated down under reduced pressure, 300 mL water was added and the mixture was extracted three times with 200 mL EtOAc. The aqueous phase was freed from the organic solvent under reduced pressure and combined with 500 mL 2 M HCl with stirring and cooling with the ice bath. The precipitate formed was suction filtered, washed with water and dried.

| | |
|---|---|
| Yield: | 67.8 g (94% of theory) |

9i) 4-(2-oxo-1,2,4,5-tetrahydro-1,3-benzodiazepin-3-yl)-piperidine-1-carboxylic acid-[(R)-1-(3,4-diethyl-benzyl)-2-(4-dimethylamino-piperidin-1-yl)-2-oxo-ethyl]-amide A mixture of 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid, 280 mg (0.87 mmol) TBTU, 0.17 mL (0.97 mmol) ethyldiisopropylamine and 45 mL THF was stirred for 1 h at RT, then combined with 130 mg (1.01 mmol) dimethyl-piperidin-4-yl-amine and 5 mL DMF and stirred overnight. The reaction mixture was diluted by the addition of 30 mL EtOAc, extracted with 30 mL of a 15% $K_2CO_3$ solution and the organic phase was dried. The product fractions were evaporated down under reduced pressure, the residue was triturated with diisopropylether, suction filtered and dried.

| Yield: | 490 mg (41% of theory) |
|---|---|
| ESI-MS: | $(M + H)^+$ 603 |
| $R_f$: | 0.61 (silica gel, DCM/MeOH/cyc/$NH_3$ 70:15:15:2) |

EXAMPLE 10

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-perhydro-azepin-1-yl-piperidin-1-yl)-ethyl]-amide

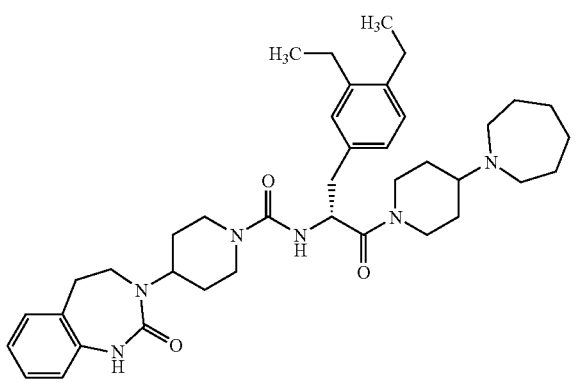

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 180 mg (0.99 mmol) 1-piperidin-4-yl-azepan.

| Yield: | 200 mg (38% of theory) |
|---|---|
| ESI-MS: | $(M + H)^+$ 657 |
| $R_f$: | 0.66 (silica gel, DCM/MeOH/cyc/$NH_3$ 70:15:15:2) |

EXAMPLE 11

4-(2-oxo-1,2,4,5-tetrahydro-1,3-benzodiazepin-3-yl)-piperidine-1-carboxylic acid-{(R)-1-(3,4-diethyl-benzyl)-2-[4-(4-methyl-perhydro-1,4-diazepin-1-yl)-piperidin-1-yl]-2-oxo-ethyl}-amide

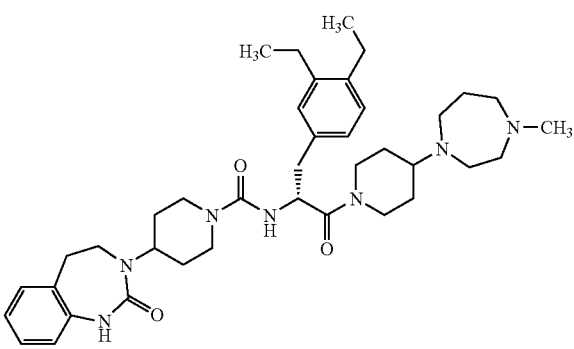

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 200 mg (1.01 mmol) 1-methyl-4-piperidin-4-yl-[1,4]diazepan.

| Yield: | 12 mg (2% of theory) |
|---|---|
| ESI-MS: | $(M + H)^+$ 672 |
| $R_f$: | 0.54 (silica gel, DCM/MeOH/cyc/$NH_3$ 70:15:15:2) |

EXAMPLE 12

4-(2-oxo-1,2,4,5-tetrahydro-1,3-benzodiazepin-3-yl)-piperidine-1-carboxylic acid-[(R)-1-(3,4-diethyl-benzyl)-2-(1'-methyl-4,4'-bipiperidinyl-1-yl)-2-oxo-ethyl]-amide

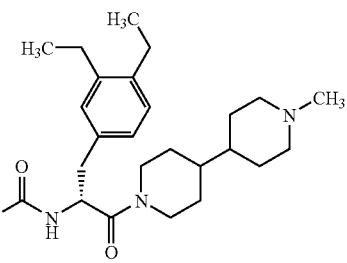

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 260 mg (1.02 mmol) 1-methyl-[4,4']bipiperidinyl.

| | |
|---|---|
| Yield: | 200 mg (38% of theory) |
| ESI-MS: | (M + H)⁺ 657 |
| R_f: | 0.60 (silica gel, DCM/MeOH/cyc/NH₃ 70:15:15:2) |

EXAMPLE 13

4-(2-oxo-1,2,4,5-tetrahydro-1,3-benzodiazepin-3-yl)-piperidine-1-carboxylic acid-{(R)-1-(3,4-diethyl-benzyl)-2-[4-(8-methyl-8-aza-bicyclo[3.2.1]oct-3-yl)-piperazin-1-yl]-2-oxo-ethyl}-amide

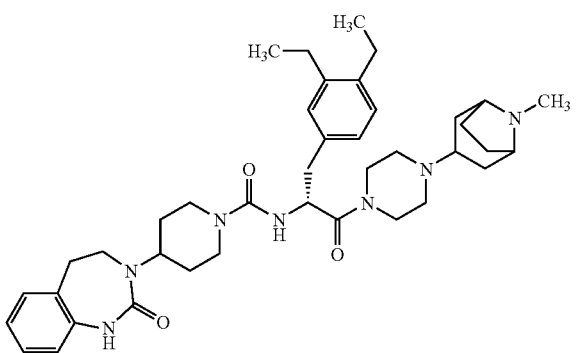

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 320 mg (1.00 mmol) 8-methyl-3-piperazin-1-yl-8-aza-bicyclo[3.2.1]octane trihydrochloride.

| | |
|---|---|
| Yield: | 160 mg (29% of theory) |
| ESI-MS: | (M + H)⁺ 684 |
| R_f: | 0.60 (silica gel, DCM/MeOH/cyc/NH₃ 70:15:15:2) |

EXAMPLE 14

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperazin-1-yl-piperidin-1-yl)-ethyl]-amide

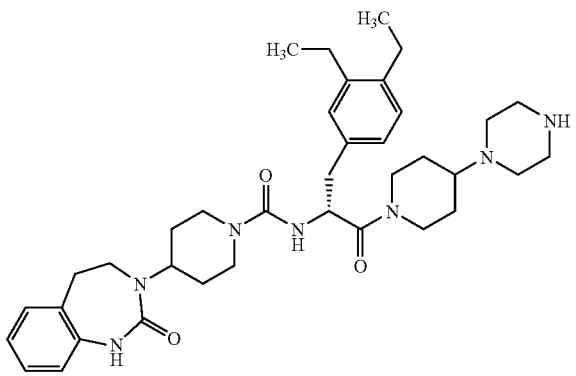

A mixture of 500 mg (1.02 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid, 320 mg (1.09 mmol) TBTU, 0.22 mL (0.97 mmol) ethyldiisopropylamine and 45 mL THF was stirred for 1 h at RT, then combined with 310 mg (1.20 mmol) 1-benzyl-4-piperidin-4-yl-piperazine and 5 mL DMF and stirred overnight. The reaction mixture was diluted by the addition of 30 mL EtOAc, extracted with 30 mL of a 15% K₂CO₃ solution and the organic phase was dried. The organic phase was evaporated down under reduced pressure and the residue purified by chromatography on silica gel. The intermediate product fractions were evaporated down under reduced pressure, the residue remaining (260 mg) was dissolved in 20 mL MeOH and hydrogenated in the autoclave in the presence of 50 mg Pd/C (10%) at 50° C. and 3 bar hydrogen pressure until the calculated volume of hydrogen had been taken up. The catalyst was filtered off, the solvent eliminated under reduced pressure and the residue purified by chromatography on silica gel. The product fractions were evaporated down under reduced pressure, the residue was triturated with diisopropylether, suction filtered and dried.

| | |
|---|---|
| Yield: | 110 mg (17% of theory) |
| ESI-MS: | (M + H)⁺ 644 |
| R_f: | 0.50 (silica gel, DCM/MeOH/cyc/NH₃ 70:15:15:2) |

EXAMPLE 15

4-(2-oxo-1,2,4,5-tetrahydro-1,3-benzodiazepin-3-yl)-piperidine-1-carboxylic acid-[(R)-2-[4-(4-acetyl-piperazin-1-yl)-piperidin-1-yl]-1-(3,4-diethyl-benzyl)-2-oxo-ethyl]-amide

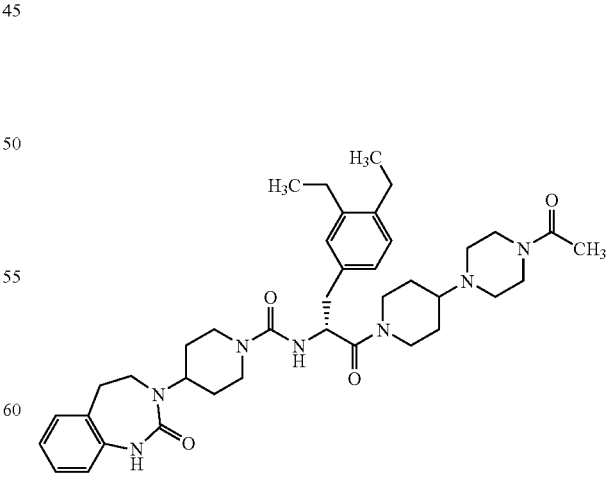

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 230 mg (1.09 mmol) 1-(4-piperidin-4-yl-piperazin-1-yl)-ethanone.

| Yield: | 280 mg (50% of theory) |
|---|---|
| ESI-MS: | (M + H)⁺ 686 |
| R$_f$: | 0.57 (silica gel, DCM/MeOH/cyc/NH₃ 70:15:15:2) |

EXAMPLE 16

4-(2-oxo-1,2,4,5-tetrahydro-1,3-benzodiazepin-3-yl)-piperidine-1-carboxylic acid-[(R)-1-(3,4-diethyl-benzyl)-2-(3-dimethylamino-piperidin-1-yl)-2-oxo-ethyl]-amide

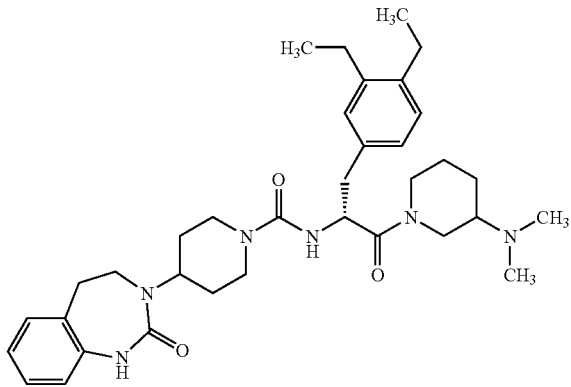

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 130 mg (1.01 mmol) dimethyl-piperidin-3-yl-amine.

| Yield: | 160 mg (33% of theory) |
|---|---|
| ESI-MS: | (M + H)⁺ 603 |
| R$_f$: | 0.59 (silica gel, DCM/MeOH/cyc/NH₃ 70:15:15:2) |

EXAMPLE 17

4-(5-oxo-3-phenyl-4,5-dihydro-1,2,4-triazol-1-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

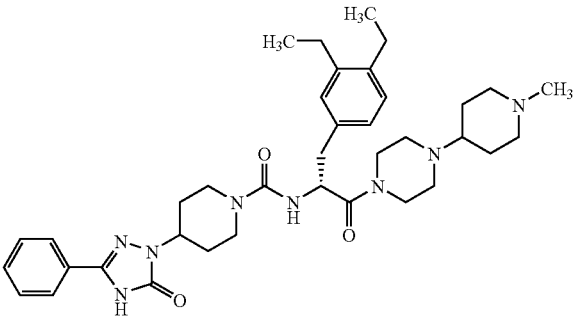

A mixture of 400 mg (1.04 mmol) (R)-2-amino-3-(3,4-diethyl-phenyl)-1-[4-(1-methyl-piperidin-4-yl)-piperazin-1-yl]-propan-1-one, 205 mg (1.25 mmol) CDT, 0.2 mL (1.15 mmol) ethyldiisopropylamine and 50 mL THF was stirred for 1 h while cooling with an ice bath and stirred for 1 h at RT, then combined with 270 mg (1.11 mmol) 5-phenyl-2-piperidin-4-yl-2,4-dihydro-[1,2,4]triazol-3-one and refluxed for 4 h. The reaction mixture was evaporated down under reduced pressure, the residue was combined with saturated NaHCO₃ solution and exhaustively extracted with DCM. The combined organic phases were dried, evaporated down under reduced pressure and the residue was purified by chromatography on silica gel. The product fractions were evaporated down under reduced pressure, the residue was triturated with diisopropylether, suction filtered and dried.

| Yield: | 180 mg (27% of theory) |
|---|---|
| ESI-MS: | (M + H)⁺ 657 |
| R$_f$: | 0.37 (silica gel, DCM/MeOH/cyc/NH₃ 70:15:15:2) |

The following were obtained accordingly:

EXAMPLE 18

4-(2-oxo-1,4-dihydro-2H-quinazolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

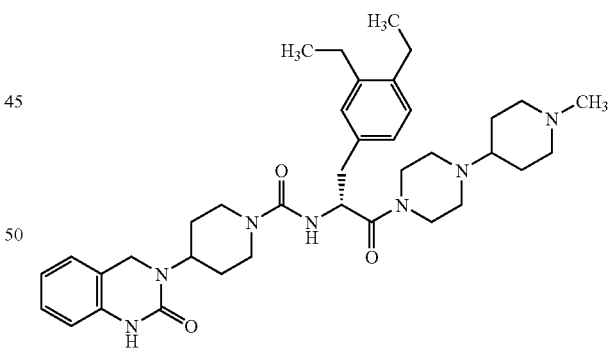

| Yield: | (50% of theory) |
|---|---|
| ESI-MS: | (M + H)⁺ 644 |
| R$_f$: | 0.29 (silica gel, DCM/MeOH/cyc/NH₃ 70:15:15:2) |

EXAMPLE 19

4-(2-oxo-1,2-dihydro-imidazo[4,5-c]quinolin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

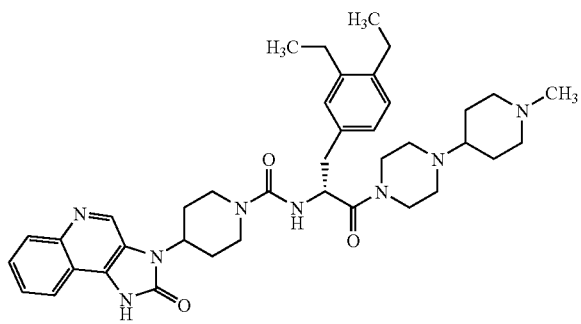

| Yield: | (45% of theory) |
|---|---|
| ESI-MS: | (M + H)+ 681 |
| R$_f$: | 0.20 (silica gel, DCM/MeOH/cyc/NH$_3$ 70:15:15:2) |

EXAMPLE 20

4-(2-oxo-1,2,4,5-tetrahydro-1,3-benzodiazepin-3-yl)-piperidine-1-carboxylic acid-[(R)-2-[4-(4-cyclopropylmethyl-piperazin-1-yl)-piperidin-1-yl]-1-(3,4-diethyl-benzyl)-2-oxo-ethyl]-amide

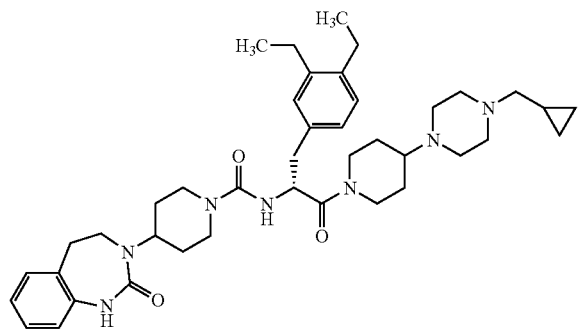

20a) tert-butyl 4-(4-cyclopropylmethyl-piperazin-1-yl)-piperidine-1-carboxylate 1.26 g (20.0 mmol) sodium cyanoborohydride was added batchwise at RT to a stirred mixture of 1.71 g (5.0 mmol) tert-butyl 4-piperazin-1-yl-piperidine-1-carboxylate dihydrochloride, 0.75 mL (10.0 mmol) cyclopropanecarbaldehyde, 30 mL EtOH and 20 mL MeOH and stirred overnight at RT. The reaction mixture was evaporated down under reduced pressure, the residue was taken up in saturated NaHCO$_3$ solution and extracted erschöpfend with EtOAc. The combined organic phases were dried over Na$_2$SO$_4$, suction filtered, evaporated down under reduced pressure and purified by column chromatography over silica gel.

| Yield: | 1.36 g (84% of theory) |
|---|---|
| EI-MS: | (M)+ 323 |

20b) 1-cyclopropylmethyl-4-piperidin-4-yl-piperazine tris-trifluoroacetate 5.0 mL TFA was added dropwise to the solution of 1.36 g (4.20 mmol) tert-butyl 4-(4-cyclopropylmethyl-piperazin-1-yl)-piperidine-1-carboxylate in 30 mL DCM while cooling with an ice bath and the reaction mixture was stirred for 4 h at RT. The solvent was eliminated under reduced pressure, the residue stirred with diethyl ether, suction filtered and dried.

| Yield: | 1.86 g (78% of theory) |
|---|---|
| EI-MS: | (M)+ 223 |

20c) 4-(2-oxo-1,2,4,5-tetrahydro-1,3-benzodiazepin-3-yl)-piperidine-1-carboxylic acid [(R)-2-[4-(4-cyclopropylmethyl-piperazin-1-yl)-piperidin-1-yl]-1-(3,4-diethyl-benzyl)-2-oxo-ethyl]-amide Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 350 mg (0.62 mmol) 1-cyclopropylmethyl-4-piperidin-4-yl-piperazine tris-trifluoroacetate.

| Yield: | 100 mg (18% of theory) |
|---|---|
| ESI-MS: | (M + H)+ 698 |
| R$_f$: | 0.73 (silica gel, DCM/MeOH/cyc/NH$_3$ 70:15:15:2) |

EXAMPLE 21

4-(2-oxo-1,2-dihydro-4H-thieno[3,4-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

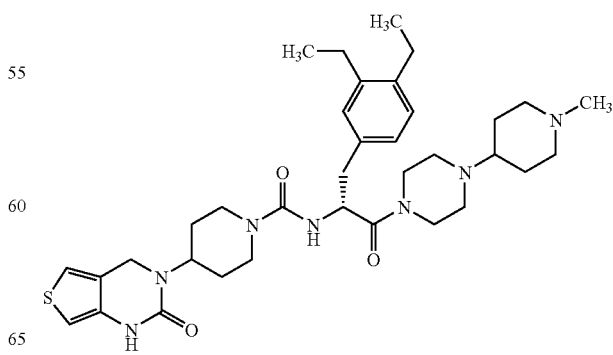

EXAMPLE 22

4-(2-oxo-1,4-dihydro-2H-thieno[3,2-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

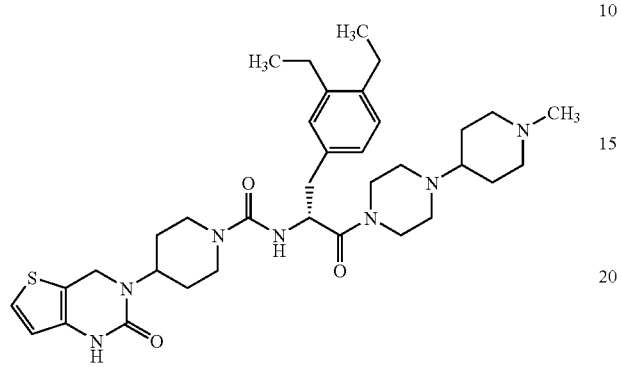

EXAMPLE 23

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyrrolidin-1-yl-piperidin-1-yl)-ethyl]-amide

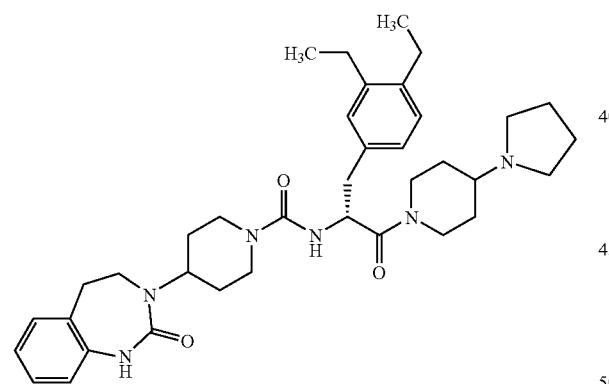

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 160 mg (0.99 mmol) 4-pyrrolidin-1-yl-piperidine.

| | |
|---|---|
| Yield: | 170 mg (33% of theory) |
| ESI-MS: | (M + H)$^+$ 629 |
| R$_f$: | 0.59 (silica gel, DCM/MeOH/cyc/NH$_3$ 70:15:15:2) |

EXAMPLE 24

4-(5-oxo-4,5,7,8-tetrahydro-2-thia-4,6-diaza-azulen-6-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

EXAMPLE 25

4-(2-oxo-1,2,4,5-tetrahydro-thieno[3,2-d]-1,3-diazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

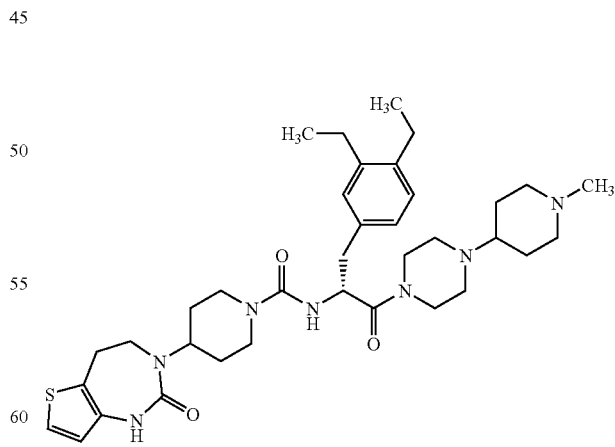

EXAMPLE 26

4-(2-oxo-1,2,4,5-tetrahydro-thieno[2,3-d]-1,3-diazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

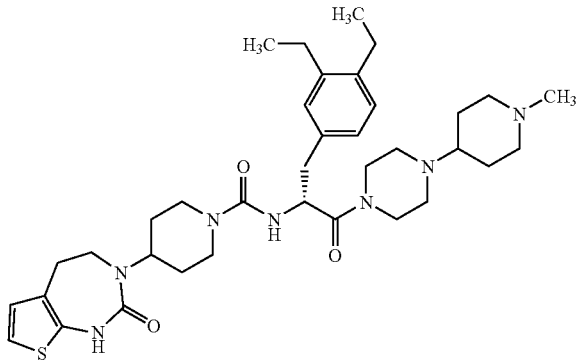

EXAMPLE 27

4-(2-oxo-1,4-dihydro-2H-thieno[2,3-d]pyrimidin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide

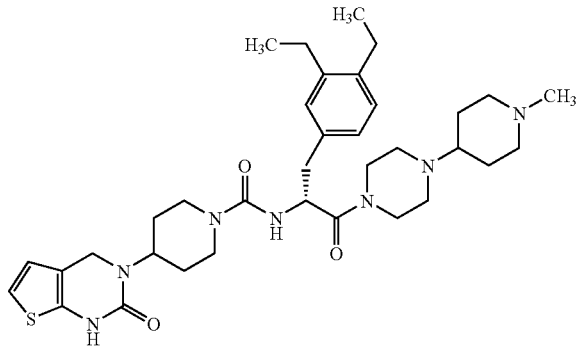

EXAMPLE 28

4-(2-oxo-1,2,4,5-tetrahydro-1,3-benzodiazepin-3-yl)-piperidine-1-carboxylic acid-{(R)-1-(3,4-diethyl-benzyl)-2-[4-(4-ethyl-piperazin-1-yl)-piperidin-1-yl]-2-oxo-ethyl}-amide

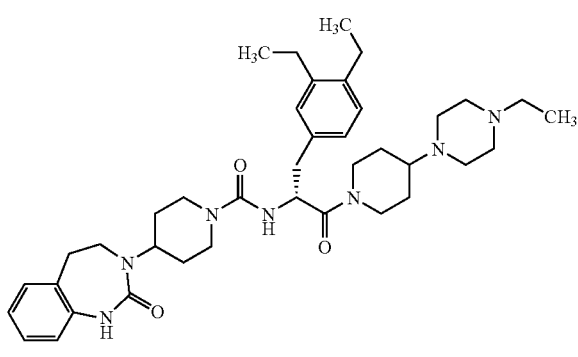

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 550 mg (1.02 mmol) 1-ethyl-4-piperidin-4-yl-piperazine-tris-trifluoroacetate.

| | |
|---|---|
| Yield: | 250 mg (46% of theory) |
| ESI-MS: | $(M + H)^+$ 672 |
| $R_f$: | 0.59 (silica gel, DCM/MeOH/cyc/$NH_3$ 70:15:15:2) |

EXAMPLE 29

4-(2-oxo-1,2,4,5-tetrahydro-1,3-benzodiazepin-3-yl)-piperidine-1-carboxylic acid-{(R)-1-(3,4-diethyl-benzyl)-2-[4-(4-isopropyl-piperazin-1-yl)-piperidin-1-yl]-2-oxo-ethyl}-amide

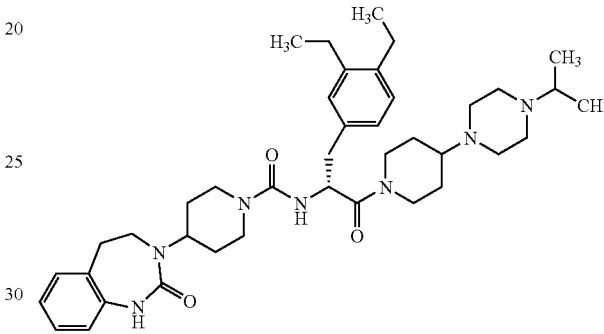

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 210 mg (0.99 mmol) 1-isopropyl-4-piperidin-4-yl-piperazine.

| | |
|---|---|
| Yield: | 80 mg (14% of theory) |
| ESI-MS: | $(M + H)^+$ 686 |
| $R_f$: | 0.59 (silica gel, DCM/MeOH/cyc/$NH_3$ 70:15:15:2) |

EXAMPLE 30

4-(2-oxo-1,2,4,5-tetrahydro-1,3-benzodiazepin-3-yl)-piperidine-1-carboxylic acid-[(R)-2-1,4'-bipiperidinyl-1'-yl-1-(3,4-diethyl-benzyl)-2-oxo-ethyl]-amide

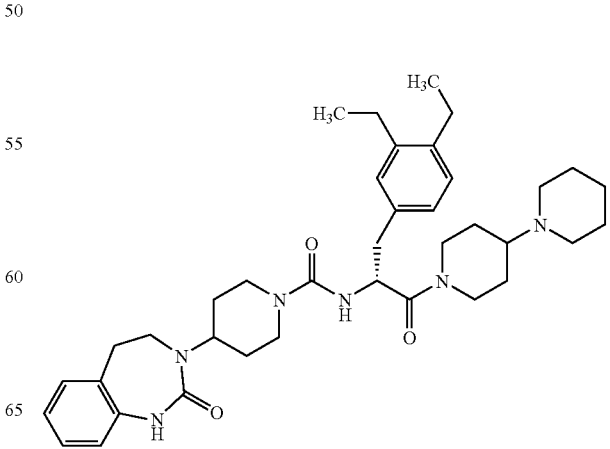

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 170 mg (1.01 mmol) [1,4']bipiperidinyl.

| Yield: | 230 mg (44% of theory) |
|---|---|
| ESI-MS: | (M + H)+ 643 |
| $R_f$: | 0.59 (silica gel, DCM/MeOH/cyc/NH$_3$ 70:15:15:2) |

EXAMPLE 31

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyridin-4-yl-piperazin-1-yl)-ethyl]-amide

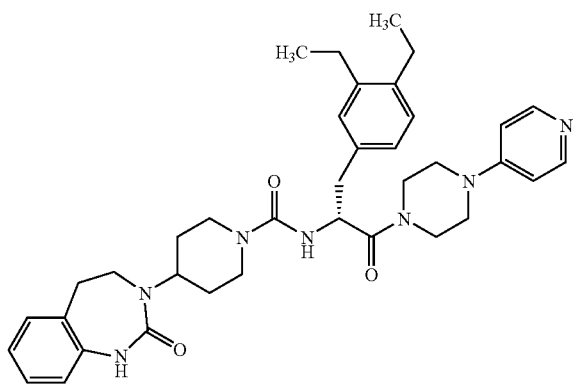

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 170 mg (1.04 mmol) 1-pyridin-4-yl-piperazine.

| Yield: | 150 mg (29% of theory) |
|---|---|
| ESI-MS: | (M + H)+ 638 |
| $R_f$: | 0.56 (silica gel, DCM/MeOH/cyc/NH$_3$ 70:15:15:2) |

EXAMPLE 32

4-(2-oxo-1,2,4,5-tetrahydro-1,3-benzodiazepin-3-yl)-piperidine-1-carboxylic acid-[(R)-1-(3,4-diethyl-benzyl)-2-oxo-2-(3,4,5,6-tetrahydro-2H-4,4'-bipyridinyl-1-yl)-ethyl]-amide

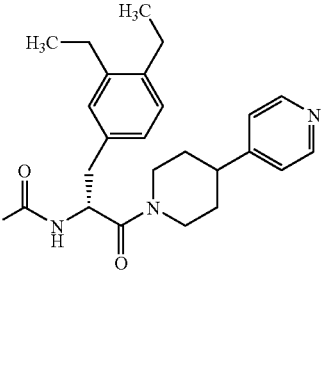

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 170 mg (1.04 mmol) 1,2,3,4,5,6-hexahydro-[4,4']bipyridinyl.

| Yield: | 280 mg (54% of theory) |
|---|---|
| ESI-MS: | (M + H)+ 637 |
| $R_f$: | 0.62 (silica gel, DCM/MeOH/cyc/NH$_3$ 70:15:15:2) |

EXAMPLE 33

4-(2-oxo-1,2,4,5-tetrahydro-1,3-benzodiazepin-3-yl)-piperidine-1-carboxylic acid-[(R)-1-(3,4-diethyl-benzyl)-2-(4,4-difluoro-1,4'-bipiperidinyl-1'-yl)-2-oxo-ethyl]-amide

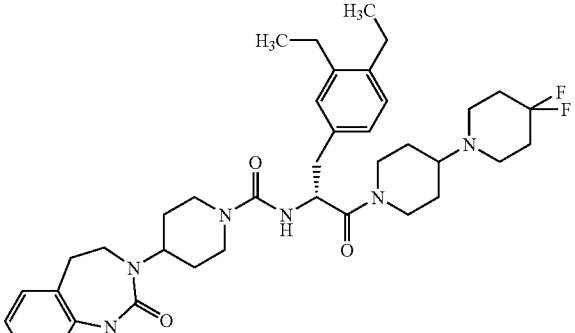

33a) 1'-benzyl-4,4-difluoro-[1,4']bipiperidinyl

Under a nitrogen atmosphere a mixture of 6.8 g (25.0 mmol) 1'-benzyl-[1,4']bipiperidinyl-4-one and 60 mL DCM was combined with stirring at RT with a solution of 7.8 mL (42.4 mmol) [bis-(2-methoxyethyl)-amino]-sulphur trifluoride in 40 mL DCM and then with 0.3 mL EtOH. The reaction mixture was stirred overnight, a further 15.6 mL [bis-(2-methoxyethyl)-amino]-sulphur trifluoride and 0.6 mL EtOH were added and the mixture was stirred for 24 h. The reaction mixture was then combined with saturated NaHCO$_3$ solution, exhaustively extracted with DCM, dried and freed from the organic solvent under reduced pressure. The residue was purified by chromatography on silica gel.

| Yield: | 2.8 g (38% of theory) |
|---|---|
| ESI-MS: | (M + H)$^+$ 295 |
| R$_f$: | 0.50 (silica gel, DCM/MeOH/NH$_3$ 90:10:1) |

33b) 4,4-difluoro-[1,4']bipiperidinyl

A solution of 2.8 g (9.5 mmol) 1'-benzyl-4,4-difluoro-[1,4']bipiperidinyl in 300 mL MeOH was hydrogenated in the presence of 1.2 g Pd/C (10%) at 50° C. and 50 psi hydrogen pressure with the addition of a few drops of 1 M HCl until the calculated volume of hydrogen had been taken up. The catalyst was filtered off and the filtrate was evaporated down under reduced pressure. The residue was triturated with diisopropylether, suction filtered and dried.

| Yield: | 0.56 g (29% of theory) |
|---|---|
| ESI-MS: | (M + H)$^+$ 204 |
| R$_f$: | 0.10 (silica gel, DCM/MeOH/NH$_3$ 90:10:1) |

33c) 4-(2-oxo-1,2,4,5-tetrahydro-1,3-benzodiazepin-3-yl)-piperidine-1-carboxylic acid-[(R)-1-(3,4-diethyl-benzyl)-2-(4,4-difluoro-1,4'-bipiperidinyl-1'-yl)-2-oxo-ethyl]-amide Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 200 mg (0.98 mmol) 4,4-difluoro-[1,4']bipiperidinyl.

| Yield: | 270 mg (49% of theory) |
|---|---|
| ESI-MS | (M + H)$^+$ 679 |
| R$_f$: | 0.65 (silica gel, DCM/MeOH/cyc/NH$_3$ 70:15:15:2) |

EXAMPLE 34

4-(2-oxo-1,2,4,5-tetrahydro-1,3-benzodiazepin-3-yl)-piperidine-1-carboxylic acid-[(R)-1-(3,4-diethyl-benzyl)-2-(4-morpholin-4-yl-piperidin-1-yl)-2-oxo-ethyl]-amide

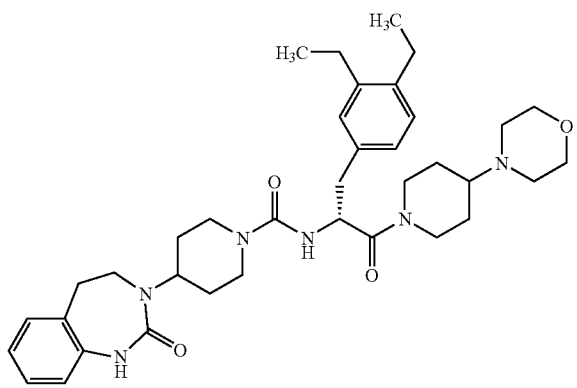

Prepared analogously to Example 9i) from 400 mg (0.81 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 170 mg (1.00 mmol) 4-piperidin-4-yl-morpholine.

| Yield: | 330 mg (63% of theory) |
|---|---|
| ESI-MS: | (M + H)$^+$ 645 |
| R$_f$: | 0.62 (silica gel, DCM/MeOH/cyc/NH$_3$ 70:15:15:2) |

The following were obtained accordingly:

EXAMPLE 35

4-(2-oxo-1,2,4,5-tetrahydro-1,3-benzodiazepin-3-yl)-piperidine-1-carboxylic acid {(R)-1-(3,4-diethyl-benzyl)-2-[4-(1-ethyl-piperidin-4-yl)-piperazin-1-yl]-2-oxo-ethyl}-amide

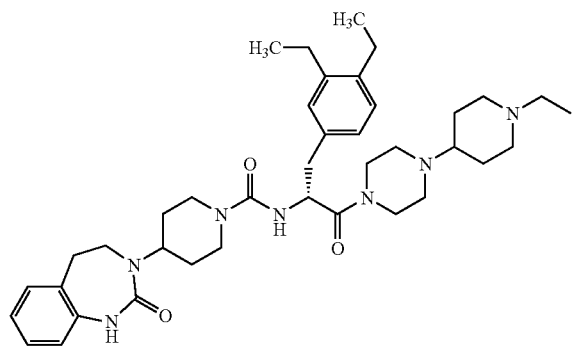

| Yield: | 7% of theory |
|---|---|
| ESI-MS: | (M + H)$^+$ 672 |
| R$_f$: | 0.60 (silica gel, DCM/MeOH/cyc/NH$_3$ 70:15:15:2) |

EXAMPLE 36

4-(2-oxo-1,2,4,5-tetrahydro-1,3-benzodiazepin-3-yl)-piperidine-1-carboxylic acid [(R)-2-(4-diethylaminomethyl-piperidin-1-yl)-1-(3,4-diethyl-benzyl)-2-oxo-ethyl]-amide

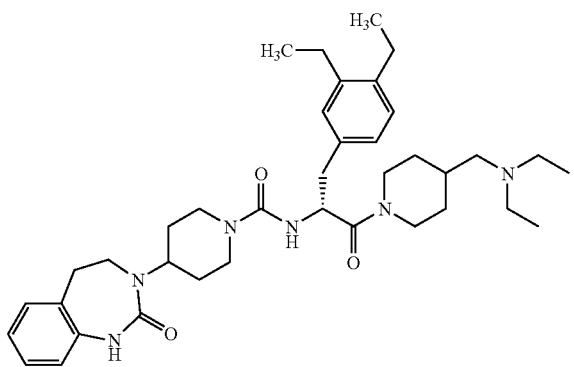

| Yield: | 15% of theory |
|---|---|
| ESI-MS: | (M + H)+ 645 |
| $R_f$: | 0.60 (silica gel, DCM/MeOH/cyc/NH$_3$ 70:15:15:2) |

EXAMPLE 37

4-(2-oxo-1,2,4,5-tetrahydro-1,3-benzodiazepin-3-yl)-piperidine-1-carboxylic acid {(R)-1-(3,4-diethyl-benzyl)-2-[4-(1-methyl-piperidin-4-yl)-[1,4]diazepan-1-yl]-2-oxo-ethyl}-amide

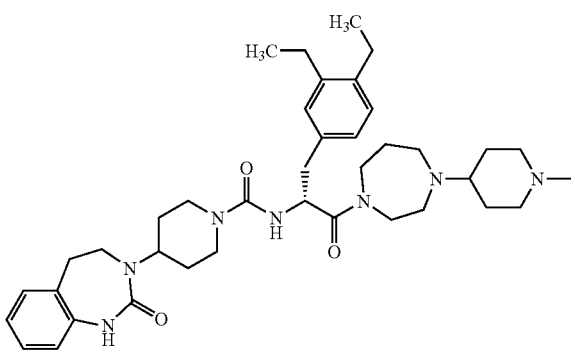

| Yield: | 59% of theory |
|---|---|
| ESI-MS: | (M + H)+ 672 |
| $R_f$: | 0.45 (silica gel, DCM/MeOH/cyc/NH$_3$ 70:15:15:2) |

EXAMPLE 38

4-(2-oxo-1,2,4,5-tetrahydro-1,3-benzodiazepin-3-yl)-piperidine-1-carboxylic acid {(R)-1-(3,4-diethyl-benzyl)-2-[3-(4-methyl-piperazin-1-yl)-azetidin-1-yl]-2-oxo-ethyl}-amide

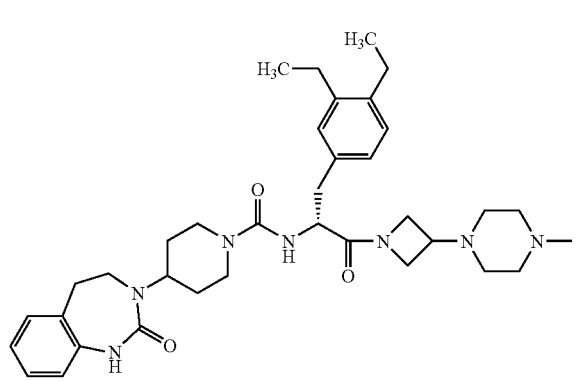

| Yield: | 33% of theory |
|---|---|
| ESI-MS: | (M + H)+ 630 |
| $R_f$: | 0.53 (silica gel, DCM/MeOH/cyc/NH$_3$ 70:15:15:2) |

EXAMPLE 39

4-(2-oxo-1,2,4,5-tetrahydro-1,3-benzodiazepin-3-yl)-piperidine-1-carboxylic acid [(R)-1-(3,4-diethyl-benzyl)-2-oxo-2-(3-piperidin-1-yl-azetidin-1-yl)-ethyl]-amide

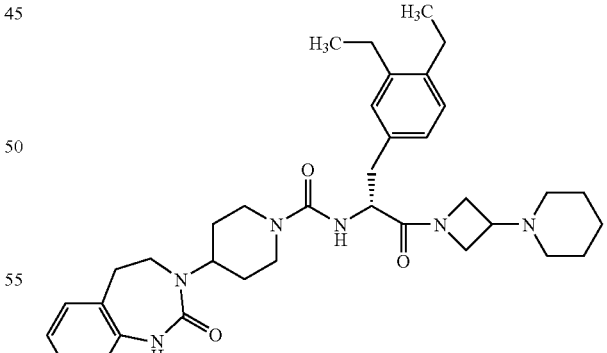

| Yield: | 42% of theory |
|---|---|
| ESI-MS: | (M + H)+ 630 |
| $R_f$: | 0.70 (silica gel, DCM/MeOH/cyc/NH$_3$ 70:15:15:2) |

EXAMPLE 40

4-(2-oxo-1,2,4,5-tetrahydro-1,3-benzodiazepin-3-yl)-piperidine-1-carboxylic acid [(R)-1-(3,4-diethyl-benzyl)-2-oxo-2-(3-pyrrolidin-1-yl-azetidin-1-yl)-ethyl]-amide

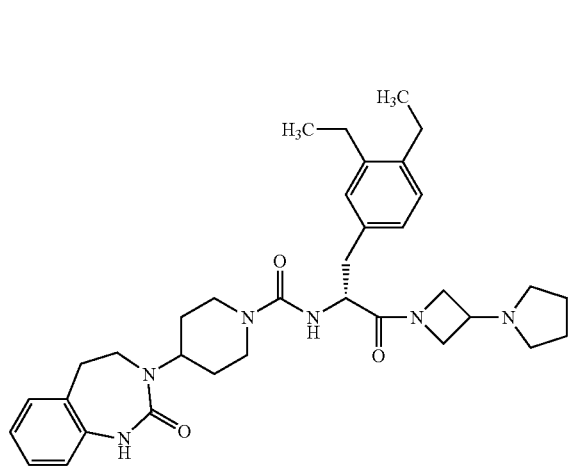

| Yield: | 49% of theory |
|---|---|
| ESI-MS: | (M + H)+ 601 |
| $R_f$: | 0.70 (silica gel, DCM/MeOH/cyc/NH$_3$ 70:15:15:2) |

EXAMPLE 41

4-(2-oxo-1,2,4,5-tetrahydro-1,3-benzodiazepin-3-yl)-piperidine-1-carboxylic acid [(R)-2-(3-diethylamino-azetidin-1-yl)-1-(3,4-diethyl-benzyl)-2-oxo-ethyl]-amide

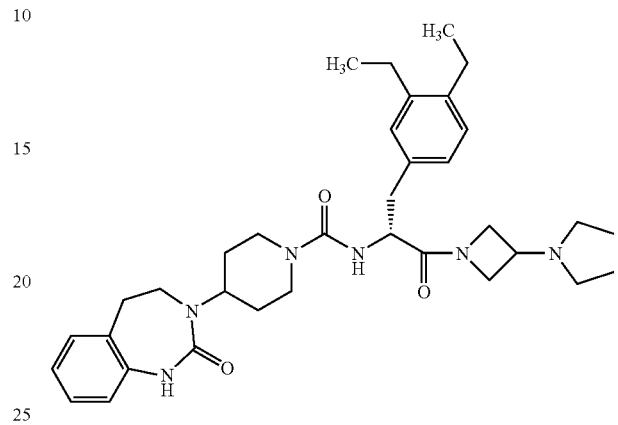

| Yield: | 29% of theory |
|---|---|
| ESI-MS: | (M + H)+ 603 |
| $R_f$: | 0.79 (silica gel, DCM/MeOH/cyc/NH$_3$ 70:15:15:2) |

EXAMPLE 42

4-(2-oxo-1,2,4,5-tetrahydro-1,3-benzodiazepin-3-yl)-piperidine-1-carboxylic acid ((R)-1-(3,4-diethyl-benzyl)-2-oxo-2-{4-[4-(2,2,2-trifluoro-acetyl)-phenyl]-piperazin-1-yl}-ethyl)-amide

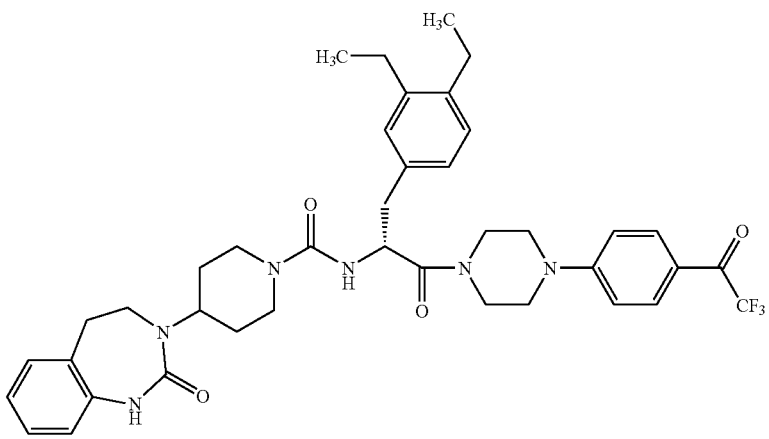

| Yield:  | 78% of theory |
|---|---|
| ESI-MS: | (M + H)+ 733 |
| $R_f$: | 0.20 (silica gel, EtOAc) |

EXAMPLE 43

4-(2-oxo-1,2,4,5-tetrahydro-1,3-benzodiazepin-3-yl)-piperidine-1-carboxylic acid [(R)-1-(3,4-diethyl-benzyl)-2-oxo-2-(4-piperidin-4-yl-piperazin-1-yl)-ethyl]-amide

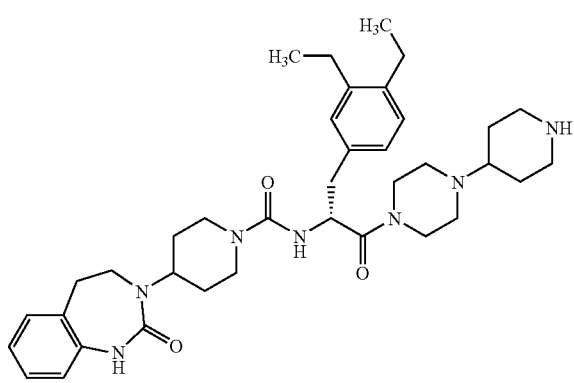

Prepared analogously to Example 14) from 500 mg (1.02 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 720 mg (1.20 mmol) 1-(1-benzyl-piperidin-4-yl)-piperazine-tris-trifluoroacetate.

| Yield:  | 160 mg (25% of theory) |
|---|---|
| ESI-MS: | (M + H)+ 644 |
| $R_f$: | 0.36 (silica gel, DCM/MeOH/cyc/NH₃ 70:15:15:2) |

EXAMPLE 44

4-(2-oxo-1,2,4,5-tetrahydro-1,3-benzodiazepin-3-yl)-piperidine-1'-carboxylic acid [(R)-1'-(3-aminomethyl-benzylcarbamoyl)-2-(3,4-diethyl-phenyl)-ethyl]-amide

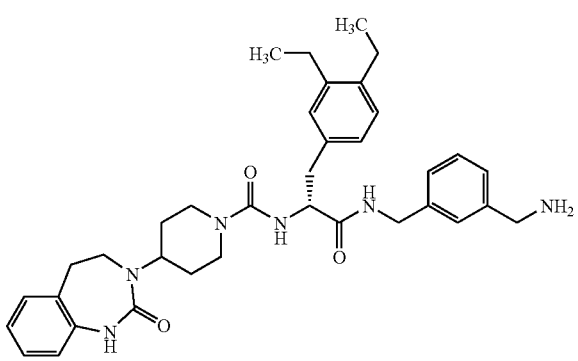

A mixture of 500 mg (1.02 mmol) (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid, 350 mg (1.09 mmol) TBTU, 0.5 mL (2.8 mmol) ethyldiisopropylamine and 45 mL THF was stirred for 1 h at RT, then combined with 290 mg (1.23 mmol) tert-butyl (3-aminomethyl-benzyl)-carbaminate and 5 mL DMF and stirred overnight. The reaction mixture was diluted by the addition of 30 mL EtOAc and extracted with 30 mL 15% K₂CO₃ solution. The organic phase was dried, evaporated down under reduced pressure and the residue purified by chromatography on silica gel. The intermediate product fractions were evaporated down, the residue remaining (600 mg) was combined with 20 mL DCM and 1.5 mL (19.6 mmol) TFA and stirred overnight. Then the reaction mixture was poured onto 60 mL 15% K₂CO₃ solution, the organic phase was separated off, dried and evaporated down under reduced pressure. The residue remaining was purified by chromatography on silica gel. The product fractions were evaporated down under reduced pressure, the residue was triturated with diisopropylether, suction filtered and dried.

| Yield:  | 90 mg (15% of theory) |
|---|---|
| ESI-MS: | (M + H)+ 611 |
| $R_f$: | 0.55 (silica gel, DCM/MeOH/cyc/NH₃ 70:15:15:2) |

The following compounds were prepared analogously:

EXAMPLE 45

4-(2-oxo-1,2,4,5-tetrahydro-1,3-benzodiazepin-3-yl)-piperidine-1-carboxylic acid [(R)-1-(5-amino-pentyl-carbamoyl)-2-(3,4-diethyl-phenyl)-ethyl]-amide

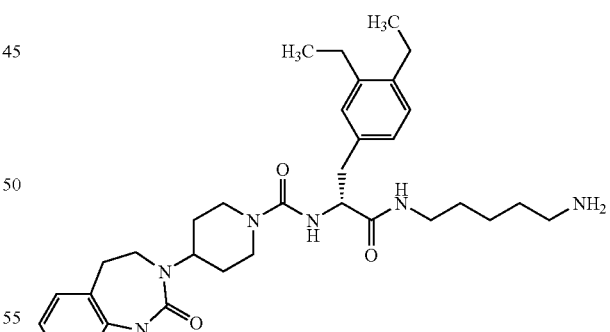

| Yield:  | 48% of theory |
|---|---|
| ESI-MS: | (M + H)+ 577 |
| $R_f$: | 0.33 (silica gel, DCM/MeOH/cyc/NH₃ 70:15:15:2) |

The following compounds may be prepared analogously:

EXAMPLE 46

4-(2-oxo-1,2,4,5-tetrahydro-1,3-benzodiazepin-3-yl)-piperidine-1-carboxylic acid-[(R)-1-(4-amino-butyl-carbamoyl)-2-(3,4-diethyl-phenyl)-ethyl]-amide

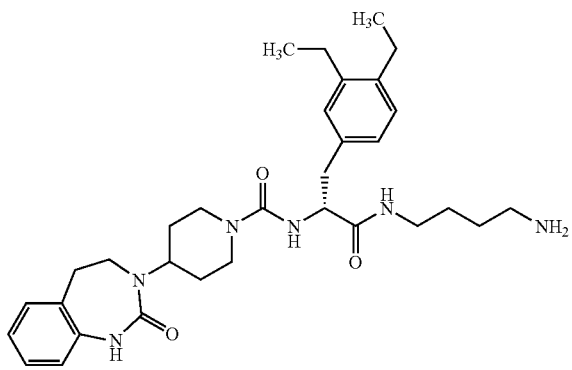

EXAMPLE 47

4-(2-oxo-1,2,4,5-tetrahydro-1,3-benzodiazepin-3-yl)-piperidine-1-carboxylic acid-[(R)-2-(3,4-diethyl-phenyl)-1-(5-methylamino-pentylcarbamoyl)-ethyl]-amide

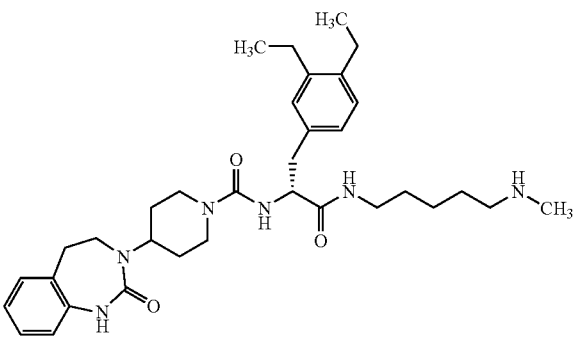

EXAMPLE 48

4-(2-oxo-1,2,4,5-tetrahydro-1,3-benzodiazepin-3-yl)-piperidine-1-carboxylic acid [(R)-2-[4-(4-methyl-piperazin-1-yl)-piperidin-1-yl]-2-oxo-1-(5,6,7,8-tetrahydro-naphthalen-2-ylmethyl)-ethyl]-amide

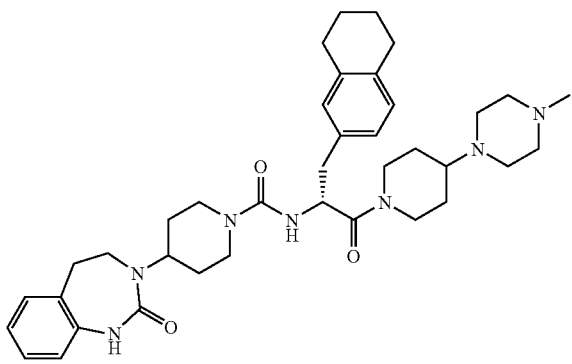

48a) monoethyl 2-acetylamino-2-(5,6,7,8-tetrahydro-naphthalen-2-ylmethyl)-malonate 19 mL 6 M NaOH (114 mmol) were added dropwise to a stirred solution of 38.5 g (106.5 mmol) diethyl 2-acetylamino-2-(5,6,7,8-tetrahydro-naphthalen-2-ylmethyl)-malonate in 250 mL EtOH. The reaction mixture was stirred overnight at RT, the solvent was eliminated under reduced pressure and the residue was taken up in 250 mL water. With stirring and cooling with the ice bath 120 mL 1 M HCl were added, the precipitate was suction filtered, suspended twice with 100 mL aliquots of water, suction filtered and dried.

| Yield: | 30.1 g (85% of theory) |
|---|---|
| ESI-MS: | $(M + H)^+$ 334 |
| $R_f$: | 0.08 (silica gel, DCM/MeOH/NH$_3$ 90:10:1) |

48b) ethyl 2-acetylamino-3-(5,6,7,8-tetrahydro-naphthalen-2-yl)-propionate

A mixture of 29.2 g (87.6 mmol) monoethyl 2-acetylamino-2-(5,6,7,8-tetrahydro-naphthalen-2-ylmethyl)-malonate and 400 mL toluene was refluxed for 5 h. The reaction mixture was then washed with 1 M NaOH and water, dried and evaporated down under reduced pressure.

| Yield: | 22.1 g (87% of theory) |
|---|---|
| ESI-MS: | $(M + H)^+$ 290 |
| $R_f$: | 0.40 (silica gel, DCM/MeOH/cyc/NH$_3$ 70:15:15:2) |

48c) ethyl (R)-2-acetylamino-3-(5,6,7,8-tetrahydro-naphthalen-2-yl)-propionate 20 mL Alcalase 2.4 L FG (Novozymes A/S; DK 2880 Bagsvaerd) were added to a solution of 28.3 g (159 mmol) disodium hydrogen phosphate dihydrate in 500 mL water at a temperature of 37° C. and by the addition of sodium dihydrogen phosphate the pH was adjusted to 7.5. Then 22.0 g (76.0 mmol) ethyl 2-acetylamino-3-(5,6,7,8-tetrahydro-naphthalen-2-yl)-propionate dissolved in 130 mL acetone was added dropwise at 37° C. with stirring. The pH value of the reaction mixture was kept in the range from pH 7.4 to pH 7.6 by the addition of 1 M NaOH. After the addition had ended the mixture was stirred for 3 h at 37° C. and overnight at RT. The reaction mixture was extracted three times with tert-butylmethylether, the combined organic extracts were washed with 15% K$_2$CO$_3$ solution, dried and evaporated down under reduced pressure.

| Yield: | 10.3 g (47% of theory) |
|---|---|
| ESI-MS: | $(M + H)^+$ 290 |
| $R_f$: | 0.75 (silica gel, DCM/MeOH/cyc/NH$_3$ 70:15:15:2) |
| ee value: | 99.8% [HPLC (Chiralpak AD, 10 µm, 4.6 × 250 mm; eluant: n-hexane/EtOH 90:10)] |

48d) (R)-2-amino-3-(5,6,7,8-tetrahydro-naphthalen-2-yl)-propionic acid

A mixture of 10.0 g (34.6 mmol) ethyl (R)-2-acetylamino-3-(5,6,7,8-tetrahydro-naphthalen-2-yl)-propionate and 120 mL 6 M HCl was refluxed for 3 h. The reaction mixture was cooled in the ice bath, the precipitate was suction filtered, washed with water and diisopropylether and dried.

| Yield: | 8.4 g (95% of theory) |
|---|---|
| ESI-MS: | (M + H)⁺ 220 |
| $R_f$: | 0.10 (silica gel, DCM/MeOH/cyc/NH₃ 70:15:15:2) |

48e) ethyl (R)-2-amino-3-(5,6,7,8-tetrahydro-naphthalen-2-yl)-propionate

A mixture of 3.7 g (14.5 mmol) (R)-2-amino-3-(5,6,7,8-tetrahydro-naphthalen-2-yl)-propionic acid and 150 mL EtOH was combined with 50 mL ethanolic HCl with stirring. The reaction mixture was stirred for 2 h, evaporated down under reduced pressure and the residue was taken up in DCM. The organic solution washed with 15% K₂CO₃ solution, dried and evaporated down under reduced pressure.

| Yield: | 3.3 g (92% of theory) |
|---|---|
| ESI-MS | (M + H)⁺ 248 |
| $R_f$: | 0.05 (silica gel, DCM/MeOH/cyc/NH₃ 70:15:15:2) |

48f) ethyl (R)-2-{[4-(2-oxo-1,2,4,5-tetrahydro-1,3-benzodiazepin-3-yl)-piperidine-1-carbonyl]-amino}-3-(5,6,7,8-tetrahydro-naphthalen-2-yl)-propionate A mixture of 20 mL THF, 1.65 g (6.7 mmol) ethyl (R)-2-amino-3-(5,6,7,8-tetrahydro-naphthalen-2-yl)-propionate and 1.25 g (7.6 mmol) CDT was stirred for 1 h in the ice bath and for 1 h at RT. Then 1.70 g (6.9 mmol) 3-piperidin-4-yl-1,3,4,5-tetrahydro-1,3-benzodiazepin-2-one was added and the mixture was refluxed for 3 h. The reaction mixture was evaporated down under reduced pressure, the residue combined with 15% K₂CO₃ solution, the precipitate was suction filtered and dried.

| Yield: | 3.4 g (98% of theory) |
|---|---|
| ESI-MS: | (M + H)⁺ 519 |
| $R_f$: | 0.47 (silica gel, DCM/MeOH/cyc/NH₃ 70:15:15:2) |

48g) (R)-2-{[4-(2-oxo-1,2,4,5-tetrahydro-1,3-benzodiazepin-3-yl)-piperidine-1-carbonyl]-amino}-3-(5,6,7,8-tetrahydro-naphthalen-2-yl)-propionic acid A mixture of 20 mL THF and 3.4 g (6.5 mmol) ethyl (R)-2-{[4-(2-oxo-1,2,4,5-tetrahydro-1,3-benzodiazepin-3-yl)-piperidine-1-carbonyl]-amino}-3-(5,6,7,8-tetrahydro-naphthalen-2-yl)-propionate was combined with a solution of 0.58 g (13.5 mmol) lithium hydroxide hydrate in 5 mL water and stirred overnight. The reaction mixture was evaporated down under reduced pressure, the residue was taken up in water and acidified by the addition of 1 M HCl. The precipitate was suction filtered and dried.

| Yield: | 2.9 g (90% of theory) |
|---|---|
| ESI-MS: | (M + H)⁺ 491 |
| $R_f$: | 0.47 (silica gel, DCM/MeOH/cyc/NH₃ 70:15:15:2) |

48h) 4-(2-oxo-1,2,4,5-tetrahydro-1,3-benzodiazepin-3-yl)-piperidine-1-carboxylic acid [(R)-2-[4-(4-methyl-piperazin-1-yl)-piperidin-1-yl]-2-oxo-1-(5,6,7,8-tetrahydro-naphthalen-2-ylmethyl)-ethyl]-amide A mixture of 500 mg (1.02 mmol) (R)-2-{[4-(2-oxo-1,2,4,5-tetrahydro-1,3-benzodiazepin-3-yl)-piperidine-1-carbonyl]-amino}-3-(5,6,7,8-tetrahydro-naphthalen-2-yl)-propionic acid, 350 mg (1.09 mmol) TBTU, 0.19 mL (1.08 mmol) ethyldiisopropylamine and 30 mL THF was stirred for 30 min at RT, then combined with 195 mg (1.06 mmol) 1-methyl-4-piperidin-4-yl-piperazin and stirred overnight. The reaction mixture was poured onto 100 mL of a 15% K₂CO₃ solution and extracted twice with DCM. The combined organic extracts were dried, evaporated down under reduced pressure and the residue was purified by chromatography on silica gel. The product fractions were evaporated down under reduced pressure, the residue was triturated with diisopropylether, suction filtered and dried.

| Yield: | 430 mg (64% of theory) |
|---|---|
| ESI-MS: | (M + H)⁺ 656 |
| $R_f$: | 0.49 (silica gel, DCM/MeOH/cyc/NH₃ 70:15:15:2) |

The following were obtained accordingly:

EXAMPLE 49

4-(2-oxo-1,2,4,5-tetrahydro-1,3-benzodiazepin-3-yl)-piperidine-1-carboxylic acid [(R)-2-[4-(1-methyl-piperidin-4-yl)-piperazin-1-yl]-2-oxo-1-(5,6,7,8-tetrahydro-naphthalen-2-ylmethyl)-ethyl]-amide

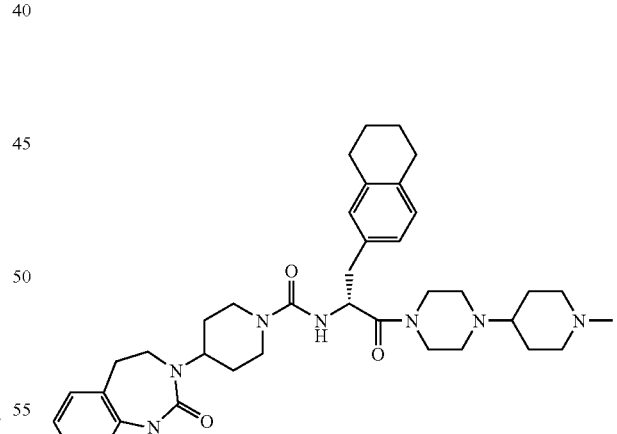

| Yield: | 52% of theory |
|---|---|
| ESI-MS: | (M + H)⁺ 656 |
| $R_f$: | 0.42 (silica gel, DCM/MeOH/cyc/NH₃ 70:15:15:2) |

EXAMPLE 50

4-(2-oxo-1,2,4,5-tetrahydro-1,3-benzodiazepin-3-yl)-piperidine-1-carboxylic acid [(R)-2-[4-(1-benzyl-piperidin-4-yl)-piperazin-1-yl]-2-oxo-1-(5,6,7,8-tetrahydro-naphthalen-2-ylmethyl)-ethyl]-amide

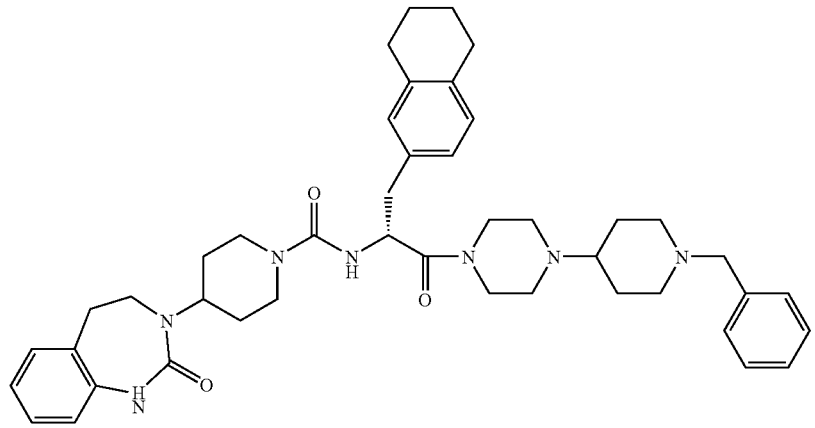

| | |
|---|---|
| Yield: | 16% of theory |
| ESI-MS: | (M + H)⁺ 732 |
| $R_f$: | 0.55 (silica gel, DCM/MeOH/cyc/NH₃ 70:15:15:2) |

EXAMPLE 51

4-(2-oxo-1,2,4,5-tetrahydro-1,3-benzodiazepin-3-yl)-piperidine-1-carboxylic acid [(R)-2-[4-(4-benzyl-piperazin-1-yl)-piperidin-1-yl]-2-oxo-1-(5,6,7,8-tetrahydro-naphthalen-2-ylmethyl)-ethyl]-amide

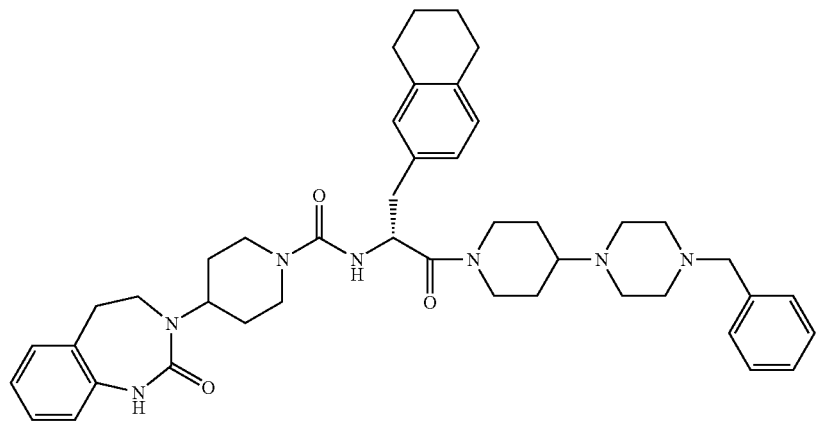

| | |
|---|---|
| Yield: | 42% of theory |
| ESI-MS: | (M + H)⁺ 732 |
| $R_f$: | 0.57 (silica gel, DCM/MeOH/cyc/NH₃ 70:15:15:2) |

EXAMPLE 52

4-(2-oxo-1,2,4,5-tetrahydro-1,3-benzodiazepin-3-yl)-piperidine-1-carboxylic acid [(R)-2-oxo-2-(4-piperidin-4-yl-piperazin-1-yl)-1-(5,6,7,8-tetrahydro-naphthalen-2-ylmethyl)-ethyl]-amide

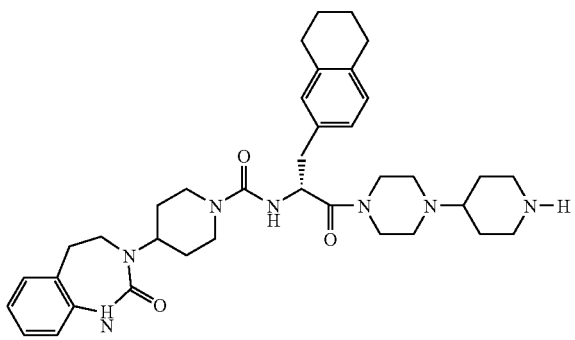

A solution of 100 mg (0.14 mmol) 4-(2-oxo-1,2,4,5-tetrahydro-1,3-benzodiazepin-3-yl)-piperidine-1-carboxylic acid [(R)-2-[4-(1-benzyl-piperidin-4-yl)-piperazin-1-yl]-2-oxo-1-(5,6,7,8-tetrahydro-naphthalen-2-ylmethyl)-ethyl]-amide (Example 50) in 10 mL MeOH was hydrogenated in the presence of 20 mg Pd/C (10%) at 50° C. and 3 bar hydrogen pressure until the calculated volume of hydrogen had been taken up. The catalyst was filtered off, the solvent eliminated under reduced pressure and the residue purified by chromatography on silica gel. The product fractions were evaporated down under reduced pressure and dried.

| Yield: | 22 mg (25% of theory) |
|---|---|
| ESI-MS: | (M + H)+ 642 |

The following was obtained accordingly:

EXAMPLE 53

4-(2-oxo-1,2,4,5-tetrahydro-1,3-benzodiazepin-3-yl)-piperidine-1-carboxylic acid [(R)-2-oxo-2-(4-piperazin-1-yl-piperidin-1-yl)-1-(5,6,7,8-tetrahydro-naphthalen-2-ylmethyl)-ethyl]-amide

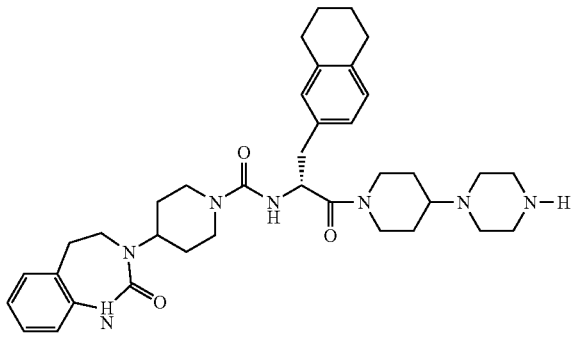

| Yield: | 10% of theory) |
|---|---|
| ESI-MS: | (M + H)+ 642 |

EXAMPLE 54

4-(2-oxo-1,2-dihydro-imidazo[4,5-c]quinolin-3-yl)-piperidine-1-carboxylic acid [(R)-2-[4-(1-methyl-piperidin-4-yl)-piperazin-1-yl]-2-oxo-1-(5,6,7,8-tetrahydro-naphthalen-2-ylmethyl)-ethyl]-amide

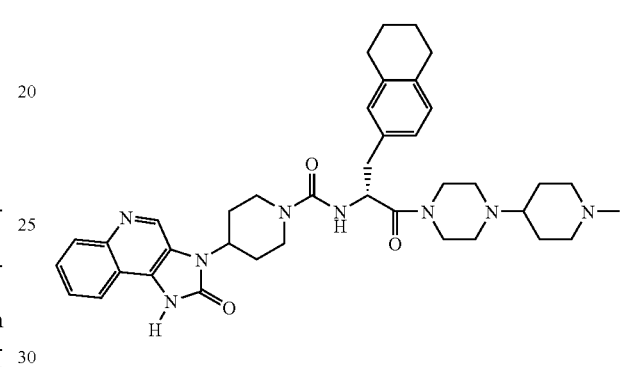

54a) (R)-2-{[4-(2-oxo-1,2-dihydro-imidazo[4,5-c]quinolin-3-yl)-piperidine-1-carbonyl]-amino}-3-(5,6,7,8-tetrahydro-naphthalen-2-yl)-propionate ethyl A mixture of 15 mL THF, 0.825 g (3.3 mmol) ethyl (R)-2-amino-3-(5,6,7,8-tetrahydro-naphthalen-2-yl)-propionate and 0.63 g (3.8 mmol) CDT was stirred for 1 h in the ice bath and for 1 h at RT. Then 0.95 g (3.5 mmol) 3-piperidin-4-yl-1,3-dihydro-imidazo[4,5-c]quinolin-2-one was added and refluxed for 3 h. The reaction mixture was evaporated down under reduced pressure, the residue combined with 15% $K_2CO_3$ solution, the precipitate was suction filtered and dried.

| Yield: | 1.65 g (91% of theory) |
|---|---|
| MS: | (M − H) 540 |
| $R_f$: | 0.30 (silica gel, DCM/MeOH/cyc/NH₃ 70:15:15:2) |

54b) (R)-2-{[4-(2-oxo-1,2-dihydro-imidazo[4,5-c]quinolin-3-yl)-piperidine-1-carbonyl]-amino}-3-(5,6,7,8-tetrahydro-naphthalen-2-yl)-propionic acid A mixture of 15 mL THF and 1.65 g (3.0 mmol) ethyl (R)-2-{[4-(2-oxo-1,2-dihydro-imidazo[4,5-c]quinolin-3-yl)-piperidine-1-carbonyl]-amino}-3-(5,6,7,8-tetrahydro-naphthalen-2-yl)-propionate was combined with a solution of 0.40 g (6.3 mmol) lithium hydroxide hydrate in 5 mL water and stirred overnight. The reaction mixture was evaporated down under reduced pressure, the residue was taken up in water and acidified by the addition of 1 M HCl. The precipitate was suction filtered and dried.

| Yield: | 1.1 g (70% of theory) |
| --- | --- |
| ESI-MS: | (M + H)⁺ 514 |
| $R_f$: | 0.14 (silica gel, DCM/MeOH/cyc/NH₃ 70:15:15:2) |

54c) 4-(2-oxo-1,2-dihydro-imidazo[4,5-c]quinolin-3-yl)-piperidine-1-carboxylic acid [(R)-2-[4-(1-methyl-piperidin-4-yl)-piperazin-1-yl]-2-oxo-1-(5,6,7,8-tetrahydro-naphthalen-2-ylmethyl)-ethyl]-amide A mixture of 500 mg (0.97 mmol) (R)-2-{[4-(2-oxo-1,2-dihydro-imidazo[4,5-c]quinolin-3-yl)-piperidine-1-carbonyl]-amino}-3-(5,6,7,8-tetrahydro-naphthalen-2-yl)-propionic acid, 350 mg (1.09 mmol) TBTU, 0.19 mL (1.08 mmol) ethyldiisopropylamine and 30 mL THF was stirred for 30 min at RT, then combined with 195 mg (1.06 mmol) 1-(1-methyl-piperidin-4-yl)-piperazine and stirred overnight. The reaction mixture was poured onto 100 mL of a 15% K₂CO₃ solution and extracted twice with DCM. The combined organic extracts were dried, evaporated down under reduced pressure and the residue was purified by chromatography on silica gel. The product fractions were evaporated down under reduced pressure, the residue was triturated with diisopropylether, suction filtered and dried.

| Yield: | 345 mg (52% of theory) |
| --- | --- |
| ESI-MS: | (M + H)⁺ 677 |
| $R_f$: | 0.38 (silica gel, DCM/MeOH/cyc/NH₃ 70:15:15:2) |

The following was obtained accordingly:

EXAMPLE 55

4-(2-oxo-1,2-dihydro-imidazo[4,5-c]quinolin-3-yl)-piperidine-1-carboxylic acid [(R)-2-[4-(4-benzyl-piperazin-1-yl)-piperidin-1-yl]-2-oxo-1-(5,6,7,8-tetrahydro-naphthalen-2-ylmethyl)-ethyl]-amide

| Yield: | 50% of theory |
| --- | --- |
| ESI-MS: | (M + H)⁺ 753 |
| $R_f$: | 0.49 (silica gel, DCM/MeOH/cyc/NH₃ 70:15:15:2) |

EXAMPLE 56

4-(2-oxo-1,2-dihydro-imidazo[4,5-c]quinolin-3-yl)-piperidine-1-carboxylic acid [(R)-2-oxo-2-(4-piperazin-1-yl-piperidin-1-yl)-1-(5,6,7,8-tetrahydro-naphthalen-2-ylmethyl)-ethyl]-amide

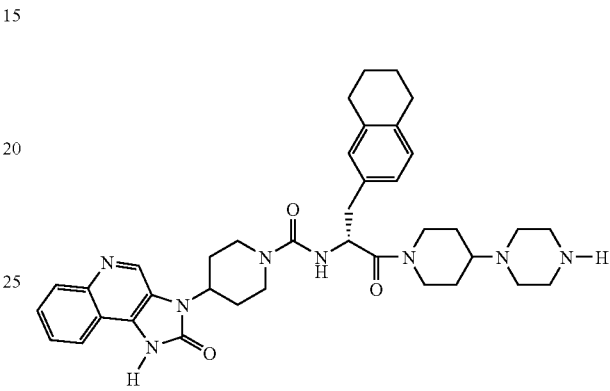

A solution of 300 mg (0.40 mmol) 4-(2-oxo-1,2-dihydro-imidazo[4,5-c]quinolin-3-yl)-piperidine-1-carboxylic acid [(R)-2-[4-(4-benzyl-piperazin-1-yl)-piperidin-1-yl]-2-oxo-1-(5,6,7,8-tetrahydro-naphthalen-2-ylmethyl)-ethyl]-amide in 10 mL MeOH was hydrogenated in the presence of 30 mg Pd/C (10%) at 50° C. and 3 bar hydrogen pressure until the calculated volume of hydrogen had been taken up. The catalyst was filtered off, the solvent eliminated under reduced pressure and the residue purified by chromatography on silica gel. The product fractions were evaporated down under reduced pressure and dried.

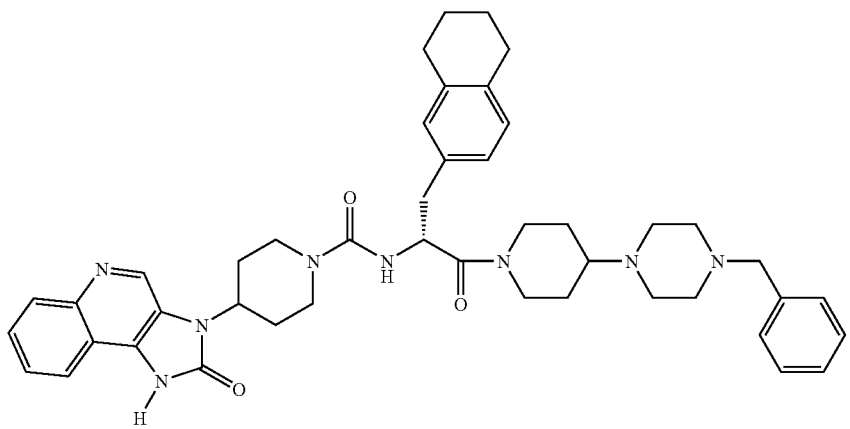

| Yield:   | 80 mg (30% of theory) |
|---|---|
| ESI-MS: | (M + H)⁺ 665 |

EXAMPLE 57

4-(5-oxo-3-phenyl-4,5-dihydro-[1,2,4]triazol-1-yl)-piperidine-1-carboxylic acid [(R)-2-[4-(1-methyl-piperidin-4-yl)-piperazin-1-yl]-2-oxo-1-(5,6,7,8-tetrahydro-naphthalen-2-ylmethyl)-ethyl]-amide

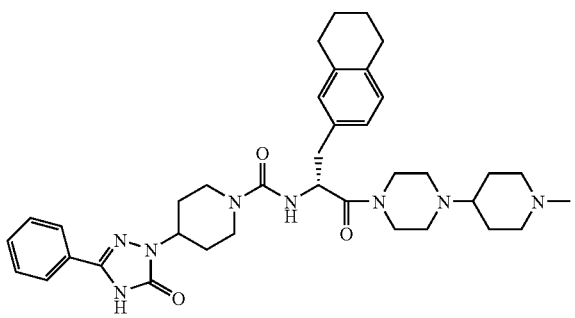

57a) ethyl (R)-2-{[4-(5-oxo-3-phenyl-4,5-dihydro-[1,2,4]triazol-1-yl)-piperidine-1-carbonyl]-amino}-3-(5,6,7,8-tetrahydro-naphthalen-2-yl)-propionate A mixture of 15 mL THF, 0.830 g (3.4 mmol) ethyl (R)-2-amino-3-(5,6,7,8-tetrahydro-naphthalen-2-yl)-propionate and 0.63 g (3.8 mmol) CDT was stirred for 1 h in the ice bath and for 1 h at RT. Then 0.83 g (3.4 mmol) 5-phenyl-2-piperidin-4-yl-2,4-dihydro-[1,2,4]triazol-3-one was added and the mixture was refluxed for 3 h. The reaction mixture was evaporated down under reduced pressure, the residue was combined with 15% K₂CO₃ solution, the precipitate was suction filtered and dried.

| Yield:   | 1.50 g (86% of theory) |
|---|---|
| ESI-MS: | (M − H)⁻ 516 |
| $R_f$: | 0.34 (silica gel, DCM/MeOH/cyc/NH₃ 70:15:15:2) |

57b) (R)-2-{[4-(5-oxo-3-phenyl-4,5-dihydro-[1,2,4]triazol-1-yl)-piperidine-1-carbonyl]-amino}-3-(5,6,7,8-tetrahydro-naphthalen-2-yl)-propionic acid Prepared analogously to Example 54b) from 1.50 g (2.9 mmol) ethyl (R)-2-{[4-(5-oxo-3-phenyl-4,5-dihydro-[1,2,4]triazol-1-yl)-piperidine-1-carbonyl]-amino}-3-(5,6,7,8-tetrahydro-naphthalen-2-yl)-propionate.

| Yield:   | 0.80 g (56% of theory) |
|---|---|
| ESI-MS: | (M + H)⁺ 490 |
| $R_f$: | 0.15 (silica gel, DCM/MeOH/cyc/NH₃ 70:15:15:2) |

57c) 4-(5-oxo-3-phenyl-4,5-dihydro-[1,2,4]triazol-1-yl)-piperidine-1-carboxylic acid-[(R)-2-[4-(1-methyl-piperidin-4-yl)-piperazin-1-yl]-2-oxo-1-(5,6,7,8-tetrahydro-naphthalen-2-ylmethyl)-ethyl]-amide Prepared analogously to Example 54c) from 300 mg (0.61 mmol) (R)-2-{[4-(5-oxo-3-phenyl-4,5-dihydro-[1,2,4]triazol-1-yl)-piperidine-1-carbonyl]-amino}-3-(5,6,7,8-tetrahydro-naphthalen-2-yl)-propionic acid and 120 mg (0.66 mmol) 1-(1-methyl-piperidin-4-yl)-piperazine.

| Yield:   | 150 mg (37% of theory) |
|---|---|
| ESI-MS: | (M + H)⁺ 653 |
| Rf: | 0.41 (silica gel, DCM/MeOH/cyc/NH₃ 70:15:15:2) |

The following was obtained accordingly:

EXAMPLE 58

4-(5-oxo-3-phenyl-4,5-dihydro-[1,2,4]triazol-1-yl)-piperidine-1-carboxylic acid-[(R)-2-[4-(4-benzyl-piperazin-1-yl)-piperidin-1-yl]-2-oxo-1-(5,6,7,8-tetrahydro-naphthalen-2-ylmethyl)-ethyl]-amide

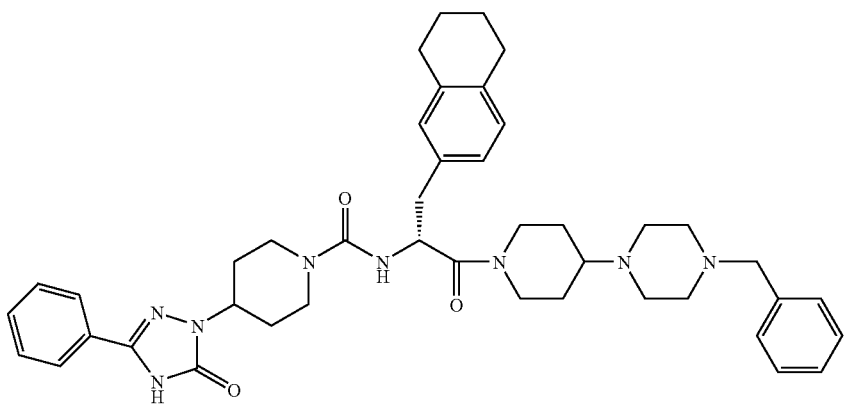

| Yield:  | 25% of theory |
| --- | --- |
| ESI-MS: | (M + H)+ 729 |
| $R_f$: | 0.54 ((silica gel, DCM/MeOH/cyc/NH₃ 70:15:15:2) |

EXAMPLE 59

4-(5-oxo-3-phenyl-4,5-dihydro-[1,2,4]triazol-1-yl)-piperidine-1-carboxylic acid-[(R)-2-oxo-2-(4-piperazin-1-yl-piperidin-1-yl)-1-(5,6,7,8-tetrahydro-naphthalen-2-ylmethyl)-ethyl]-aide

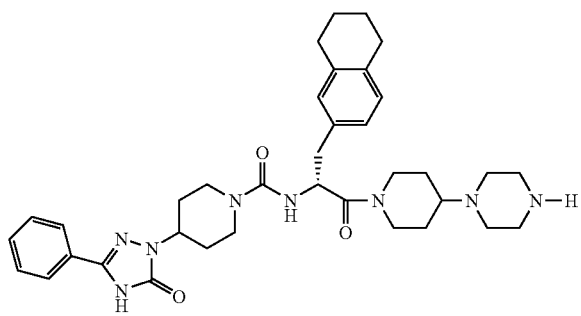

A solution of 80 mg (0.11 mmol) 4-(5-oxo-3-phenyl-4,5-dihydro-[1,2,4]triazol-1-yl)-piperidine-1-carboxylic acid [(R)-2-[4-(4-benzyl-piperazin-1-yl)-piperidin-1-yl]-2-oxo-1-(5,6,7,8-tetrahydro-naphthalen-2-ylmethyl)-ethyl]-amide in 10 mL MeOH was hydrogenated in the presence of 10 mg Pd/C (10%) at 50° C. and 3 bar hydrogen pressure until the calculated volume of hydrogen had been taken up. The catalyst was filtered off, the solvent eliminated under reduced pressure and the residue purified by chromatography on silica gel. The product fractions were evaporated down under reduced pressure and dried.

| Yield: | 15 mg (22% of theory) |
| --- | --- |
| ESI-MS: | (M + H)+ 641 |

EXAMPLE 60

(R)-1-(3,4-diethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

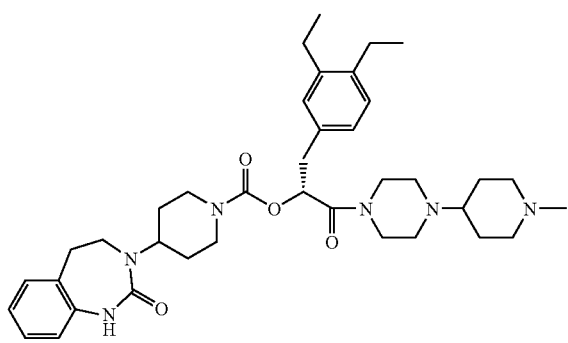

60a) (R)-3-(3,4-diethyl-phenyl)-2-hydroxy-propionic acid

A solution of 3.2 g (47 mmol) sodium nitrite in 20 mL water was slowly added dropwise with stirring to an ice-cooled mixture of 2.0 g (7.8 mmol) (R)-2-amino-3-(3,4-diethyl-phenyl)-propionic acid in 60 mL 0.5 M H₂SO₄. The reaction mixture was stirred for 3 h while cooling with ice and for 3 days at RT, combined with 80 mL diethyl ether, vigorously stirred and the organic phase is separated off. The aqueous phase was again extracted with 80 mL diethyl ether, the combined organic phases were dried and evaporated down under reduced pressure. The residue was purified by chromatography on silica gel and the product fractions were evaporated down under reduced pressure.

| Yield: | 0.64 g (37% of theory) |
| --- | --- |
| ESI-MS: | (M − H)⁻ 221 |

60b) benzyl (R)-2-amino-3-(3,4-diethyl-phenyl)-propionate 0.64 g (2.9 mmol) (R)-3-(3,4-diethyl-phenyl)-2-hydroxy-propionic acid was dissolved in 10 mL MeOH and 1 mL water and adjusted to a pH of 7.0 by the addition of 20% Cs₂CO₃ solution. The reaction mixture was evaporated down, the residue taken up in 10 mL DMF and the solution was again evaporated down under reduced pressure. The oily residue was taken up in 10 mL DMF and the ice-cooled solution was combined with 0.34 mL (2.9 mmol) benzylbromide under an argon atmosphere. The reaction mixture was stirred for 2 h while cooling with an ice bath and for two days at RT, then combined with 10 mL water and extracted twice with 20 mL diethyl ether. The combined organic phases were dried, evaporated down and purified by chromatography on silica gel.

| Yield: | 0.67 g (74% of theory) |
| --- | --- |
| ESI-MS: | (M − H)⁻ 311 |
| $R_f$: | 0.40 (silica gel, cyc/EtOAc 8:2) |

60c) 4-(2-oxo-1,2,4,5-tetrahydro-1,3-benzodiazepin-3-yl)-piperidine-1-carbonylchloride 6 g (12.1 mmol) phosgene (20 percent by weight in toluene) were added to a solution of 2.5 g (10.2 mmol) 3-piperidin-4-yl-1,3,4,5-tetrahydro-1,3-benzodiazepin-2-one and 2.6 mL (14.9 mmol) ethyldiisopropylamine in 75 mL DCM cooled to 0° C. and the reaction mixture was stirred for 30 min at this temperature. It was allowed to come up to RT, evaporated down i.vac. to approx. 50 mL and filtered through silica gel, this washed with 200 mL DCM/EtOAc (1:1) and the combined filtrates were again evaporated down i.vac. The residue was stirred with diisopropylether, suction filtered and dried i.vac.

| Yield: | 2.42 g (77% of theory) |
|---|---|
| $R_f$ = | 0.43 (silica gel, DCM/EtOAc 1:1) |

60d) (R)-1-benzyloxycarbonyl-2-(3,4-diethyl-phenyl)-ethyl 4-(2-oxo-1,2,4,5-tetrahydro-1,3-benzodiazepin-3-yl)-piperidine-1-carboxylate 87 mg (2.0 mmol) sodium hydride (55% in mineral oil) were added to an ice-cooled mixture of 600 mg (1.9 mmol) benzyl (R)-2-amino-3-(3,4-diethyl-phenyl)-propionate and 40 mL THF, stirred for 30 min at RT, cooled in the ice bath and 660 mg (2.1 mmol) 4-(2-oxo-1,2,4,5-tetrahydro-1,3-benzodiazepin-3-yl)-piperidine-1-carbonylchloride in 20 mL THF were added dropwise within 10 min. The reaction mixture was stirred for a further 30 min while cooling with ice and for 1 h at RT and then evaporated down under reduced pressure. The residue was taken up in EtOAc and purified by chromatography on silica gel.

| Yield: | 0.36 g (32% of theory) |
|---|---|
| ESI-MS: | (M + H)+ 584 |
| $R_f$: | 0.56 (silica gel, EtOAc/cyc 2:1) |

60e) (R)-1-carboxy-2-(3,4-diethyl-phenyl)-ethyl 4-(2-oxo-1,2,4,5-tetrahydro-1,3-benzodiazepin-3-yl)-piperidine-1-carboxylate A mixture of 350 mg (0.60 mmol) (R)-1-benzyloxycarbonyl-2-(3,4-diethyl-phenyl)-ethyl 4-(2-oxo-1,2,4,5-tetrahydro-1,3-benzodiazepin-3-yl)-piperidine-1-carboxylate and 30 mL MeOH was hydrogenated in the presence of 50 mg Pd/C (5%) at RT and 3 bar hydrogen pressure until the calculated volume of hydrogen had been taken up. The catalyst was filtered off, the solvent was eliminated under reduced pressure.

| Yield: | 0.30 g (100% of theory) |
|---|---|
| ESI-MS: | (M + H)+ 494 |
| retention time (HPLC): | 8.97 min (method A) |

60f) (R)-1-(3,4-diethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A mixture of 150 mg (0.30 mmol) (R)-1-carboxy-2-(3,4-diethyl-phenyl)-ethyl 4-(2-oxo-1,2,4,5-tetrahydro-1,3-benzodiazepin-3-yl)-piperidine-1-carboxylate, 98 mg (0.30 mmol) TBTU, 0.2 mL (1.1 mmol) ethyldiisopropylamine and 15 mL THF as well as 3 mL DMF was stirred for 1 h at RT, then combined with 56 mg (0.30 mmol) 1-(1-methyl-piperidin-4-yl)-piperazin and stirred for 2 h. The reaction mixture was combined with 30 mL of a semisaturated NaHCO₃ solution and extracted with 30 mL EtOAc. The organic phase was dried, evaporated down under reduced pressure and the residue was purified by chromatography on silica gel. The product fractions were evaporated down under reduced pressure, the residue was triturated with diisopropylether, suction filtered and dried.

| Yield: | 39 mg (20% of theory) |
|---|---|
| ESI-MS: | (M + H)+ 659 |
| $R_f$: | 0.37 (silica gel, EtOAc/MeOH/NH₃ 80:20:2) |

EXAMPLE 61

4-(2-oxo-1,2,4,5-tetrahydro-1,3-benzodiazepin-3-yl)-piperidine-1-carboxylic acid-[(R)-1-(3,4-diethyl-benzyl)-2-(7-dimethylaminomethyl-1,2,4,5-tetrahydro-3-benzazepin-3-yl)-2-oxo-ethyl]-amide

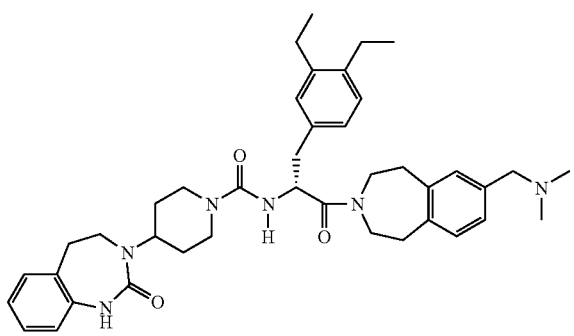

61a) 1-(7-dimethylaminomethyl-1,2,4,5-tetrahydro-3-benzazepin-3-yl)-2,2,2-trifluoroethanone 11.7 mL (23.4 mmol) of a 2 M dimethylamine solution in THF were added to a solution of 4.5 g (16.59 mmol) 3-(2,2,2-trifluoro-acetyl)-2,3,4,5-tetrahydro-1H-3-benzazepine-7-carbaldehyde in 150 mL THF and the solution was adjusted to pH 5 with 1 mL glacial acetic acid. After 30 min 4.62 g (21.79 mmol) sodium triacetoxyborohydride were added and the reaction mixture was stirred overnight at RT. The reaction solution was carefully combined with saturated NaHCO₃ solution, stirred for 30 min, exhaustively extracted with EtOAc, the organic phase was separated off and dried over Na₂SO₄. After the desiccant and solvent had been eliminated the desired product was obtained, which was further reacted without purification.

| Yield: | 4.5 g (90% of theory) |
|---|---|
| ESI-MS: | (M + H)+ 301 |
| $R_f$ = | 0.76 (silica gel, DCM/MeOH/cyc/NH₃ 70:15:15:2) |

61b) dimethyl-(2,3,4,5-tetrahydro-1H-3-benzazepin-7-ylmethyl)-amine 50 mL water and 8.5 g (61.51 mmol) K₂CO₃ were added to a solution of 4.5 g (14.98 mmol) 1-(7-dimethylaminomethyl-1,2,4,5-tetrahydro-3-benzazepin-3-yl)-2,2,2-trifluoroethanone in 50 mL MeOH and the reaction mixture was stirred for 72 h at RT. The reaction solution was evaporated down i.vac., the residue was combined with DCM, filtered to remove insoluble ingredients and evaporated down i.vac. The desired product was obtained in the form of a light-brown oil.

| Yield: | 2.9 g (95% of theory) |
|---|---|
| ESI-MS: | (M + H)$^+$ = 205 |
| R$_f$ = | 0.39 (silica gel, DCM/MeOH/cyc/NH$_3$ 70:15:15:2) |

61c) 4-(2-oxo-1,2,4,5-tetrahydro-1,3-benzodiazepin-3-yl)-piperidine-1-carboxylic acid [(R)-1-(3,4-diethyl-benzyl)-2-(7-dimethylaminomethyl-1,2,4,5-tetrahydro-3-benzazepin-3-yl)-2-oxo-ethyl]-amide Prepared analogously to Example 34 from (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and dimethyl-(2,3,4,5-tetrahydro-1H-3-benzazepin-7-ylmethyl)-amine.

| Yield: | 45% of theory |
|---|---|
| ESI-MS: | (M + H)$^+$ 679 |
| R$_f$: | 0.56 (silica gel, DCM/MeOH/cyc/NH$_3$ 70:15:15:2) |

EXAMPLE 62

4-(2-oxo-1,2,4,5-tetrahydro-1,3-benzodiazepin-3-yl)-piperidine-1-carboxylic acid-[(R)-2-(4-azetidin-1-yl-piperidin-1-yl)-1-(3,4-diethyl-benzyl)-2-oxo-ethyl]-amide

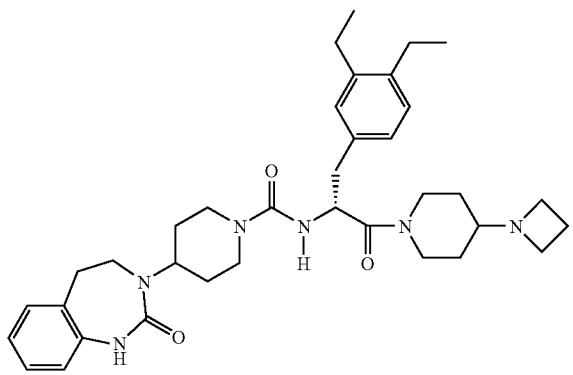

62a) 4-azetidin-1-yl-1-benzyl-piperidine 1.0 mL (17.5 mmol) glacial acetic acid were added to the stirred mixture of 3.0 mL (16.5 mmol) 1-benzyl-4-piperidone, 1.0 g (17.5 mmol) azetidine and 100 mL DCM. Then 6.0 g (39.5 mmol) sodium triacetoxy-borohydride was added batchwise within one hour while cooling with an ice bath and the mixture was stirred for a further 12 h at RT. The reaction mixture was extracted with 200 mL EtOAc, the organic phase was dried, evaporated down under reduced pressure and the residue was purified by chromatography.

| Yield: | 3.2 g (84% of theory) |
|---|---|
| ESI-MS: | (M + H)$^+$ 231 |
| R$_f$: | 0.57 (silica gel, DCM/MeOH/cyc/NH$_3$ 70:15:15:2) |

62b) 4-azetidin-1-yl-piperidine 3.2 g (13.9 mmol) 4-azetidin-1-yl-1-benzyl-piperidine dissolved in 50 mL MeOH were hydrogenated in the autoclave in the presence of 0.5 g Pd/C (10%) at 50° C. and 3 bar hydrogen pressure until the calculated volume of hydrogen had been taken up. The catalyst was filtered off and the solvent was eliminated under reduced pressure.

| Yield: | 1.9 g (98% of theory) |
|---|---|
| ESI-MS: | (M + H)$^+$ 141 |
| R$_f$: | 0.19 (silica gel, DCM/MeOH/NH$_3$ 75:25:5) |

62c) 4-(2-oxo-1,2,4,5-tetrahydro-1,3-benzodiazepin-3-yl)-piperidine-1-carboxylic acid [(R)-2-(4-azetidin-1-yl-piperidin-1-yl)-1-(3,4-diethyl-benzyl)-2-oxo-ethyl]-amide Prepared analogously to Example 34 from (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 4-azetidin-1-yl-piperidine.

| Yield: | 36% of theory |
|---|---|
| ESI-MS: | (M + H)$^+$ 615 |
| R$_f$: | 0.53 (silica gel, DCM/MeOH/cyc/NH$_3$ 70:15:15:2) |

EXAMPLE 63

4-(2-oxo-1,2,4,5-tetrahydro-1,3-benzodiazepin-3-yl)-piperidine-1-carboxylic acid [(R)-2-(3-azepan-1-yl-azetidin-1-yl)-1-(3,4-diethyl-benzyl)-2-oxo-ethyl]-amide

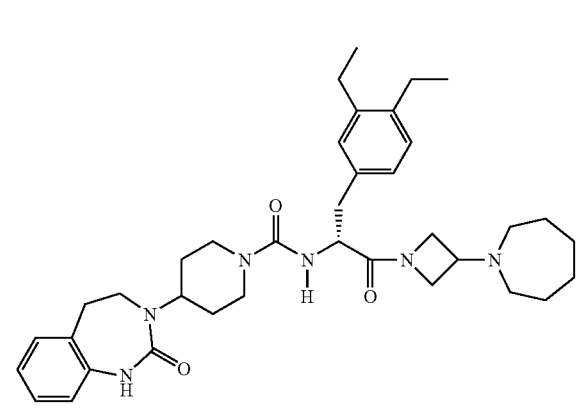

Prepared analogously to Example 34 from (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and 1-azetidin-3-yl-perhydro-azepine.

| Yield: | 37% of theory |
|---|---|
| ESI-MS: | (M + H)$^+$ 629 |
| R$_f$: | 0.66 (silica gel, DCM/MeOH/cyc/NH$_3$ 70:15:15:2) |

EXAMPLE 64 ethyl [1'-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-[4,4']bipiperidinyl-1-yl]-acetate

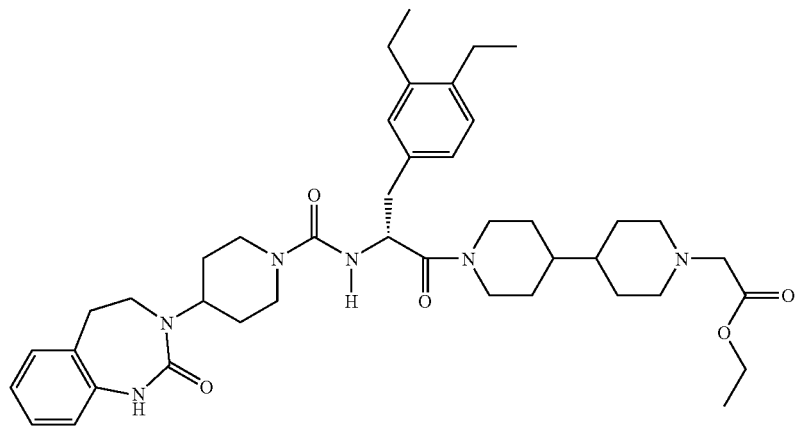

Prepared analogously to Example 34 from (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and ethyl [4,4']bipiperidinyl-1-yl-acetate

| Yield: | 42% of theory |
|---|---|
| ESI-MS: | $(M + H)^+$ 729 |

EXAMPLE 65 ethyl {4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetate

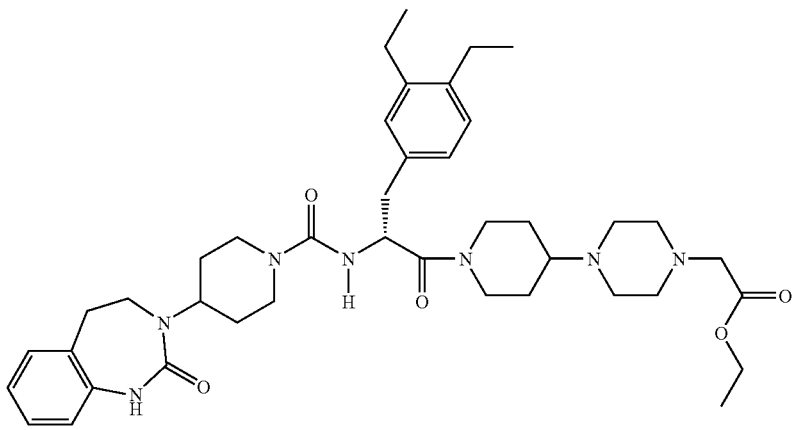

Prepared analogously to Example 34 from (R)-3-(3,4-diethyl-phenyl)-2-{[4-(2-oxo-1,2,4,5-tetrahydro-1,3-benzodiazepin-3-yl)-piperidine-1-carbonyl]-amino}-propionic acid and ethyl (4-piperidin-4-yl-piperazin-1-yl)-acetate

| Yield: | 33% of theory |
|---|---|
| ESI-MS: | $(M + H)^+$ 730 |

EXAMPLE 66

[1'-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-[4,4']bipiperidinyl-1-yl]-acetic acid

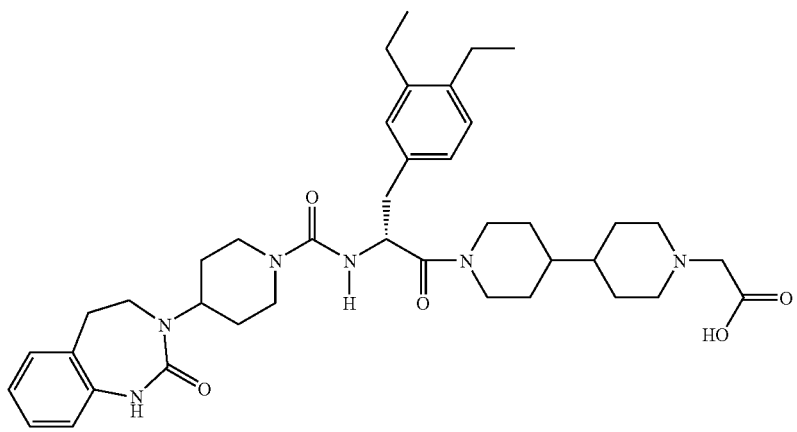

A mixture of 150 mg (0.21 mmol) ethyl [1'-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-[4,4']bipiperidinyl-1-yl]-acetate, 20 mL THF and 2.5 mL 0.1 M NaOH was stirred for 12 h at RT. The organic solvent was eliminated under reduced pressure and the pH of the reaction mixture was adjusted to exactly 7.0 by the addition of 0.1 M HCl. The precipitate was suction filtered, washed with a little water and dried.

| Yield: | 139 mg (90% of theory) |
|---|---|
| ESI-MS: | (M + H)+ 701 |

EXAMPLE 67

{4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetic acid

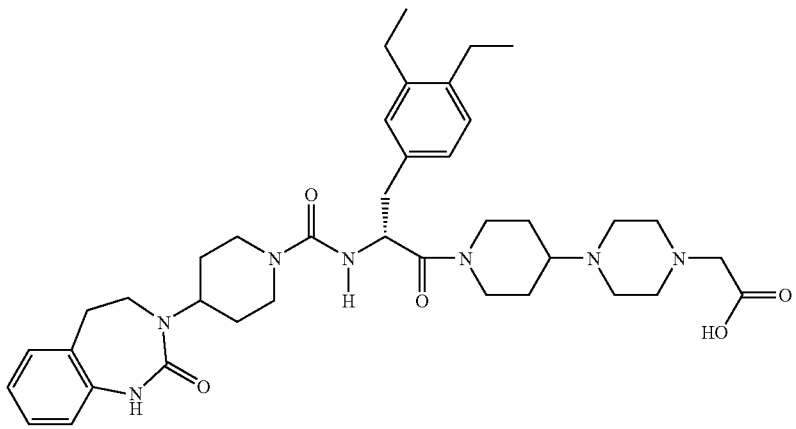

Prepared analogously to Example 66 from ethyl {4-[1-((R)-3-(3,4-diethyl-phenyl)-2-{[4-(2-oxo-1,2,4,5-tetrahydro-1,3-benzodiazepin-3-yl)-piperidine-1-carbonyl]-amino}-propionyl)-piperidin-4-yl]-piperazin-1-yl}-acetate

| Yield: | 99% of theory |
|---|---|
| ESI-MS: | (M + H)+ 702 |

EXAMPLE 68 ethyl {4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetate

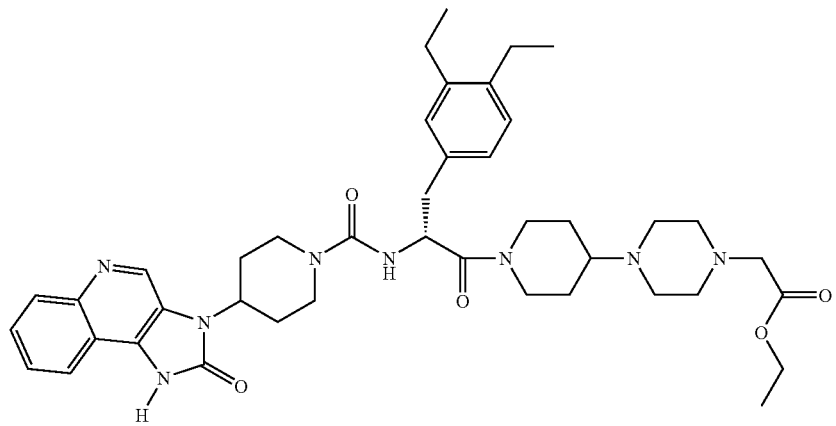

Prepared analogously to Example 1i) from 3-piperidin-4-yl-1,3-dihydro-imidazo[4,5-c]quinolin-2-one and ethyl (4-{1-[(R)-2-amino-3-(3,4-diethyl-phenyl)-propionyl]-piperidin-4-yl}-piperazin-1-yl)-acetate

| Yield: | 64% of theory |
|---|---|
| ESI-MS: | (M + H)+ 753 |

EXAMPLE 69 ethyl [1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetate

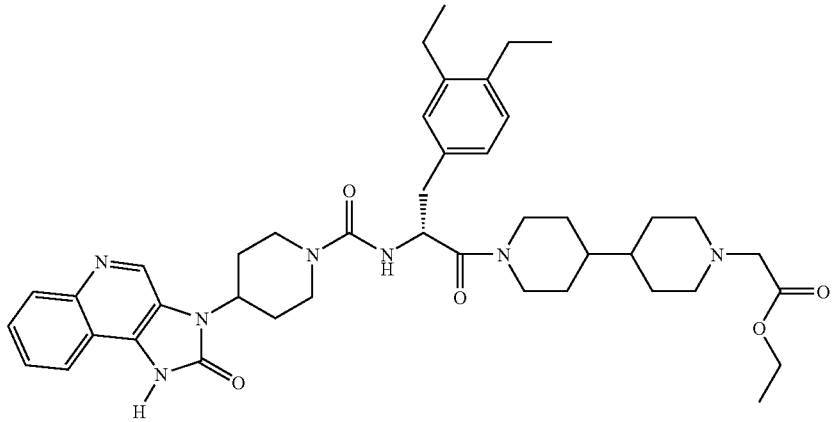

Prepared analogously to Example 1i) from 3-piperidin-4-yl-1,3-dihydro-imidazo[4,5-c]quinolin-2-one and ethyl {1'-[(R)-2-amino-3-(3,4-diethyl-phenyl)-propionyl]-[4,4']bipiperidinyl-1-yl}-acetate

| Yield: | 49% of theory |
|---|---|
| ESI-MS: | (M + H)+ 752 |

EXAMPLE 70

{4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetic acid

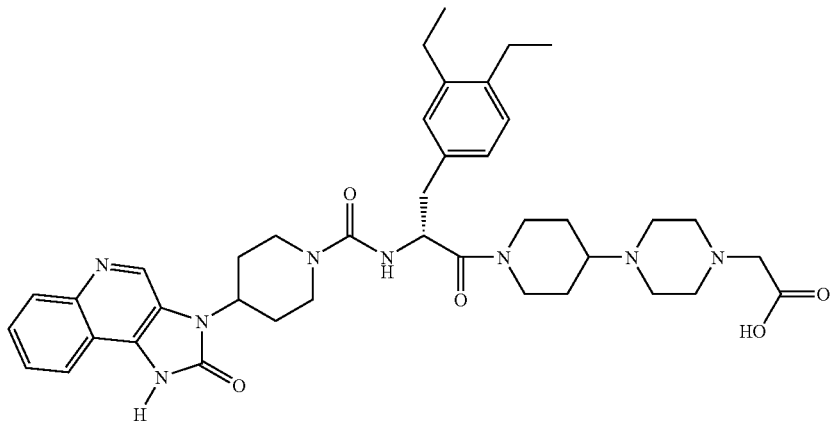

Prepared analogously to Example 66 from ethyl {4-[1-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-piperidin-4-yl]-piperazin-1-yl}-acetate

| Yield: | 42% of theory |
|---|---|
| ESI-MS: | (M + H)+ 725 |

EXAMPLE 71

[1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetic acid

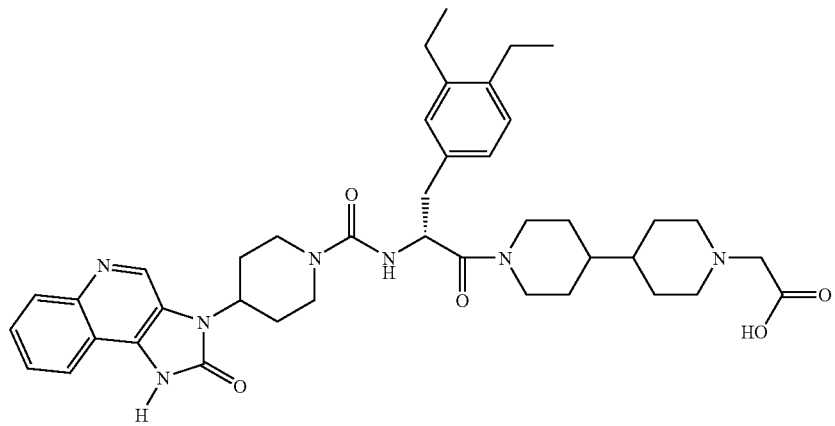

Prepared analogously to Example 66 from ethyl [1'-((R)-3-(3,4-diethyl-phenyl)-2-{[4-(2-oxo-1,2-dihydro-imidazo[4,5-c]quinolin-3-yl)-piperidine-1-carbonyl]-amino}-propionyl)-[4,4']bipiperidinyl-1-yl]-acetate

| Yield: | 69% of theory |
|---|---|
| ESI-MS: | (M + H)+ 724 |

EXAMPLE 72

4-(2-oxo-1,2-dihydro-imidazo[4,5-c]quinolin-3-yl)-piperidine-1-carboxylic acid {(R)-1-(3,4-diethyl-benzyl)-2-[4-(4-methyl-piperazin-1-yl)-piperidin-1-yl]-2-oxo-ethyl}-amide

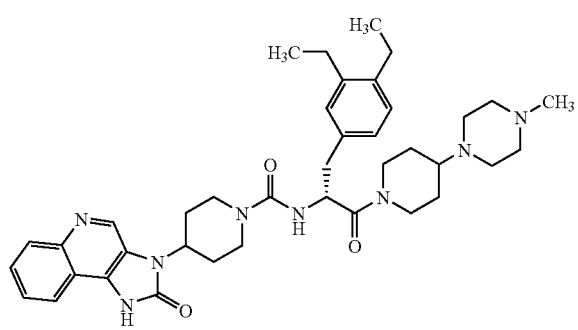

Prepared analogously to Example 17) from (R)-2-amino-3-(3,4-diethyl-phenyl)-1-[4-(4-methyl-piperazin-1-yl)-piperidin-1-yl]-propan-1-one and 3-piperidin-4-yl-1,3-dihydroimidazo[4,5-c]quinolin-2-one

| Yield: | 25% of theory) |
|---|---|
| ESI-MS: | (M + H)⁺ 681 |

EXAMPLE 73

N-[1-{(R)-1-(3,4-diethyl-benzyl)-2-[4-(1-methyl-piperidin-4-yl)-piperazin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide

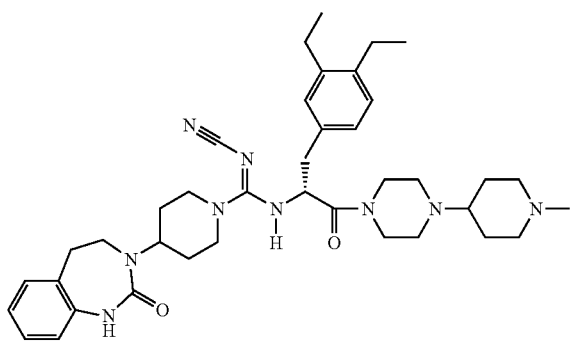

A mixture of 390 mg (1.01 mmol) (R)-2-amino-3-(3,4-diethyl-phenyl)-1-[4-(1-methylpiperidin-4-yl)-piperazin-1-yl]-propan-1-one, 270 mg (1.01 mmol) diphenylcyano-carbonimidate and 50 mL DCM was stirred for 4 h at RT and then evaporated down under reduced pressure. The residue was combined with 30 mL acetonitrile and 270 mg (1.10 mmol) 3-piperidin-4-yl-1,3,4,5-tetrahydro-1,3-benzodiazepin-2-one and refluxed for 14 h. The reaction mixture was evaporated down under reduced pressure and the residue was purified by chromatography. The product fractions were evaporated down, the residue was triturated with PE and suction filtered.

| Yield: | 200 mg (29% of theory) |
|---|---|
| ESI-MS: | (M + H)⁺ 682 |
| R_f: | 0.33 (silica gel, DCM/MeOH/cyc/NH₃ 70:15:15:2) |

EXAMPLE 74

N-[1-{(R)-1-(3,4-diethyl-benzyl)-2-[4-(4-methyl-piperazin-1-yl)-piperidin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide

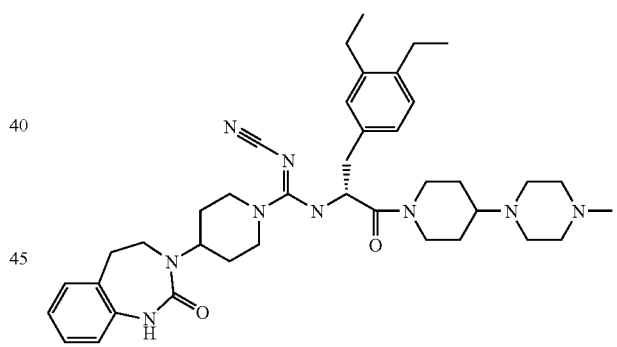

Prepared analogously to Example 73 from 3-piperidin-4-yl-1,3,4,5-tetrahydrobenzo[d][1,3]diazepin-2-one and (R)-2-amino-3-(3,4-diethyl-phenyl)-1-[4-(4-methylpiperazin-1-yl)-piperidin-1-yl]-propan-1-one

| Yield: | 26% of theory |
|---|---|
| ESI-MS: | (M + H)⁺ 682 |
| R_f: | 0.47 (silica gel, DCM/MeOH/cyc/NH₃ 70:15:15:2) |

EXAMPLE 75

N-[1-[(R)-2-[1,4']bipiperidinyl-1'-yl-1-(3,4-diethyl-benzyl)-2-oxo-ethylamino]-1-[4-(2-oxo-1,2,4,5-tetrahydro-1,3-benzodiazepin-3-yl)-piperidin-1-yl]-meth-(Z)-ylidene]-cyanamide

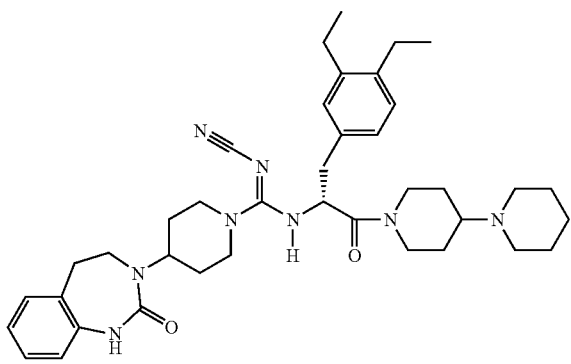

Prepared analogously to Example 73 from 3-piperidin-4-yl-1,3,4,5-tetrahydrobenzo[d][1,3]diazepin-2-one and (R)-2-amino-1-[1,4']bipiperidinyl-1'-yl-3-(3,4-diethylphenyl)-propan-1-one

| Yield: | 15% of theory |
| --- | --- |
| ESI-MS: | (M + H)+ 667 |
| $R_f$: | 0.49 (silica gel, DCM/MeOH/cyc/NH$_3$ 70:15:15:2) |

EXAMPLE 76

1-[1,4']bipiperidinyl-1'-yl-2-(3,4-dimethyl-benzyl)-4-[4-(2-oxo-1,4-dihydro-2H-quinazolin-3-yl)-piperidin-1-yl]-butan-1,4-dione

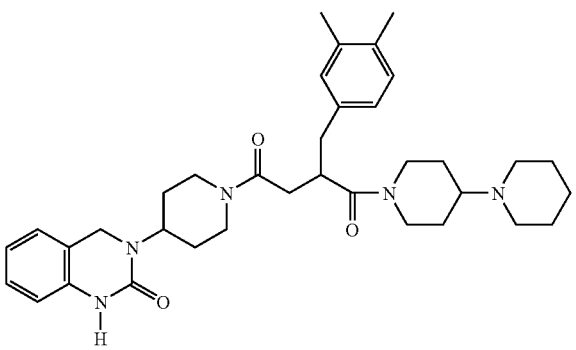

76a) tert-butyl 4-(3,4-dimethyl-phenyl)-3,3-bis-ethoxycarbonyl-butanoate 1.56 g (35.7 mmol) sodium hydride (55% in mineral oil) was added batchwise to the solution of 8.80 mL (34.0 mmol) 4-tert-butyl 2-ethoxycarbonyl-succinate in 140 mL THF while cooling with ice and the mixture was stirred for 1 h. Then 6.5 g (32.6 mmol) 4-bromomethyl-1,2-dimethyl-benzene dissolved in 70 mL THF was slowly added dropwise to the ice-cooled mixture and stirred for 1 h at RT. The reaction mixture was evaporated down under reduced pressure, the residue was combined with 20% citric acid solution and extracted three times with EtOAc. The combined organic phases were dried and evaporated down under reduced pressure.

Yield: 11.6 g (91% of theory)
$R_f$: 0.6 (silica gel, PE/EtOAc/glacial acetic acid 8:2:0.5)

76b) 4-(3,4-dimethyl-phenyl)-3,3-bis-ethoxycarbonyl-butanoic acid

A mixture of 11.6 g (29.5 mmol) tert-butyl 4-(3,4-dimethyl-phenyl)-3,3-bis-ethoxycarbonyl-butanoate and 100 mL DCM was combined with 20 mL TFA, the reaction mixture was stirred for 3 h at RT and evaporated down under reduced pressure.

| Yield: | 10.0 g (100% of theory) |
| --- | --- |
| Rf: | 0.35 (silica gel, PE/EtOAc/glacial acetic acid 8:2:0.5) |

76c) diethyl 2-(3,4-dimethyl-benzyl)-2-{2-oxo-2-[4-(2-oxo-1,4-dihydro-2H-quinazolin-3-yl)-piperidin-1-yl]-ethyl}-malonate A mixture of 10.0 g (29.7 mmol) 4-(3,4-dimethyl-phenyl)-3,3-bis-ethoxycarbonyl-butanoic acid, 10.5 g (32.7 mmol) TBTU, 4.2 g (30.5 mmol) HOBt, 5.8 mL (32.4 mmol) ethyldiisopropylamine, 270 mL THF and 30 mL water was stirred for 15 min at RT and then combined with 7.6 g (32.9 mmol) 3-piperidin-4-yl-3,4-dihydro-1H-quinazolin-2-one. The reaction mixture was stirred for 5 h at RT and evaporated down under reduced pressure. The residue was stirred with 150 mL saturated NaHCO$_3$ solution, suction filtered, washed with water and dried in the circulating air dryer.

| Yield: | 15.6 g (96% of theory) |
| --- | --- |
| $R_f$: | 0.77 (silica gel, DCM/MeOH/cyc/NH$_3$ 70:15:15:2) |

76d) 2-(3,4-dimethyl-benzyl)-4-oxo-4-[4-(2-oxo-1,4-dihydro-2H-quinazolin-3-yl)-piperidin-1-yl]-butanoic acid A solution of 15.5 g (28.2 mmol) diethyl 2-(3,4-dimethyl-benzyl)-2-{2-oxo-2-[4-(2-oxo-1,4-dihydro-2H-quinazolin-3-yl)-piperidin-1-yl]-ethyl}-malonate in 100 mL EtOH was combined with 11.2 g (169.7 mmol) KOH dissolved in 150 mL water and the mixture was refluxed for 5 h. After the addition of another 11.2 g (169.7 mmol) KOH dissolved in 150 mL water the mixture was refluxed again for 5 h, then combined with 150 mL water and the precipitate was suction filtered. The filter cake was dissolved in 500 mL water, washed twice with 100 mL EtOAc and adjusted to pH 4 by the addition of conc. HCl. The precipitate formed was suction filtered and dried in the circulating air dryer.

| Yield: | 6.7 g (53% of theory) |
| --- | --- |
| $R_f$: | 0.18 (silica gel, DCM/MeOH/cyc/NH$_3$ 70:15:15:2) |

76e) 1-[1,4']bipiperidinyl-1'-yl-2-(3,4-dimethyl-benzyl)-4-[4-(2-oxo-1,4-dihydro-2H-quinazolin-3-yl)-piperidin-1-yl]-butan-1,4-dione A mixture of 0.9 g (2.0 mmol) 2-(3,4-dimethyl-benzyl)-4-oxo-4-[4-(2-oxo-1,4-dihydro-2H-quinazolin-3-yl)-piperidin-1-yl]-butanoic acid, 0.71 g (2.2 mmol) TBTU, 0.28 g (2.1 mmol) HOBt, 0.39 mL (2.2 mmol) ethyldiisopropylamine, 45 mL THF and 5 mL water was stirred for 10 min at RT, combined with 0.37 g (2.1 mmol) [1,4']bipiperidinyl and stirred for a further 4 h. The reaction mixture was evaporated down under reduced pressure, the residue was combined with saturated NaHCO$_3$ solution and extracted three times with DCM/MeOH (95:5). The combined organic phases were dried, evaporated down under reduced pressure and purified by chromatography over silica gel. The product fractions were evaporated down under reduced pressure, the residue was triturated with diisopropylether and suction filtered.

| Yield: | 0.6 g (50% of theory) |
|---|---|
| R$_f$: | 0.52 (silica gel, DCM/MeOH/cyc/NH$_3$ 70:15:15:2) |

EXAMPLE 77

2-(3,4-dimethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione

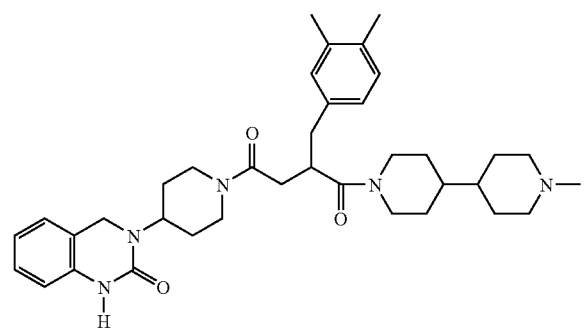

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-methyl-[4,4']bipiperidinyl

| Yield: | 33% of theory |
|---|---|
| R$_f$: | 0.36 (silica gel, DCM/MeOH/cyc/NH$_3$ 70:15:15:2) |

EXAMPLE 78

2-(3,4-dimethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione

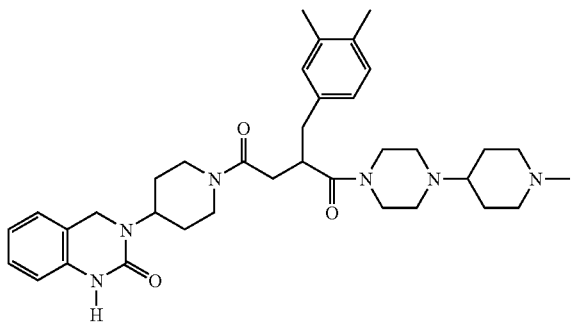

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-(1-methyl-piperidin-4-yl)-piperazine.

| Yield: | 27% of theory |
|---|---|
| R$_f$: | 0.35 (silica gel, DCM/MeOH/cyc/NH$_3$ 70:15:15:2) |

EXAMPLE 79

2-(3,4-dimethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

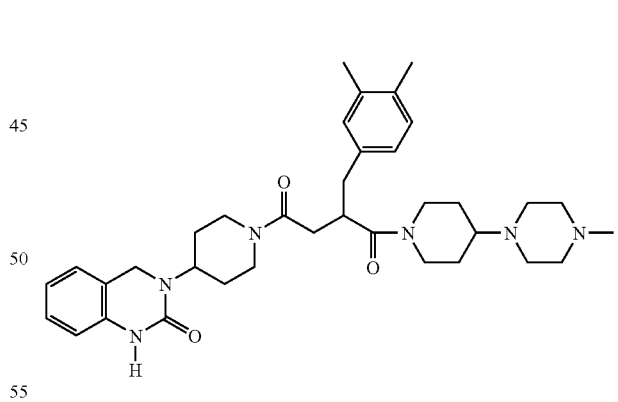

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-methyl-4-piperidin-4-yl-piperazine

| Yield: | 33% of theory |
|---|---|
| R$_f$: | 0.53 (silica gel, DCM/MeOH/cyc/NH$_3$ 70:15:15:2) |

EXAMPLE 80

2-(3,4-dimethyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione

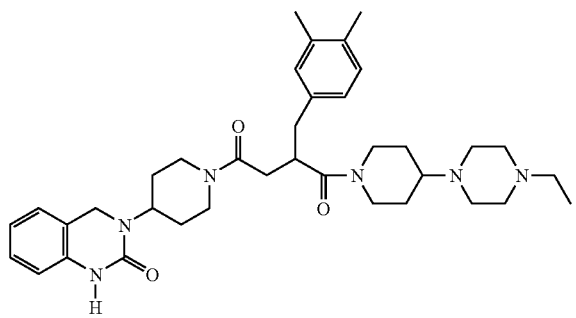

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-ethyl-4-piperidin-4-yl-piperazine

| Yield: | 29% of theory |
|---|---|
| $R_f$: | 0.61 (silica gel, DCM/MeOH/cyc/NH$_3$ 70:15:15:2) |

EXAMPLE 81

2-(3,4-dimethyl-benzyl)-1-[4-(4-isopropyl-piperazin-1-yl)-piperidin-1-yl]-4-[4-(2-oxo-1,4-dihydro-2H-quinazolin-3-yl)-piperidin-1-yl]-butan-1,4-dione

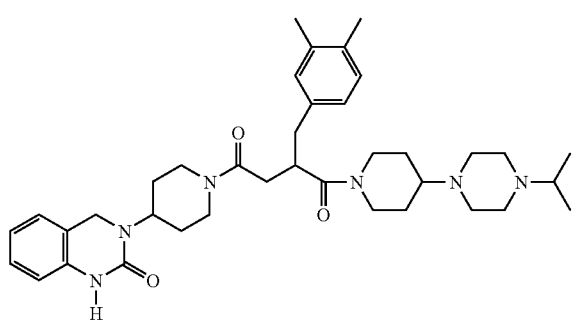

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-isopropyl-4-piperidin-4-yl-piperazine

| Yield: | 18% of theory |
|---|---|
| $R_f$: | 0.59 (silica gel, DCM/MeOH/cyc/NH$_3$ 70:15:15:2) |

EXAMPLE 82

2-(3,4-dimethyl-benzyl)-1-[4-(4-methanesulphonyl-piperazin-1-yl)-piperidin-1-yl]-4-[4-(2-oxo-1,4-dihydro-2H-quinazolin-3-yl)-piperidin-1-yl]-butan-1,4-dione

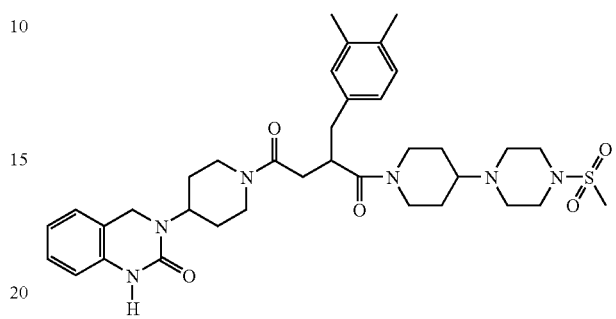

Prepared analogously to Example 76e) from 2-(3,4-dimethyl-benzyl)-4-oxo-4-[4-(2-oxo-1,4-dihydro-2H-quinazolin-3-yl)-piperidin-1-yl]-butanoic acid and 1-methanesulphonyl-4-piperidin-4-yl-piperazine.

| Yield: | 45% of theory |
|---|---|
| $R_f$: | 0.65 (silica gel, DCM/MeOH/cyc/NH$_3$ 70:15:15:2) |

EXAMPLE 83

4-(2-oxo-1,4-dihydro-2H-quinazolin-3-yl)-piperidine-1-carboxylic acid {1-(3,4-dimethyl-benzyl)-2-[4-(4-methyl-piperazin-1-yl)-piperidin-1-yl]-2-oxo-ethyl}-amide

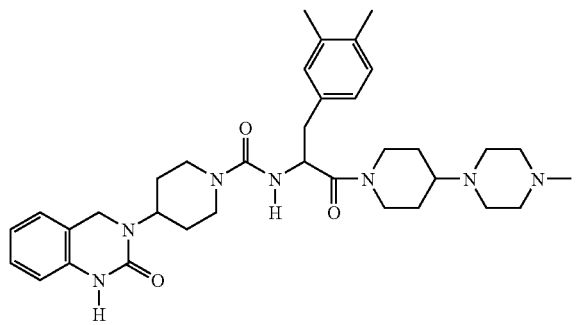

83a) ethyl 2-amino-3-(3,4-dimethyl-phenyl)-propionate

A mixture of 18.6 g (93.5 mmol) 4-bromomethyl-1,2-dimethyl-benzene, 25.0 g (93.5 mmol) ethyl(diphenylmethylidene-amino)-acetate, 3.29 g (10.0 mmol) tetrabutylammonium bromide, 41.3 g (250 mmol) K$_2$CO$_3$×1.5H$_2$O and 600 mL acetonitrile was refluxed overnight. The reaction mixture was filtered, the filtrate was evaporated down under reduced pressure, the residue was taken up in 500 mL diethyl ether and combined with 250 mL semiconc. HCl with vigorous stirring.

Then the organic phase was separated off, the aqueous phase was extracted twice with diethyl ether and neutralised by the addition of solid NaHCO₃. The aqueous phase was extracted by shaking three times with 200 mL EtOAc, the combined organic phases were washed once with water, dried over Na₂SO₄, filtered and evaporated down under reduced pressure.

| Yield: | 11.3 g (55% of theory) |
|---|---|
| R_f: | 0.62 (silica gel, DCM/MeOH/cyc/NH₃ 70:15:15:2) |

83b) ethyl 3-(3,4-dimethyl-phenyl)-2-{[4-(2-oxo-1,4-dihydro-2H-quinazolin-3-yl)-piperidine-1-carbonyl]-amino}-propionate 10.0 g (57.9 mmol) CDT were added to the solution of 11.0 g (49.7 mmol) ethyl 2-amino-3-(3,4-dimethyl-phenyl)-propionate in 250 mL THF cooled in the ice bath, stirred for 1 h while cooling with an ice bath and for 1 h at RT. Then 12.7 g (54.7 mmol) 3-piperidin-4-yl-3,4-dihydro-1H-quinazolin-2-one was added, the reaction mixture was refluxed for 2.5 h and evaporated down under reduced pressure. The residue was distributed between saturated NaHCO₃ solution and EtOAc and the aqueous phase was extracted twice more with EtOAc. The combined organic phases were dried over Na₂SO₄, filtered and evaporated down under reduced pressure.

| Yield: | 17.5 g (74% of theory) |
|---|---|
| R_f: | 0.6 (silica gel, DCM/MeOH/cyc/NH₃ 70:15:15:2) |

83c) 3-(3,4-dimethyl-phenyl)-2-{[4-(2-oxo-1,4-dihydro-2H-quinazolin-3-yl)-piperidine-1-carbonyl]-amino}-propionic acid 17.5 g (36.6 mmol) ethyl 3-(3,4-dimethyl-phenyl)-2-{[4-(2-oxo-1,4-dihydro-2H-quinazolin-3-yl)-piperidine-1-carbonyl]-amino}-propionate dissolved in 100 mL MeOH was combined with 200 mL 1 M NaOH and stirred overnight at RT. The reaction mixture was filtered, the filtrate washed three times with tert-butylmethylether and combined with 200 mL 1 M HCl. The aqueous phase was extracted three times with EtOAc, the combined organic phases were dried, filtered and evaporated down under reduced pressure. The residue was triturated with diisopropylether, suction filtered, stirred with diethyl ether and dried at 50° C. in the circulating air dryer.

| Yield: | 6.0 g (36% of theory) |
|---|---|

83d) 4-(2-oxo-1,4-dihydro-2H-quinazolin-3-yl)-piperidine-1-carboxylic acid {1-(3,4-dimethyl-benzyl)-2-[4-(4-methyl-piperazin-1-yl)-piperidin-1-yl]-2-oxo-ethyl}-amide 0.90 g (2.80 mmol) TBTU, 0.35 g (2.55 mol) HOBt, 0.49 mL (2.80 mmol) ethyldiisopropylamine was added to a mixture of 1.15 g (2.55 mol) 3-(3,4-dimethyl-phenyl)-2-{[4-(2-oxo-1,4-dihydro-2H-quinazolin-3-yl)-piperidine-1-carbonyl]-amino}-propionic acid and 100 mL THF and the mixture was stirred for 30 min at RT. Then 20 mL DMF was added, the mixture was stirred for 15 min and combined with 0.49 g (2.65 mmol) 1-methyl-4-piperidin-4-yl-piperazine. The reaction mixture was stirred overnight at RT, evaporated down under reduced pressure and the residue was combined with 70 mL saturated NaHCO₃ solution. The aqueous phase was extracted three times with DCM, the combined organic phases were dried over Na₂SO₄, filtered and evaporated down under reduced pressure. The residue was purified by column chromatography over silica gel, the product fractions were evaporated down under reduced pressure, triturated with diethyl ether and suction filtered.

| Yield: | 0.45 g (29% of theory) |
|---|---|
| EI-MS | (M)⁺ 615 |
| R_f: | 0.49 (silica gel, DCM/MeOH/cyc/NH₃ 70:15:15:2) |

EXAMPLE 84

4-(2-oxo-1,4-dihydro-2H-quinazolin-3-yl)-piperidine-1-carboxylic acid {1-(3,4-dimethyl-benzyl)-2-[4-(1-methyl-piperidin-4-yl)-piperazin-1-yl]-2-oxo-ethyl}-amide

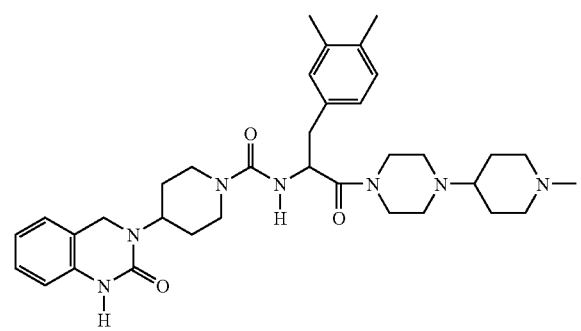

Prepared analogously to Example 83d) from 3-(3,4-dimethyl-phenyl)-2-{[4-(2-oxo-1,4-dihydro-2H-quinazolin-3-yl)-piperidine-1-carbonyl]-amino}-propionic acid and 1-methyl-4-piperidin-4-yl-piperazine

| Yield: | 19% of theory |
|---|---|
| EI-MS | (M)⁺ 615 |
| R_f: | 0.25 (silica gel, DCM/MeOH/cyc/NH₃ 70:15:15:2) |

EXAMPLE 85

4-(2-oxo-1,4-dihydro-2H-quinazolin-3-yl)-piperidine-1-carboxylic acid [1-(3,4-dimethyl-benzyl)-2-(1'-methyl-[4,4']bipiperidinyl-1-yl)-2-oxo-ethyl]-amide

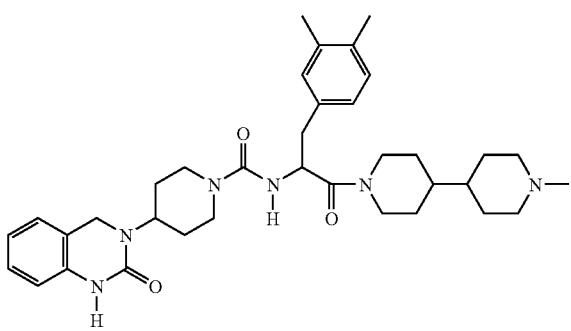

Prepared analogously to Example 83d) from 3-(3,4-dimethyl-phenyl)-2-{[4-(2-oxo-1,4-dihydro-2H-quinazolin-3-yl)-piperidine-1-carbonyl]-amino}-propionic acid and 1-methyl-[4,4']bipiperidinyl.

| Yield: | 35% of theory |
|---|---|
| EI-MS | (M)⁺ 614 |
| $R_f$: | 0.42 (silica gel, DCM/MeOH/cyc/NH$_3$ 70:15:15:2) |

EXAMPLE 86

2-(3,4-diethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

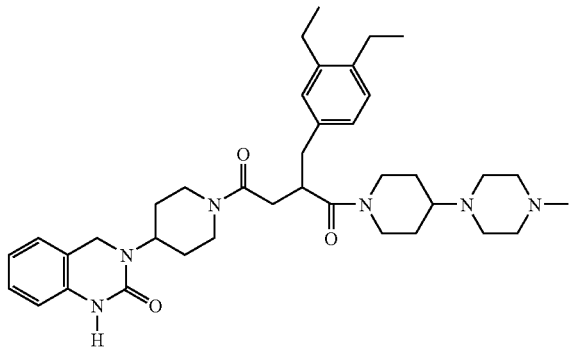

86a) tert-butyl 4-(3,4-diethyl-phenyl)-3,3-bis-ethoxycarbonyl-butanoate

Prepared analogously to Example 76a) from 4-tert-butyl 2-ethoxycarbonyl-succinate and 4-bromomethyl-1,2-diethyl-benzene.

| Yield: | 97% of theory |
|---|---|
| $R_f$: | 0.35 (silica gel, PE/EtOAc 4:1) |

86b) 4-(3,4-diethyl-phenyl)-3,3-bis-ethoxycarbonyl-butanoic acid

Prepared analogously to Example 76b) from tert-butyl (3,4-diethyl-phenyl)-3,3-bis-ethoxycarbonyl-butanoate. Yield: 100% of theory

86c) diethyl 2-(3,4-diethyl-benzyl)-2-{2-oxo-2-[4-(2-oxo-1,4-dihydro-2H-quinazolin-3-yl)-piperidin-1-yl]-ethyl}-malonate Prepared analogously to Example 76c) from 4-(3,4-diethyl-phenyl)-3,3-bis-ethoxycarbonyl-butanoic acid and 3-piperidin-4-yl-3,4-dihydro-1H-quinazolin-2-one.

| Yield: | 50% of theory |
|---|---|
| $R_f$: | 0.6 (silica gel, EtOAc) |

86d) 2-(3,4-diethyl-benzyl)-4-oxo-4-[4-(2-oxo-1,4-dihydro-2H-quinazolin-3-yl)-piperidin-1-yl]-butanoic acid Prepared analogously to Example 76d) from diethyl (3,4-diethyl-benzyl)-2-{2-oxo-2-[4-(2-oxo-1,4-dihydro-2H-quinazolin-3-yl)-piperidin-1-yl]-ethyl}-malonate

| Yield: | 67% of theory |
|---|---|
| $R_f$: | 0.6 (silica gel, PE/EtOAc/glacial acetic acid 7:3:0.3) |

86e) 2-(3,4-diethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione Prepared analogously to Example 76e) from 2-(3,4-diethyl-benzyl)-4-oxo-4-[4-(2-oxo-1,4-dihydro-2H-quinazolin-3-yl)-piperidin-1-yl]-butanoic acid and 1-methyl-4-piperidin-4-yl-piperazine

| Yield: | 16% of theory |
|---|---|
| ESI-MS: | (M + H)⁺ 643 |
| $R_f$: | 0.3 (silica gel, MeOH) |

EXAMPLE 87

2-(3,4-diethyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione

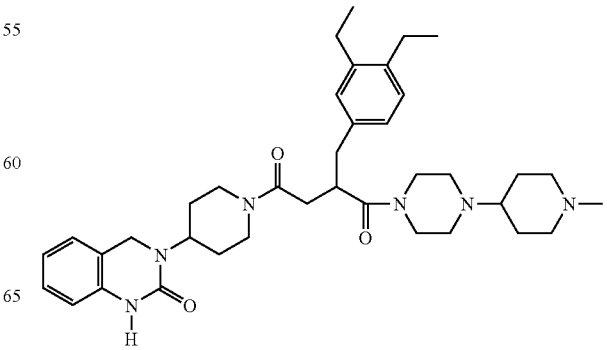

Prepared analogously to Example 76e) from 2-(3,4-diethyl-benzyl)-4-oxo-4-[4-(2-oxo-1,4-dihydro-2H-quinazolin-3-yl)-piperidin-1-yl]-butanoic acid and 1-(1-methyl-piperidin-4-yl)-piperazine.

| Yield: | 18% of theory |
|---|---|
| ESI-MS: | (M + H)⁺ 643 |
| $R_f$: | 0.15 (silica gel, MeOH/NH₃ 10:0.3) |

EXAMPLE 88 methyl {1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetate 88c) diethyl 2-{2-oxo-2-[4-(2-oxo-1,4-dihydro-2H-quinazolin-3-yl)-piperidin-1-yl]-ethyl}-2-(5,6,7,8-tetrahydro-naphthalen-2-ylmethyl)-malonate Prepared analogously to Example 76c) from 3,3-bis-ethoxycarbonyl-4-(5,6,7,8-tetrahydro-naphthalen-2-yl)-butanoic acid and 3-piperidin-4-yl-3,4-dihydro-1H-quinazolin-2-one.

| Yield: | 71% of theory |
|---|---|

88d) 4-oxo-4-[4-(2-oxo-1,4-dihydro-2H-quinazolin-3-yl)-piperidin-1-yl]-2-(5,6,7,8-tetrahydro-naphthalen-2-ylmethyl)-butanoic acid Prepared analogously to Example 76d) from diethyl 2-{2-oxo-2-[4-(2-oxo-1,4-dihydro-2H-quinazolin-3-yl)-piperidin-1-yl]-ethyl}-2-(5,6,7,8-tetrahydro-naphthalen-2-ylmethyl)-malonate.

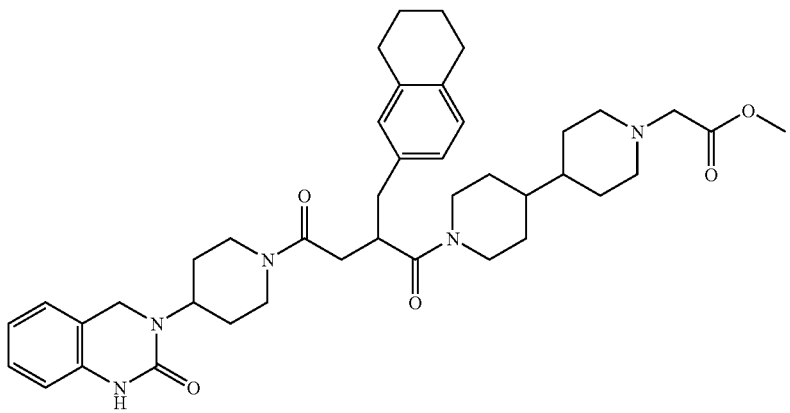

| Yield: | 95% of theory |
|---|---|

88a) tert-butyl 3,3-bis-ethoxycarbonyl-4-(5,6,7,8-tetrahydro-naphthalen-2-yl)-butanoate Prepared analogously to Example 76a) from 4-tert-butyl 2-ethoxycarbonyl-succinate and 6-bromomethyl-1,2,3,4-tetrahydro-naphthalene.

| Yield: | 66% of theory |
|---|---|

88b) 3,3-bis-ethoxycarbonyl-4-(5,6,7,8-tetrahydro-naphthalen-2-yl)-butanoic acid Prepared analogously to Example 76b) from tert-butyl 3,3-bis-ethoxycarbonyl-4-(5,6,7,8-tetrahydro-naphthalen-2-yl)-butanoate

| Yield: | 100% of theory |
|---|---|

88e) methyl {1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetate Prepared analogously to Example 76e) from 4-oxo-4-[4-(2-oxo-1,4-dihydro-2H-quinazolin-3-yl)-piperidin-1-yl]-2-(5,6,7,8-tetrahydro-naphthalen-2-ylmethyl)-butanoic acid and methyl [4,4']bipiperidinyl-1-yl-acetate.

| Yield: | 6% of theory |
|---|---|
| EI-MS: | (M)⁺ 697 |

EXAMPLE 89

{1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetic acid

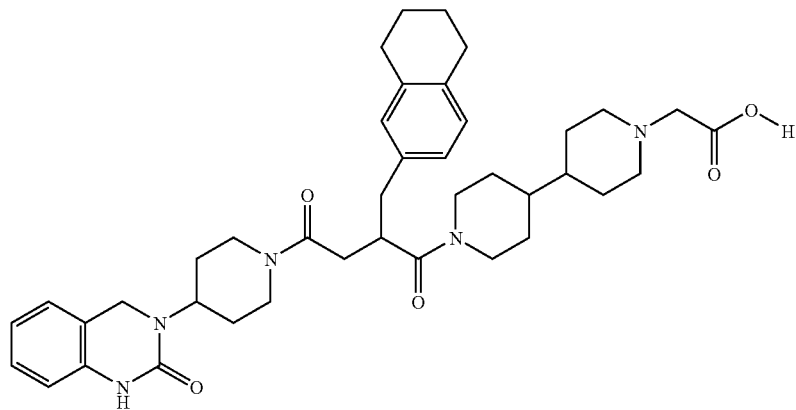

Prepared analogously to Example 66) from methyl {1'-[4-oxo-4-[4-(2-oxo-1,4-dihydro-2H-quinazolin-3-yl)-piperidin-1-yl]-2-(5,6,7,8-tetrahydro-naphthalen-2-ylmethyl)-butyryl]-[4,4']bipiperidinyl-1-yl}-acetate

| Yield: | 17% of theory |
|---|---|
| ESI-MS: | (M + H)+ 684 |

EXAMPLE 90 methyl (1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetate

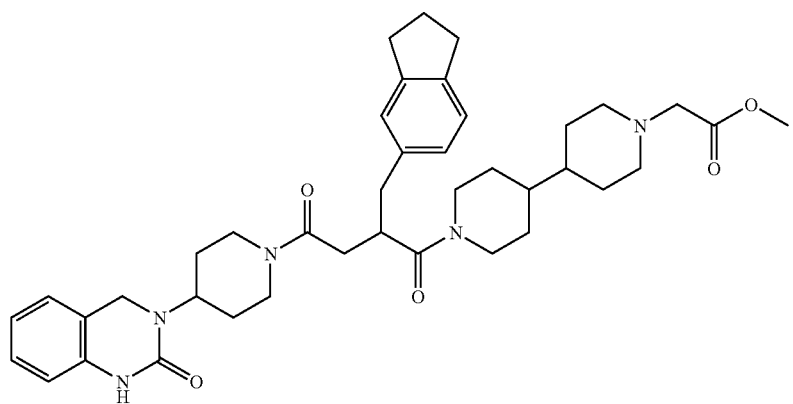

90a) tert-butyl 3,3-bis-ethoxycarbonyl-4-indan-5-yl-butanoate

Prepared analogously to Example 76a) from 4-tert-butyl 2-ethoxycarbonyl-succinate and 5-bromomethyl-indane.

| Yield: | 100% of theory |
|---|---|

90b) 3,3-bis-ethoxycarbonyl-4-indan-5-yl-butanoic acid

Prepared analogously to Example 76b) from tert-butyl 3,3-bis-ethoxycarbonyl-4-indan-5-yl-butanoate

| Yield: | 100% of theory |
|---|---|

90c) diethyl 2-indan-5-ylmethyl-2-{2-oxo-2-[4-(2-oxo-1,4-dihydro-2H-quinazolin-3-yl)-piperidin-1-yl]-ethyl}-malonate Prepared analogously to Example 76c) from 3,3-bis-ethoxycarbonyl-4-indan-5-yl-butanoic acid and 3-piperidin-4-yl-3,4-dihydro-1H-quinazolin-2-one.

| Yield: | 61% of theory |
|---|---|

90d) 2-indan-5-ylmethyl-4-oxo-4-[4-(2-oxo-1,4-dihydro-2H-quinazolin-3-yl)-piperidin-1-yl]-butanoic acid Prepared analogously to Example 76d) from diethyl 2-indan-5-ylmethyl-2-{2-oxo-2-[4-(2-oxo-1,4-dihydro-2H-quinazolin-3-yl)-piperidin-1-yl]-ethyl}-malonate

| Yield: | 100% of theory |
|---|---|

90e) methyl (1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetate Prepared analogously to Example 76e) from and 2-indan-5-ylmethyl-4-oxo-4-[4-(2-oxo-1,4-dihydro-2H-quinazolin-3-yl)-piperidin-1-yl]-butanoic acid and methyl[4,4']bipiperidinyl-1-yl-acetate.

| Yield: | 5% of theory |
|---|---|
| ESI-MS: | (M + H)$^+$ 684 |

EXAMPLE 91

((1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetic acid

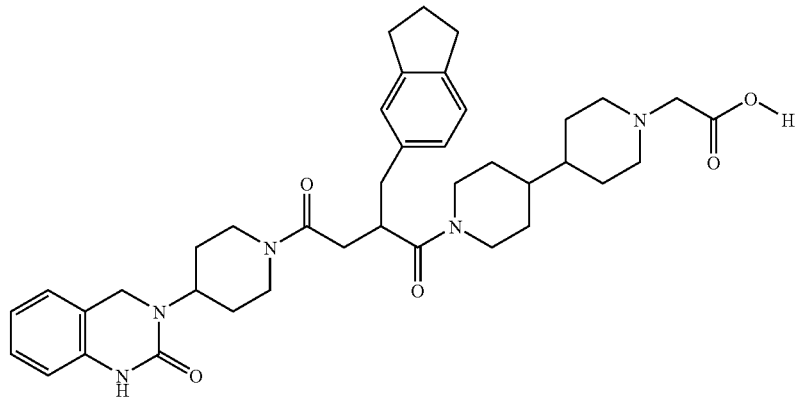

Prepared analogously to Example 66) from methyl (1'-{2-indan-5-ylmethyl-4-oxo-4-[4-(2-oxo-1,4-dihydro-2H-quinazolin-3-yl)-piperidin-1-yl]-butyryl}-[4,4']bipiperidinyl-1-yl)-acetate

| Yield: | 10% of theory |
|---|---|
| ESI-MS: | (M + H)$^+$ 670 |

EXAMPLE 92

[4-(4-methyl-piperazin-1-yl)-piperidin-1-yl]-4-[4-(2-oxo-1,4-dihydro-2H-quinazolin-3-yl)-piperidin-1-yl]-2-(5,6,7,8-tetrahydro-naphthalen-2-ylmethyl)-butan-1,4-dione

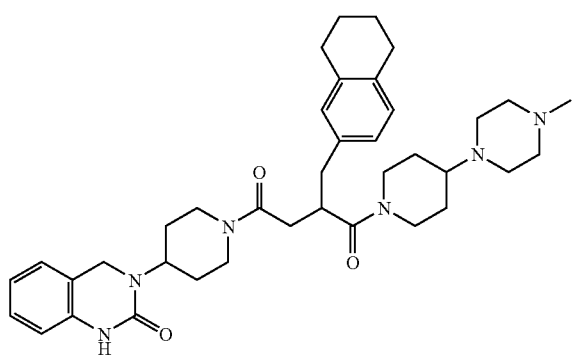

Prepared analogously to Example 76e) from 4-oxo-4-[4-(2-oxo-1,4-dihydro-2H-quinazolin-3-yl)-piperidin-1-yl]-2-(5,6,7,8-tetrahydro-naphthalen-2-ylmethyl)-butanoic acid and 1-methyl-4-piperidin-4-yl-piperazine.

| Yield: | 46% of theory |
|---|---|
| retention time (HPLC): | 6.0 min (method A) |

EXAMPLE 93

1-(1'-methyl-[4,4']bipiperidinyl-1-yl)-4-[4-(2-oxo-1,4-dihydro-2H-quinazolin-3-yl)-piperidin-1-yl]-2-(5,6,7,8-tetrahydro-naphthalen-2-ylmethyl)-butan-1,4-dione

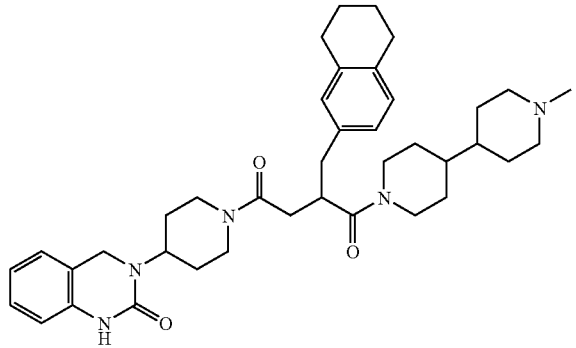

Prepared analogously to Example 76e) from 4-oxo-4-[4-(2-oxo-1,4-dihydro-2H-quinazolin-3-yl)-piperidin-1-yl]-2-(5,6,7,8-tetrahydro-naphthalen-2-ylmethyl)-butanoic acid and 1-methyl-[4,4']bipiperidinyl.

| Yield: | 44% of theory |
|---|---|
| retention time (HPLC): | 6.5 min (method A) |

EXAMPLE 94

2-indan-5-ylmethyl-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

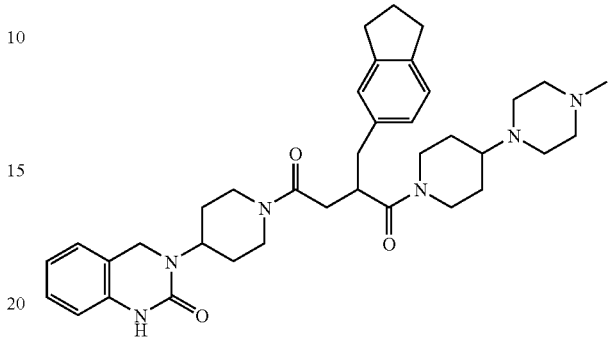

Prepared analogously to Example 76e) from and 2-indan-5-ylmethyl-4-oxo-4-[4-(2-oxo-1,4-dihydro-2H-quinazolin-3-yl)-piperidin-1-yl]-butanoic acid and 1-methyl-4-piperidin-4-yl-piperazine

| Yield: | 51% of theory |
|---|---|
| retention time (HPLC): | 5.7 min (method A) |

EXAMPLE 95

2-indan-5-ylmethyl-1-(1'-methyl-[4,4']bipiperidinyl-1-yl)-4-[4-(2-oxo-1,4-dihydro-2H-quinazolin-3-yl)-piperidin-1-yl]-butan-1,4-dione

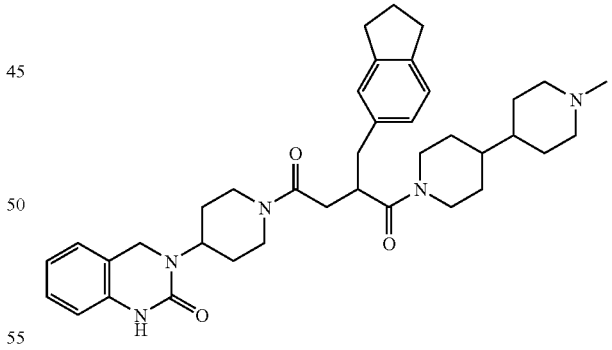

Prepared analogously to Example 76e) from and 2-indan-5-ylmethyl-4-oxo-4-[4-(2-oxo-1,4-dihydro-2H-quinazolin-3-yl)-piperidin-1-yl]-butanoic acid and 1-methyl-[4,4']bipiperidinyl.

| Yield: | 51% of theory |
|---|---|
| retention time (HPLC): | 6.2 min (method A) |

The following compounds may be prepared by the processes described:

EXAMPLE 96

1-(1'-methyl-[4,4']bipiperidinyl-1-yl)-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione

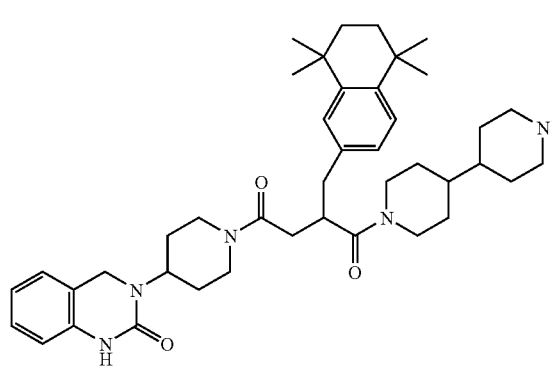

EXAMPLE 97

1-[4-(4-methyl-piperazin-1-yl)-piperidin-1-yl]-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione

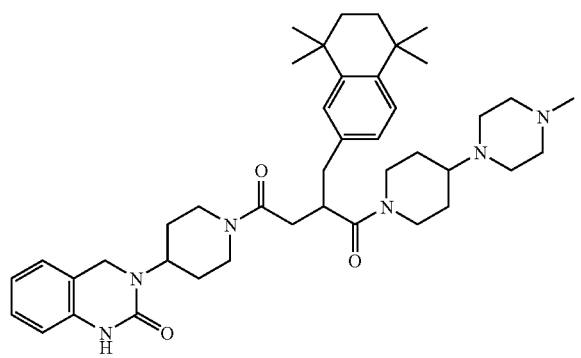

EXAMPLE 98

1-[1,4']bipiperidinyl-1'-yl-4-[4-(2-oxo-1,4-dihydro-2H-quinazolin-3-yl)-piperidin-1-yl]-2-(5,5,8,8-tetramethyl-5,6,7,8-tetrahydro-naphthalen-2-ylmethyl)-butan-1,4-dione

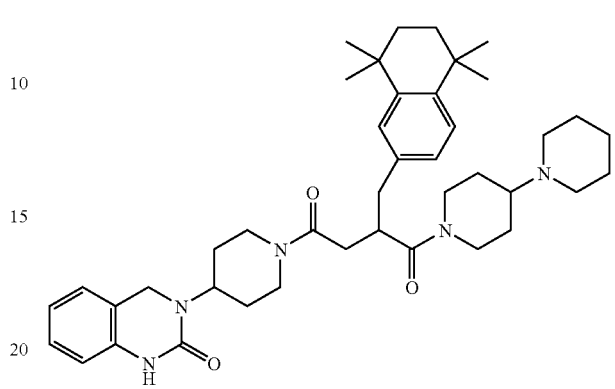

EXAMPLE 99

4-(2-oxo-1,2,4,5-tetrahydro-1,3-benzodiazepin-3-yl)-piperidine-1-carboxylic acid {(R)-1-(3,4-bis-pentafluoroethyl-benzyl)-2-[4-(4-methyl-piperazin-1-yl)-piperidin-1-yl]-2-oxo-ethyl}-amide

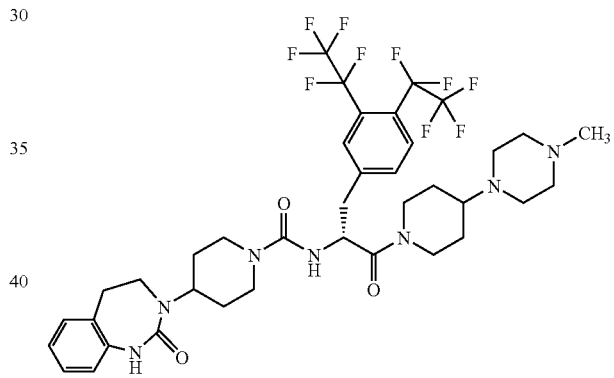

EXAMPLE 100

4-(2-oxo-1,2,4,5-tetrahydro-1,3-benzodiazepin-3-yl)-piperidine-1-carboxylic acid {(R)-1-(3-ethyl-4-methyl-benzyl)-2-[4-(4-methyl-piperazin-1-yl)-piperidin-1-yl]-2-oxo-ethyl}-amide

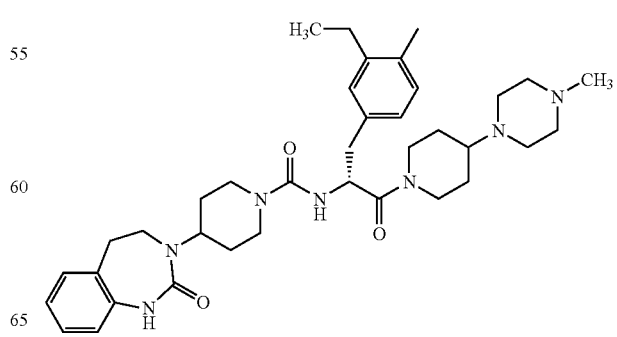

EXAMPLE 101

(R)-1-(3,4-diethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

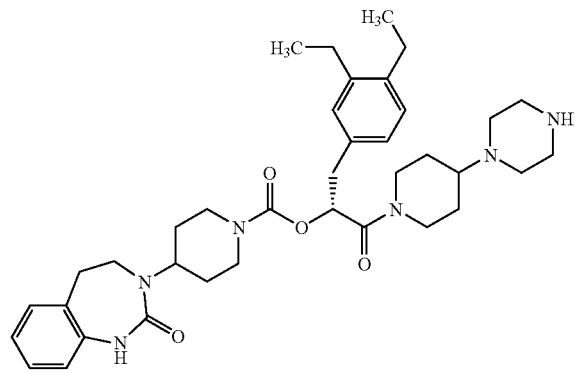

EXAMPLE 102

(R)-1-(3,4-diethyl-benzyl)-2-[4-(1-ethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

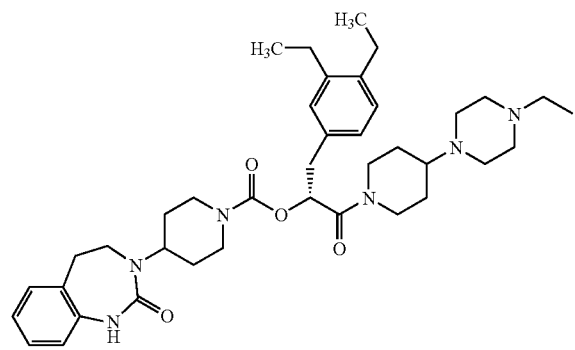

EXAMPLE 103

(R)-2-oxo-2-(4-piperazin-1-yl-piperidin-1-yl)-1-(5,6,7,8-tetrahydro-naphthalen-2-ylmethyl)-ethyl 4-(2-oxo-1,2,4,5-tetrahydro-1,3-benzodiazepin-3-yl)-piperidine-1-carboxylate

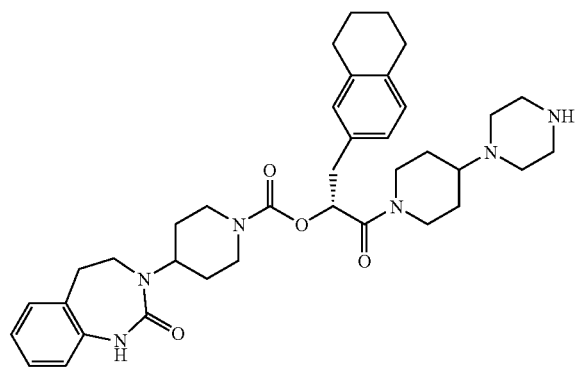

EXAMPLE 104

(S)-2-(3,4-diethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione

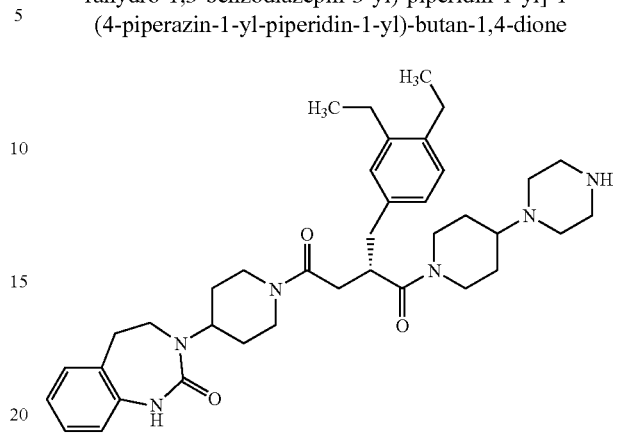

EXAMPLE 105

(S)-2-(3,4-diethyl-benzyl)-4-[4-(2-oxo-1,2,4,5-tetrahydro-1,3-benzodiazepin-3-yl)-piperidin-1-yl]-1-(4-piperidin-4-yl-piperazin-1-yl)-butan-1,4-dione

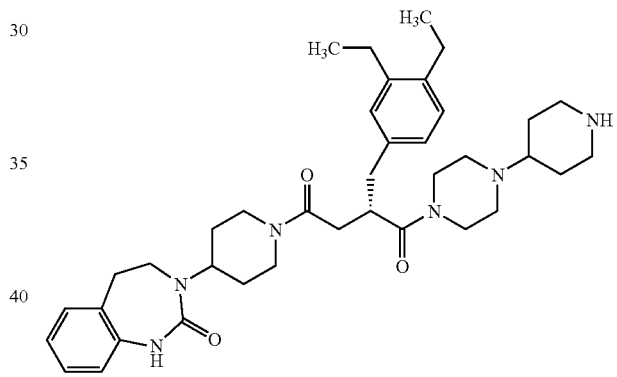

EXAMPLE 106

(S)-2-(3,4-diethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione

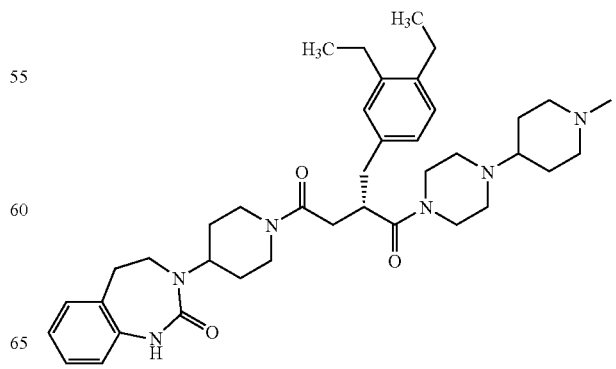

EXAMPLE 107

(S)-2-(3,4-diethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione

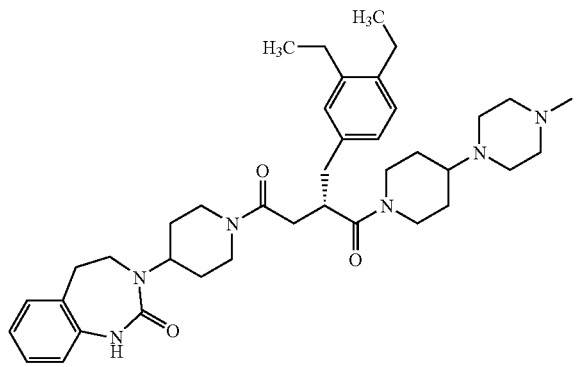

EXAMPLE 108

(S)-1-[1,4']bipiperidinyl-1'-yl-2-(3,4-diethyl-benzyl)-4-[4-(2-oxo-1,2,4,5-tetrahydro-1,3-benzodiazepin-3-yl)-piperidin-1-yl]-butan-1,4-dione

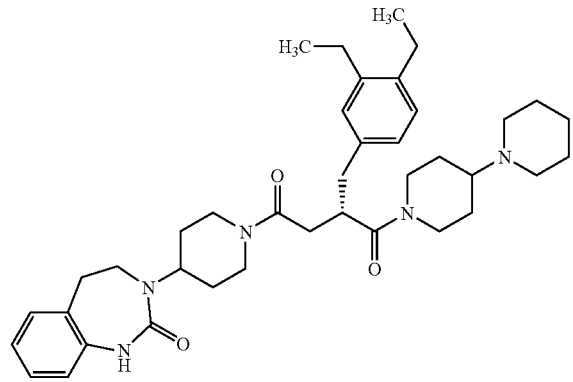

EXAMPLE 109

4-(2-oxo-1,2,4,5-tetrahydro-1,3-benzodiazepin-3-yl)-piperidine-1-carboxylic acid {(R)-1-(3,4-bis-trifluoromethyl-benzyl)-2-[4-(4-methyl-piperazin-1-yl)-piperidin-1-yl]-2-oxo-ethyl}-amide

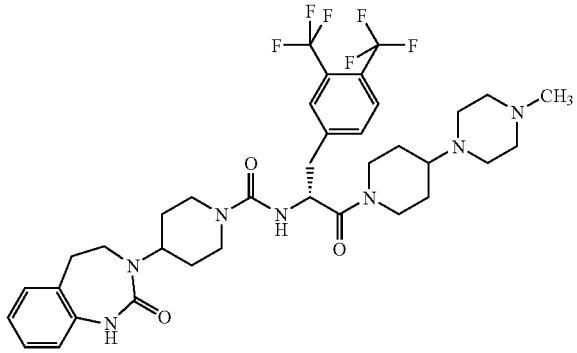

EXAMPLE 110

(S)-2-(3,4-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione

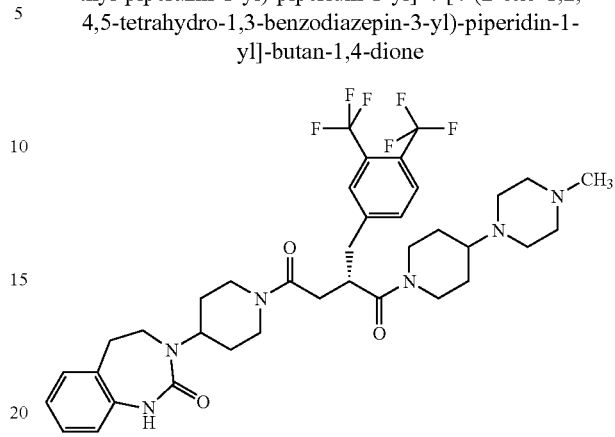

EXAMPLE 111

(R)-1-(3,4-bis-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

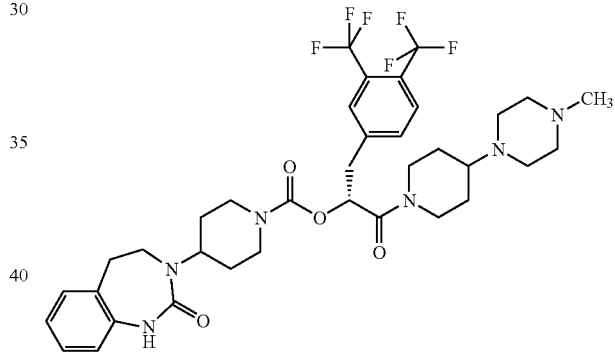

EXAMPLE 112

(S)-2-(3,4-diethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione

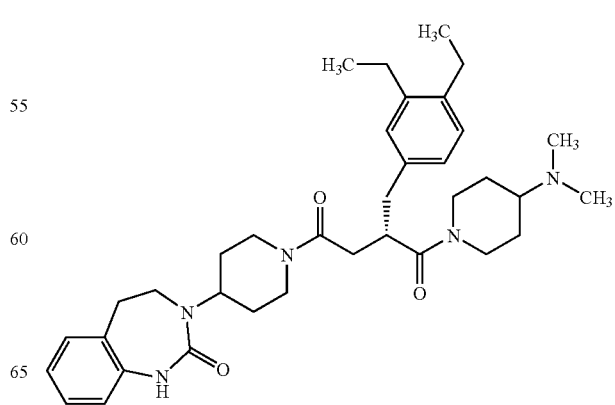

EXAMPLE 113

(R)-1-(3,4-diethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate

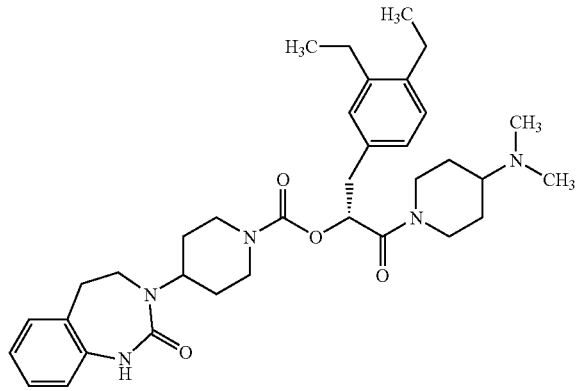

EXAMPLE 114

[(R)-2-(4-amino-piperidin-1-yl)-1-(3,4-diethyl-benzyl)-2-oxo-ethyl]-amide 4-(2-oxo-1,2,4,5-tetrahydro-1,3-benzodiazepin-3-yl)-piperidine-1-carboxylate

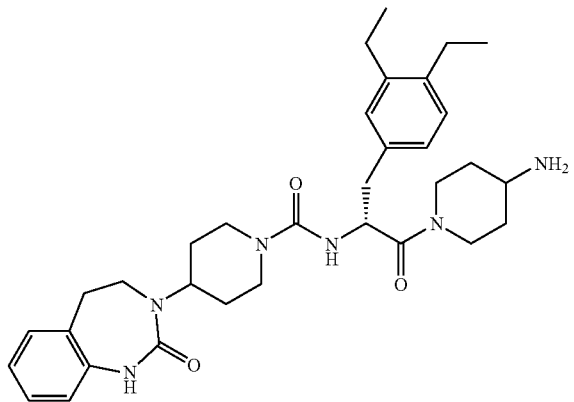

EXAMPLE 115

4-(2-oxo-1,4-dihydro-2H-quinazolin-3-yl)-piperidine-1-carboxylic acid [2-[1,4']bipiperidinyl-1'-yl-1-(3,4-dimethyl-benzyl)-2-oxo-ethyl]-amide

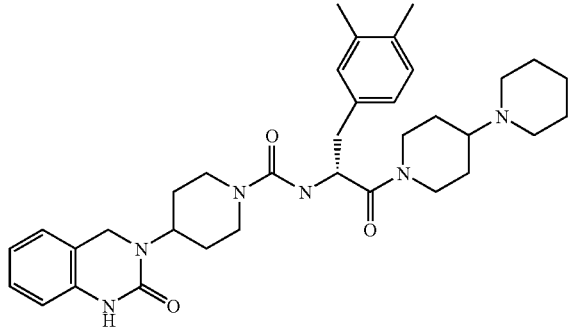

EXAMPLE 116

(S)-2-(3,4-diethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione

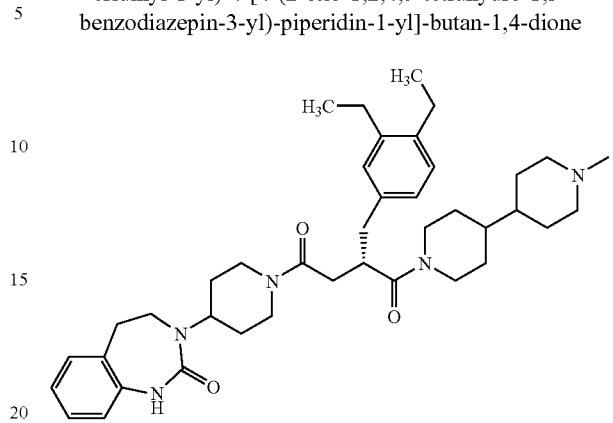

EXAMPLE 117

(S)-1-4,4'-bipiperidinyl-1-yl-2-(3,4-diethyl-benzyl)-4-[4-(2-oxo-1,2,4,5-tetrahydro-1,3-benzodiazepin-3-yl)-piperidin-1-yl]-butan-1,4-dione

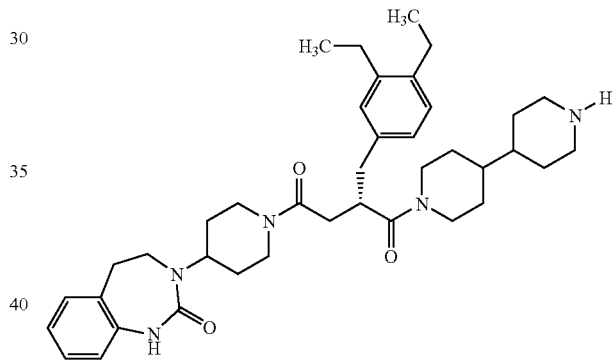

EXAMPLE 118

4-(2-oxo-1,2,4,5-tetrahydro-1,3-benzodiazepin-3-yl)-piperidine-1-carboxylic acid-{(R)-1-(4-ethyl-3-trifluoromethyl-benzyl)-2-[4-(4-methyl-piperazin-1-yl)-piperidin-1-yl]-2-oxo-ethyl}-amide

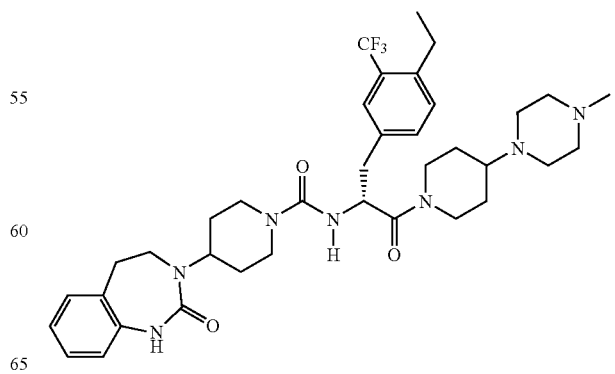

EXAMPLE 119

4-(2-oxo-1,2,4,5-tetrahydro-1,3-benzodiazepin-3-yl)-piperidine-1-carboxylic acid-{(R)-1-(4-ethyl-3-trifluoromethyl-benzyl)-2-[4-(1-methyl-piperidin-4-yl)-piperazin-1-yl]-2-oxo-ethyl}-amide

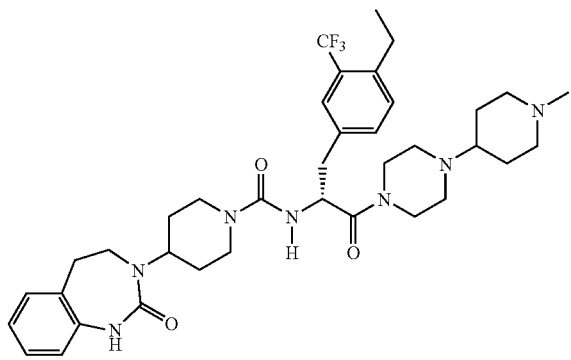

EXAMPLE 120

4-(2-oxo-1,2,4,5-tetrahydro-1,3-benzodiazepin-3-yl)-piperidine-1-carboxylic acid-[(R)-1-(4-ethyl-3-trifluoromethyl-benzyl)-2-(1'-methyl-4,4'-bipiperidinyl-1-yl)-2-oxo-ethyl]-amide

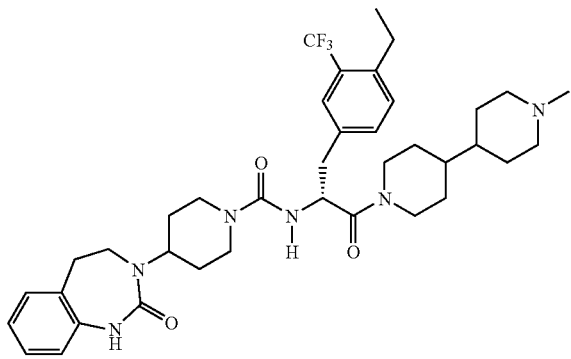

EXAMPLE 121

4-(2-oxo-1,2,4,5-tetrahydro-1,3-benzodiazepin-3-yl)-piperidine-1-carboxylic acid-[(R)-2-1,4'-bipiperidinyl-1'-yl-1-(4-ethyl-3-trifluoromethyl-benzyl)-2-oxo-ethyl]-amide

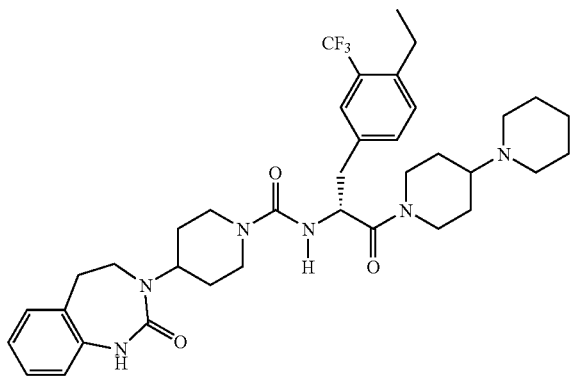

EXAMPLE 122

4-(2-oxo-1,2,4,5-tetrahydro-1,3-benzodiazepin-3-yl)-piperidine-1-carboxylic acid-[(R)-2-(4-dimethylamino-piperidin-1-yl)-1-(4-ethyl-3-trifluoromethyl-benzyl)-2-oxo-ethyl]-amide

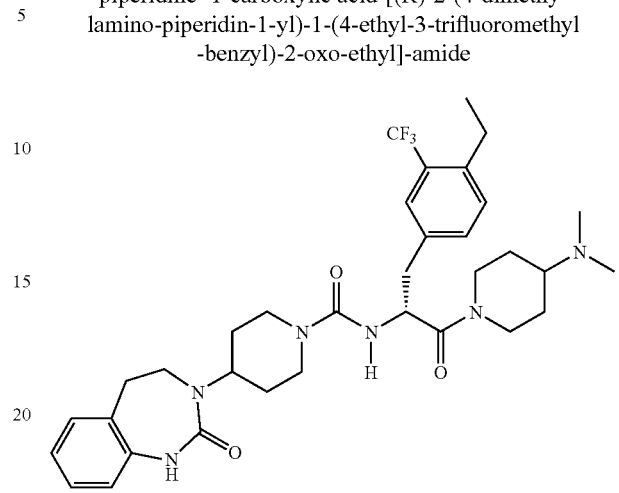

EXAMPLE 123

4-(2-oxo-1,2,4,5-tetrahydro-1,3-benzodiazepin-3-yl)-piperidine-1-carboxylic acid-{(R)-1-(3-ethyl-4-trifluoromethyl-benzyl)-2-[4-(4-methyl-piperazin-1-yl)-piperidin-1-yl]-2-oxo-ethyl}-amide

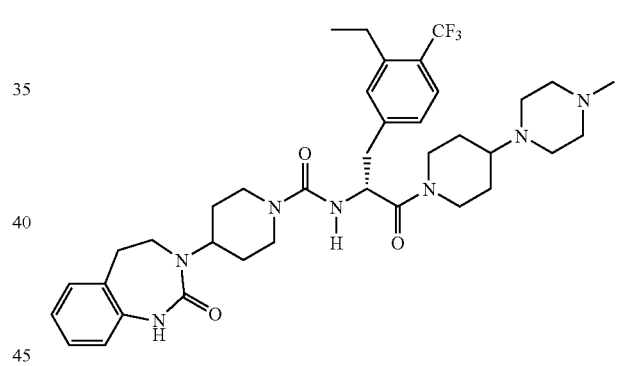

EXAMPLE 124

4-(2-oxo-1,2,4,5-tetrahydro-1,3-benzodiazepin-3-yl)-piperidine-1-carboxylic acid-{(R)-1-(3-ethyl-4-trifluoromethyl-benzyl)-2-[4-(1-methyl-piperidin-4-yl)-piperazin-1-yl]-2-oxo-ethyl}-amide

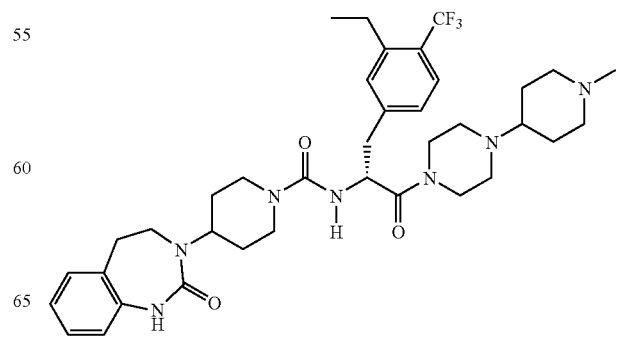

EXAMPLE 125

4-(2-oxo-1,2,4,5-tetrahydro-1,3-benzodiazepin-3-yl)-piperidine -1-carboxylic acid-[(R)-1-(3-ethyl-4-trifluoromethyl-benzyl)-2-(1'-methyl-4,4'-bipiperidinyl-1-yl)-2-oxo-ethyl-amide

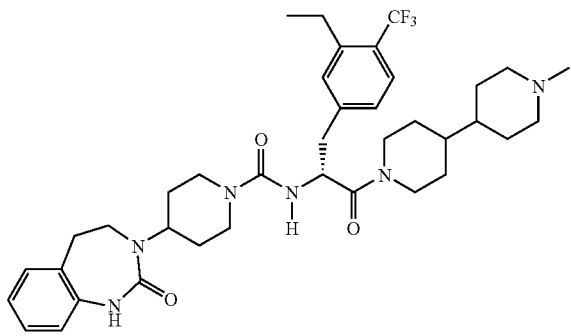

EXAMPLE 126

4-(2-oxo-1,2,4,5-tetrahydro-1,3-benzodiazepin-3-yl)-piperidine -1-carboxylic acid-[(R)-2-1,4'-bipiperidinyl-1'-yl-1-(3-ethyl-4-trifluoromethyl-benzyl)-2-oxo-ethyl]-amide

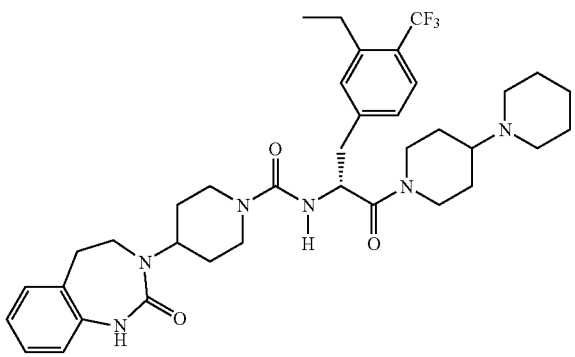

EXAMPLE 127

4-(2-oxo-1,2,4,5-tetrahydro-1,3-benzodiazepin-3-yl)-piperidine -1'-carboxylic acid-[(R)-2-(4-dimethylamino-piperidin-1-yl)-1-(3-ethyl-4-trifluoromethyl-benzyl)-2-oxo-ethyl]-amide

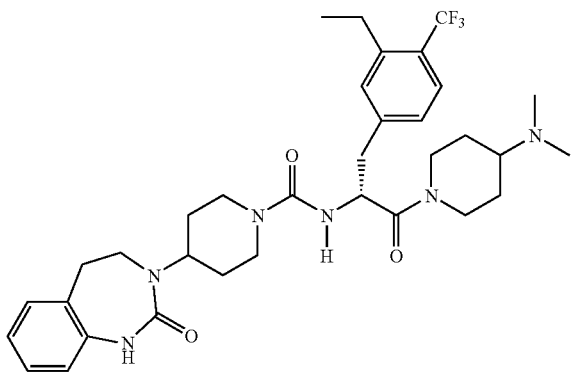

The following Examples describe the preparation of pharmaceutical formulations which contain as active substance any desired compound of general formula (I):

EXAMPLE I

| Capsules for powder inhalation containing 1 mg of active ingredient | |
|---|---|
| Composition: | |
| 1 capsule for powder inhalation contains: | |
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

| Inhalable solution for Respimat ® containing 1 mg of active ingredient | |
|---|---|
| Composition: | |
| 1 puff contains: | |
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

EXAMPLE III

| Inhalable solution for nebulisers containing 1 mg of active ingredient | |
|---|---|
| Composition: | |
| 1 vial contains: | |
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE IV

| Propellant gas-operated metering aerosol containing 1 mg of active ingredient Composition: 1 puff contains: | |
| --- | --- |
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

EXAMPLE V

| Nasal spray containing 1 mg of active ingredient Composition: | |
| --- | --- |
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

| Injectable solution containing 5 mg of active substance per 5 ml Composition: | |
| --- | --- |
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

| Injectable solution containing 100 mg of active substance per 20 ml Composition: | |
| --- | --- |
| active substance | 100 mg |
| monopotassium dihydrogen phosphate = $KH_2PO_4$ | 12 mg |
| disodium hydrogen phosphate = | 2 mg |

| Injectable solution containing 100 mg of active substance per 20 ml Composition: | |
| --- | --- |
| $Na_2HPO_4 \cdot 2H_2O$ | |
| sodium chloride | 180 mg |
| human serum albumin | 50 mg |
| Polysorbate 80 | 20 mg |
| water for injections ad | 10 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

EXAMPLE VIII

| Lyophilisate containing 10 mg of active substance Composition: | |
| --- | --- |
| Active substance | 10 mg |
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

| Solvent for lyophilisate: | |
| --- | --- |
| Polysorbate 80 = Tween 80 | 20 mg |
| mannitol | 200 mg |
| water for injections ad | 10 ml |

Preparation:

Polysorbate 80 and mannitol are dissolved in water for injections (WfI); transferred into ampoules.

EXAMPLE IX

| Tablets containing 20 mg of active substance Composition: | |
| --- | --- |
| active substance | 20 mg |
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE X

| Capsules containing 20 mg active substance Composition: | |
|---|---|
| active substance | 20 mg |
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size for 3 hard gelatine capsules in a capsule filling machine.

EXAMPLE XI

| Suppositories containing 50 mg of active substance Composition: | |
|---|---|
| active substance | 50 mg |
| hard fat (*Adeps solidus*) q.s. ad | 1700 mg |

Preparation:
Hard fat is melted at about 38° C.; ground active substance is homogeneously dispersed in the molten hard fat; after cooling to about 35° C. it is poured into chilled moulds.

EXAMPLE XII

| Injectable solution containing 10 mg of active substance per 1 ml Composition: | |
|---|---|
| active substance | 10 mg |
| mannitol | 50 mg |
| human serum albumin | 10 mg |
| water for injections ad | 1 ml |

Preparation:
Mannitol is dissolved in water for injections (WfI); human serum albumin is added; active ingredient is dissolved with heating; made up to specified volume with WfI; transferred into ampoules under nitrogen gas.

What is claimed is:
1. A compound selected from the group consisting of:
(1) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,
(6) 4-(2-oxo-1,2,4,5-tetrahydro-1,3-benzodiazepin-3-yl)-piperidine-1-carboxylic acid-[1-(3,4-diethyl-benzyl)-2-oxo-2-(4-pyridin-4-yl-piperazin-1-yl)-ethyl]-amide,
(13) 4-(2-oxo-1,2,4,5-tetrahydro-1,3-benzodiazepin-3-yl)-piperidine-1-carboxylic acid-{(R)-1-(3,4-diethyl-benzyl)-2-[4-(8-methyl-8-aza-bicyclo [3.2.1]oct-3-yl)-piperazin-1-yl]-2-oxo-ethyl}-amide,
(31) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyridin-4-yl-piperazin-1-yl)-ethyl]-amide,
(35) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-ethyl-piperidin-4-yl)-piperazin-1-yl]-2-oxo-ethyl}-amide,
(42) 4-(2-oxo-1,2,4,5-tetrahydro-1,3-benzodiazepin-3-yl)-piperidine-1-carboxylic acid-((R)-1-(3,4-diethyl-benzyl)-2-oxo-2-{4-[4-(2,2,2-trifluoro-acetyl)-phenyl]-pipera-zin-l-yl}-ethyl)-amide,
(43) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperidin-4-yl-piperazin-1-yl)-ethyl]-amide,
(49) 4-(2-oxo-1,2,4,5-tetrahydro-1,3-benzodiazepin-3-yl)-piperidine-1-carboxylic acid-[(R)-2-[4-(1-methyl-piperidin-4-yl)-piperazin-1-yl]-2-oxo-1-(5,6,7,8-tetrahydro-naphthalen-2-ylmethyl)-ethyl]-amide,
(50) 4-(2-oxo-1,2,4,5-tetrahydro-1,3-benzodiazepin-3-yl)-piperidine-1-carboxylic acid-[(R)-2-[4-(1-benzyl-piperidin-4-yl)-piperazin-1-yl]-2-oxo-1-(5,6,7,8-tetrahydro-naphthalen-2-ylmethyl)-ethyl]-amide,
(52) 4-(2-oxo-1,2,4,5-tetrahydro-1,3-benzodiazepin-3-yl)-piperidine-1-carboxylic acid-[(R)-2-oxo-2-(4-piperidin-4-yl-piperazin-1-yl)-1-(5,6,7,8-tetrahydro-naphthalen-2-ylmethyl)-ethyl]-amide,
(60) (R)-1-(3,4-diethyl-benzyl)-2-[4-(1-methyl-piperidin-4-yl)-piperazin-1-yl]-2-oxo-ethyl4-(2-oxo-1,2,4,5-tetrahydro-1,3-benzodiazepin-3-yl)-piperidine-1-carboxylate,
(73) N-[1-{(R)-1-(3,4-diethyl-benzyl)-2-[4-(1-methyl-piperidin-4-yl)-piperazin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide,
(102) (R)-1-(3,4-diethyl-benzyl)-2-[4-(1-ethyl-piperidin-4-yl)-piperazin-1-yl]-2-oxo-ethyl4-(2-oxo-1,2,4,5-tetrahydro-1,3-benzodiazepin-3-yl)-piperidine-1-carboxylate,
(105) (S)-2-(3,4-diethyl-benzyl)-4-[4-(2-oxo-1,2,4,5-tetrahydro-1,3-benzodiazepin-3-yl)-piperidin-1-yl]-1-(4-piperidin-4-yl-piperazin-1-yl)-butan-1,4-dione,
(106) (S)-2-(3,4-diethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,
(119) 4-(2-oxo-1,2,4,5-tetrahydro-1,3-benzodiazepin-3-yl)-piperidine-1-carboxylic acid-{(R)-1-(4-ethyl-3-trifluoromethyl-benzyl)-2-[4-(1-methyl-piperidin-4-yl)-piperazin-1-yl]-2-oxo-ethyl}-amide, and
(124) 4-(2-oxo-1,2,4,5-tetrahydro-1,3-benzodiazepin-3-yl)-piperidine-1-carboxylic acid-{(R)-1-(3-ethyl-4-trifluoromethyl-benzyl)-2-[4-(1-methyl-piperidin-4-yl)-piperazin-1-yl]-2-oxo-ethyl}-amide,
or a salt thereof.
2. A compound selected from the group consisting of:
(1) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide,
(5) 4-(2-oxo-1,2,4,5-tetrahydro-1,3-benzodiazepin-3-yl)-piperidine-1-carboxylic acid-[1-(3,4-diethyl-benzyl)-2-oxo-2-(4-pyridine-4-yl-piperazin-1-yl)-ethyl]-amide,

(12) 4-(2-oxo-1,2,4,5-tetrahydro-1,3-benzodiazepin-3-yl)-piperidine-1-carboxylic acid-{(R)-1-(3,4-diethyl-benzyl)-2-[4-(8-methyl-8-aza-bicyclo[3.2.1]oct-3-yl)-piperazin-1-yl]-2-oxo-ethyl}-amide,

(25) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-pyridine-4-yl-piperazin-1-yl)-ethyl]-amide,

(28) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-ethyl-piperidin-4-yl)-piperazin-1-yl]-2-oxo-ethyl}-amide,

(32) 4-(2-oxo-1,2,4,5-tetrahydro-1,3-benzodiazepin-3-yl)-piperidine-1-carboxylic acid-[(R)-1-(3,4-diethyl-benzyl)-2-oxo-2-(4-piperidin-4-yl-piperazin-1-yl)-ethyl]-amide,

(34) 4-(2-oxo-1,2,4,5-tetrahydro-1,3-benzodiazepin-3-yl)-piperidine-1-carboxylic acid-[(R)-2-[4-(1-methyl-piperidin-4-yl)-piperazin-1-yl]-2-oxo-1-(5,6,7,8-tetrahydro-naphthalen-2-ylmethyl)-ethyl]-amide,

(35) 4-(2-oxo-1,2,4,5-tetrahydro-1,3-benzodiazepin-3-yl)-piperidine-1-carboxylic acid-[(R)-2-oxo-2-(4-piperidin-4-yl-piperazin-1-yl)-1-(5,6,7,8-tetrahydro-naphthalen-2-ylmethyl)-ethyl]-amide,

(42) (R)-1-(3,4-diethyl-benzyl)-2-[4-(1-methyl-piperidin-4-yl)-piperazin-1-yl]-2-oxo-ethyl4-(2-oxo-1,2,4,5-tetrahydro-1,3-benzodiazepin-3-yl)-piperidine-1-carboxylate, and

(49) N-[1-{(R)-1-(3,4-diethyl-benzyl)-2-[4-(1-methyl-piperidin-4-yl)-piperazin-1-yl]-2-oxo-ethylamino}-1-[4-(2-oxo-1,2,4,5-tetrahydro-1,3-benzodiazepin-3-yl)-piperidin-1-yl]-meth-(Z)-ylidene]-cyanamide, or a salt thereof.

3. A physiologically acceptable salt of a compound according to claims 1 or 2, formed with inorganic or organic acid or base.

4. A pharmaceutical composition containing a compound according to claims 1 or 2, or a physiologically acceptable salt thereof, together with one or more inert carriers and/or diluents.

5. A method for the treatment of migraine or cluster headaches, which comprises administering to a host prone to or currently suffering from the same a therapeutically effective amount of a compound according to claims 1 or 2, or a physiologically acceptable salt thereof.

6. A method for the treatment of migraine headaches, which comprises administering to a host prone to or currently suffering from the same a therapeutically effective amount of a compound according to claims 1 or 2, or a physiologically acceptable salt thereof.

* * * * *